United States Patent
Hanson et al.

(10) Patent No.: US 7,164,058 B2
(45) Date of Patent: Jan. 16, 2007

(54) RESTORATION OF FERTILITY TO CYTOPLASMIC MALE STERILE PETUNIA

(75) Inventors: Maureen Hanson, Ithaca, NY (US); Stephane Bentolila, Ithaca, NY (US); Antonio A. Alfonso, Nueva Ecija (PH)

(73) Assignee: Cornell Research Foundation, Inc., Ithaca, NY (US)

( * ) Notice: Subject to any disclaimer, the term of this patent is extended or adjusted under 35 U.S.C. 154(b) by 275 days.

(21) Appl. No.: 10/341,200

(22) Filed: Jan. 10, 2003

(65) Prior Publication Data

US 2003/0177535 A1 Sep. 18, 2003

Related U.S. Application Data

(60) Provisional application No. 60/347,996, filed on Jan. 10, 2002.

(51) Int. Cl.
- *A01H 5/00* (2006.01)
- *A01H 5/10* (2006.01)
- *C12N 15/82* (2006.01)
- *C12N 15/29* (2006.01)

(52) U.S. Cl. .......... 800/298; 800/290; 536/23.6; 435/418; 435/252.3

(58) Field of Classification Search .......... 536/23.6; 424/93.2; 800/279, 290, 301, 323; 435/252.3
See application file for complete search history.

(56) References Cited

U.S. PATENT DOCUMENTS 5,981,833 A 11/1999 Wise et al.

OTHER PUBLICATIONS

Bellaoui et al, 1999, Plant Mol. Biol. 40:893-902.*
Schnable et al, 1998, Trends Plant Sci. 3:175-180.*
Guo et al, 2004, Proc. Natl. Acad. Sci. USA 101: 9205-9210.*
Hill et al, 1998, Biochem. Biophys. Res. Comm. 244:573-577.*
Lazar et al, 1988, Mol. Cell. Biol. 8:1247-1252.*
Wise et al, 2002, Proc. Natl. Acad. Sci. USA 99:10240-10242.*
Alcala et al, 2001, GenBank Accession No. AW618552.*
Alcala et al, 2001, GenBank Accession No. AI487633.*
Alcala et al, 2001, GenBank Accession No. BE432107.*
van der Hoeven et al, 2001, GenBank Accession No. BI925982.*
van der Hoeven et al, 2001, GenBank Accession No. BG128263.*
Chao et al, 2001, GenBank Accession No. AAF88093.*
Akagi et al, 2004, Theor. Appl. Genet. 108:1449-1457.*
Komori et al, 1005, Plant. Cell, Environ. 28:425-431.*
Bentolila et al., "Locating the Petunia *Rf* Gene on a 650-kb DNA Fragment," *Theor. Appl. Genet.*, 96:980-988 (1998).
Hanson et al., "Mitochondrial Gene Organization and Expression in Petunia Male Fertile and Sterile Plants," *J. Hered.*, 90(3):362-368 (1999).
Bentolila et al., "Identification of a BIBAC Clone That Co-Segregates With the Petunia Restorer of Fertility (*Rf*) Gene," *Mol. Genet. Genomics*, 266:223-230 (2001).
Bentolila et al., "Pentatricopeptide Repeat-Containing Gene Restores Fertility to Cytoplasmic Male-Sterile Plants," *PNAS*, 99(16):10887-10892 (2002).

* cited by examiner

*Primary Examiner*—Anne Kubelik
(74) *Attorney, Agent, or Firm*—Nixon Peabody LLP

(57) ABSTRACT

The present invention relates to isolated nucleic acid molecules which restore fertility to cytoplasmic male sterile plants and modify expression of toxic mitochondria proteins by the plant. The present invention also relates to methods of identifying a candidate plant suitable for breeding with a cytoplasmic male sterile plant and methods of identifying a candidate gene restoring fertility in plants by analyzing for the candidate plant and candidate gene, respectively, for the presence of the nucleic acid molecule of the present invention. Also disclosed are methods of producing hybrid plant seed, methods of directing gene expression to plant mitochondria, and method of expressing a gene preferentially in roots of a plant. Promoters and terminators from plant genes which restore fertility to cytoplasmic male sterile plants and modify expression of toxic mitochondria proteins are also disclosed. Finally, methods of producing plants with a cytoplasmic male sterile plant restoration system are disclosed.

21 Claims, 9 Drawing Sheets

A B.

Diagram of a plant genotype 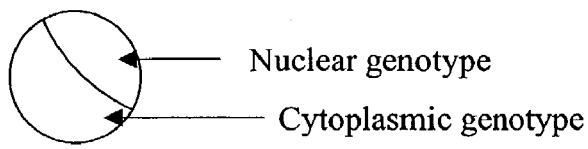 — Nuclear genotype
— Cytoplasmic genotype

 Wild-type plant with wild-type nuclear alleles of gene Ms, a PPR motif gene needed for male fertility ↓ Mutagenesis of the Ms gene (e.g by an insertional element, radiation, chemicals, etc.

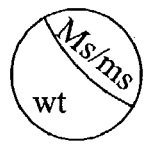 Heterozygous mutant at Ms locus

↓ Self-cross

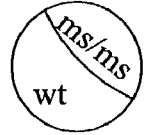 Mutant male sterile plant

↓ By sexual crosses or cybridization with genotypes carrying different organelle genomes than the initial wt genome, or by mutagenesis of genome(s) in the wt cytoplasm, create a genotype with mutant ms/ms nuclear alleles that is male fertile

 Male fertile plant

These genotypes are then utilized as a CMS/restorer system for hybrid seed production and breeding as follows:

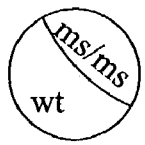   

CMS line      Fertile maintainer line      Fertility restorer lines

Figure 7A

Examples illustrating how new lines can be used as a CMS/restorer system

CMS line     Fertile maintainer line     Maintained CMS line

CMS line     Fertility restorer lines     Fertile Hybrid

RESTORATION OF FERTILITY TO CYTOPLASMIC MALE STERILE PETUNIA

This application claims the benefit of U.S. patent application Ser. No. 60/347,996, filed Jan. 10, 2002, which is hereby incorporated by reference in its entirety.

This invention arose out of research sponsored by the USDA NRI (Grant No. 98-35300-6171). The U.S. Government may have certain rights in this invention.

FIELD OF THE INVENTION

The present invention relates to improving productivity or usefulness of plants by altering mitochondrial gene expression and to the production of hybrid seed. Specifically, the present invention relates to the use of genes that affect mitochondrial gene expression, some of which ameliorate male sterility and others which cause male sterility or altered floral development. The invention also provides a method of facilitating the identification of genes with similar functions in other plant species.

BACKGROUND OF THE INVENTION

A widely used method for producing hybrid seeds involves crossing a cytoplasmic male sterile (CMS) plant line with a fertile plant line. Typically, the fertile line contains a fertility restorer gene in its nuclear genome, so that all of the progeny are male fertile. All seeds collected from a CMS plant must result from cross-pollination. However, the hybrid seed so generated will itself be male sterile unless the male parent has brought a nuclear fertility-restorer gene into the next generation. The fertility of the progeny is important for productivity in plant varieties where self-pollination is responsible for production of the desirable crop. For example, a fruit crop of a self-pollinated species requires male fertility, while an ornamental species will produce attractive flowers or plant morphology even when no pollen is produced.

While a number of naturally occurring CMS/restorer systems exist and are currently in use for hybrid seed production, there are a number of crop species which lack known CMS and fertility restorer genes. For example, a hybrid seed of tomato is typically made by hand emasculation of plants to be used as female parents. This hand-made method of cross-pollination is quite labor intensive and cost-prohibitive for many crops. In addition, certain naturally occurring CMS/restorer systems have some drawbacks. For example, corn plants carrying the CMS-T cytoplasm are more susceptible to a blight disease.

Fertility restorer genes that have been particularly useful for hybrid seed production are active as single dominant alleles at a locus, though multigenic systems are sometimes used. A *Petunia* fertility restorer locus termed Rf is known to be effective with no additional helper genes to restore fertility (Edwardson et al., "Fertility Restoration in Cytoplasmic Male Sterile *Petunia*," *J. Hered.*, 58:195–196 (1967); Izhar, "Cytoplasmic Male Sterility in *Petunia*. III. Genetic Control on Microsporogenesis and Male Fertility Restoration," *J. Hered.*, 69:22–26 (1978)).

Nuclear fertility restoration genes confer normal pollen development upon plants carrying sterility-encoding mitochondria. The mitochondrial genes responsible for causing the male sterility have been identified in a number of species, including *Petunia*, maize, *Brassica*, and common bean. The expression of these CMS-encoding mitochondrial genes is affected by the nuclear restorer genes, as shown for Rf in *Petunia* (Pruitt et al., "Cytochrome Oxidase Subunit II Sequences in *Petunia* Mitochondria: Two Intron-Containing Genes and an Intron-Less Pseudogene Associated With Cytoplasmic Male Sterility," *Curr. Genet.*, 16:281–91 (1989); Nivison et al., "Identification of a Mitochondrial Protein Associated With Cytoplasmic Male Sterility in *Petunia*," *Plant Cell*, 1:1121–30 (1989); Nivision et al., "Sequencing, Processing, and Localization of the *Petunia* CMS-Associated Mitochondrial Protein," *Plant J.*, 5:613–623 (1994); Hanson et al., "Mitochondrial Gene Organization and Expression in *Petunia* Male Fertile and Sterile Plants," *J. Hered.*, 90:362–368 (1999)); Rf1 in CMS-T maize (Dewey et al., "Novel Recombinations in the Maize Mitochondrial Genome Produce a Unique Transcriptional Unit in the Texas Male-Sterile Cytoplasm," *Cell*, 44:439–49 (1986); Wise et al., "Mitochondrial Transcript Processing and Restoration of Male Fertility in T-Cytoplasm Maize," *J Hered*, 90:380–385 (1999); Kennell et al., "Influence of Nuclear Background on Transcription of a Maize Mitochondrial Region Associated With Texas Male Sterile Cytoplasm," *Mol. Gen. Genet.*, 210:399–406 (1987); Kennell et al., "Initiation and Processing of atp6, T-urf13, and ORF221 Transcripts From Mitochondria of T Cytoplasm Maize," *Mol. Gen. Genet.*, 216:16–24 (1989)); Rfp1 and rfp1 in *Brassica* (Singh et al., Suppression of Cytoplasmic Male Sterility by Nuclear Genes Alters Expression of a Novel Mitochondrial Gene Region," *Plant Cell*, 3:1349–1362 (1991); Singh et al., "Nuclear Genes Associated With a Single *Brassica* CMS Restorer Locus Influence Transcripts of Three Different Mitochondrial Gene Regions," *Genetics*, 143:505–516 (1996)); restorers in radish (Krishnasamy et al., "Organ-Specific Reduction in the Abundance of a Mitochondrial Protein Accompanies Fertility Restoration in Cytoplasmic Male-Sterile Radish," *Plant Molec. Biol.*, 26:935–946 (1994)); restorers in sunflower (Horn et al., "A Mitochondrial 16 kDa Protein is Associated With Cytoplasmic Male Sterility in Sunflower," *Plant Molec. Biol.*, 17:29–36 (1991); Laver et al., "Mitochondrial Genome Organization and Expression Associated With Cytoplasmic Male Sterility in Sunflower (*Helianthus annuus*)," *Plant J.*, 1:185–193 (1991); Monéger et al., "Nuclear Restoration of Cytoplasmic Male Sterility in Sunflower is Associated With the Tissue-Specific Regulation of a Novel Mitochondrial Gene," *EMBO J.*, 13:8–17 (1994); Smart et al., "Cell-Specific Regulation of Gene Expression in Mitochondria During Anther Development in Sunflower," *Plant Cell*, 6:811–825 (1994)); restorers in rice (Akagi et al., "A Unique Sequence Located Downstream From the Rice Mitochondrial atp6 May Cause Male Sterility," *Curr. Genet.*, 25:52–58 (1994); Kadowaki et al., "A Chimeric Gene Containing the 5' Portion of atp6 is Associated With Cytoplasmic Male Sterility of Rice," *Mol. Gen. Genet.*, 224:10–16 (1990)); and Fr2 in broad bean (Chase, "Expression of CMS-Unique and Flanking Mitochondrial DNA Sequencs in *Phaseolus vulgaris,*" *L. Curr. Genet.*, 25:245–251 (1993); He et al., "Pollen Fertility Restoration by Nuclear Gene Fr in CMS Bean: Nuclear-Directed Alteration of a Mitochondrial Population," *Genetics*, 139:995–962 (1995)). The expression of various nuclear restorer genes has been reported to be either enhanced in reproductive tissue, as in the case of sunflower, or, as in the case of *Petunia*, expressed in both vegetative and reproductive tissues. Thus, different fertility restorer genes carry different promoters and nuclear expression regulatory elements which may confer very limited tissue-specific expression or very broad expression in the plant.

Reduction in the amount of the protein product of the CMS-encoding gene is the usual effect of these restorers whose target mitochondrial genes are known. These genes may possibly act by affecting the transcription or translation rate, the transcript or protein stability, processing, splicing, etc. Alleles of some restorer genes may up-regulate while others may down-regulate the expression of particular mitochondrial genes. Fertility restorer genes and their alleles or homologous counterparts in other species may thus be extremely valuable in engineering the expression of genes introduced into higher plant mitochondria.

The cloning and sequencing of the restorer gene Rf2 in maize has been reported in Cui et al., "The rf2 Nuclear Restorer Gene of Male-Sterile T-Cytoplasm Maize," *Science*, 272:1334–1336 (1996) and U.S. Pat. No. 5,981,833 to Wise et al. This restorer gene acts in conjunction with a second required gene, Rf1, the gene that reduces the amount of the toxic protein, to restore fertility to plants carrying the maize CMS-T cytoplasm (Dewey et al., "Novel Recombinations in the Maize Mitochondrial Genome Produce a Unique Transcriptional Unit in the Texas Male-Sterile Cytoplasm," *Cell*, 44:439–49 (1986); Dewey et al., "A Mitochondrial Pprotein Associated With Cytoplasmic Male Sterility in the T Cytoplasm of Maize," *Proc. Natl. Acad. Sci. USA*, 84:5374–78 (1987); Wise et al., "Urf13-T of T Cytoplasm Maize Mitochondria Encodes a 13 kD Polypeptide," *Plant Mol. Biol.* 9:121–26 (1987)). Plants of genotype Rf1rf2, though sterile, have greatly reduced amounts of the URF13 protein. In contrast, sterile plants of genotype rf1Rf2 have abundant amounts of the URF13 protein. The Rf2 gene is, thus, unusual in that no effect on the expression of the maize T-CMS-associated protein, URF13, has been detected. The sequence of the gene bore out the absence of observable effect on mitochondrial gene expression; according to sequence analysis, Rf2 is apparently an aldehyde dehydrogenase (Liu et al., "Mitochondrial Aldehyde Dehydrogenase Activity is Required for Male Fertility in Maize," *The Plant Cell*, 13:1063–1078 (2001)). It has been proposed that Rf2 acts by compensating for a metabolic defect caused by the low levels of the URF13 protein that remain despite the presence of Rf1, the gene that reduces the amount of the toxic protein (Dewey et al., "A Mitochondrial Protein Associated With Cytoplasmic Male Sterility in the T Cytoplasm of Maize," *Proc. Natl. Acad. Sci. USA*, 84:5374–78 (1987)) and also alters the T-urf13 transcript profile (Kennell et al., "Influence of Nuclear Background on Transcription of a Maize Mitochondrial Region Associated With Texas Male Sterile Cytoplasm," *Mol. Gen. Genet.*, 210:399–406 (1987)).

An abnormal recombinant mitochondrial gene in *Petunia* CMS lines (termed pcf) has been genetically correlated with CMS (Young et al., "A Fused Mitochondrial Gene Associated With Cytoplasmic Male Sterility is Developmentally Regulated," *Cell*, 50:41–49 (1987)). Because plant mitochondrial RNA is edited from C to U in some locations, the edited RNA sequence for the pcf gene has been determined, allowing the prediction of the pcf-encoded protein (Wintz et al., "A Termination Codon is Created by RNA Editing in the *Petunia* Mitochondrial atp9 Gene Transcript," *Curr. Genet.*, 19:61–64 (1990); Sutton et al., "Editing of Pre-mRNAs Can Occur Before cis- and trans-Splicing in *Petunia* Mitochondria," *Mol. Cell Biol.*, 11:4274–4277 (1991); Nivision et al., "Sequencing, Processing, and Localization of the *Petunia* CMS-Associated Mitochondrial Protein," *Plant J.*, 5:613–623 (1994); Hanson et al., "Mitochondrial Gene Organization and Expression in *Petunia* Male Fertile and Sterile Plants," *J. Hered.*, 90:362–368 (1999)). Antibodies to synthetic peptide sequences have revealed the presence of a 19.5 kD PCF protein located in both the membrane and soluble fraction of mitochondria (Nivison et al., "Identification of a Mitochondrial Protein Associated With Cytoplasmic Male Sterility in *Petunia*," Plant Cell, 1:1121–30 (1989)). The PCF protein is processed from a longer precursor protein and is entirely encoded by the urfS region of the pcf gene (Nivision et al., "Sequencing, Processing, and Localization of the *Petunia* CMS-Associated Mitochondrial Protein," *Plant J.*, 5:613–623 (1994)). The PCF protein is strongly expressed in sporogenous cells of premeiotic *petunia* anthers in CMS lines, but undetectable in CMS-Rf lines (Conley et al., "Tissue-Specific Protein Expression in Plant Mitochondria," *Plant Cell*, 6:85–91 (1994)). Abnormalities in *Petunia* pollen development are first observed in meiosis, and by the developmental stage where fertile plants are releasing pollen, CMS anthers are hollow shells (Conley et al., "Effects of *Petunia* Cytoplasmic Male Sterile (CMS) Cytoplasm on the Development of Sterile and Fertility-Restored *P. parodii* Anthers," *Am. J. Bot.*, 81:630–640 (1994)). It is evident that the pcf gene product is disrupting mitochondrial function, leading to death of the sporogenous cells, though the exact mechanism at the molecular level is not known.

In maize T, *Petunia*, rice, and *Brassica* Pol CMS systems, particular transcripts of CMS-associated genes have been reported to be altered in restored lines (Pruitt et al., "Transcription of the *Petunia* Mitochondrial CMS-Associated pcf Locus in Male Sterile and Fertility-Restored Lines," *Mol. Gen. Genet.*, 227:348–355 (1991); Dewey et al., "Novel Recombinations in the Maize Mitochondrial Genome Produce a Unique Transcriptional Unit in the Texas Male-Sterile Cytoplasm," *Cell*, 44:439–49 (1986); Kennell et al., "Initiation and Processing of atp6, T-urf13, and ORF221 Transcripts From Mitochondria of T Cytoplasm Maize," *Mol. Gen. Genet.*, 216:16–24 (1989); Kennell et al., "Influence of Nuclear Background on Transcription of a Maize Mitochondrial Region Associated With Texas Male Sterile Cytoplasm," *Mol. Gen. Genet.*, 210:399–406 (1987); Singh et al., "Suppression of Cytoplasmic Male Sterility by Nuclear Genes Alters Expression of a Novel Mitochondrial Gene Region," *Plant Cell*, 3:1349–1362 (1991); Singh et al., "Nuclear Genes Associated With a Single *Brassica* CMS Restorer Locus Influence Transcripts of Three Different Mitochondrial Gene Regions," *Genetics*, 143:505–516 (1996); Wise et al., "Mitochondrial Transcript Processing and Restoration of Male Fertility in T-Cytoplasm Maize," *J. Hered.*, 90:380–385 (1999)). In *Brassica*, the presence of either one of two restorer genes results in monocistronic transcripts of atp6, instead of the dicistronic orf224/atp6 transcripts found in CMS lines (Singh et al., "Suppression of Cytoplasmic Male Sterility by Nuclear Genes Alters Expression of a Novel Mitochondrial Gene Region," *Plant Cell*, 3:1349–1362 (1991)). A UG-rich sequence appears to be the target of the *Brassica* restorer alleles (Singh et al., "Nuclear Genes Associated With a Single *Brassica* CMS Restorer Locus Influence Transcripts of Three Different Mitochondrial Gene Regions," *Genetics*, 143:505–516 (1996)). In *Petunia*, pcf transcripts with 5' termini at −121 are specifically reduced in restored lines (Pruitt et al., "Transcription of the *Petunia* Mitochondrial CMS-Associated pcf Locus in Male Sterile and Fertility-Restored Lines," *Mol. Gen. Genet.*, 227:348–355 (1991)), while transcripts terminating at −266 and −522 remain at normal levels. In maize T cytoplasm, a sequence unlike either the *Brassica* restorer target or the *Petunia* −121 transcript terminus is the putative recognition signal for the Rf1 gene (Dill et al., "Rf8 and Rf*

Mediate Unique T-urf13-Transcript Accumulation, Revealing a Conserved Motif Associated With RNA Processing and Restoration of Pollen Fertility in T-cytoplasm Maize," *Genetics*, 147:1367–1379 (1997)).

The steady-state amounts of the *Petunia* pcf-encoded protein and the maize urf13-encoded protein decrease greatly in restored lines compared to unrestored lines (Nivison et al., "Identification of a Mitochondrial Protein Associated With Cytoplasmic Male Sterility in *Petunia*," *Plant Cell*, 1:1121–30 (1989); Dewey et al., "Novel Recombinations in the Maize Mitochondrial Genome Produce a Unique Transcriptional Unit in the Texas Male-Sterile Cytoplasm," *Cell*, 44:439–49 (1986); Wise et al., "Urf13-T of T Cytoplasm Maize Mitochondria Encodes a 13 kD Polypeptide," *Plant Mol. Biol.*, 9:121–26 (1987)). Abundance of CMS-associated proteins is also reduced in sunflower and radish (Horn et al., "A Mitochondrial 16 kDa Protein is Associated With Cytoplasmic Male Sterility in Sunflower," *Plant Mol. Biol.* 17:29–36 (1991); Laver et al., "Mitochondrial Genome Organization and Expression Associated With Cytoplasmic Male Sterility in Sunflower (*Helianthus annuus*)," *Plant J.*, 1:185–193 (1991); Krishnasamy et al., "Organ-Specific Reduction in the Abundance of a Mitochondrial Protein Accompanies Fertility Restoration in Cytoplasmic Male-Sterile Radish," *Plant Mol. Biol.*, 26:935–946 (1994)). The mechanism behind the reduction in quantity of CMS-associated proteins in restored lines is not understood. For example, absence of transcripts that could potentially encode the PCF protein is not the explanation; only the shortest transcript is reduced in restored lines (Pruitt et al., "Transcription of the *Petunia* Mitochondrial CMS-Associated pcf Locus in Male Sterile and Fertility-Restored Lines," *Mol. Gen. Genet.*, 227:348–355 (1991)).

In *Petunia* and in some other CMS/restorer systems, the abnormal gene is co-transcribed with known mitochondrial genes. One possible mechanism for CMS in *Petunia* and its restoration, which is also consistent with current data, is that the restorer gene not only results in decrease in the expression of PCF, but also improves the expression of the co-transcribed genes nad3 and rps12 in some way. For example, it remains possible that an RNA processing event results in little translation of PCF but enhanced production of NAD3 and RPS12 protein.

In sum, with the exception of maize Rf2, in those systems where analysis has reached the molecular level, restorer genes have been found to affect the abundance of mitochondrial-encoded DNAs, RNAs, and proteins.

Cytoplasmic male sterility/restorer systems have been proven to be an invaluable tool in the production of hybrid seeds. Despite their importance for both the production of major crops such as rice and sunflower and the study of organelle/nuclear interactions in plants, none of the nuclear fertility-restorer genes that reduce the expression of aberrant mitochondrial proteins have been cloned.

The present invention is directed to overcoming these deficiencies in the art.

SUMMARY OF THE INVENTION

The present invention relates to an isolated nucleic acid molecule which restores fertility to cytoplasmic male sterile plants and modifies expression of toxic mitochondria proteins by the plant. The nucleic acid molecule encodes a protein having an amino acid sequence of SEQ ID NOs: 2, 21, 23, 25, 27, 29, 31, 33, 35, 37, 39, or 41. Alternatively, the nucleic acid molecule encodes a protein containing a motif having an amino acid sequence corresponding to any of SEQ ID NOs: 3 to 18 or an amino acid sequence identified with a METAMEME software using the amino acid sequence of SEQ ID NO: 2 as input or an amino acid sequence identified as significantly similar to SEQ ID NO: 2 using a NCBI BLAST software (threshold=E less than or equal to 15) with SEQ ID NO: 2 as input. Alternatively, the nucleic acid molecule hybridizes to a nucleotide sequence of from nucleotide 1982 to 3760 of SEQ ID NO: 1, SEQ ID NO: 19, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40 under stringent conditions of a hybridization buffer containing 20% formamide in 0.9M saline/0.09M SSC buffer at a temperature of 42° C. Alternatively, the nucleic acid molecule has a nucleotide sequence of from nucleotide 1982 to 3760 of SEQ ID NO: 1, SEQ ID NO: 19, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40.

Another aspect of the present invention relates to a method of identifying a candidate plant suitable for breeding with a cytoplasmic male sterile plant. The method involves analyzing the candidate plant for the presence, in its genome, of the above nucleic acid molecule of the present invention.

Yet another aspect of the present invention relates to a method of identifying a candidate gene restoring fertility in plants. The method involves analyzing the candidate gene for the presence of the above nucleic acid molecule in accordance with the present invention.

The present invention also relates to a method of producing hybrid plant seed. The method first involves providing a cytoplasmic male sterile plant. Next, a second plant containing the above nucleic acid molecule in accordance with the present invention is provided. Finally, the cytoplasmic male sterile plant and the second plant are bred under conditions effective to produce hybrid progeny seed which yield fertile plants.

Another aspect of the present invention relates to a method of producing plant seeds for an inbred line of plants. The method first involves providing a cytoplasmic male sterile plant. Next, a second plant containing the above nucleic acid molecule in accordance with the present invention is provided. Then, the cytoplasmic male sterile plant and the second plant are bred under conditions effective to produce hybrid progeny seed which yield fertile plants. Next, hybrid fertile plants are produced from the hybrid progeny seeds. Finally, the hybrid fertile plants and the second plant are backcrossed to produce seed which yiled inbred progeny plants.

Yet another aspect of the present invention relates to a method of directing gene expression to plant mitochondria. The method involves transforming a plant with a chimeric nucleic acid molecule containing a transgene operatively linked to a promoter or a terminator from a plant gene which restores fertility to cytoplasmic male sterile plants and modifies expression of toxic mitochondria proteins by the plant under conditions effective to direct expression of the transgene in the mitochondria of the transformed plant. The promoter has a nucleotide sequence of from nucleotide 1 to 1981 of SEQ ID NO: 1. The terminator has a nucleotide sequence of from nucleotide 3761 to 4593 of SEQ ID NO: 1.

The present invention also relates to a promoter from a plant gene which restores fertility to cytoplasmic male sterile plants and modifies expression of toxic mitochondria proteins by the plant under conditions effective to direct expression of the transgene in the mitochondria of the transformed plant. The promoter has a nucleotide sequence of from nucleotide 1 to 1981 of SEQ ID NO: 1.

Another aspect of the present invention relates to a terminator from a plant gene which restores fertility to cytoplasmic male sterile plants and modifies expression of toxic mitochondria proteins by the plant under conditions effective to direct expression of the transgene in the mitochondria of the transformed plant. The terminator has a nucleotide sequence of from nucleotide 3761 to 4593 of SEQ ID NO: 1.

Yet another aspect of the present invention relates to a nucleic acid construct. The nucleic acid construct includes: (i) a promoter or a terminator from a plant gene which restores fertility to cytoplasmic male sterile plants and modifies expression of toxic mitochondria proteins by the plant under conditions effective to direct expression of the transgene in the mitochondria of the transformed plant and (ii) a nucleic acid heterologous to and operatively coupled to the promoter or the terminator. The promoter has a nucleotide sequence of from nucleotide 1 to 1981 of SEQ ID NO: 1. The terminator has a nucleotide sequence of from nucleotide 3761 to 4593 of SEQ ID NO: 1.

The present invention also relates to a method of expressing a gene preferentially in roots of a plant. The method involves transforming a plant with a nucleic acid construct. The nucleic acid construct includes a promoter suitable for driving expression preferentially in roots having a nucleotide sequence of from 1 to 1388 of SEQ ID NO: 44; a nucleic acid heterologous to the promoter, where the promoter is operatively coupled 5' to the nucleic acid to induce transcription of the nucleic acid; and a terminator having a nucleotide sequence of from nucleotide 3168 to 4016 of SEQ ID NO: 44, where the terminator is operably coupled 3' to the nucleic acid.

Another aspect of the present invention relates to a method of altering plant floral morphology in ornamental plants. The method involves transforming an ornamental plant with the above nucleic acid molecule in accordance with the present invention.

Another aspect of the present invention relates to a method of producing plants with a cytoplasmic male sterile plant restoration system. The method first involves transforming a first plant in its chloroplast genome with a nucleic acid which causes the plant to become male sterile. Next a second plant is transformed with the above nucleic acid molecule in accordance with the present invention whose protein product is targeted to the chloroplast. Finally, the first and second plants are crossed to produce progeny plants possessing a cytoplasmic male sterile plant restoration system.

Another aspect of the present invention relates to a method of producing plants with a cytoplasmic male sterile plant restoration system. The method first involves mutagenizing a first plant having a nucleic acid which encodes a protein. The protein has a motif having an amino acid sequence corresponding to any of SEQ ID NOs: 3 to 18 or an amino acid sequence identified with a METAMEME software using the amino acid sequence of SEQ ID NO: 2 as input or an amino acid sequence identified as significantly similar to SEQ ID NO: 2 using a NCBI BLAST software (threshold=E less than or equal to 15) with SEQ ID NO: 2 as input. Next, the mutagenized first plant is crossed with a wild-type plant having mitochondrial DNA polymorphisms compared to mitochondrial DNA in the mutagenized first plant to produce progeny plants. Finally, it is determined if the progeny plants are fertile, whereby fertile progeny plants can be used as a fertile maintainer line, where the mutagenized first plant, the fertile maintainer line, and a wild-type allele present in the first plant before mutagenesis comprises a new cytoplasmic male sterile plant restoration system.

The present invention also relates to an isolated nucleic acid sequence corresponding to SEQ ID NO: 42 or SEQ ID NO: 44.

The present invention identifies nucleic acid sequences which encode the gene for restoration of fertility to cytoplasmic male sterile plants. This gene modifies the expression of the mitochondrial genome and is the first such gene sequence that has been identified. In *petunia*, the gene may be transferred to lines lacking the gene in order to restore fertility. More importantly, the gene sequence has characteristics that can be used to identify comparable genes from economically important species. Thus, the gene and the sequence information may be used to develop hybrid seed production systems in economically important plants. Furthermore, the information may be used in crop improvement by controlling mitochondrial gene expression.

BRIEF DESCRIPTION OF THE DRAWINGS

FIG. 1A illustrates the genomic organization of the region containing the Rf-PPR592 and Rf-PPR591 genes. Duplicated blocks are indicated by similar shading. Arrows indicate the direction of transcription 1 and 2 show locations of the primers used to amplify the rf-PPR592 gene from a CMS plant. FIG. 1B shows a single onion epidermal cell expressing a known mitochondrially targeted green fluorescent protein (GFP) after DNA bombardment. FIG. 1C shows a single onion epidermal cell transiently expressing 44 N-terminal amino acids of Rf-PPR592 fused to GFP. FIG. 1D shows a comparison of PPR motifs found in Rf-PPR592 with the MEME-derived consensus from 1,303 PPR motifs ("1303 PPR"; SEQ ID NO: 3). The 14 PPR repeats ("PPR 230–264" (SEQ ID NO: 10); "PPR 265–299" (SEQ ID NO: 11); "PPR 370–404" (SEQ ID NO: 14); "PPR 300–334" (SEQ ID NO: 12); "PPR 335–369" (SEQ ID NO: 13); "PPR 475–509" (SEQ ID NO: 17); "PPR 510–544" (SEQ ID NO: 18); "PPR 440–474" (SEQ ID NO: 16); "PPR 195–229" (SEQ ID NO: 9); "PPR 405–439" (SEQ ID NO: 15); "PPR 160–194" (SEQ ID NO: 8); "PPR 124–158" (SEQ ID NO: 7); "PPR 54–88" (SEQ ID NO: 5); and "PPR 89–123" (SEQ ID NO: 6)) are sorted by decreasing statistical significance, with PPR 230–264 showing the highest match to the consensus motif ("Consensus"; SEQ ID NO: 4) that is generated by retaining only the amino acids that occur at least in 6 of the 14 repeats.

FIG. 2A illustrates that a comparison of Rf-PPR592 and rf-PPR592 reveals a size polymorphism. The first lane was loaded with the Rf-PPR592 PCR amplicon obtained from a restorer line (Rf/Rf), the adjacent lane was loaded with the rf-PPR592 PCR amplicon obtained with the same primer pair from a CMS line (rf/rf). FIG. 2B illustrates that a comparison of Rf-PPR592, Rf-PPR591, and rf-PPR592 reveals five similarity blocks. For each block, (I to V), the two blocks that exhibit the greatest similarity are shown with the same shading. Overall all three sequences are greater than 90% identical at the nucleotide level except in block V, where Rf-PPR591 exhibits only 23% identity to the other two genes. The locations of 47- and 49-nt deletions in Rf-PPR591 and 47- and 530-nt deletions in rf-PPR592 with respect to the Rf-PPR592 sequence in blocks I and II are shown as lines.

FIG. 3A depicts the examination of floral bud RNA for expression of rf-PPR592 and Rf-PPR592. RT-PCR of floral bud RNA of a CMS plant (S) with primers specific to rf-PPR592, and RT-PCR of floral bud RNA of an RfRf (nontransgenic) fertile plant with primers specific for Rf-PPR592 (R). DNA, positive control for the amplification where the substrate is leaf DNA from a CMS plant; M, mass markers; 0, no template added, negative control. FIG. 3B depicts the examination of different tissues for expression of rf-PPR592. RT-PCR of RNA from different tissues of a CMS plant with primers specific to rf-PPR592. DNA, M, and 0 are same as in FIG. 3A.

FIG. 4A shows the flower of *P. parodii* CMS line 3688. FIG. 4B shows the regenerant carrying Rf-PPR592. FIG. 4C shows the *P. hybrida* CMS line 2423. FIG. 4D shows the regenerant carrying Rf-PPR592.

FIG. 5A shows the DNA blot hybridized with an npt II transgene-specific probe. Lane 1, *P. parodii* CMS line 3688; lanes 2- and 3, sterile $T_1$ progeny of transformed *P. parodii;* lanes 4–9, fertile $T_1$ progeny. FIG. 5B shows the immunoblot of floral bud proteins probed with anti-PCF antibody. Lanes are as in FIG. 5A.

FIG. 6A shows a petaloid flower on a plant carrying a recombination event near the Rf locus, affecting the region 5' to Rf-PPR592. FIG. 6B shows an abnormal flower on a plant carrying the CMS cytoplasm and the 4.5 kb Rf-PPR592 transgene.

FIGS. 7A–B show methods for creating a new CMS/restorer system.

DETAILED DESCRIPTION OF THE INVENTION

Figure 1:
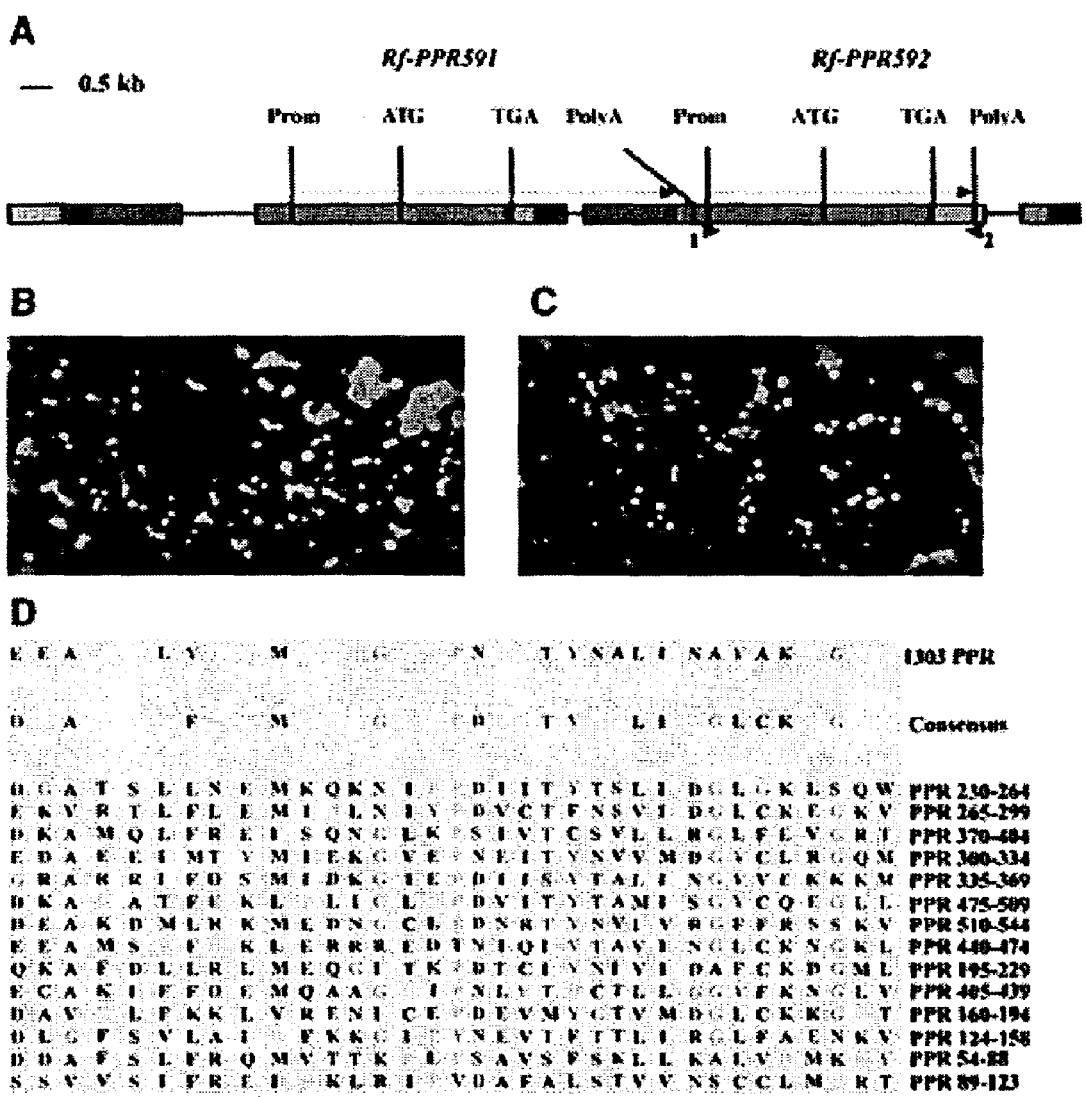
FIGS. 1A–D show that the Rflocus contains two tandem mitochondrially targeted PPR motif genes.

The present invention relates to an isolated nucleic acid molecule which restores fertility to cytoplasmic male sterile plants and modifies expression of toxic mitochondria proteins by the plant.

One form of the nucleic acid molecule of the present invention is a nucleotide sequence of from nucleotide 1982 to 3760 of SEQ ID NO: 1, identified herein as Rf-PPR592, as follows:

```
   1 ATATATATATACAAACTGATTTTTTCT-
     GTCTATTTGCACAGTGTTATATTTACATACCCTTGAAAAAGGGTAGCTCCGCT

81 AATAATGTTATCTTTACAAAAAATAA-
     CAATAATTTTTTTACATAATATATACAAAACTCATTGTTATGTATTGTAAATAT

161 GATAAAAATATTGTTATTTTTTG-
     TAATATAGCTATTAGGTAGTCATGTGGTGTAATATTTCCTAAAAATATTTACCTGAG

241 TCGGCCATTTGGCTAAAAATATTT-
     TATTTTATAGTCGCATATACTCCAAGCTTGTATATCCCATAGCGACAGTATACCTA

321 TACGATATCTTCTATTATTTACCTTTT-
     TAGTATTCGTATACCCCCAATAGTATACAAGTTTCACACCGCAATAGTGTACC

401 CCAATGTTGTGGTTGTGTGGC-
     TATAAAATGTTTAAACAAAATTTGAGTGATGGTAGTGTAATTTTTTAGTGTAAGCTGGG

481 TAGTTTTAAAAACATTCTTTTTGAAAAT-
     TGTAGTTCAAGTCATAGTACAAAAAACTGAAATATTTATATGTTTCTTGATT

561 TTGGCTGGTCTTCTAAAAATTTTGAAAT-
     GCTGGCTAGTTTTCATTTAGCGAGGGGCAAATAGACTACATGGCCAAATTTT

641 TACGTTAAAAGAAGTGTTGTCTGG-
     GAAAGTATTCGAAAAGATTCTACGGACAAGTGTTGCCTAGACAACACGTCAAATTA

721 TGTAGAAAAATGTAGGAAGAAAT-
     TCAAAAGCAAATATTGCTTAAGCAAAAGGCAGTCAAAGACAATGCTGCCTTAGGGAG

801 TGAGAAATGGGCATCACTATAAGATTG-
     TATTTCCATTCGATATTTATTCATTATAAACTTAAGGAAAAGTGCAAGGAAAA

881 GCCACTTTTTGGCTTGCCTTTACCGT-
     TGAAGCTACTTTCAAAGAAAAAGAGCTAGTTTTTAGCTTTTTTGGAACTTTAAT

961 CATTGTGGGCCGAACTTCAGACCT-
     TGTGGGCCGAACTTCATACATTCACAAGTAAAAAATTAGCTCACAGGCCACTTTTA

1041 CCACTAGTATTTGGTTTGAAGT-
     CATTTTTTTATTGGTTTTACATGAGAGACCACTTTTTGGAACTTCAATCTTTGTGCGC

1121 TTGAACTTCATGCCTAAGTTATTAAGT-
     TCAACTTCAATCCGTAAGGGCTGAATTTTTAGGCATAGATGCGTAAACTTCAA

1201 CCTTGTGGACTGAAGTTGAACTTCGC-
     CCCTTATGGTGGCCTGAAGTTGAACTTCAATCCTTGTGGGCTGAACTTGTGTGA
```

```
                                    -continued
1281  AGTTCAACCCACAAGGAT-
      TAAAGTTTCAAAAAATGACCTCTCAAGCAAAATCTGCAAAAAAAAGTGGTCTCTCATGCACT 1361  TTTACCCATTCGCAAAGTAGGCTGAAGT-
      TCAGCCCACAATTATTCAAGTTCCAAAAAATTTCACAATATATACCTCCTTA 1441  TCTCGGTTATGATCTTTTGTATGATT-
      TAGCAAAATGGACGGGCAAAGTGCACGAAAGACCACTTTTGCCATTGGTCTTTG 1521  GGTACAGGCCACTAATACCAAAATATT-
      TAGTTTCTGGCTACTTTTGCTTAAAGAGATAGAACTTCAGTCCAGAGGCCGGA 1601  TTGAAGTTCAGTCCTTAAAGATTGAACT-
      TCGATCCAGTGCCATATGGACTGAAGTTCAGTCAAGTCCTTAAGATGGAACT 1681  TCAGTCCAGAGCCATATGGACTGAAGT-
      TCAATCCTTAAAGATAGAACTTCAGTCCAGCCGCCGTATGGACTGAAGTTCAG 1761  TCAATTATCAGAACTTAAGTCAGTATT-
      TATTTAGTAAAGGCCCAAAAGTGGTTAGTATAAGACCAATAAAAATAGAGGCC 1841  TAAAACTAAATAACAGTGTTAAAAGTG-
      GCTGATGGACGAAATTTCTACAAAATGGACTCGAGGTAGCAATTCAACTTCAA 1921  CCTATGGTGTCATAGTCGTACAATTCT-
      TCCAATCACCCCTACTAAGTGAAGTGAAGCGAAGATGATGAGAATTGCACTGC 2001  GTTACTGTCTCAATGGTAATC-
      CCTTTTTCTCATTCTTTGCTTATTCAATTGCACCCCGACATTATTCTACCAATACATGT 2081  TCCATTTCAGTTAAAGG-
      GAATTTTGGGGTTTCTAATGAATTTGAGAATGTTAAGTGTTTAGATGATGCTTTCAGTTTGTT 2161  CCGTCAAATGGTTACAACTAAGCCTCT-
      TCCTTCTGCTGTCTCTTTCTCTAAATTGTTGAAAGCTTTGGTACATATGAAGC 2241  ATTACTCTTCTGTTGTTTCTATTTTTC-
      GAGAAATCCACAAATTACGTATTCCTGTTGATGCTTTCGCCTTGAGCACTGTG 2321  GTTAACAGTTGTTGCCTTATGCATCG-
      TACCGATCTCGGATTTTCTGTATTAGCCATTCACTTCAAGAAAGGTATTCCATA 2401  TAATGAAGTCACCTTTACTACCT-
      TAATAAGGGGACTTTTTGCTGAAAATAAGGTCAAAGATGCTGTTCATTTGTTCAAAA 2481  AGTTGGTGAGGGAGAATATATGTGAGC-
      CTGATGAAGTCATCTATGGGACGGTCATGGATGGGCTTTGCAAGAAGGGCCAT 2561  ACTCAAAAAGCTTTTGATTTGCTCCGGT-
      TAATGGAACAAGGAATTACTAAGCCCGATACATGCATCTACAACATTGTTAT 2641  CGATGCCTTTTGCAAAGATGGGATGCTA-
      GATGGTGCTACCAGCCTTTTGAACGAGATGAAACAAAAAAACATTCCTCCAG 2721  ACATTATTACATATACCTCATTGATC-
      GATGGTTTGGGTAAGTTAAGTCAGTGGGAAAAGGTTAGGACTTTGTTCCTTGAG 2801  ATGATACATCTTAATATTTATCCAGAT-
      GTGTGCACCTTCAACTCCGTCATTGATGGACTATGCAAAGAGGGGAAAGTTGA 2881  AGATGCCGAGGAAATAATGACATACAT-
      GATCGAAAAAGGTGTAGAACCTAATGAGATAACCTACAATGTGGTAATGGATG 2961  GATATTGCTTGCGTGGTCAAATGGGTA-
      GAGCGAGGAGAATTTTTGATTCCATGATAGATAAGGGCATTGAGCCTGATATC 3041  ATTAGCTATACCGCACTAATAAATG-
      GATACGTCGAGAAAAGAAAATGGATAAGGCCATGCAATTGTTTCGTGAAATTTC 3121  TCAAAATGGATTGAAACCTAGTATTGT-
      TACCTGCAGTGTTCTCTTGCGTGGTCTTTTTGAAGTTGGAAGAACTGAATGTG 3201  CAAAAATATTCTTTGATGAGATG-
      CAAGCTGCGGGGCACATACCTAATTTATACACTCATTGCACTTTGCTTGGTGGTTAT 3281  TTTAAGAATGGACTTGTTGAAGAGGC-
      TATGTCACACTTCCATAAGTTGGAAAGGAGGAGAGAAGATACAAATATTCAAAT 3361  TTACACGGCTGTCATTAATGGATTGTG-
      CAAAAAATGGTAAGCTCGACAAAGCTCATGCTACGTTTGAGAAGCTTCCCTTGA 3441  TAGGCTTACATCCTGATGTGATAACATA-
      CACTGCAATGATTAGTGGATATTGTCAAGAAGGGTTGTTAGATGAAGCTAAA
```

-continued

```
3521 GATATGCTAAGGAAAATGGAGGACAATG-
     GTTGTTTGCCAGACAACCGAACATACAATGTTATTGTGCGGGGATTTTTCAG

3601 AAGCAGTAAAGTTAGTGAAATGAAG-
     GCTTTTCTGAAGGAAATAGCTGGGAAGAGCTTCTCATTTGAGGCAGCTACTGTAG

3681 AGTTATTGATGGATATTATAGCACAG-
     GATCCTTCTTTGCTTAACATGATTCCAGAATTTCACCGGGATAATAAGAAGTGA

3761 ATAACTTTTGCACCTGTTTTTTTTGAC-
     GATATCACCATTATTCTGCTATTTCCTTTCATCTTAGCAAAAGAAATTGCATC

3841 CAGTGGAATTGCGGAAGCTGAAAAAATG-
     GCAAGAAGAACATTGCTTAAGCTTTCCTGGCAAGCTTATATCGGAGGGACAT

3921 CATTTTGGTTGTTTTGGCTCTCTTCTT-
     TATCTTGGAAATCAAATGTTCTGCGCTCTTAATATCAGAAACAATGTGAACTC

4001 CCATATATGTACGAGTTATAAGTTTCG-
     GAATATGATTTCAATGGTTTCAGTATTCTATTTTTGATATGGAATTAATTTTT

4081 GAGCGACCCAGTGTTGACCATTGCCTAC-
     CTTCGGTTATTATATGATTGAAATTCCCTCCAATCTCCAATACTCACTTCAT

4161 TTTGTCTTGT-
     TGAATTTTTCAATTTTTCTTTTTCTGT-
     TACGATTGTCATTTTCACCGCCTTGAGTATCCATCAGGTTCCA

4241 GTTGAAAAAGAATCATTTTTTGCCAT-
     GACCATCATGCTTTCTGAGTGCAAGATCAAGAGAGGTACTTTTCTCTCTAAGAA

4321 CCTCTTGGTTTTTTAAGTGTTCTGGGT-
     TCTTTCAGTACTTTTAAGCTATTTTCTAATCCTTTGAAGAGATTCATACATAT

4401 CTGTGCATGT-
     GTTTGTTTCTTTTTTTCGGGT-
     GATACTTTGTTTTATAGCTAAGGATTGAAAAGGTAATTTTCATTTTCAT

4481 TAGCAATAGATATGAAACAGCTTTG-
     TAAGGACTCTGGAGTCTCCTAAAAATTTTGGCTATGCAAATAGCCTATTGCATCA

4561 ATTTGTCGTTGAAATCCATGTATCATAAAAAAA
```

Rf-PPR592, isolated from *Petunia* has an open reading frame ("ORF") of 1779 bp, extending between nucleotides 1982–3760.

The nucleic acid molecule of the present invention which has the nucleotide sequence of from nucleotide 1982 to 3760 of SEQ ID NO: 1 encodes a protein or polypeptide having a deduced amino acid sequence of SEQ ID NO: 2, as follows:

tide repeat motifs (PPRs). These repeats extend from the amino acid in position 54 to the amino acid in position 544 and are organized in two sets of tandem repeats, one set containing 3 PPRs from amino acid 54 to amino acid 158, the other set containing 11 PPRs from amino acid 160 to amino acid 544. Thus, another suitable nucleic acid molecule in accordance with the present invention encodes a protein containing a motif having an amino acid sequence

MMRIAVRYCLNGNPFFSFFAYSIAPRHYSTNTCSISVKGNFGVSNEFENVKCLDDAFSLFRQMVTTKPLPSAVSFS

KLLKALVHMKHYSSVVSIFREIHKLRIPVDAFALSTVVNSCCLMHRTDLGFSVLAIHFKKGIPYNEVTFTTLIRGL

FAENKVKDAVHLFKKLVRENICEPDEVMYGTVMDGLCKKGHTQKAFDLLRLMEQGITKPDTCIYNIVIDAFCKDGM

LDGATSLLNEMKQKNIPPDIITYTSLIDGLGKLSQWEKVRTLFLEMIHLNIYPDVCTFNSVIDGLCKEGKVEDAEE

IMTYMIEKGVEPNEITYNVVMDGYCLRGQMGRARRIFDSMIDKGIEPDIISYTALINGYVEKKKMDKAMQLFREIS

QNGLKPSIVTCSVLLRGLFEVGRTECAKIFFDEMQAAGHIPNLYTHCTLLGGYFKNGLVEEAMSHFHKLERRREDT

NIQIYTAVINGLCKNGKLDKAHATFEKLPLIGLHPDVITYTAMISGYCQEGLLDEAKDMLRKMEDNGCLPDNRTYN

VIVRGFFRSSKVSEMKAFLKEIAGKSFSFEAATVELLMDIIAEDPSLLNMIPEFHRDNKK

As shown in FIG. 1D, most of the predicted mature protein (87%) of Rf-PPR592 consists of 14 pentatricopepcorresponding to any of the PPR motifs (SEQ ID NOs: 3 to 18), where SEQ ID NO: 3 is as follows:

where SEQ ID NO: 3 is as follows:
E E A . . L Y . . M . . . G . . P N . . T Y N A L I N A Y A K . G . .

where SEQ ID NO: 4 is as follows:
D . A . . . F . . M . . . G . . P D . . T Y . . L I . G L C K . G . .

where SEQ ID NO: 5 is as follows:
D D A F S L F R Q M V T T K P L P S A V S F S K L L K A L V H M K H Y where SEQ ID NO: 6 is as follows:
S S V V S I F R E T H K L R I P V D A F A L S T V V N S C C L M H R T where SEQ ID NO: 7 is as follows:
D L G F S V L A T H F K K G I P Y N E V T F T T L I R G L F A E N K V where SEQ ID NO: 8 is as follows:
D A V H L F K K L V R E N I C E P D E V M Y G T V M D G L C K K G H T where SEQ ID NO: 9 is as follows:
Q K A F D L L R L M E Q G T T K P D T C T Y N I V I D A F C K D G M L where SEQ ID NO: 10 is as follows:
D G A T S L L N E M K Q K N I P P D I I T Y T S L I D G L G K L S Q W where SEQ ID NO: 11 is as follows:
E K V R T L F L E M I H L N I Y P D V C T F N S V I D G L C K E G K V where SEQ ID NO: 12 is as follows:
E D A E E I M T Y M I E K G V E P N E I T Y N V V M D G Y C L R G Q M where SEQ ID NO: 13 is as follows:
G R A R R I F D S M I D K G I E P D I I S Y T A L I N G Y V E K K K M where SEQ ID NO: 14 is as follows:
D K A M Q L F R E I S Q N G L K P S I V T C S V L L R G L F E V G R T where SEQ ID NO: 15 is as follows:
E C A K I F F D E M Q A A G H I P N L Y T H C T L L G G Y F K N G L V where SEQ ID NO: 16 is as follows:
E E A M S H F H K L E R R R E D T N I Q I Y T A V I N G L C K N G K L where SEQ ID NO: 17 is as follows:
D K A H A T F E K L P L I G L H P D V I T Y T A M I S G Y C Q E G L L and where SEQ ID NO: 18 is as follows:
D E A K D M L R K M E D N G C L P D N R T Y N V I V R G F F R S S K V A PPR motif-containing gene can be identified if it contains the consensus sequence (SEQ ID NOs: 3 or 4) or if it is found with a MEME software (Bailey et al., "Fitting a Mixture Model by Expectation Maximization to Discover Motifs in Biopolymers," *Proceedings of the Second International Conference on Intelligent Systems for Molecular Biology* pp. 28–36, AAAI Press, Menlo Park, Calif. (1994), which is hereby incorporated by reference in its entirety). To find whether a protein has a PPR motif with the MEME software, the parameters for motif searching should be set as minimum width=35, maximum width=35. MEME (Multiple Em for Motif Elicitation) is a software tool for discovering motifs in a group of related DNA or protein sequences (Bailey et al., "Fitting a Mixture Model by Expectation Maximization to Discover Motifs in Biopolymers," *Proceedings of the Second International Conference on Intelligent Systems for Molecular Biology*, pp. 28–36, AAAI Press, Menlo Park, Calif. (1994), which is hereby incorporated by reference in its entirety). MEME takes as input a group of DNA or protein sequences (the "training set") and outputs as many motifs as requested. MEME uses statistical modeling techniques to automatically choose the best width, number of occurrences, and description for each motif. MEME represents motifs as position-dependent letter-probability matrices which describe the probability of each possible letter at each position in the pattern. Individual MEME motifs do not contain gaps. Patterns with variable-length gaps are split by MEME into two or more separate motifs.

Another suitable nucleic acid molecule for the present invention is a nucleic acid molecule which encodes a protein having an amino acid sequence identified with a METAMEME software using the amino acid sequence of SEQ ID NO: 2 as input. Meta-MEME is a software toolkit for building and using motif-based hidden Markov models of DNA and proteins. The input to Meta-MEME is a set of similar protein sequences, as well as a set of motif models discovered by MEME. Meta-MEME combines these models into a single, motif-based hidden Markov model and uses this model to produce a multiple alignment of the original set of sequences and to search a sequence database for homologs (Grundy et al., "Meta-MEME: Motif-based Hidden Markov Models of Biological Sequences," *Computer Applications in the Biosciences*, 13(4):397–406 (1997), which is hereby incorporated by reference in its entirety).

Also suitable for the present invention is a nucleic acid molecule which encodes a protein having an amino acid sequence identified as significantly similar to SEQ ID NO: 2 using a NCBI BLAST software (threshold=E less than or equal to 15) with SEQ ID NO: 2 as input for comparison (Fulton et al., "Identification, Analysis, and Utilization of Conserved Ortholog Set Markers for Comparative Genomics in Higher Plants," *Plant Cell*, 14:1457–1467 (2002), which is hereby incorporated by reference in its entirety).

Also suitable in the present invention is a nucleic acid molecule which has a nucleotide sequence of SEQ ID NO: 19, an 8.5 kb fragment containing Rf-PPR592 capable of transforming cytoplasmic male sterile plants, as follows:

```
GGATCCAAAATTTCACTAAAGGTTAAACGCGAGGATACTGAAGTTGGAGAGCAATGTGGTATCTTGGTGCATGGAC
GGAGTCATGGGGGTATAGTTGCTGGCTATTTAGCTAACTGGAGAACTGTTGTGAGGAATTATTTAAAGAATGCTAC
TTTCTCGTCCACATAAACATGTCCAAATATTTTCTACTTGATAGAGAGTTCAAGGAAATAGTGTGGATTTCTTCCC
AAACACAAACGATTTGAGAAAACTGAAGTGAAGGCTGAAGAGAAAACTAAAGAGAACTGGAAGCTAAGAAACACAG
AAGCACAAACCTATAAACATAGACACTGGCATGTTGCAGAAAATTTTAACTTTCGATTCTCCAGTAGAAAGACACA
AATACATCAGTAAATTTTCTTTAGGCTCAAGCAAGGATACATCTTGGTAGAATTTGCATTATACCAACATAATAAG
CTCAAAAAAATAACTAAGCTGCAACTAGCTACTTGGTCCGAGAAGCTTTTGCTATCAGGAAGTTCCACAGTTCCAA
AACCAAGGTAGACTATCAAGCTAGTTCCCACCAGTCATTTTCTTAGACTTTGCTCTCACGATAAACTAAGATCATT
TTTTTATGATACATGGATTTCAACGACAAATTGATGCAATAGGCTATTTGCATAGCCAAAATTTTTAGGAGACTCC
AGAGTCCTTACAAAGCTGTTTCATATCTATTGCTAATGAAAATGAAAATTACCTTTTCAATCCTTAGCTATAAAAC
AAAGTATCACCCGAAAAAAAGAAACAAACACATGCACAGATATGTATGAATCTCTTCAAAGGATTAGAAAATAGCT
TAAAAGTACTGAAAGAACCCAGAACACTTAAAAAACCAAGAGGTTCTTAGAGAGAAAAGTACCTCTCTTGATCTTG
CACTCAGAAAGCATGATGGTCATGGCAAAAAATGATTCTTTTTCAACTGGAACCTGATGGATACTCAAGGCGGTGA
AAATGACAATCGTAACAGAAAAAGAAAAATTGAAAAATTGAACAAGACAAAATGAAGTGAGTATTGGAGATTGGAG
GGAATTTCAATCATATAATAACCGAAGGTAGGCAATGGTCAACACTGGGTCGCTCAAAAATTAATTCCATATCAAA
AATAGAATACTGAAACCATTGAAATCATATTCCGAAACTTATAACTCGTACATATATGGGAGTTCACATTGTTTCT
GATATTAAGAGCGCAGAACATTTGATTTCCAAGATAAAGAAGAGAGCCAAAACAACCAAAATGATGTCCCTCCGAT
ATAAGCTTGCCAGGAAAGCTTAAGCAATGTTCTTCTTGCCATTTTTTCAGCTTCCGCAATTCCACTGGATGCAATT
TCTTTTGCTAAGATGAAAGGAAATAGCAGAATAATGGTGATATCGTCAAAAAAAACAGGTGCAAAAGTTATTCACT
TCTTATTATCCCGGTGAAATTCTGGAATCATGTTAAGCAAAGAAGGATCCTCTGCTATAATATCCATCAATAACTC
TACAGTAGCTGCCTCAAATGAGAAGCTCTTCCCAGCTATTTCCTTCAGAAAAGCCTTCATTTCACTAACTTTACTG
CTTCTGAAAAATCCCCGCACAATAACATTGTATGTTCGGTTGTCTGGCAAACAACCATTGTCCTCCATTTTCCTTA
GCATATCTTTAGCTTCATCTAACAACCCTTCTTGACAATATCCACTAATCATTGCAGTGTATGTTATCACATCAGG
ATGTAAGCCTATCAAGGGAAGCTTCTCAAACGTAGCATGAGCTTTGTCGAGCTTACCATTTTTGCACAATCCATTA
ATGACAGCCGTGTAAATTTGAATATTTGTATCTTCTCTCCTCCTTTCCAACTTATGGAAGTGTGACATAGCCTCTT
CAACAAGTCCATTCTTAAAATAACCACCAAGCAAAGTGCAATGAGTGTATAAATTAGGTATGTGCCCCGCAGCTTG
CATCTCATCAAAGAATATTTTTGCACATTCAGTTCTTCCAACTTCAAAAAGACCACGCAAGAGAACACTGCAGGTA
ACAATACTAGGTTTCAATCCATTTTGAGAAATTTCACGAAACAATTGCATGGCCTTATCCATTTTCTTTTTCTCGA
CGTATCCATTTATTAGTGCGGTATAGCTAATGATATCAGGCTCAATGCCCTTATCTATCATGGAATCAAAAATTCT
CCTCGCTCTACCCATTTGACCACGCAAGCAATATCCATCCATTACCACATTGTAGGTTATCTCATTAGGTTCTACA
CCTTTTTCGATCATGTATGTCATTATTTCCTCGGCATCTTCAACTTTCCCCTCTTTGCATAGTCCATCAATGACGG
AGTTGAAGGTGCACACATCTGGATAAATATTAAGATGTATCATCTCAAGGAACAAAGTCCTAACCTTTTCCCACTG
ACTTAACTTACCCAAACCATCGATCAATGAGGTATATGTAATAATGTCTGGAGGAATGTTTTTTGTTTCATCTCG
TTCAAAAGGCTGGTAGCACCATCTAGCATCCCATCTTTGCAAAAGGCATCGATAACAATGTTGTAGATGCATGTAT
CGGGCTTAGTAATTCCTTGTTCCATTAACCGGAGCAAATCAAAAGCTTTTTGAGTATGGCCCTTCTTGCAAAGCCC
ATCCATGACCGTCCCATACATGACTTCATCAGGCTCACATATATTCTCCCTCACCAACTTTTTGAACAAATGAACA
GCATCTTTGACCTTATTTTCAGCAAAAAGTCCCCTTATTAAGGTAGTAAAGGTGACTTCATTATATGGAATACCTT
```

-continued

```
TCTTGAAGTGAATGGCTAATACAGAAAATCCGAGATCGGTACGATGCATAAGGCAACAACTGTTAACCACAGTGCT
CAAGGCGAAAGCATCAACAGGAATACGTAATTTGTGGATTTCTCGAAAAATAGAAACAACAGAAGAGTAATGCTTC
ATATGTACCAAAGCTTTCAACAATTTAGAGAAAGAGACAGCAGAAGGAAGAGGCTTAGTTGTAACCATTTGACGGA
ACAAACTGAAAGCATCATCTAAACACTTAACATTCTCAAATTCATTAGAAACCCCAAAATTCCCTTTAACTGAAAT
GGAACATGTATTGGTAGAATAATGTCGGGGTGCAATTGAATAAGCAAAGAATGAGAAAAAGGGATTACCATTGAGA
CAGTAACGCACTGCAATTCTCATCATCTTCGCTTCACTTCACTTAGTAGGGGTGATTGGAAGAATTGTACGACTAT
GACACCATAGGTTGAAGTTGAATTGCTACCTCGAGTCCATTTTGTAGAAATTTCGTCCATCAGCCACTTTTAACAC
TGTTATTTAGTTTTAGGCCTCTATTTTTATTGGTCTTATACTAACCACTTTTGGGCCTTTACTAAATAAATACTGA
CTTAAGTTCTGATAATTGACTGAACTTCAGTCCATACGGCCCCTGGACTGAAGTTCTATCTTTAAGGATTGAACTT
CAGTCCATATGGCTCTGGACTGAAGTTCCATCTTAAGGACTTGACTGAACTTCAGTCCATATGGCACTGGATCGAA
GTTCAATCTTTAAGGACTGAACTTCAATCCGGCCTCTGGACTGAAGTTCTATCTCTTTAAGCAAAAGTAGCCACAA
ACTAAATATTTTGGTATTAGTGGCCTGTACCCAAAGACCAATGGCAAAAGTGGTCTTTCGTGCACTTTCCCCGTCC
ATTTTGCTAAATCATACAAAAGATCATAACCGAGATAAGGAGGTATATATTGTGAAATTTTTTGGAACTTGAATAA
TTGTGGGCTGAACTTCAGCCTACTTTGCGAATGGGTAAAAGTGCATGAGAGACCACTTTTTTTTGCAGATTTTGCT
TGAGAGGTCATTTTTTGAAACTTTAATCCTTGTGGGTTGAACTTCACACAAGTTCAGCCCACAAGGATTGAAGTTC
AACTTCAGGCCACCATAAGGGGCGAAGTTCAACTTCAGTCCACAAGGTTGAAGTTTACGCATCTATGCCTAAAAAT
TCAGCCCTTACGGATTGAAGTTGAACTTAATAACTTAGGCATGAAGTTCAAGCGCACAAAGATTGAAGTTCCAAAA
AGTGGTCTCTCATGTAAAACCAATAAAAAAATGACTTCAAACCAAATACTAGTGGTAAAAGTGGCCTGTGAGCTAA
TTTTTTACTTGTGAATGTATGAAGTTCGGCCCACAAGGTCTGAAGTTCGGCCCACAATGATTAAAGTTCCAAAAAA
GCTAAAAACTAGCTCTTTTTCTTTGAAAGTAGCTTCAACGGTAAAGGCAAGCCAAAAAGTGGCTTTTCCTTGCACT
TTTCCTTAAGTTTATAATGAATAAATATCGAATGGAAATACAATCTTATAGTGATGCCCATTTCTCACTCCCTAAG
GCAGCATTGTCTTTGACTGCCTTTTGCTTAAGCAATATTTGCTTTTGAATTTCTTCCTACATTTTTCTACATAATT
TGACGTGTTGTCTAGGCAACACTTGTCCGTACAATCTTTTCGAATACTTTCCCAGACAACACTTCTTTTAACGTAA
AAATTTGGCCATGTAGTCTATTTGCCCCTCGCTAAATGAAAACTAGCCAGCATTTCAAAATTTTTAGAAGACCAGC
CAAAATCAAGAAACATATAAATATTTCAGTTTTTTGTACTATGACTTGAACTACAATTTTCAAAAAGAATGTTTTT
AAAACTACCCAGCTTACACTAAAAAATTACACTACCATCACTCAAATTTTGTTTAAACATTTTATAGCCACACAAC
CACAACATTGGGTACACTATTGCGGTGTCAAACTTGTATACTATTGGGGGTATACGAATACTAAAAAGGTAAATA
ATAGAAGATATCGTATAGGTATACTGTCGCTATGGGATATACAAGCTTGGAGTATATGCCACTATAAAATAAAATA
TTTTTAGCCAAATGGCCGACTCAGGTAAATATTTTTAGGAAATATTACACCACATGACTACCTAATAGCTATATTA
CAAAAAATAACAATATTTTTATCATATTTACAATACATAACAATGAGTTTTGTATATATTATGTAAAAAAATTATT
GTTATTTTTGTAAAGATAACATTATTAGCGGAGCTACCCTTTTTCAAGGGTATGTAAATATAACACTGTGCAAAT
AGACAGAAAAAATCAGTTTGTATATATATATCAGATATTGATTCCCCCTTCATTTTTTCGTATGTTTACTTTTTTA
TATTTATATATCCCTTAGTAAAAATACTGGCTCCGCCACTGCCAGTAAGGTAGTATTAGTTTGCGTCGCTCAATAA
AGTAACATCTATCGTTTATTTTTCATCAACATTAAAAAGGAAGATTCACTATCCACATAGGCATCATCATTATCAA
AGAATATCAGTTCATACATTGTATATATATAACTTTCTCAAATAAACTAACTTTAAAATGAAGTACATTAAAAAGG
AAGATTCACTATCCTTTTAATATTTCGTATATTTACTTATTTATATTTTGATACTCCTTAGTAAAAATACTGGCTC
CGCCACTACCAGTGATGTAATATTAATTCGCGTCCCTCACTAAAGTAACACCTATAATTTAATTTTCATGAAGTCA
GAGTTAGCATTGGAAAGGGATATAAGCACATGCATTGTGTATATATATATAACTTGCTCAAATAAACTAACTTAAA
AATGAAATTTTACTTTTCCTAGTACAATGAACTATGCATCAATGCGTAATTAGTTGAGGTCGGCTATATGAATATG
TTATTAATTTGAAAGCAAAACATAATAACTGATAGAAGAATTTTGCACCTAAAAATTGAACTTGAGCTGCTTCAGT
```

-continued

```
TACTATCTCATTTTTCACTATATATGTGTGTATCAGCTAATTCTATGATTTAATTAAACAAATTGTAAGTATTAAC
AAAATAACGAATAAATATGGAAAATAAGTACTTGATGAACGTAGGGCCGGAGTTGGCCGAGGTGACCGGAGACAAT
GGAAAGCAGAGTTACTATTTTTGACTAAATAGCCACAAAAGAATCATTGTTTTTACAATGTAGCAAGTTGGCACGA
TTATGATTCTTGACACAATAGCCACATTATAGAAAGATAATGTGGCACTAATGAGGTAATTTTCATTATGGAATGA
TAACAAACAAATAAGTACACGATTAAAACAAACTGAAAGGGTTTTGCGCGATAATTTAATCATTGTTTTACGAAAA
TACTCATCAAAATCAAAATATTTATCTGCCTCTGCATGTAAGTTTCATATTTACTCGTCTTGCCATAATTTATATG
AAAAAATTTACTCACACCGGATATATATACCTAACCATAGCAATTAACTATGGTAATGTGATGTAATGAAGAGAGA
ATGTCTATTAATTAATTATGGCTAAGTGATAGTAGTGTATTGTAAACAAATGACGTGCATTTGTTGATTAGACACT
TACAAAAATACCCACGAAATCTAAAATAATTACAGCCACTATCCACTACTTTCAAATATTATCTGGCCTACCCATT
AAAATATTTACTCACTCTACCCCTCCAGACTTATATATTATAAGGTATAAAAAGGTAAACAATAATAAATGGTCCT
CCAGACTTTTATACCATAATTTATGCAGCCTTAAAGGTATACACCTATAAACAAAGGTATACAATAAAAAATGGGT
ATGTTGGGTAAATACTTTTAGTTTTATGGGTAGAGTAATTTTTAATGGGTATGACTTGTAAATACTTTAAATTTCA
TGGGTATAGAGTGTAAAAATTCCTTTGTTGATTGGGTATATACACCCGATGTGGGTAAGTACTTGCCTAATTTTTG
CCCTAAGGTAAATATAGACTTATAGTATAAAAAAAAATACGCAGTGTGATAGATACTTTGAATTTCATGAGTAATG
TAATTTTTAATAGGTATAGTAAGGTAAATACTTTATATTCCAAGGGTACACATTGTAAAAAGCTCAATATTTTATT
CCAAAGAATAAGAGACCAAACAATGTGTTTGAGATTTATTACTTTGTTGTCCACCAAACTAAAAAGAAAACTTTAG
AAGTCTAAATTACAATAATCTTAACATGCATTTTACGAATAAATATCACAAAATCTCAAACTATTAGAGATAATGT
CGTGGATGATGTTAACATATTGGACTACACAACCCATTGTACAATAATTTTGAAGCATGTATATGCACGACCAAGA
CTCCATCATCATAGATCAAATGAATGTTCATTTTAATGCATGAAACCTAAGTAGAACATTTATGCCTTAATGAACT
AAAACCAAGCAAAAAGATACATCTACTTGTGCAATTGAATGAATTCTACCGTATATACTAATATACACCAGAGGTT
AGTTTAACACTTGGAACTTCAAAAGGTGTACAACCATAGAGTTTCCTTTACATTGATGGTTTCTTTCATTTCACTA
ACTGATAAAATGAAGGCTGGTATAGTCTACCAAATCCCTAGTTCCCTGTGAACTTGCATCCCTTCTAGCTACATGC
AGAACATGTCCTTTAGATCCCATAGGTGTATTGCCATTTGCCACTGAACAATGGAGGACAATGTATAATTGTCCTC
CTCACCCATTGCACATACTCTGTCATTTGCTGCACATCTACATGCCTTTTCTGAATATTCTTCTGAGTCAAATAAG
CATCATGAGACATCTGTCAAGTATCTTTGAATGGGATAATCACATTTCCAAATCGAAAGGTTCTTGTCTTAACAAG
TCAAGCTGCATCTCGACAAAGAGACTTCGTTGATGAAATGCGACCATAAAGAGCACATGCAAACCAGTTGTTAAAA
GCATTGTACACATATACCTACTTCTGATGTGAATAAAAGAAAGTCGATCAATGACAGAGGAAAACAGTCAATCTAT
AACCACAAAAATACTTTTCTTTAAAAGTACGACCACATAGATAACTATAATTTCCCGTAGATGTCAAACTCTTATT
GAATAAAAAATAAACAAACATGTACTATTTGCTCATTTATCCGACTGTCACAAGGATTTTCTTAATGATGGTATAA
TAGGAGCAATCCCTTTTATGACAGATGCACTAATTTGTTTGGGTGCATATTTCAATGCAGAACTGTGGGTATATA
ATCTAAAATATCATTCAAATCAAACCTGGGAACGATTGAGAGAAGATTAGCATGGCCTCTGCACAAGGATGACACG
CATAAATCGAGAAATGTTCCAAATAAAGGAAATATATATATTACCTGTTTCAATTGGCATAGTTCTTAAAGAAGTT
TTGGCAGTTAAAGTATTAATAGTTTACCTTGTTTCGATTGTGGGATTTAGCCTTGGGGTTGTCTGGGACGGACCTG
TGATTATTCTGCTAATCTCCTTGTATATTCATGCAATGTGCAGTTTAATCCAGTGCATTTTGCGTGTTATGGATGG
ATCC
```

Another suitable nucleic acid molecule in accordance with the present invention is isolated from rice and identified herein as Rhpr1, which has a nucleotide sequence of SEQ ID NO: 20, as follows:

```
ATGGCGCGCCGCGTCCCTACCCGCCCGCGCGGCGGTGGCGGCGGCGGCGTCCCACGCTCGGAGGGCTCGATCCAAG
GGCGAGGAGGCCGCGCGGGGGGCAGTGGCGCCGAGGACGCACGCCACGTGTTCGACGAATTGCTCCGGCGTGGCAG
GGGCGCCTCGATCTACGGCTTGAACCGCGCCCTCGCCGACGTCGCGCGTCACAGCCCCGCGGCCGCCGTGTCCCGC
TACAACCGCATGGCCCGAGCCGGCGCCGGCAAGGTAACTCCCACCGTGCACACCTATGCCATCCTCATCGGCTGCT
GCTGCCGTGCGGGCCGCTTGGACCTCGGTTTCGCGGCCTTGGGCAATGTCGTCAAGAAGGGATTTAGAGTGGATGC
CATCACCTTCACTCCTCTGCTCAAGGGCCTCTGTGCCGACAAGAGGACGAGCGACGCAATGGACATAGTGCTCCGC
AGAATGACCGAGCTCGGCTGCATACCAGATGTCTTCTCCTACAATAATCTTCTCAAGGGTCTGTGTGATGAGAACA
GAAGCCAAGAAGCTCTCGAGCTGCTGCACATGATGGCTGATGATCGAGGAGGAGGTAGCCCACCTGATGTGGTGTC
GTATAACACTGTCCTCAATGGCTTCTTCAAAGAGGGGGATTCAGACAAGCTTACAGTACATACCATGAAAATGCTG
GACCGGGGATTTTACCAGATGTTGTGACCTACAGCTCTATTATTGCTGCGTTATGCAAGGCTCAAGCTATGGACA
AAGCCATGGAGGTACTTAACACCATGGTTAAGAATGGTGTCATGCCTGATTGCATGACATATAATAGTATTCTGCA
TGGATATTGCTCTTCAGGGCAGCCAAAAGAGGCTATTGGAACACTCAAAAAGATGCGCAGTGATGGCGTCGAACCA
AATGTTGTTACTTATAGTTCACTGATGAATTATCTTTGCAAGAATGGAAGATCCACCGAAGCTAGAAAGATTTTCG
ATTCTATGACCAAGAGGGGCCTAGAGCCTGATATTGCTACCTATCGTACCCTGCTTCAGGGGTATGCTACCAAAGG
AGCCCTTGTTGAGATGCATGCTCTCTTGGATTTGATGGTACGAAATGGTATCCAACCGGATCATCATGTATTCAAC
ATTCTAATATGTGCATACGCTAAACAAGAGAAAGTAGATCAGGCAATGCTTGTATTCAGCAAAATGAGGCAGCATG
GATTGAATCCGAATGTAGTGTGCTATGGAACAGTTATAGATGTACTTTGCAAGTCAGGCAGTGTAGATGATGCTAT
GCTTTATTTTGAGCAGATGATCGATGAAGGACTAACCCCTAACATTATTGTGTATACCTCCCTAATTCATGGTCTG
TGCACCTGTGACAAATGGGACAAGGCTGAAGAGTTAATTCTTGAAATGTTGGATCGAGGCATCTGTCTGAACACTA
TTTTCTTTAATTCAATAATTGACAGTCATTGCAAAGAAGGGAGGGTTATAGAATCTGAAAAACTCTTTGACTTGAT
GGTACGAATTGGTGTGAAGCCCGATATCATTACGTACAATACACTCATCGATGGATGCTGCTTAGCTGGTAAGATG
GATGAAGCAACGAAGTTACTTGCCAGCATGGTCTCAGTTGGGGTGAAACCTGATATTGTTACCTATGGCACCTTGA
TTAATGGCTACTGTAGAGTTAGCAGGATGGATGACGCATTAGCTCTTTTCAAAGAGATGGTGAGCAGTGGTGTTAG
TCCTAATATTATTACGTATAACATAATTCTGCAAGGTTTATTTCATACCAGAAGAACTGCTGCTGCAAAAGAACTC
TATGTCAGTATTACCAAAAGTGGAACACAGCTTGAACTTAGCACGTACAACATAATCCTTCATGGACTTTGCAAAA
ACAATCTCACTCACGAGGCACTTCGAATGTTTCAGAACCTATGTTTGACGGATTTACAGCTGGAGACTAGGACTTT
TAACATTATGATTCGTGCCTTACTTAAATGTGGAAGAATGGATGAAGCTAAGGATTTGTTTGCTGCTCACTCGGCT
AACGGTTTAGTGCCAGATGTTAGGACCTACAGTTTAATGGCAGAAAATCTTATAGAGCAGGGGTCGCTAGAAGAAT
TGGATGATCTATTTCTTTCAATGGAGGAGAATGCCTGTTCCGCCGACTCCCGCATGCTAAATTCCATTGTTAGGAA
ACTGTTACAGAGGGGTGATATAACCAGGGCTGGCACTTACCTGTTCATGATTGATGAGAAGCACTTCTCCCTCGAA
GCATCCACTGCTTCCTTCTTGTTAGAATCTTCCCCAATCGTCTGGGAGCAAATATCAAGAATATCACACTTGTCTG
TAAATTTGAAATTAATTAAGCAGCCCAAATGCACCTGTGAGTTAGGCCCAAAGTGGTCCCAAAATCTGCCTAAACC
TGGCACAAATTCGGTCGGTAGTGTCGCACAGTTTCACTTATCGCGCGGCGGTTATCGCGCTTACCGCGGGGTACG
ACGGTTACCGCACTACCGCAGGGTGACGGTAACCCCGGCCCAAACGATAAGGTAAACCCTGGTCGCACAAATTTGG
CCCAAAACCGACCAGTTATCGCGCTACCGCGGGATGCCTCAGTAGGACCTTAG
```

Rhpr1 is a rice homolog of the *Petunia* Rf-PPR592 gene.

The nucleic acid molecule of the present invention which has the nucleotide sequence of SEQ ID NO: 20 encodes a protein or polypeptide having a deduced amino acid sequence corresponding to SEQ ID NO: 21 as follows:

```
MARRVPTRPRGGGGGGVPRSEGSIQGRGGRAGGSGAEDARHVFDELLRRGRGASIYGLNRALADVARHSPAAAVSR
YNRMARAGAGKVTPTVHTYAILIGCCCRAGRLDLGFAALGNVVKKGFRVDAITFTPLLKGLCADKRTSDAMDIVLR
RMTELGCIPDVFSYNNLLKGLCDENRSQEALELLHMMADDRGGGSPPDVVSYNTVLNGFFKEGDSDKAYSTYHEML
DRGILPDVVTYSSIIAALCKAQAMDKAMEVLNTMVKNGVMPDCMTYNSILHGYCSSGQPKEAIGTLKKMRSDGVEP
NVVTYSSLMNYLCKNGRSTEARKIFDSMTKRGLEPDIATYRTLLQGYATKGALVEMHALLDLMVRNGIQPDHHVFN
ILICAYAKQEKVDQAMLVFSKMRQHGLNPNVVCYGTVIDVLCKSGSVDDAMLYFEQMIDEGLTPNIIVYTSLIHGL
CTCDKWDKAEELILEMLDRGICLNTIFFNSIIDSHCKEGRVIESEKLFDLMVRIGVKPDIITYNTLIDGCCLAGKM
DEATKLLASMVSVGVKPDIVTYGTLINGYCRVSRMDDALALFKEMVSSGVSPNIITYNIILQGLFHTRRTAAAKEL
YVSITKSGTQLELSTYNIILHGLCKNNLTDEALRMFQNLCLTDLQLETRTFNIMIGALLKCGRMDEAKDLFAAHSA
NGLVPDVRTYSLMAENLIEQGSLEELDDLFLSMEENGCSADSRMLNSIVRKLLQRGDITRAGTYLFMIDEKHFSLE
ASTASFLLESSFIVWEQISRISHLSVNLKLIKQPKCTCELGPKWSQNLPKPGTNSVGSVAQFHLSRGGYRAYRGGT
TVTALPQGDGNPGPNDKVNPGRTNLAQNRPVIALPRDASVGP
```

Another suitable nucleic acid molecule in accordance with the present invention is isolated from rice and identified herein as Rhpr2, which has a nucleotide sequence of SEQ ID NO: 22, as follows:

```
ATGGCGCCGCCGCCGCTTCCCGCGTCCGCGCCGGCGCTGTTGGCGCCCTTCGCTCGGAGGGCTCGACCCAAGGGC
GAGGGGGCCGCACGGGGGGCAGTGGCGCCGAGGACGCACGCCACGTGTTCGACGAATTGCTCCGGCGTGGCAGGGG
CGCCTCGATCTACGGCTTGAACTGCGCCCTCGCCGACGTCGCGCGTCACAGCCCCGCGGCCGCCGTGTCCCGCTAC
AACCGCATGGCCCGAGCCGGCGCCGACGAGGTAACTCCCAACTTGTGCACCTACGGCATTCTCATCGGTTCCTGCT
GCTGCGCGGGCCGCTTGGACCTCGGTTTCGCGGCCTTGGGCAATGTCATTAAGAAGGGATTTAGAGTGGACGCCAT
CGCCTTCACTCCTCTGCTCAAGGGCCTCTGTGCTGACAAGAGGACGAGCGACGCAATGGACATAGTGCTCCGCAGA
ATGACCCAGCTTGGCTGCATACCAAATGTCTTCTCCTACAATATTCTTCTCAAGGGGCTGTGTGATGAGAACAGAA
GCCAAGAAGCTCTCGAGCTGCTCCAAATGATGCCTGATGATGGAGGTGACTGCCCACCTGATGTGGTGTCGTATAC
CACTGTCATCAATGGCTTCTTCAAGGAGGGGATCTGGACAAAGCTTACGGTACATACCATGAAATGCTGGACCGG
GGGATTTTACCAAATGTTGTTACCTACAGCTCTATTATTGCTGCGTTATGCAAGGCTCAAGCTATGGACAAAGCCA
TGGAGGTACTTACCAGCATGGTTAAGAATGGTGTCATGCCTAATTGCAGGACGTATAATAGTATCGTGCATGGGTA
TTGCTCTTCAGGGCAGCCGAAAGAGGCTATTGGATTTCTCAAAAAGATGCACAGTGATGGTGTCGAACCAGATGTT
GTTACTTATAACTCGCTCATGGATTATCTTTGCAAGAACGGAAGATGCACGGAAGCTAGAAAGATGTTCGATTCTA
TGACCAAGAGGGGCCTAAAGCCTGAAATTACTACCTATGGTACCCTGCTTCAGGGGTATGCTACCAAAGGAGCCCT
TGTTGAGATGCATGGTCTCTTGGATTTGATGGTACGAAACGGTATCCACCCTAATCATTATGTTTTCAGCATTCTA
ATATGTGCATACGCTAAACAAGGGAAAGTAGATCAGGCAATGCTTGTGTTCAGCAAAATGAGGCAGCAAGGATTGA
ATCCGGATACAGTGACCTATGGAACAGTTATAGGCATACTTTGCAAGTCAGGCAGAGTAGAAGATGCTATGCGTTA
TTTTGAGCAGATGATCGATGAAAGACTAAGCCCTGGCAACATTGTTTATAACTCCCTAATTCATAGTCTCTGTATC
TTTGACAAATGGGACAAGGCTAAAGAGTTAATTCTTGAAATGTTGGATCGAGGCATCTGTCTGGACACTATTTTCT
TTAATTCAATAATTGACAGTCATTGCAAAGAAGGGAGGGTTATAGAATCTGAAAAACTCTTTGACCTGATGGTACG
TATTGGTGTGAAGCCCGATATCATTACGTACAGTACTCTCATCGATGGATATTGCTTGGCAGGTAAGATGGATGAA
GCAACGAAGTTACTTGCCAGCATGGTCTCAGTTGGAATGAAACCTGATTGTGTTACATATAATACTTTGATTAATG
GCTACTGTAAAATTAGCAGGATGGAAGATGCGTTAGTTCTTTTTAGGGAGATGGAGAGCAGTGGTGTTAGTCCTGA
TATTATTACGTATAATATAATTCTGCAAGGTTTATTTCAAACCAGAAGAACTGCTGCTGCAAAAGAACTCTATGTC
GGGATTACCGAAAGTGGAACGCAGCTTGAACTTAGCACATACAACATAATCCTTCATGGGCTTTGCAAAAAGAATC
```

-continued

```
TCACTGACGAGGCACTTCGAATGTTTCAGAACCTATGTTTGACGGATTTACAGCTGGAGACTAGCACTTTTAACAT
TATGATTGGTGCATTGCTTAAAGTTGGCAGAAATGATGAAGCCAAGGATTTGTTTGCAGCTCTCTCGCCTAACGGT
TTAGTGCCAGATGTTAGGACCTACAGTTTAATGGCAGAAAATCTTATAGAGCAGGGGTTGCTAGAAGAATTGGATG
ATCTATTTCTTTCAATGGAGGAGAATGGCTGTACTGCCAACTCCCGCATGCTAAATTCCATTGTTAGGAAACTGTT
ACAGAGGGGTGATATAACCAGGGCTGGCACTTACCTGTTCATGATTGATGAGAAGCACTTCTCCCTCGAAGCATCC
ACTGCTTCCTTGTTTTTAGATCTTTTGTCTGGGGGAAAATATCAAGAATATCATAGTTGTATTAGAGGAGGGATCT
TCTCTTTATGTGTAAATAGCGAGGTTCAAGAAAATCATTTGTTGGATTCAGAATCTGGTGTCCATTTTCTTCTTAA
ATTATTAAATCCTCCAGTGAATCTTGTTGATTCCAAAGCACCATCGATAGGTTCCAAACTTCTTGGAATCAGTAAA
GTTCAAATGCTTAATGGATCAAATAAGGATTCTGACTGCATTTCAGAGGAAATCCTTTCAAAAGTTGAAGAGATTC
TCTTAAGCTGTCAAGTGATCAAGTCGCTCGACAAAGATGACAAGAAAACAACAAGGCCAGAACTGTGTCCAAAGTG
GCTTGCTTTGTTGACAATGGAAAATGCATGCTTGTCTGCTGTTTCAGTAGAGGAGACTTCTGACACAGTGTCCAGA
GTTGGAGGAAATTTTAAAGAGACATTAAGGGAGATGGGAGGTCTTGATAGTATTTTTGACGTTATGGTGGATTTTC
ATTCAACATTGGAGAATCTCATAAAGGATACATCCACTTCAGCTTTGGACCGAAATGAAGGAACATCTTTGCAAAG
TGCTGCTCTCCTCTTGAAATGTTTGAAAATATTGGAAAATGCCATATTTCTAAGCGATGATAACAAGACCCATTTG
CTTAATATGAGTAGAAAATTGAACCCGAAACGCTCCTTGCTTTCTTTTGTTGGTGTCATTATCAATACTATTGAGT
TATTATCAGCTCTTTCAATACTTCAGAATTCTTCTGTTGTTTCCAGCTCTACATATCCGAAATCGTCTAAAGTCTC
TCAACAGAGTTACTCTGTGGTCATGGCGGGGGGCGACCGTGGCCGAGGCGTGGAGTGCCATCCGCATCAGGGTGTA
TCGGCCGCGCTGCTCCGCCCTGGTCCGCAGGCTTTGGCGGCGAGCTGGCGGCGGAGGGAGACTGTGGTGAGATCGG
ATTTCGCCGCTGGTGGTGTCGCTACCATGGGGGATTCGCCGCAGGCGCTCTCAGATCGGTTATGCGGGAGCGCAAC
AAAAGTATGGCGTGGCGGCGCGGAGTGGACGGCCGAGGCGTTCGCGCGGAATGGGGCTGCGGGACCGAGCCAGTCT
CGCTTGCCGGTAACGCGGAACCGAGCTCAGCACTACATTGCAAAGATTTGGGCAACTCTGACAATTTCCATGTTCT
ACAAGCTTGACGTCGAGGGAATGGAGAACCTGCCACCGAATAGTAGCCCTGCTATCTATGTTGCGAACCATCAGAG
TTTTTTGGATATCTATACCCTTCTAACTCTAGGAAGGTGTTTCAAGTTTATAAGCAAGACAAGTATATTTATGTTC
CGAATTATTTGA
```

Rhpr2 is a rice homolog of the *Petunia* Rf-PPR592 gene.

The nucleic acid molecule of the present invention which has the nucleotide sequence of SEQ ID NO: 22 encodes a protein or polypeptide having a deduced amino acid sequence corresponding to SEQ ID NO: 23 as follows:

```
MARRAASRVRAGAVGALRSEGSTQGRGGRTGGSGAEDARHVFDELLRRGRGASIYGLNCALADVARHSPAAAVSRY
NRMARAGADEVTPNLCTYGILIGSCCCAGRLDLGFAALGNVIKKGFRVDAIAFTPLLKGLCADKRTSDAMDIVLRR
MTQLGCIPNVFSYNILLKGLCDENRSQEALELLQMMPDDGGDCPPDVVSYTTVINGFFKEGDLDKAYGTYHEMLDR
GILPNVVTYSSIIAALCKAQANDKAMEVLTSMVKNGVMPNCRTYNSIVHGYCSSGQPKEAIGFLKKMHSDGVEPDV
VTYNSLMDYLCKNGRCTEARKMFDSMTKRGLKPEITTYGTLLQGYATKGALVEMHGLLDLMVRNGIHPNHYVFSIL
ICAYAKQGKVDQAMLVFSKMRQQGLNPDTVTYGTVTGILCKSGRVEDAMRYFEQMIDERLSPGNIVYNSLIHSLCI
FDKWDKAKELTLEMLDRGTCLDTIFFNSIIDSHCKEGRVIESEKLFDLMVRIGVKPDIITYSTLIDGYCLAGKMDE
ATKLLASMVSVGMKPDCVTYNTLINGYCKISRMEDALVLFREMESSGVSPDIITYNIILQGLFQTRRTAAAKELYV
GITESGTQLELSTYNIILHGLCKNNLTDEALRMFQNLCLTDLQLETRTFNIMIGALLKVGRNDEAKDLFAALSANG
LVPDVRTYSLMAENLIEQGLLEELDDLFLSMEENGCTANSRMLNSIVRKLLQRGDITRAGTYLFMIDEKHESLEAS
TASLFLDLLSGGKYQEYHSCIRGGIFSLCVNSEVQENHLLDSESGVHFLLKLLNPPVNLVDSKAPSIGSKLLGISK
VQMLNGSNKDSDCISEEILSKVEEILLSCQVIKSLDKDDKKTTRPELCPKWLALLTMENACLSAVSVEETSDTVSR
```

-continued

```
VGGNFKETLREMGGLDSIFDVMVDFHSTLENLIKDTSTSALDRNEGTSLQSAALLLKCLKILENAIFLSDDNKTHL
LNMSRKLNPKRSLLSFVGVIINTIELLSALSILQNSSVVSSSTYPKSSKVSQQSYSVVMAGGDRGRGVECHPHQGV
SAALLRPGPQALAASWRRRETVVRSDFAAGGVATMGDSPQALSDRLCGSATKVWRGGAEWTAEAFARNGAAGPSQS
RLPVTRNRAQHYIAKIWATLTISMFYKLDVEGMENLPPNSSPAIYVANHQSFLDIYTLLTLGRCFKFISKTSIFMF
RII
```

Another suitable nucleic acid molecule in accordance with the present invention is isolated from rice and identified herein as Rhpr3, which has a nucleotide sequence of SEQ ID NO: 24, as follows:

```
ATGGCGCCGCGCCGCTTCCCGCGCTGTTGGCGCCCTTCGCTCGGACGGCTCGATCCAAGGGCGAGGAGGCCGCG
CGGGGGGCAGTGGCGCCGAGGACGCACGCCACGTGTTCGACGAATTGCTCCGGCGTGGCAGGGGCGCCTCGATCTA
CGGCTTGAACCGCGCCCTCGCCGACGTCGCGCGTCACAGCCCCGCGGCCGCCGTGTCCCGCTACAACCGCATGGCC
CGAGCTGGCGCCGACGAGGTAACTCCCGACTTGTGCACCTACGGCATTCTCATCGGTTGCTGCTGCCGCGCGGGCC
GCTTGGACCTCGGTTTCGCGGCCTTGGGCAATGTCATTAAGAAGGCATTTAGAGTGGAAGCCATCACCTTCACTCC
TCTGCTCAAGGGCCTCTGTGCCGACAAGAGGACGAGCGACGCAATGGACATAGTGCTCCGCAGAATGACCGAGCTC
GGTTGCATACCAAATGTCTTCTCCTACAATAATCTTCTCAACGGGCTGTGTGATGAGAACAGAAGCCAAGAACCTC
TCGAGTTGCTGCACATGATGGCTGATGATCGAGGAGGAGGTAGCCCACCTGATGTGGTGTCGTATACCACTGTCAT
CAATGGCTTCTTCAAAGAGGGGGATTCAGACAAAGCTTACAGTACATACCATGAAATGCTGGACCGGGGGATTTTA
CCTGATGTTGTGACCTACAGCTCTATTATTGCTGCGTTATGCAAGGGTCAAGCTATGGACAAGCCATGGAGTCATT
GCAAAGAAGGGAGGGTTATAGAATCTGAAAAACTCTTTGACCTGATGGTACGTATTGGTGTGAAGCCTGATATCAT
TACATACAGTACACTCATCGATGGATATTGCTTGGCAGGTAAGATGGATGAAGCAATGAAGTTACTTTCTGGCATG
GTCTCAGTTGGGTTGAAACCTAATACTGTTACTTATAGCACTTTGATTAATGGCTACTGCAAAATTAGTAGGATGG
AAGACGCGTTAGTTCTTTTTAAGGAGATGGAGAGCAGTGGTGTTAGTCCTGATATTATTACGTATAACATAATTCT
GCAAGGTTTATTTCAAACCAGAAGAACTGCTGCTGCAAAAGAACTCTATGTCACCATTACCGAAAGTGGAACGCAG
ATTGAACTTAGCACATACAACATAATCCTTCATGOACTTTGCAAAAACAAACTCACTGATCATGCACTTCAGATGT
TTCAGAACCTATGTTTGATGGATTTGAAGCTTGAGGCTAGGACTTTCAACATTATGATTGATCCATTGCTTAAAGT
TGGCAGAAATGATGAAGCCAAGGATTTGTTTGTTGCTTTCTCGTCTAACGGTTTAGTGCCGAATTATTGGACGTAC
AGGTTGATGGCTGAAAATATTATAGGACAGGGGTTGCTAGAAGAATTGGATCAACTCTTTCTTTCAATGGACGACA
ATGGCTGTACTGTTGACTCTGGCATGCTAAATTTCATTGTTAGGGAACTGTTGCAGAGAGGAGTAGTGGTGGTGGT
GAGTGGTGAATCTGCCACCACCCCACCACCAACTCTCAAAATTCTGACATGTGGGATCACTGTCAATCCCTTCTCC
AAGACATGTGGGATCACTGTCAATCCCTTCTCCAAACCAATTGTGCAGACAGGTGCTTGCGGTCAGGTTAAAGAAG
TTGGCAAAAATGCTTCTGAAGAAAGGTTAATTGTTGTTTCATCTCAGGAGATTCCAGATGATCCAGTGTCTCCAAC
AATTGAGGCGCTTATTTTGCTCCATAGTAAAGCAAGTACACTTGCTGAGAACCACCAGTTGACAACACGGCTTGTT
GTACCATCAAACAAAGTTGGTTGTATTCTTGGGGAAGGTGGAAAGGTAATTACTGAAATGAGAAGACGGACTGGGG
CTGAAATCCGAGTCTACTCAAAAGCAGATAAACCTAAGTACCTGTCTTTTGATGAGGAGCTTGTGCAGCATATCAG
CCTTATCTTGGTTGATCCGCATGCTGGACGAGCACATCTGTTCTCGCATCAACTGCTGACTGCTATATATGTGCTG
GTGCTGAATCGATCGATTGTCGTCGCGGAAGTGAAGAACAACCACGGCACTGCTGCCTGCTGGGCTCTAGCCGCCA
TCAGTTATAACCGTACAAACTTCAGTGATTTGCTGGTTTCACATTGGTTTATAATAAAGGCCTCCGTTTTTAGTTT
CACGCTGGGCCTTCAGAATCTCAGGACCCGCCCTGCTCATGATCCTTACACCGTGTATCCTGTAGAGTACTTCTCT
AAAAGAGAGTACCCTAGTGGAAGTAGCAAAGTTGCACCATCTGCTTCATACGAAAGATATGCAGCAACTACTCGCT
```

-continued

```
TGCCTAATGGACAACTGCCCTCATCTATTAGTCCTGGTGCCGATTATATGTCCTGCCGTTCTTATCTTGACCAAGT

ACCTACTGATAGGTACTCTAATAGGGTTACACTACAATTAGGCCTCTCGAGAGCCGGGAATAGTAATGTGCAACAA

TTAGGAATCACCAGAGCTGGAAATTCCAATGCTTATGATTATACTGAGGCTGCTGAGCAGATCCATGGACGTGAGG

ATTACCGAAGACTGTCAGGTCTCACTGGGTATCCAGGTGGCTCTTCGAATTGTGGATTCCAAATAGTTAACTGGAG

TCTGTCATTGGTGTTGGTGATCTCTGGTGCGAGAGTGAAGTTGCACGAAGCCCATCCTGGTTCTTCCGAGTCCATT

GTGGAGATCCAGGGCATTCCGGATCAAGTGAAAGCCGCACAGAGCCTTCTGCAAGGCTTCATCGGCGCAAGCAGCA

ACAGCAGGCAGGCGCCCCAGTCCTCTCGCATGGCCCATTATTTTTAG
```

Rhpr3 is a rice homolog of the *Petunia* Rf-PPR592 gene.
The nucleic acid molecule of the present invention which has the nucleotide sequence of SEQ ID NO: 24 encodes a protein or polypeptide having a deduced amino acid sequence corresponding to SEQ ID NO: 25 as follows:

```
MARRAASRAVGALRSDGSIQGRGGRAGGSGAEDARHVFDELLRRGRGASIYGLNRALADVARHSPAAAVSRYNRMA

RAGADEVTPDLCTYGILIGCCCRAGRLDLGFAALGNVIKKGFRVEAITFTPLLKCLCADKRTSDAMDIVLRRMTEL

GCIPNVFSYNNLLNGLCDENRSQEALELLHMMADDRGGGSPPDVVSYTTVINGFFKEGDSDKAYSTYHEMLDRGIL

PDVVTYSSIIAALCKGQANDKPWSHCKEGRVIESEKLFDLMVRIGVKPDIITYSTLIDGYCLACKMDEAMKLLSGM

VSVCLKPNTVTYSTLINGYCKISRMEDALVLFKEMESSGVSPDIITYNIILQGLFQTRRTAAAKELYVRITESGTQ

IELSTYNIILHGLCKNKLTDDALQMFQNLCLMDLKLEARTFNIMIDALLKVGRNDEAKDLFVAFSSNGLVPNYWTY

RLMAENIIGQGLLEELDQLFLSMEDNGCTVDSGMLNFIVRELLQRGVVVVVSGESATTPPPTLKILTCGITVNPFS

KTCGITVNPFSKPIVQTGACGQVKEVGKNASEERLIVVSSQEIPDDPVSPTIEALILLHSKASTLAENHQLTTRLV

VPSNKVGCILGECGKVITEMRRRTGAEIRVYSKADKPKYLSFDEELVQHTSLILVDRHAGRAHLLSHQLLTAIYVL

VLNRSIVVAEVKNNHGTAACWALAAISYNRTNFSDLLVSHWFIIKASVFSFTLGLQNLRTGPAHDPYTVYPVEYFS

KREYPSGSSKVAPSASYERYAATTRLPNGELPSSISPGADYMSCRSYLDQVPTDRYSNRVTLQLGLSRACNSNVQQ

LGITRAGNSNAYDYTEAAEQIHGREDYRRLSGLTGYPGGSSNCGFQIVNWSLSLVLVISGARVKLHEAHPGSSESI

VEIQGIPDQVKAAQSLLQGFIGASSNSRQAPQSSRMAHYF
```

Another suitable nucleic acid molecule in accordance with the present invention is isolated from rice and identified herein as Rhpr4, which has a nucleotide sequence of SEQ ID NO: 26, as follows:

```
ATGCCGCTCGCCACGCTGCTCGGCCACCTCGCCGCCGGCCGCTTCCGCCTCGTCCAGGCGCTCACCGGCGCCGCGA

CCGCGGCGGCCGCGCACCGACTCCTCCACCTCCTCCTCCGCACAGCGCCGCCGCCTCCCCTCCCGGACCTCGTCTC

CCTCGCGCGGTGGTCGCGCGCCCACTTCCGCGCGCCGCTCCCGCTCCGGCTCCACGGGCTCCTCCTCGCCCGCCTC

GCCTCCAAGGGGCTCTACCCCCTCCTCCGCTCCGAGCTCCACGTCCTCGCCGCGCCGCGCCTCCACTCCCCCGCAT

CCATCCTCCGCGCTCTCCCCTCCCCGTCCGCGTCCGCGTCCGCATCCACGCCGCTCATCGCCGACATGCTCGTCCT

CGCCCTCGCCAGGGCATCCCAGCCCCTCAGGGCGTACGACGCGTTCCTCCTCGCCGGGGAGAGCCACCCGCGGCAC

CGCCCCTCCACCTCCTCCGTGAACGCCCTTCTCGCCGGCCTCGTCGGCGCCAAGCGGGTCGACCTCGCCGAGAAGG

CGTTCAGGAGCGCGCTGCGGCGGCGCGTGTCACCGGACATCTACACCTTCAACACCGTCATCTCCGGCCTCTCCAG

GATCGGCCAGCTCCGCAAAGCCGGCGATGTCGCCAAGGACATCAAGGCATGGGGTCTGGCTCCCTCTGTGGCCACC

TACAATAGCCTCATCGATGGGTACTGCAAGAAGGGTGGAGCTGGGAACATGTACCATGTCGACATGCTTTTGAAGG
```

-continued

```
AGATGGTCGAAGCCGGGATCTCACCGACTGCAGTTACATTTGGTGTGTTGATCAATGGGTATTGCAAGAACTCGAA

TACTGCGGCCGCAGTGAGAGTCTTCGAGGAGATGAAGCAGCAGGGGATCGCTGCGAGTGTCGTGACGTATAATTCG

CTAATTTCAGGTCTCTGCAGTGAGGGTAAGGTGGAGGAAGGGGTGAAGCTGATGGAGGAGATGGAGGATTTGGGGC

TGTCACCCAATGAAATCACCTTTGGCTGTGTTCTGAAAGGGTTTTGTAAGAAGGGAATGATGGCAGATGCCAATGA

TTGGATTGATGGTATGACAGAGAGGAATGTGGAACCTGATGTGGTTATTTACAATATCTTGATCGATGTGTATCGC

CGTCTTGGAAAAATGGAGGATGCAATGGCGGTGAAGGAGGCAATGGCAAAGAAGGGGATCAGTCCCAATGTCACAA

CATATAATTGCTTGATAACAGGGTTTAGCCGCAGTGGGGATTGGAGGAGTGCTTCTGGCCTTCTGGATGAGATGAA

GGAGAAAGGTATTGAAGCAGACGTCGTCACTTACAATGTGCTTATTGGTGCTTTGTGCTGCAAAGGTGAGGTACGG

AAAGCTGTAAAGCTCTTGGATGAAATGTCGGAAGTTGGATTGGAACCAAACCATCTGACCTACAATACCATAATAC

AGGGGTTCTGTGATAAGGGTAACATTAAGTCTGCCTATGAAATTAGAACCAGGATGGAAAAATGTCGGAAACGGGC

AAATGTGGTTACGTACAATGTGTTCATCAAGTATTTCTGCCAGATAGGGAAGATGGATGAAGCTAATGATCTACTC

AATGAGATGTTGGACAAATGTCTAGTTCCAAACGGGATCACTTATGAAACGATAAAAGAGGGGATGATGGAAAAAG

GCTATACACCAGATATTAGAGGGTGCACTGTCTCACAAGCTTCTGAAAACCCAGCATCATCCTGA
```

Rhpr4 is a rice homolog of the *Petunia* Rf-PPR592 gene. The nucleic acid molecule of the present invention which has the nucleotide sequence of SEQ ID NO: 26 encodes a protein or polypeptide having a deduced amino acid sequence corresponding to SEQ ID NO: 27 as follows:

```
MPLATLLGHLAAGRFGLVQALTGAATAAAAHRLLHLLLRTAPPPPLPDLVSLARWSRAHFRAPLPLRLHGLLLARL

ASKGLYPLLRSELHVLAAARLHSPASILRALPSPSASASASTPLIADMLVLALARASQPLRAYDAFLLAGESHPRH

RPSTSSVNALLAGLVGAKRVDLAEKAFRSALRRRVSPDIYTFNTVISGLCRIGQLRKAGDVAKDIKAWGLAPSVAT

YNSLIDGYCKKGGAGNMYHVDMLLKEMVEAGISPTAVTFGVLINGYCKNSNTAAAVRVFEEMKQQGIAASVVTYNS

LISGLCSEGKVEEGVKLMEEMEDLGLSPNEITFGCVLKGFCKKGMMADANDWIDGMTERNVEPDVVIYNILIDVYR

RLGKMEDAMAVKEAMAKKGISPNVTTYNCLITGFSRSGDWRSASGLLDEMKEKGIEADVVTYNVLIGALCCKGEVR

KAVKLLDEMSEVGLEPNHLTYNTIIQGFCDKGNIKSAYEIRTRMEKCRKRANVVTYNVFIKYFCQIGKMDEANDLL

NEMLDKCLVPNGITYETIKEGMMEKGYTPDIRGCTVSQASENPASS
```

Another suitable nucleic acid molecule in accordance with the present invention is isolated from rice and identified herein as Rhpr5, which has a nucleotide sequence of SEQ ID NO: 28, as follows:

```
ATGGCTGATGATGGTCGCTGCCCACCTGATGTGGTGTCGTATAATACCATCATTGATGGTCTCTTCAAAGAGGGTG

ATGTGGACAAAGCTTACATCACATACCATGAAATGCTGGACCGGAGGGTTTCTCCAGATGCTGTGACTTACAACTC

TATCATTGCTGCCTTAAGCAAGGCTCAAGCTATGGACAGGGCCATGGAGGTACTTACAGTGATGGTTATGCCCAAT

TGCTTCACATATAATAGTATTATGCATGGATATTGTTCTTCAGGACAGTCGGAAAAGGCTATTGGTATTTTCAGAA

AGATGTGCAGTGATGGTATTGAACCAGATGTTGTTACTTATAACTCGTTGATGGACTATCTCTGCAAGAACGGAAA

ATGCACAGAAGCCAGAAAGATTTTTGATTCTATGGTCAAGAGGGGTCTCAAGCCTGATATTACTACCTATGGTACC

CTGCTTCATGGGTATGCTTCCAAAGGAGCTCTTGTTGAGATGCATGATCTCTTAGCTTTGATGGTACAAAATGGCA

TGCAACTTGATCATCATGTCTTCAACATATTAATATGTGCATACACTAAACAAGAAAAAGTAGACGAGGTCGTGCT

TGTATTCAGCAAAATGAGGCAGCAAGGATTGACTCCGAACGCAGTGAACTATAGAACAGTGATAGATGGACTTTGC
```

-continued

```
AAGTTAGGTAGACTAGATGATGCTATGCTTAATTTTGAGCAGATGATTGATAAAGGACTGACACCTAACGTTGTTG

TTTATACCTCCCTAATTCATGCTCTCTGTACCTATGACAAATGGGAGAAGGCCGAGGAGTTAATTTTTGAAATATT

GGATCAAGGTATCAATCCCAACATTGTGTTTTTTAATACAATATTGGACAGTCTTTGCAAAGAAGGGAGGGTTATA

GAATCTAAAAAACTCTTTGACCTGTTGGGACATATTGGTGTGAATCCTGATCTCATTACATACAGTACACTCATCG

ATGGATATTGCTTAGCTGGTAAGATGGATGGAGCATGAAGTTACTCACTGGCATGGTCTCAGTTGGGTTGAAAACC

TGATAGTGTTACATATAGCACTTTGATTAATGGTTACTGTAAAATTAATAGAATGGAGGACGCATTAGCTCTTTTC

AAGGAGATGGAAAGCAATGGTGTTAATCCTGATATTATTACATATAACATAATTCTGCATGGTTTATTTCGCACCA

GAAGAACTGCTGCTGCAAAAGAACTATATGCCAGGATTACCGAAAGTGGAACGCAGCTTGAACTTAGCACATACAA

CATAATCCTCATGGACTTTGCAAAAACAAACTCACTGATGATGCACTTCGGATGTTTCAGAACCTATGTTTGA
```

Rhpr5 is a rice homolog of the *Petunia* Rf-PPR592 gene.

The nucleic acid molecule of the present invention which has the nucleotide sequence of SEQ ID NO: 28 encodes a protein or polypeptide having a deduced amino acid sequence corresponding to SEQ ID NO: 29 as follows:

```
MADDGRCPPDVVSYNTIIDGLEKECDVDKAYITYHEMLDRRVSPDAVTYNSIIAALSKAQAMDRAMEVLTVMVMPN

CFTYNSIMHGYCSSGQSEKAIGIFRKMCSDGIEPDVVTYNSLMDYLCKNGKCTEARKIFDSMVKRGLKPDITTYGT

LLHGYASKGALVEMHDLLALMVQNGMQLDHHVFNILICAYTKQEKVDEVVLVFSKMRQQGLTPNAVNYRTVIDGLC

KLGRLDDAMLNFEQMIDKGLTPNVVVYTSLIHALCTYDKWEKAEELIFEILDQGINPNIVFFNTILDSLCKEGRVI

ESKKLFDLLGHIGVNPDVITYSTLIDGYCLAGKMDGAMKLLTGMVSVGLKPDSVTYSTLINGYCKINRMEDALALF

KEMESNGVNPDIITYNIILHGLFRTRRTAAAKELYARITESGTQLELSTYNIILMDFAKTNSLMMHFGCFRTYV
```

Another suitable nucleic acid molecule in accordance with the present invention is isolated from rice and identified herein as Rhpr6, which has a nucleotide sequence of SEQ ID NO: 30, as follows:

```
ATGGCGCGCCGCGCCGCTTCCCGCGCTGTTGGCTCGGAGGGCTCGATCCAAGGGCGAGGGGCCGCGCGGGGGCA

ATGGCGCCGAGGACGCACGCCACGTGTTCGACGAATTGCTTCGGCGTGGCAAGGGCGCCACGATCTACGGCTTGAA

CCGCGCCCTCGACGACGTCGCGCGTCACAGCCCCGCGGCCGCCGTGTCCCGCTACAACCGCATGGCCCGAGCCGGC

GCCGACGAGGTAACTCCCAACTTGTACACCTACAGCGTTCTCATCGGTTGCTGCTGCCGGGCGGGCCGCTTGGACC

TCGGTTTCGCGGCCTTGGGCAATGTCATTAAGAAGGGATTTAGAGTGGAAGCCATCACCTTCACTCCTCTGCTCAA

GGGCCTCTGTGCCGACAAGAGGACGAGCGACGCAATGGACATAGTGCTCTGCAGAATGACCCAGCTCGGCTGCATA

CCAAATGTCTTCTCCTGCACCATTCTTCTCAAGGGTCTGTGTGATGAGAACAGAAGCCAAGAAGCTCTCGAGCTGC

TCCAAATGATGCCTGATGATGGAGGTGACTGCCCACCTGATGTGGTGTTGTACAACACCGTCATCAATGGCTTCTT

CAAAGAGGGGGATCCGGACAAAGCTTACGCTACATACCATGAAATGTTTGACCAGGGGATTTTGCCAGATGTTGTG

ACTTACAGCTCTATTATCGCTGCCTTATGCAAGGCTCAAGCTATGGACAAGGCCATGGAGGTACTTAACACCATGG

TTAAGAATGGTGTCATGCCTAATTGCAGGACATATAATAGTATTGTGCACGGATATTGCTCTTCAGGGCAGTTGAC

AGAGGCTATTGGATTTCTCAAAATGATGTGCAGTGATGGTGTCGAACCAGATGTTGTTACTTGTAACTTCCTGATG

GATTATCTTTGCAAGAACAGAAGATGCACGGAAGCTAGAAAGATTTTCAATTCTATGACCAAGTGTGGCCTAAAGC

CTGATATTACTACCTATTGTACCCTGCTTCAGGGGTATGCTACCAAAGGAGCCCTTGTTGAGATCCATGATCTCCT

GGATTTGATGGTATGGAACGGTATCCAACCTAATCATCATGTATTCAACATTCTAATATGTGCATACGCTAAACAA
```

-continued
```
GAAAAAGTAGATGAGGCGATGCTTGTATTCAGCAAAATGAGGCAGCAAGGATTGAGTCCGAATGCAGTGAACTACA

GAACAGTCATAGATGTACTCTGCAAGCTAGGCAGAGTATACGATGCAGTGCTTACCTTAAAGCAGATGATCAATGA

AGGACTAACCCCTGACATCATTGTATATACCCCCCTAATTCATGGTTTTTGTACCTGTGACAAATGGGAGAAGGCT

GAGGAGTTAATTTTTTAA
```

Rhpr6 is a rice homolog of the *Petunia* Rf-PPR592 gene.

The nucleic acid molecule of the present invention which has the nucleotide sequence of SEQ ID NO: 30 encodes a protein or polypeptide having a deduced amino acid sequence corresponding to SEQ ID NO: 31 as follows:

```
MARRAASRAVGSEGSIQGRGGRAGGNGAEDARHVFDELLRRGKGATIYGLNRALDDVARHSPAAAVSRYNRMARAG

ADEVTPNLYTYSVLIGCCCRAGRLDLGFAALGNVIKKGFRVEAITFTPLLKGLCADKRTSDAMDIVLCRMTQLGCI

PNVFSCTILLKGLCDENRSQEALELLQMMPDDGGDCPPDVVLYNTVINGFFKEGDPDKAYATYHEMFDQGILPDVV

TYSSIIAALCKAQAMDKAMEVLNTMVKNGVMPNCRTYNSIVHGYCSSGQLTEAIGFLKMMCSDGVEPDVVTCNLLM

DYLCKNRRCTEARKIFNSMTKCGLKPDITTYCTLLQGYATKGALVEMHDLLDLMVWNGIQPNHHVFNILICAYAKQ

EKVDEAMLVFSKMRQQGLSPNAVNYRTVIDVLCKLGRVYDAVLTLKQMINEGLTPDIIVYTPLTHGFCTCDKWEKA

EELIF
```

Another suitable nucleic acid molecule in accordance with the present invention is isolated from rice and identified herein as Rhpr7, which has a nucleotide sequence of SEQ ID NO: 32, as follows:

```
ATGGCACGCCGCGTCGCTGCCCGCGCCCGCGCCCGCGCCGGCGGCGTCCCGCGCTCGGAGGGTACGATCCAAGACC

GAGCACGCGTTGGGAGCGGTGGCGCCGAGGACGCACTCGACGTGTTCGACGAATTGCTCCGGCGAGGCATCGGCGC

TCCGATCCGCAGCTTGAACGGCGCTCTCGCCGACGTCGCGCGCGACAACCCCGCGGCCGCTGTGTCCCGCTTCAAC

CGCATGGCACGAGCTGGTGCCAGCATGGTAACTCCCACCGTGCACACCTATGGCATCCTCATCGGCTGCTGCTGCA

GTGCGGGCCGCTTAGACCTCGGTTTCGCGGCCTTGGGCCATGTCGTTAAGAAGGGATTCAGAGTGGAACCCATCAT

CTTTAATCCTCTGCTCAAGGGCCTCTGTGCAGACAAGAGGACGGACGACGCAATGGACATAGTGCTCCGTGGAATG

ACCGAGCTCAGCTGCGTGCCAAATGTCTTCTCCCACACCATTATTCTCAAGGGACTCTGTCATGAGAACAGAAGCC

AAGAAGCTCTCGAGCTGCTCCACATGATGGCTGATGATGGAGGAGGCTGCTTACCTAATGTTGTGTCATACAGCAC

CGTCATCGATGGCCTCTTGAAAGGAGGGGATCCGGACAAAGCCTACGCTACATACCGTGAAATGCTTGACCGGAGG

ATTTTGCCAAATGTTGTGATTTACAGCTCCATTATTGCTGCCCTATGCAAGGGTCAAGCAATGGACAAGGCCATGG

AGGTACACGATAGGATGGTTAAGAATGGAGTTACACCCAATTGCTTCACGTATACTAGTCTTGTGCATGGATTTTG

CTCTTCAGGGCAGTTGACAGAGGCTATTAAATTTCTAGAAAAGATGTGCAGCAATGGTGTTGAACCAAATGTTGTT

ACTTATAGCTCGTTTATGGACTATCTCTGCAAGAACGGAAGATGCACAGAAGCTAGAAAGATTTTTGATTCTATGG

TCAAGAGGGGCCTAAAGCCTGATATTACTACCTACAGTAGCTTACTTCATGGGTATGCTATCGAAGGAGCTCTTGT

TGAGATGCATGGTCTCTTTGATTTGATGGTACAAAGTGATATGCAACCCGATCATTATGTCTTCAACACACTAATA

TATGCATCCGCCAAGCAAGGAAAAGTAGATGAGGCCATGCTTGTATTTAGCAAAATGAGGCAGCAAGGATTGAAAC

CTAATTGTGTTACGTATAGCACTTTGATTAATGGCTACTGTAAAATTACTAGGATGGAGAATGCTTTAGCACTTTT

CCAAGAGATGGTGAGCAATGGTGTTAGTCCTAATTTTATCACATATAACATAATGCTGCAAGGTTTATTTCGTACA
```

-continued

```
GGAAGAACTGCTACTGCAAAAGAATTCTATGTACAGATTATCAAAAGTGGCAAAAAAGATCTTATAGAACAGGGGT

TGCTAGAAGAATTGGATGATCTATTTCTTTCAATGGAGGACAATGACTGTAGTACTGTGTCGACTCCTGCATGCTA

A
```

Rhpr7 is a rice homolog of the *Petunia* Rf-PPR592 gene.

The nucleic acid molecule of the present invention which has the nucleotide sequence of SEQ ID NO: 32 encodes a protein or polypeptide having a deduced amino acid sequence corresponding to SEQ ID NO: 33 as follows:

```
MARRVAARARARAGGVPRSEGTIQDRARVGSGGAEDALDVFDELLRRGIGAPIRSLNGALADVARFNPAAAVSRFN

RMARAGASMVTPTVHTYGILIGCCCSAGRLDLGFAALGHVVKKGFRVEPIIFNPLLKGLCADKRTDDAMDIVLRGM

TELSCVPNVFSHTIILKGLCHENRSQEALELLHMMADDGGGCLPNVVSYSTVIDGLLKGGDPDKAYATYREMLDRR

ILPNVVIYSSIIAALCKGQAMDKAMEVHDRMVKNGVTPNCFTYTSLVHGFCSSGQLTEAIKFLEKMCSNGVEPNVV

TYSSFMDYLCKNGRCTEARKIFDSMVKRGLKPDITTYSSLLHGYAIEGALVEMHGLFDLMVQSDMQPDHYVFNTLI

YASAKQGKVDEAMLVFSKMRQQGLKPNCVTYSTLINGYCKITRMENALALFQEMVSNGVSPNFITYNIMLQGLFRT

GRTATAKEFYVQIIKSGKKDLIEQGLLEELDDLFLSMEDNDCSTVSTPAC
```

Another suitable nucleic acid molecule in accordance with the present invention is isolated from rice and identified herein as Rhpr8, which has a nucleotide sequence of SEQ ID NO: 34, as follows:

```
ATGGCGCGCCGCGCCGCTTCCCGCGCTGCTGGCGCCCTTCGCTCGGAGGGCTCGATCCAAGGGCGAGGGGCCGCG

CGGGGGGCAGTGGCGGTGGCGCGGAGGACGCACGCCACGTGTTCCACGAATTGCTCCGTCGTGGCATACCAGATGT

CTTCTCCTACAATATTCTTCTCAACGGGCTGTGTGATGAGAACAGAAGCCAAGAAGCTCTCGAGTTACTGCACATA

ATGGCTGATGATGGAGGTGACTGCCCACCTGATGTGGTGTCGTACAGCACCGTCATCAATGGCTTCTTCAAGGAGG

GGGATCTGGACAAAATGCTTGACCAGAGGATTTCGCCAAATGTTGTGACCTACAACTCTATTATTGCTGCGCTATG

CAAGGCTCAAACTGTGGACAAGGCCATGGAGGTACTTACCACCATGGTTAAGAGTGGTGTCATGCCTGATTGCATG

ACATATAATAGTATTGTGCATGGGTTTTGCTCTTCAGGGCAGCCGAGAGGCTATTGTATTTCTCAAAAAAAGATGC

GCAGTGATGGTGTCGAACCAGATGTTGTTACTTATAACTCGCTCATGGATTATCTTTGCAAGAACGGAAGATGCAC

GGAAGCAAGAAAGATTTTTGATTCTATGACCAAGAGGGGCCTAAAGCCTGATATTACTACCTATGGTACCCTGCTT

CAGGGGTATGCTACCAAAGGAGCCCTTGTTGAGATGCATGGTCTCTTGGATTTGATGGTACGAAACGGTATCCACC

CTAATCATTATGTTTTCAGCATTCTAGTATGTGCATACGCTAAACAAGAGAAAGTAGAAGAGGCAATGCTTGTATT

CAGCAAAATGAGGCAGCAAGGATTGAATCCGAATGCAGTGACCTATGGAACAGTTATAGATGTACTTTGCAAGTCA

GGTAGAGTAGAAGATGCTATGCTTTATTTTGAGCAGATGATCGATGAAGGACTAAGACCTGACAGCATTGTTTATA

ACTCCCTAATTCATAGTCTCTGTATCTTTGACAAATGGGAGAAGGCTGAAGAGTTATTTCTTGAAATGTTGGATCG

AGGCATCTGTCTTAGCACTATTTTCTTTAATTCAATAATTGACAGTCATTGCAAAGAAGGGAGGGTTATAGAATCT

GGAAAACTCTTTGACTTGATGGTACGAATTGGTGTGAAGCCCGATATCATTACCCTTGGCAGGTTTTTGGGGAGCG

CAAGGCGCGACTACTCACTGTTCGTCAACATCTACTTCATCTTCACCAACATGTCGAACACTGGAGACAAGGAGAA

GGAGACTCCCGTCAACACCAACGGAGGCAATACTGCCTCAAACTCCAGCGGAGGACCATTCTTGGGCACATACAAC

ATAATCCTTCATGGACTTTGCAAAAACAAACTCACTGATGATGCACTTCGAATGTTTCAGAACCTATGTTTGATGG

ATTTGAAGCTTGAGGCTAGGACTTTCAACATTATGATTGATGCATTGCTTAAAGTTGGCAGAAATGATGAAGCCAA
```

-continued

```
GGATTTGTTTGTTGCTTTCTCGTCTAACGGTTTAGTGCCGAATTATTGGACGTACAGATTGATGGCTGAAAATATT
ATAGGACAGGGGTTGCTAGAAGAATTGGATCAACTCTTTCTTTCAATGGAGGACAATGGCTGTACTGTTGACTCTG
GCATGCTAAATTTCATTGTTAGGGAACTGTTGCAGAGAGGTGAGATAACCAGGGCTGGCACTTACCTTTCCATGAT
TGATGAGAAGCACTTTTCCCTCGAAGCATCCACTGCTTCCTTGTTTATAGATCTTTTGTCTGGGGGAAAATATCAA
GAATATCATATATTTCTCCCTGAAAAATACAAGTCCTTTATAGAATCTTTGAGCTGCTGA
```

Rhpr8 is a rice homolog of the *Petunia* Rf-PPR592 gene.

The nucleic acid molecule of the present invention which has the nucleotide sequence of SEQ ID NO: 34 encodes a protein or polypeptide having a deduced amino acid sequence corresponding to SEQ ID NO: 35 as follows:

```
MARRAASRAAGALRSEGSIQGRGGRAGGSGGGAEDARHVFDELLRRGIPDVFSYNILLNGLCDENRSQEALELLHI
MADDGGDCPPDVVSYSTVINGFFKEGDLDKMLDQRISPNVVTYNSIIAALCKAQTVDKAMEVLTTMVKSGVMPDCM
TYNSIVHGFCSSGQPKEAIVFLKKMRSDGVEPDVVTYNSLMDYLCKNGRCTEARKIFDSMTKRGLKPDITTYGTLL
QGYATKGALVEMHGLLDLMVRNGIHPNHYVFSILVCAYAKQEKVEEAMLVFSKMRQQGLNPNAVTYGTVIDVLCKS
GRVEDAMLYFEQMIDEGLRPDSIVYNSLIHSLCIFDKWEKAEELFLEMLDRGICLSTIFFNSIIDSHCKEGRVIES
GKLFDLMVRTGVKPDIITLGRFLGSARRDYSLFVNIYFIFTNMSNTGDKEKETPVNTNGGNTASNSSGGPFLGTYN
IILHGLCKNKLTDDALRMFQNLCLMDLKLEARTFNIMIDALLKVGRNDEAKDLFVAFSSNGLVPNYWTYRLMAENI
IGQGLLEELDQLELSMEDNGCTVDSGMLNFIVRELLQRGEITRAGTYLSMIDEKHFSLEASTASLFIDLLSGGKYQ
EYHIFLPEKYKSFIESLSC
```

Another suitable nucleic acid molecule in accordance with the present invention is isolated from rice and identified herein as Rhpr9, which has a nucleotide sequence of SEQ ID NO: 36, as follows:

```
ATGGCGAGAAGAGGACGACGATACTGTAGAGCAGAGGGAACAGAGGAGCGGGCACTGGTGCTCCGGTGGCTGGGA
GGTGGCGACGTCGGCGGCCGAATGTGTTCCCGAGCGCCGCGCTGGAGAGCCCCGAGCTGCGACGGCATCACGCCGA
CTACCGGCCGTGGCGGCGCACATGGAGGCAAAGCCGGTCTACTTCGCGTCGAGGCGTGCCTCCGGGCGGCCCGAG
CTGCAGCAGCAGCTCGTCCGGCCCACCCCAATCTGGGCCGATTGGGCCGATCTCAGCCTCCCGGAGCGGAGACCGA
TCTGGGCCGTCCATCCGCGCCGCCCAGCCAATCGGACCGTGGGTGTATTACTGTACTGCCAGGTCGGTGACCCTCC
GCCGCCGGCGGCGGCGGCGGCGGCGGCAGGCATGGCGCGCCGTGTCACCACCCTTACCCGCGCCCGCACCCGCGCC
CGCGGCGGCGGCGTCCCCAGCGCGCAGGGTGGTACGACCCAAGACCTAGGGCGCGCGGGGGGCAGTGGCACCGAGG
GCGCACGCCACGTGCTCGACGAATTGCCGCTACGGGGCTGGGGCGCCTCGATCTACAGCTTCAACCGCACCCTCAC
CGACGTCGCGCGTGACAGCCCAGCCGCAGCAGTTTCGCTCTTCAACCGCATGGCCCGAGCCGGCGCCGACGAGGTA
ACTCCCGACTTGTGCACCTACAGCATTCTCATCGGTTGCTGCTGCCGCGCGGGCCGCTTGGACCTCGGTTTCGCGG
CCTTGGGCAATGTCATTAAGAAGGGATTTAGAGTGGAAGCCATCACCTTCGCTCCTCTGCTCAAGGGCCTCTGTGC
CGACAAGAGGACGAGCGACGCAATGGACATAGTGCTCCGCAGAATGACCGAGCTCAGCTGCATGCCAGATGTTTTC
TCCTGCACCATTCTTCTCAAGGGTCTGTGTGATGAGAACAGAAGCCAAGAAGCTCTCGAGCTGCTGCACATGATGG
CTGATGATCGAGGAGGAGGTAGCCCACCTGATGTGGTGTCGTATACCACTGTCATCAATGGCTTCTTCAAAGAGGG
GGATTCAGACAAAGCTTACAGTACATACCATGAAATGCTTGATCGGAGGATTTCACCAAATGTTGTGACCTACAGC
TCTATTATTGCTGCGTTATGCAAGGCTCAAGCTATGGACAAAGCCATGGAGGTACTTAACACCATGGTTAAGAATG
```

-continued

```
GTGTCATGCCTGATTGCATGACATATAATAGTATTCTGCATGGATATTGCTCTTCAGGGCAGCCAAAAGAGGCTAT

TGGAACACTCAAAAAGATGCGCAGTGATGGCGTCGAACCAAATGTTGTTACTTATAGATCACTGATGAATTATCTT

TGCAAGAATGGAAGATGCACCGAAGCTAGAAAGATTTTCGATTCTATGACCAAGAGGGGCCTAGAGCCTGATATTG

CTACCTATCGTACCCTGCTTCAGGGGTATGCTACCAAAGGAGCCCTTGTTGAGATGCATGCTCTCTTGGATTTGAT

GGATCCTGAGTTCTACAAGTATTTGGAGAAGTGA
```

Rhpr9 is a rice homolog of the *Petunia* Rf-PPR592 gene.

The nucleic acid molecule of the present invention which has the nucleotide sequence of SEQ ID NO: 36 encodes a protein or polypeptide having a deduced amino acid sequence corresponding to SEQ ID NO: 37 as follows:

```
MARRGRRYCRAEGTEERGTGAPVAGRWRRRRPNVFPSAALESPELRRHHADYRPWAAHMEAKPVYFASRRASGRPE

LQQQLVRPTPIWADWADLSLPERRPIWAVHPRRPANRTVGVLLYCQVGDPPPPAAAAAAAGMARRVTTLTRARTRA

RGGGVPSAQGGTTQDLGRAGGSGTEGARHVLDELPLRGWGASIYSFNRTLTDVARDSPAAAVSLFNRMARAGADEV

TPDLCTYSILIGCCCRAGRLDLGFAALGNVIKKGFRVEAITFAPLLKGLCADKRTSDAMDIVLRRMTELSCMPDVF

SCTILLKGLCDENRSQEALELLHMMADDRGGGSPPDVVSYTTVINGFFKEGDSDKAYSTYHEMLDRRISPNVVTYS

SIIAALCKAQAMDKAMEVLNTMVKNGVMPDCMTYNSILHGYCSSGQPKEAIGTLKKMRSDGVEPNVVTYRSLMNYL

CKNGRCTEARKIFDSMTKRGLEPDIATYRTLLQGYATKGALVEMHALLDLMDPEFYKYLEK
```

Another suitable nucleic acid molecule in accordance with the present invention is isolated from rice and identified herein as Rhpr10, which has a nucleotide sequence of SEQ ID NO: 38, as follows:

```
ATGCCCTTCCGACCGCGCCTCCCGCTCCCCCTCCTCCTCCTCCTGCCTCACCTCCGGCGCCGCCGCTCCTCCC

CCCGCCCGCCCGTGCCCGCGTGGAGACCGCTCTCGTATTATCCCTCGGCGGCGGCCGCGGCGGCGGAGGTGACGGA

GTCCGAGGAGGACGCGGCGGCTGTTGGCAGGGACACCCGAGCCCCTCCCTCCATCGGCGGGATTGCACGGGAGCG

CCTAGGGTTGGCTGCAATGGCGGGGGGGCTGCCGATGACGAGGAGGTCGAGAGGAAGGCCCGCGCTGTCGCGCGGA

TCAAGCTCTGCCATGAGCTTCTGCGGGAGAGGAGGTGGCGCGCGATGCGGGCAGCCTTGGCGCAGCTGGTGACTGA

GCAAGGTGAGCATGCTATGAATTTTCCCCATTCTGATTATCAACTCTACTCATGTGGTATCTGAATAACTATGGTG

ATTGGTGTGAGGAGGCGTAGGAATGGCATCGGTAGTTTTGAACTTCTGATCGATATGAATGTGTGACACAGGATAT

ATTGTTTTTCCAGAGGCATTATCAATTGATCATTACCATATAAAAAACAGTAAGAAAAGGGTCGAAAGCAATGCAT

ACATAGTTGTATTTGGTGTAGTATTATTACTGTAATTCGTTTTTTACTAGAAGGTCTCTGCAAGTATGACAAACTA

GTAACATAAAAATTGTTCGCGTTTAATCTTATTGCGCTTCCTGCTGTAGGATCTGGGTCTGCAGCTGCTCTCTGTG

ACATCTTATGGAACAGATTCAGAGAGTGTGATTCCAACGGTTGTGTATGGGATGCTCTAGCGAACAGTTATGCTAG

AGCTCAGATGGTTCATGATGCCCTTTACGTTCTTAGTAAAATGAGCAGCCTAAACATGCAAATCTCGGTGTTCACC

TATGACAGTTTATTGCACGGCTTAAGGATGACAGACGTGGCATTGGAGCTTTTTGAAGAAATGGAGTCTTGTGGTG

TCTCTCCCAGTGAATATTCGCATAGTATTATTATTAATGGCCTCTGTAAGCAAGATAAGGTTGGAGAAGCTTTATC

TTTCCTTCAGGAAGCTAGGAAGGAGGGAAAGTTTAAACCCTTGGGAATGACCTTTAACATTCTTATGTCTGCATTG

TGTAATTGGGGGTTTGTTCAGTCTGCAAAATCATTTTTATGCCTGATGCTGAAATATGGATTAGTCCCTGACAGGT
```

-continued

```
ATACCTTTTCTACCCTTATACACGGTCTATGTAAAGTAGGTTCAATGGAGGAAGCATTGGATCTTTTCGAGAGAGT

GACAAAAGAAGGAATGGAACTTGAGATTGTGACCTACAATAGCCTTATCAATGGGTACCGATTGCTTGGTTTAACA

AAAGAAATTCCTAAAATCATCCAGATGATGAGAGGCCAAGGTGTTGAACCTGATCTTGTTACATATACTATACTTA

TTGCTGGTCACTGCGAAAGTGGTGATGTTGAAGAAGGAATGAAGGTAAGGAAGGATGTCCTAGACCAAGGTTTGCA

GTTGAATATTGTCACATATAGTGTCCTTCTCAATGCTCTCTTCAAAAAAGGCATGTTCTGCGAAATTGACAACCTA

CTCGGCGAGATCTACAATATTGGTTTGGATATGGATGTTATCGCATATTCCATCCTTATCCATGGGTATTGCAAGC

TAGGGGAAATTGAAAAGGCTCTTCAAGTATGTAATGCAATGTGCAGTTCTCAGAGGGTAATGCCAACATCACTGAA

CCATTTTTCTATTCTTCTAGGACTTTGCAAGAAAGGATTGTTAGTTGAAGCAAGGTGGTATTTGGAAAATGTAGCT

AGAAAATATCAGCCAACTGATGTAGTGTTCTATAATGTCGTTATTGATGGTTATGCAAAACTTGGTGATATTGTAA

ATGCTGTTCGTTTGTATGATCAGATCACTGTAGCTGGTATGCACCCAACCATTGTCACATGCAATTCTCTTCTATA

TGGGTATTGTAAAATTGGGGATCTGCAACTTGCCGAGAGCTATTTTAGGGCTATTCAGCTAAGTGGACTTCTACCA

ACAGCAGTGACATACACTACCTTGATGGATGCACTCTCTGAAGCTGGAGAAGTTAATACCATGCTAAGTCTTTTTG

ATGAAATGGTTGCAAAGAGGATCAAGGCAAATGCAGTAACTTACAGTGTCATTGTTAAAGGGCTTTGTAAGCAGCT

CAGATTTGATGAGGCTATCAATGTTCTCAAAGATATGGATAGCAAAGGTATTAATGCTGACCCGATAACTTACAAT

ACCCTTATACAAGGTTTCTGTGAATCAGAAAACGTTCAGATGGCTTTCCACATACATGACATCATGTTATGCCGTG

GCCTTGTGCCGACACCTGTTACTTATAACTTGCTTATTAATGTGCTGTGTTTGAAGGGAAAAGTTATTCAAGCAGA

AATACTTTTGGAGTCCCTCAGAGAAAATGGCATTAAGTTGAGAAAATTTGCGTACACAACACTTATCAAAGCTCAG

TGCGCAAAAGGAATGCCTATCAATGCTGTTTTGTTAGTTGGTAAGCTTCTAGATGCAGGATTTGAAGCTTCTATTG

AAGATTTCAGTGCAGCAATCAATCGACTTTCCAAAAGACAATTTGCCAAAGAAGCCTTTATGTTTGTCCCGATTAT

GCTATCTCTTGGTATTTACCCAGATACTCAAATATATTGTGTGCTAGGCAGAGCTCTGCAGAAAAATAGTGAGCTT

GTCTATCTACCCATATTAAATGCACTTGCTGTTAAAACTGGTATTTAA
```

Rhpr10 is a rice homolog of the *Petunia* Rf-PPR592 gene.

The nucleic acid molecule of the present invention which has the nucleotide sequence of SEQ ID NO: 38 encodes a protein or polypeptide having a deduced amino acid sequence corresponding to SEQ ID NO: 39 as follows:

```
MPFRPRLPLPLLLLLLPHLRRRRSSPRPPVPAWRPLSYYPSAAAAAAEVTESEEDAAAVGRDTRAPPSIGGIARGA

PRVGCNGGGAADDEEVERKARAVARIKLCHELLRERRWRAMRAALAQLVTEQGSGSAAALCDILWNRFRECDSNGC

VWDALANSYARAQMVHDALYVLSKMSSLNMQISVFTYDSLLHGLRMTDVALELFEEMESCGVSPSEYSHSIIINGL

CKQDKVGEALSFLQEARKEGKFKPLGMTFNILMSALCNWGFVQSAKSFLCLMLKYGLVPDRYTFSTLIHGLCKVGS

MEEALDLFERVTKEGMELEIVTYNSLINGYRLLGLTKEIPKIIQMMRGQGVEPDLVTYTILIAGHCESGDVEEGMK

VRKDVLDQGLQLNIVTYSVLLNALFKKGMFCEIDNLLGEIYNIGLDMDVIAYSILIHGYCKLGEIEKALQVCNAMC

SSQRVMPTSLNHFSILLGLCKKGLLVEARWYLENVARKYQPTDVVFYNVVIDGYAKLGDIVNAVRLYDQITVAGMH

PTIVTCNSLLYGYCKIGDLQLAESYFRAIQLSGLLPTAVTYTTLMDALSEAGEVNTMLSLFDEMVAKRIKANAVTY

SVIVKGLCKQLRFDEAINVLKDMDSKGINADPITYNTLIQGFCESENVQMAFHIHDIMLCRGLVPTPVTYNLLINV
```

-continued

LCLKGKVIQAEILLESLRENGIKLRKFAYTTLIKAQCAKGMPINAVLLVGKLLDAGFEASIEDFSAAINRLCKRQF

AKEAFMFVPIMLSVGIYPDTQTYCVLGRALQKNSELVYLPILNALAVKTGI

Another suitable nucleic acid molecule in accordance with the present invention is isolated from *Arabidopsis thaliana*, which has a nucleotide sequence of SEQ ID NO: 40, as follows:

ATGAAGGCTTTGAGATTGATTCAGCCTCATCTCTTGAAGACAGGTAGTCTTAGAACTGATTTGCTCTGTACCATTT

CGAGTTTCTTTTCTAGCTGCGAACGAGACTTTTCAAGTATTAGCAATGGGAATGTCTGTTTCAGAGAGAGATTGAG

AAGTGGTATTGTTGATATTAAGAAAGATGATGCTATTGCTCTGTTCCAAGAAATGATTAGGTCTCGTCCTCTTCCT

AGTCTTGTTGATTTCAGTAGATTCTTTAGTGCCATTGCCAGAACAAAACAGTTCAATCTCGTGTTAGATTTCTGCA

AGCAACTGGAATTGAATGGGATTGCTCATAACATCTACACTTTGAATATCATGATCAACTGCTTTTGCCGGTGTTG

TAAAACTTGTTTTGCTTATTCTGTTTTGGGAAAAGTAATGAAGCTTGGGTATGAGCCTGACACAACCACGTTTAAC

ACTCTGATCAAAGGACTCTTTCTTGAGGGTAAAGTGTCTGAAGCTGTGGTTTTAGTCGATAGGATGGTGGAAAACG

GATGTCAACCTGATGTGGTTACTTATAATTCGATTGTAAATGGGATATGTAGATCAGGAGATACTTCTTTGGCCTT

GGATTTGCTCAGAAAGATGGAAGAAAGAAATGTTAAGGCTGATGTGTTTACTTACAGTACAATCATTGATAGTCTT

TGTAGAGATGGTTGCATAGACGCTCCAATTAGCCTTTTCAAGGAAATGGAGACGAAAGGGATTAAATCTAGTGTTG

TTACGTATAATTCTCTTGTGAGAGGTCTTTGTAAAGCCGGTAAATGGAATGATGGGGCACTGTTGTTGAAGGATAT

GGTGAGTAGGGAAATCGTCCCTAATGTCATCACTTTCAATGTATTACTTGATGTTTTTGTCAAAGAAGGGAAGCTT

CAGGAGGCTAATGAATTGTACAAAGAGATGATCACAAGAGGTATATCACCTAATATTATTACTTATAATACCTTGA

TGGATGGGTATTGTATGCAGAACCGTCTTAGTGAGGCCAACAATATGTTGGATCTTATGGTTAGGAATAAGTGCAG

TCCTCATATCGTGACTTTTACAAGTCTCATCAAAGGATATTGTATGGTGAAAAGAGTTGACGATGGTATGAAGGTC

TTCCGCAATATTTCTAAGAGAGGCTTGGTTGCCAATGCAGTTACTTATAGCATTCTTGTCCAAGGGTTTTGTCAAT

CCGGGAAAATAAAGCTCGCAGAGGAACTTTTCCAAGAAATGGTTTCACACGGTGTTCTTCCTGATGTTATGACGTA

TGGTATTTTGCTTGATGGCTTGTGTGACAATGGGAAGCTTGAAAAGGCATTGGAAATTTTTGAGGATTTACAAAAG

AGTAAGATGGATCTTGGTATTGTTATGTATACAACCATCATCCAGGGGATGTGCAAGGGTGGAAAAGTGGAAGATC

CCTGGAATTTATTCTGTAGCCTACCTTGTAAAGGAGTGAAGCCTAATGTTATGACATACACCGTGATGATTTCAGG

ATTATGTAAGAAAGGGTCACTGTCTGAAGCAAACATCTTGCTTAGAAAAATGGAGGAAGATGGGAATGCGCCAAAT

GATTGTACATACAACACACTAATCCGGGCACATCTCCGAGATGGTGACTTAACTGCATCAGCTAAACTTATTGAAG

AAATGAAGAGTTGTGGGTTCTCAGCAGATGCTTCCAGTATTAAGATGGTTATCGATATGTTATTGAGTGGTGAATT

GGACAAAAGCTTTCTAGATATGCTTTCGTAA

SEQ ID NO: 40 is a *Arabidopsis* homolog of the *Petunia* Rf-PPR592 gene.

The nucleic acid molecule of the present invention which has the nucleotide sequence of SEQ ID NO: 40 encodes a protein or polypeptide having a deduced amino acid sequence corresponding to SEQ ID NO: 41 as follows:

MKALRLIQPHLLKTGSLRTDLLCTISSFFSSCERDFSSISNGNVCFRERLRSGIVDIKKDDAIALFQEMIRSRPLP

SLVDFSRFFSAIARTKQFNLVLDFCKQLELNGIAHNIYTLNIMINCFCRCCKTCFAYSVLGKVMKLGYEPDTTTFN

TLTKGLFLEGKVSEAVVLVDRMVENGCQPDVVTYNSIVNGICRSGDTSLALDLLRKMEERNVKADVFTYSTIIDSL

-continued

```
CRDGCIDAAISLFKEMETKGIKSSVVTYNSLVRGLCKAGRWNDGALLLKDMVSREIVPNVITFNVLLDVFVKEGKL

QEANELYKEMITRGISPNIITYNTLMDGYCMQNRLSEANNMLDLMVRNKCSPDIVTFTSLIKGYCMVKRVDDGMKV

FRNISKRGLVANAVTYSILVQGFCQSGKIKLAEELFQEMVSHGVLPDVMTYGILLDGLCDNGKLEKALEIFEDLQK

SKMDLGIVMYTTIIEGMCKGGKVEDAWNLFCSLPCKGVKPNVMTYTVMISGLCKKGSLSEANILLRKMEEDGNAPN

DCTYNTLIRAHLRDGDLTASAKLIEEMKSCGFSADASSIKMVIDMLLSGELDKSFLDMLS
```

Another nucleic acid molecule in accordance with the present invention has a nucleotide sequence of SEQ ID NO: 42, identified herein as Rf-PPR591, as follows:

```
   1 ATATATATATACAAACTCATTTTTTCTGTCTATTTGCACAGTGTTATTTTTACATACCCTTGAAAAAGGGTACCTCCGCT
  81 AATAATGTTATCTTTACAAAAAATAACAATACTTTTTTTACATAATATATACAAAACTCATTCTTATGTATTGTAAATAT
 161 GATAAAAATATTGTTATTTTTTGTAATATAGCTATTAGGTAGTCATCTTGTGTAAATTTTCCTAAAAATATTTACCTGAG
 241 TCGGCCATTTGGCTAAAAATATTTCATTTTATAGTCGCATATACTCCAAGCTTGTATATCCCAGAGCGACAGTATACTTC
 321 AATGGTATACGATATCTTCTATTATACACCTTTTTAGTATTCGTATACCCCCAATAGTATACAAGTTTGACACCGCAATA
 401 GTGTACCCCAATGTTGTGGTTGTGTCGCTACAAAATTTGAGTGATGGTAGTGTAATTTTTTAGTGTAAGCTGGGTAGTTT
 481 TGAAAACATTCTTTTTGAAAATTGTAGTTCAAGTCATAGTACAAAAAACTGAAATATTTATATGTTTCTTGATTCTGGCT
 561 GGTCTTCTAAAAATTTTGAAATGCTGGCTAGTTTTCATTTAGCGAGGGCAAATAGGCTACATGGCCAAATTTTTACGTT
 641 AAAAGATAAGTGTTGTCTGGGAAAGTATTCGAAAAGATTGTAGGGACAAGTGTTGCCTAGACAACACGTCAAATTATGTA
 721 GAAAAATGCACGAAGAAATTCAAAAGCAAATATTGCTTAAGCAAGAGGCAGTCAAAGACAAGTGCTGCCTTAGGGAGTGA
 801 GAAATGGGCATCACTATAAGATTGTATTTCCATCCGATATTTATTCATTATAAACTTAAGGAAAAGTGCAGGAAAAACCA
 881 CTAGTTTTTAGCTATTTTTTGGAACTTTAATCATTATGGGCTGAACTTCACACTTTGTGGGCCGAACTTCATACATTCGC
 961 AAGTAAAAATTTAGCTCACAGGCCACTTTTACCACTAGTATTTGGTTTGAAGTCATTTTTTATTGGTTTTACATGAGAGA
1041 CCACTTTTTGGAACTTCAATCTTTGTGCGCTTGAACTTCATGCCTAAGTTATTAAGTTCAACTTCAATCCGTAAGGGCTG
1121 AATTTTTAGGCATAGATGCGTAAACTTCAACCTTGTGGACTGAAGTTGAACTTCGCCCCTTATGGTGGCCTGAAGTTGAA
1201 CTTCAATCCTTGTGGGCTGAACTTGTGTGAAGTTCAACCCACAAGGATTAAAGTTTCAAAAAATGACCTCTCAAGCAAAA
1281 TCTGTAAAAAAAAGTGGTCTCTCATGCACTTTTACCCATTCGCAAAGTAGGCTGAAGTTCAGCCCACAATTATTCAAGTT
1361 CCAAAAAATTTCACAATATATACCTCCTTATCTCGGTTATGATCTTTTGTATGATTTAGCAAAATGGACCGGGAAAGTGC
1441 ACGAAAGACCACTTTTGCCATTGGTCTTTGGGTACAGGCCACTAATACCAAAATATTTAGTTTGTGGCTACTTTTGCTTA
1521 AAGAGTTGAACTTCAGTCCAGAGGCCGGATTGAAGTTCAGTCCTTAAAGATTGAACTTCGATCCAGTGCCATATGGACTG
1601 AAGTTCAGTCAAGTCCTTAAGATGGAACTTCAGTCCAGAGCCATATGGACTGAAGTTCAGTCAATTATCAGAACTTAAGT
1681 CAATATTTATTTAGTAAAGGCCCAAAAGTGGTTAGTATAAGACCAATAAAAATAGCGGCCTAAAACTAAATAACAGTGTT
1761 AAAAGTGGCTGATGGACGAAATTTCTACAAAATGGACTCGAGGTAGCAATTCAACTTCAACCTATGGTCTCATAGTTGTA
1841 CAATTCTTCCAATCACCCCTACTAAGTGAAGTGAAGCGAAGATGATGAGAATTTCAGTGCGTTACTGTCTCAATGGTAAT
1921 CCCTTTTTCTCATTCTTTGCTTATTCAATTGCACCCCGACATTATTCTACCAATACATGTTCCATTTCAGTTAAAGGGAA
2001 TTTTGGGGTTTCTAATGAATTTCAGAATCTTAAGTGTTTAGATGATGCTTTCAGTTTGTTCCGTCAAATGGTTAGAACTA
2081 AGCCTCTTCCTTCTGTTGCCTCTTTCTCTAAATTGTTGAAAGCTATGGTACATATGAAGCATTACTCTTCTGTTGTTTCT
2161 CTTTTTCGAGAAATCCACAAATTACGAATTCCTGTTCATGAATTCATCTTGAGCATTGTGGTTAACAGTTGTTGCCTTAT
2241 GCATCGTACCGATCTCGGATTTTCTGTATTAGCCATTCACTTCAAGAAAGGCATTCCATATAATGAAGTCACCTTTACTA
2321 CCTTAATAAGGGACTTTTTGCTGAAAATAAGGTCAAAGATGCTGTTCATTTGTTCAAAAAGTTGGTGAGGGAGAATATA
2401 TGTGAGCCTAATGAAGTCATGTATGGAACGGTCATGAATGGGCTTTGCAAAAAGGGCCATACTCAAAAAGCTTTTGATTT
```

-continued

```
2481 CCTCCGGTTAATGGAACAAGGAAGCACTAAGCCCAATACACGCACTTACACCATTGTCATAGACGCCTTTTGCAAAGATG
2561 GGATGCTAGATGCTGCTACCAGCCTTTTGAATGAGATGAAACAAAAAAGCATTCCTCCCGACATTTTTACTTATAGCACT
2641 TTAATTGATGCTTTGTGTAAGTTAAGTCAGTGGGAAAATGTTAGGACTTTGTTCCTTGAGATGATACATCTTAATATTTA
2721 TCCAAATGTGTGCACCTTCAACTCCGTCATTGATGGACTATGCAAAGAGGGGAAAGTAGAAGACGCTGAGGAAATAATGA
2801 GATACATGATTGAAAAAGGTGTAGACCCTGATGTGATCACCTATAATATGATAATTGACGGATATGGCTTGCGTGGTCAA
2881 GTGGATAGAGCACGGGAAATTTTTGATTCCATGATCAATAAGAGCATTGAGCCCGATATTATTAGCTATAATATACTAAT
2961 AAATGGATATGCCAGGCAAAAGAAAATAGACGAGGCAATGCAAGTCTGCCGTGAAATTTCTCAAAAGGGATTGAAACCTA
3041 GTATTGTTACCTGCAATGTTCTCTTGCATGGTCTTTTTGAACTTGGAAGAACTAAATCTGCACAAAATTTCTTTGATGAG
3121 ATGCTATCTGCGGGGCACATCCCTGATTTATACACTCATTGTACTTTGCTTGGTGGTTATTTTAAGAATGGACTTGTTGA
3201 AGAGGCTATGTCACACTTCCATAAGTTGGAAAGAAGGAGAGAAGATACAAATATTCAAATTTACACGGCTGTCATTGATG
3281 GATTGTGCAAAAATGGTAAGCTCGACAAAGCTCATGCTACGTTTGAGAAGCTTCCCTTGATAGGCTTACATCCTGATGTG
3361 ATAACATACACTGCAATGATTAGTGGATATTGTCAAGAAGGGTTGTTAGATGAAGCTAAAGATATGCTAAGGAAAATGGA
3441 GGACAATGGTTGTTTGGCAGACAACCGAACATACAATGTTATTGTGCGGGATTTCTCAGAAGCAATAAAGTTAGTGAAA
3521 TGAAGGCTTTTCTGGAGGAAATAGCTGGGAAGAGCTTCTCATTTGAGGCAGCTACTGTAGAGTTATTGATGGATATTATA
3601 GCAGAGGATCCATCCATAACACGCAAAATGCACTGGATTAAACTGCACATTGCATGAATATACAAGGAGATTAGCAGAAT
3681 AATCACAGGTCCGTCCCAGACAACCCCAAGGCTAAATCCCACAATCGAAACAAGGTAAACTATTAATACTTTAACTGCCA
3761 AAACTTCTTTAAGAACTATGCCAATTGAAACAGGTAATATATATATTTCCTTTATTTGGAACATTTCTCGATTTATGCGT
3841 GTCATCCTTGTGCAGAGGCCATGCTAATCTTCTCTCAATCGTTCCCAGGTTTGATTTGAATGATATTTTAGATTATATAC
3921 CCCACAGTTCTGCATTCAAATATGCACCCAAACAAATTAGTGCATCTGTCATAAAAGGGATTGCTCCTATTATACCATCA
4001 TTAAGAAAATCCTTGTGACAGTCGGATAAATGAGCAAATAGTACATGTTTGTTTATTTTTTATTCAATAAGAGTTTGACA
4081 TCTACGGGAAATTATAGTTATCTATGTGGTCGTACTTTTAAAGAAAAGTATTTTTGTCGTTATAGATTGACTGTTTTCCT
4161 CTGTCATTGATCGACTTTCTTTTATTCACATCAGAAGTAGGTATATGTGTACAATGCTTTTAACAACTGGTTTGCATGTG
4241 CTCTTTATGGTCGCATTTCATCAACGAAGTCTCTTTGTCGAGATGCAGCTTGACTTGTTAAGACAAGAACCTTTCGATTT
4321 GGAAATGTGATTATCCCATTCAAAGATACTTGACAGATGTCTCATGATGCTTATTTGACTCAGAAGAATATTCAGAAAAG
4401 GCATGTAGATGTGCAGCAAATGACAGAGTATGTGCAATGGGTGAGGAGGACAATTATACATTGTCCTCCATTGTTCAGTG
4481 GCAAATGGCAATACACCTATGGGATCTAAAGGACATGTTCTGCATGTAGCTAGAAGGGATGCAAGTTCACAGGGAACTAG
4561 GGATTTGGTAGACTATACCAGCCTTCATTTTATCAGTTAGTGAAATGAAAGAAACCATCAATGTAAAGGAAACTCTATGG
4641 TTGTACACCTTTTGAAGTTCCAAGTGTTAAACTAACCTCTGGTGTATATTAGTATATACGGTAGAATTCATTCAATTGCA
4721 CAAGTAGATGTATCTTTTTGCTTGGTTTTAGTTCATTAAGGCATAAATGTTCTACTTAGGTTTCATGCATTAAAATGAAC
4801 ATTCATTTGATCTATGATGATGGAGTCTTGGTCGTGCATATACATGCTTCAAAATTATTGTACAATGGGTTGTGTAGTCC
4881 AATATGTTAACATCATCCACGACATTATCTCTAATAGTTTGAGATTTTGTGATATTTATTCGTAAAATGCATGTTAAGAT
4961 TATTGTAATTTAGACTTCTAAAGTTTTCTTTTTAGTTTGGTGGACAACAAAGTAATAAATCTCAAACACATTGTTTGGTC
5041 TCTTATTCTTTGGAATAAAATATTGAGCTTTTTACAATGTGTACCCTTGGAATATAAAGTATTTACCTTACTATACCTAT
5121 TAAAAATTACATTACTCATGAAATTCAAAGTATCTATCACACTGCGTATTTTTTTTATACTATAAGTCTATATTTACCT
5201 TAGGGCAAAAATTAGGCAAGTACTTACCCACATCGGGTGTATATACCCAATCAACAAAGGAATTTTTACACTCTATACCC
5281 ATGAAATTTAAAGTATTTACAAGTCATACCCATTAAAAATTACTCTACCCATAAAACTAAAAGTATTTACCCAACATACC
5361 CATTTTTTATTGTATACCTTTGTTTATAGGTGTATACCTTAAGGCTGCATAAATTATGGTATAAAAGTCTGGAGGACCA
5441 TTTATTATTGTTTACCTTTTTATACCTTATAATATATAAGTCTGGAGGGGTAGAGTGAGTAAATATTTTAATGGGTAGGC
5521 CAGATAATATTTGAAAGTAGTGGATAGTGGCTGTAATTATTTTAGATTTCGTGGGTATTTTTGTAAGTGTCTAATCAACA
5601 AATGCACGTCATTTGTTTACAATACACTACTATCACTTAGCCATAATTAATTAATAGACATTCTCTCTTCATTACATCAC
```

```
-continued
5681  ATTACCATAGTTAATTGCTATGGTTAGGTATATATATCCGGTGTGAGTAAATTTTTTCATATAAATTATGGCAAGACGAG 5761  TAAATATGAAACTTACATGCAGAGGCAGATAAATATTTTGATTTTGATGAGTATTTTCGTAAAACAATGATTAAATTATC 5841  GCGCAAAACCCTTTCAGTTTGTTTTAATCGTGTACTTATTTGTTTGTTATCATTCCATAATGAAAATTACCTCATTAGTG 5921  CCACATTATCTTTCTATAATGTGGCTATTGTGTCAAGAATCATAATCGTGCCAACTTGCTACATTGTAAAAACAATGATT 6001  CTTTTGTGGCTATTTAGTCAAAAATAGTAACTCTGCTTTCCATTGTCTCCGGTCACCTCGGCCAACTCCGGCCCTACGTT 6081  CATCAAGTACTTATTTTCCATATTTATTCGTTATTTTGTTAATACTTACAATTTGTTTAATTAAATCATACAATTAGCTG 6161  ATACACACATATATAGTGAAAAATGAGATAGTAACTGAAGCAGCTCAAGTTCAATTTTTAGCTGCAAAATTCTTCTATCA 6241  GTTATTATGTTTTGCTTTCAAATTAATAACATATTCATATAGCCGACCTCAACTAATTACGCATTGATGCATAGTTCATT 6321  GTACTAGGAAAAGTAAAATTTCATTTTTAAGTTAGTTTATTTGAGCAAGTTATATATATATACACAATCCATGTGCTTAT 6401  ATCCCTTTCCAATGCTAACTCTGACTTCATGAAAATTAAATTATAGGTGTTACTTTAGTGAGGGACGCGAATTAATATTA 6481  CATCACTGGTAGTGGCGGAGCCAGTATTTTTACTAAGGAGTATCAAAATATAAATAAGTAAATATACGAAATATTAAAAG 6561  GATAGTGAATCTTCCTTTTTAATGTACTTCATTTTAAAGTTAGTTTATTTGAGAAAGTTATATATATACAATGTATGAAC

6641  TGATATTCTTTGATAATGATGATGCCTATGTGGATAGTGAATCTTCCTTTTTAATGTGATGAAAAATAAA
```

Rf-PPR591, isolated from *Petunia*, has an open reading frame ("ORF") of 1776 bp, extending between nucleotides 1882–3657, which is homologous to that of Rf-PPR592.

The nucleotide sequence of SEQ ID NO: 42 encodes a protein or polypeptide having a deduced amino acid sequence of SEQ ID NO: 43, as follows:

```
MMRISVRYCLNGNPFFSFFAYSIAPRHYSTNTCSISVKGNFGVSNEFQNVKCLDDAFSLFRQMVRTKPLPSVASFS

KLLKAMVHMKHYSSVVSLFREIHKLRIPVHEFILSIVVNSCCLMHRTDLGFSVLAIHFKKGIPYNEVTFTTLIRGL

FAENKVKDAVHLFKKLVRENICEPNEVMYGTVMNGLCKKGHTQKAFDLLRLMEQGSTKPNTRTYTIVIDAFCKDGM

LDGATSLLNEMKQKSIPPDIFTYSTLIDALCKLSQWENVRTLFLEMIHLNIYPNVCTFNSVIDGLCKEGKVEDAEE

IMRYMIEKGVDPDVITYNMIIDGYGLRGQVDRAREIFDSMINKSIEPDIISYNILINGYARQKKIDEAMQVCREIS

QKGLKPSIVTCNVLLHGLFELGRTKSAQNFFDEMLSAGHIPDLYTHCTLLGGYFKNGLVEEAMSHFHKLERRREDT

NIQIYTAVIDGLCKNGKLDKAHATFEKLPLIGLHPDVITYTAMISGYCQEGLLDEAKDMLRKMEDNGCLADNRTYN

VIVRGFLRSNKVSEMKAFLEEIAGKSFSFEAATVELLMDIIAEDPSITRKMHWIKLHIA
```

Yet another nucleic acid molecule in accordance with the present invention has a nucleotide sequence of SEQ ID NO: 44, identified herein as rf-PPR592, as follows:

```
ATGATGAGAATTGCAGTGCGTTACTGTCTCAATGGTAATCCCTTTTTCTCATTCTTTGCTTATTCAATTGCACCCC

GACATTATTCTACCAATACACGTTCCATTTCAGTTAAAGGGAATTTTGGGGTTTCTAATGAATTTGAGAATGTTAA

GTGTTTAGATGATGCTTTCAGTTTGTTCCGTCAAATGGTTAGAACTAAGCCTCTTCCTTCTGTTGTCTCTTTCTCT

AAATTGTTGAAAGCTTTGGTACATATGAAGCATTACTCTTCTGTTGTTTCTCTTTTTCGAGAAATCCACAAATTAC

GTATTCCTGTTCATGAATTCATCTTGAGCATTGTGGTTAACAGTTGTTGCCTTATGCATCGTACCGATCTCGGATT

TTCTGTATTAGCCATTCACTTCAAGAAAGGTATTCCATTTAATCAAGTTATCTTTAACACCTTACTAACGGGACTC

TTTGCTGAAAATAAGGTTAAAGATGCTGTTCATTTGTTCAAAAAGTTGGTGAGGGAGAATATATGTGACCCTAATG

AAGTCATGTATGGAACGGTCATGAATGGGCTTTCCAAAAAGGGCCATACTCAAAAAGCTTTTGATTTGCTCCGGTT

AATGGAACAAGGAAGTACTAAGCCCAATACATGTATCTATAGCATTGTTATCGATGCCTTTTGCAAAGATGGGATG
```

-continued

```
CTAGATGGTGCTACCAGCCTTTTGAATGAGATGAAACAAAAAAGCATTCCTCCCGACATTTTTACTTATAGCACTT

TAATTGATGCTTTGTGTAAGTTAAGTCAGTGGGAAAATGTTAGGACTTTGTTCCTTGAGATGATACATCTTAATAT

TTATCCAAATGTGTGCACCTTCAACTCCGTCATTGATGGACTATGCAAAGAGGGGAAAGTAGAAGACGCTGAGGAA

ATAATGAGATACATGATTGAAAAAGGTGTAGACCCTGATGTGATCACCTATAATATGATAATTGACGGATATGGCT

TGCGTGGTCAAGTGGATAGAGCACGGGAAATTTTTGATTCCATGATCAATAAGAGCATTGAGCCCAATATTATTAG

CTATAATATACTAATAAATGGATATGCCAGGCAAAAGAAAATAGACGAGGCAATGCAAGTCTGCCGTGAAATTTCT

CAAAAGGGATTGAAACCTAGTATTGTTACCTGCAATGTTCTCTTGCATGGTCTTTTTGAACTTGGAAGAACTAAAT

CTGCACAAAATTTCTTTGATGAGATGCTATCTGCGGCGCACATACCTGATTTATACACTCATTGTACTTTGCTTGG

TGGTTATTTTAAGAATGGACTTGTTGAAGAGGCTATGTCACACTTCCATAAGTTGGAAAGAAGGAGAGAAGATACA

AATATTCAAATTTACACGGCTGTCATTGATGGATTGTGCAAAAATGGTAAGCTCGACAAAGCTCATGCTACGTTTG

AGAAGCTTCCCTTGATAGGCTTACATCCTGATGTGATAACATACACTGCAATGATTAGTGGATATTGTCAAGAAGG

GTTGTTAGATGAAGCTAAAGATATGCTAAGGAAAATGGAGGACAATGGTTGTTTGGCAGACAACCGAACATACAAT

GTTATTGTGCGGGGATTTCTCAGAAGCAATAAAGTTAGTGAAATGAAGGCTTTTCTGGAGGAAATAGCTGGGAAGA

GCTTCTCATTTGAGGCACCTACTGTAGAGTTATTGATGGATATTATAGCAGAGGATCCTTCTTTGCTTAACATGAT

TCCAGAATTTCACCGGGATAATAAGAAGTGA
``` rf-PPR592 is a gene homologous to Rf-PPR592 and is isolated from a non-restoring *Petunia* line.

The nucleotide sequence of SEQ ID NO: 44 encodes a protein or polypeptide having a deduced amino acid sequence of SEQ ID NO: 45, as follows:

```
MMRIAVRYCLNGNPFFSFFAYSIAPRHYSTNTRSISVKGNFGVSNEFENVKCLDDAFSLFRQMVRTKPLPSVVSFS

KLLKALVHMKHYSSVVSLFREIHKLRIPVHEFILSIVVNSCCLMHRTDLGFSVLAIHFKKGIPFNQVIFNTLLRGL

FAENKVKDAVHLFKKLVRENICEPNEVMYGTVMNGLCKKGHTQKAFDLLRLMEQGSTKPNTCIYSIVIDAFCKDGM

LDGATSLLNEMKQKSIPPDIFTYSTLIDALCKLSQWENVRTLFLEMIHLNIYPNVCTFNSVIDGLCKEGKVEDAEE

IMRYMIEKGVDPDVITYNMIIDGYGLRGQVDRAREIFDSMINKSIEPNIISYNILINGYARQKKIDEAMQVCREIS

QKGLKPSIVTCNVLLHGLFELGRTKSAQNFFDEMLSAGHIPDLYTHCTLLGGYFKNGLVEEAMSHFHKLERRREDT

NIQIYTAVIDGLCKNGKLDKAHATFEKLPLIGLHPDVITYTAMISGYCQEGLLDEAKDMLRKMEDNGCLADNRTYN

VIVRGFLRSNKVSEMKAFLEEIAGKSFSFEAATVELLMDIIAEDPSLLNMIPEFHRDNKK
```

Also suitable in the present invention are other forms of the nucleic acid molecules shown above. An example of a nucleic acid suitable in the present invention is a nucleic acid molecule which hybridizes to a nucleotide sequence of from nucleotide 1982 to 3760 of SEQ ID NO: 1, SEQ ID NO: 19, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40 under stringent conditions of a hybridization buffer comprising 20% formamide in 0.9M saline/0.09M SSC buffer at a temperature of 42° C.

For the purposes of defining the level of stringency, reference can conveniently be made to Sambrook et al., *Molecular Cloning: A Laboratory Manual*, 2nd Edition, Cold Spring Harbor, N.Y., Cold Spring Harbor Laboratory Press, at 11.45 (1989) which is hereby incorporated by reference in its entirety. An example of low stringency conditions is 4–6×SSC/0.1–0.5% w/v SDS at 37°–45° C. for 2–3 hours. Depending on the source and concentration of the nucleic acid involved in the hybridization, alternative conditions of stringency may be employed such as medium stringent conditions. Examples of medium stringent conditions include 1–4×SSC/0.25% w/v SDS at >45° C. for 2–3 hours. An example of high stringency conditions includes 0.1–1×SSC/0.1% w/v SDS at 60 C for 1–3 hours. The skilled artisan is aware of various parameters which may be altered during hybridization and washing and which will either maintain or change the stringency conditions. For example, another stringent hybridization condition is hybridization at 4×SSC at 65° C., followed by a washing in 0.1×SSC at 65° C. for about one hour. Alternatively, an exemplary stringent hybridization condition is in 50% formamide, 4×SSC, at 42° C. Still another example of stringent conditions include hybridization at 62° C. in 6×SSC, 0.05× BLOTTO, and washing at 2×SSC, 0.1% SDS at 62° C.

The isolated nucleic acid molecule of the present invention can be from *petunia, Arabidopsis thaliana,* or rice.

The present invention also relates to an isolated protein encoded by the isolated nucleic acid molecule of the present invention which restores fertility to cytoplasmic male sterile plants and modifies expression of toxic mitochondria proteins by the plant.

The present invention also relates to an isolated expression system that contains the nucleic acid molecule of the present invention which restores fertility to cytoplasmic male sterile plants and modifies expression of toxic mitochondria proteins by the plant. This involves incorporating the nucleic acid molecules of the present invention into host cells using conventional recombinant DNA technology. Generally, this involves inserting the nucleic acid molecule into an expression system to which the nucleic acid molecule is heterologous (i.e., not normally present). The heterologous nucleic acid molecule is inserted into the expression system which includes the necessary elements for the transcription and translation of the inserted protein coding sequences. In one embodiment, the isolated expression system of the present invention contains the nucleic acid molecule of the present invention in proper sense orientation.

The nucleic acid molecules of the present invention may be inserted into any of the many available expression vectors and cell systems using reagents that are well known in the art. Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference in its entirety), pQE, pIH821, pGEX, pET series (see Studier et al., "Use of T7 RNA Polymerase to Direct Expression of Cloned Genes," *Gene Expression Technology*, vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, 2nd Edition, Cold Spring Harbor, N.Y., Cold Spring Harbor Laboratory Press (1989); and Ausubel et al., *Current Protocols in Molecular Biology*, John Wiley & Sons, New York, N.Y., (1989) which are hereby incorporated by reference in their entirety.

In preparing a DNA vector for expression, the various DNA sequences may normally be inserted or substituted into a bacterial plasmid. Any convenient plasmid may be employed, which will be characterized by having a bacterial replication system, a marker which allows for selection in a bacterium and generally one or more unique, conveniently located restriction sites. Numerous plasmids, referred to as transformation vectors, are available for plant transformation. The selection of a vector will depend on the preferred transformation technique and target species for transformation. A variety of vectors are available for stable transformation using *Agrobacterium tumefaciens*, a soilborne bacterium that causes crown gall. Crown gall are characterized by tumors or galls that develop on the lower stem and main roots of the infected plant. These tumors are due to the transfer and incorporation of part of the bacterium plasmid DNA into the plant chromosomal DNA. This transfer DNA (T-DNA) is expressed along with the normal genes of the plant cell. The plasmid DNA, pTi or Ti-DNA, for "tumor inducing plasmid," contains the vir genes necessary for movement of the T-DNA into the plant. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *Agrobacterium tumefaciens* (Fraley et al., "Expression of Bacterial Genes in Plant Cells," *Proc. Nat'l Acad. Sci.*, 80:4803–4807 (1983), which is hereby incorporated by reference in its entirety).

Further improvement of this technique led to the development of the binary vector system (Bevan, "Binary *Agrobacterium* Vectors for Plant Transformation," *Nucleic Acids Res.*, 12:8711–8721 (1984), which is hereby incorporated by reference in its entirety). In this system, all the T-DNA sequences (including the borders) are removed from the pTi, and a second vector containing T-DNA is introduced into *Agrobacterium tumefaciens*. This second vector has the advantage of being replicable in *E. coli* as well as *A. tumefaciens*, and contains a multiclonal site that facilitates the cloning of a transgene. An example of a commonly used vector is pBin19 (Frisch et al., "Complete Sequence of the Binary Vector Bin19, " *Plant Molec. Biol.*, 27:405–409 (1995), which is hereby incorporated by reference in its entirety). Any appropriate vectors now known or later described for genetic transformation are suitable for use with the present invention.

U.S. Pat. No. 4,237,224 issued to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Certain "control elements" or "regulatory sequences" are also incorporated into the vector-construct. These include non-translated regions of the vector, promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used.

A constitutive promoter is a promoter that directs expression of a gene throughout the development and life of an organism. Examples of some constitutive promoters that are widely used for inducing expression of transgenes include the nopoline synthase ("NOS") gene promoter, from *Agrobacterium tumefaciens* (U.S. Pat. No. 5,034,322 issued to Rogers et al., which is hereby incorporated by reference in its entirety), the cauliflower mosaic virus ("CaMV") 35S and 19S promoters (U.S. Pat. No. 5,352,605 issued to Fraley et al., which is hereby incorporated by reference in its entirety), those derived from any of the several actin genes, which are known to be expressed in most cells types (U.S. Pat. No. 6,002,068 issued to Privalle et al., which is hereby incorporated by reference in its entirety), and the ubiquitin promoter ("ubi"), which is the promoter of a gene product known to accumulate in many cell types.

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, growth regulator, herbicide or phenolic compound, or a physiological stress directly imposed upon the plant such as cold, heat, salt, toxins, or through the action of a pathogen or disease agent such as a virus or fungus. A plant cell containing an inducible promoter may be exposed to an inducer by externally applying the inducer to the cell or plant such as by spraying, watering, heating, or by exposure to the operative pathogen. An example of an appropriate inducible promoter for use in the present invention is a glucocorticoid-inducible promoter (Schena et al., "A Steroid-Inducible Gene Expression System for Plant Cells," *Proc. Natl. Acad. Sci.*, 88:10421–5 (1991), which is hereby incorporated by reference in its entirety). Expression of the transgene-encoded protein is induced in the transformed plants when the transgenic plants are brought into contact with nanomolar concentrations of a glucocorticoid, or by contact with dexamethasone, a glucocorticoid analog (Schena et al., "A Steroid-Inducible Gene Expression System for Plant Cells," *Proc. Natl. Acad. Sci. USA*, 88:10421–5 (1991); Aoyama et al., "A Glucocorticoid-Mediated Transcriptional Induction System in Transgenic Plants," *Plant J.*, 11: 605–612 (1997), and McNellis et al., "Glucocorticoid-Inducible Expression of a Bacterial Avirulence Gene in Transgenic *Arabidopsis* Induces Hypersensitive Cell Death, *Plant J.*, 14(2):247–57 (1998), which are hereby incorporated by reference in their entirety). In addition, inducible promoters include promoters that function in a tissue specific manner to regulate the gene of interest within selected tissues of the plant. Examples of such tissue specific promoters include seed, flower, or root specific promoters as are well known in the field (U.S. Pat. No. 5,750,385 issued to Shewmaker et al., which is hereby incorporated by reference in its entirety). In the preferred embodiment of the present invention, a heterologous promoter is linked to the nucleic acid of the construct, where "heterologous promoter" is defined as a promoter to which the nucleic acid of the construct is not linked in nature.

The nucleic acid construct also includes an operable 3' regulatory region, selected from among those which are capable of providing correct transcription termination and polyadenylation of mRNA for expression in the host cell of choice, operably linked to a DNA molecule which encodes for a protein of choice. A number of 3' regulatory regions are known to be operable in plants. Exemplary 3' regulatory regions include, without limitation, the nopaline synthase ("nos") 3' regulatory region (Fraley et al., "Expression of Bacterial Genes in Plant Cells," *Proc. Nat'l Acad. Sci. USA*, 80:4803–4807 (1983), which is hereby incorporated by reference in its entirety) and the cauliflower mosaic virus ("CaMV") 3' regulatory region (Odell et al., "Identification of DNA Sequences Required for Activity of the Cauliflower Mosaic Virus 35S Promoter," *Nature*, 313(6005):810–812 (1985), which is hereby incorporated by reference in its entirety). Virtually any 3' regulatory region known to be operable in plants would suffice for proper expression of the coding sequence of the nucleic acid of the present invention.

The vector of choice, suitable promoter, and an appropriate 3' regulatory region can be ligated together to produce the nucleic acid construct which contains the nucleic acid molecule of the present invention, or suitable fragments thereof, using well known molecular cloning techniques as described in Sambrook et al., *Molecular Cloning: A Laboratory Manual*, 2nd Edition, Cold Spring Harbor, N.Y., Cold Spring Harbor Laboratory Press (1989); Ausubel et al., *Current Protocols in Molecular Biology*, John Wiley & Sons, New York, N.Y. (1989), which are hereby incorporated by reference in their entirety.

Once the nucleic acid construct has been prepared, it is ready to be incorporated into a host cell. Accordingly, in another embodiment, the present invention is an isolated host cell containing the nucleic acid molecule of the present invention which restores fertility to cytoplasmic male sterile plants and modifies expression of toxic mitochondria proteins by the plant. Basically, this method is carried out by transforming a host cell with the expression system of the present invention under conditions effective to yield transcription of the nucleic acid molecule in the host cell, using standard cloning procedures known in the art, such as described by Sambrook et al., *Molecular Cloning: A Laboratory Manual* 2nd Edition, Cold Spring Harbor, N.Y., Cold Spring Harbor Laboratory Press, (1989), which is hereby incorporated by reference in its entirety. Suitable host cells include, but are not limited to, bacteria, virus, yeast, mammalian cells, insect, plant, and the like. Preferably the host cells are either a bacterial cell or a plant cell. Methods of transformation may result in transient or stable expression of the DNA under control of the promoter. Preferably, the nucleic acid construct of the present invention is stably inserted into the genome of the recombinant plant cell as a result of the transformation, although transient expression can serve an important purpose, particularly when the plant under investigation is slow-growing. Plant tissue suitable for transformation include leaf tissue, root tissue, meristems, zygotic and somatic embryos, callus, protoplasts, tassels, pollen, embryos, anthers, and the like. The means of transformation chosen is that most suited to the tissue to be transformed.

An appropriate method of stably introducing the nucleic acid construct into plant cells is to infect a plant cell with *Agrobacterium tumefaciens* or *Agrobacterium rhizogenes* previously transformed with the nucleic acid construct. As described above, the Ti (or RI) plasmid of *Agrobacterium* enables the highly successful transfer of a foreign DNA into plant cells. Another approach to transforming plant cells with a gene which imparts resistance to pathogens is particle bombardment (also known as biolistic transformation) of the host cell, as disclosed in U.S. Pat. Nos. 4,945,050, 5,036,006, and 5,100,792, all to Sanford et al., and in Emerschad et al., "Somatic Embryogenesis and Plant Development from Immature Zygotic Embryos of Seedless Grapes (*Vitis vinifera*)," *Plant Cell Reports*, 14:6–12 (1995), which are hereby incorporated by reference in their entirety. Yet another method of introduction is fusion of protoplasts with other entities, either minicells, cells, lysosomes or other fusible lipid-surfaced bodies (Fraley et al., *Proc. Natl. Acad. Sci. USA*, 79:1859–63 (1982), which is hereby incorporated by reference in its entirety). The DNA molecule may also be introduced into the plant cells by electroporation (Fromm et al., *Proc. Natl. Acad. Sci. USA*, 82:5824 (1985), which is hereby incorporated by reference in its entirety). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate. The precise method of transformation is not critical to the practice of the present invention. Any method that results in efficient transformation of the host cell of choice is appropriate for practicing the present invention.

After transformation, the transformed plant cells must be regenerated. Plant regeneration from cultured protoplasts is described in Evans et al., *Handbook of Plant Cell Cultures*, Vol. 1, MacMillan Publishing Co., NY (1983); Vasil (ed.), *Cell Culture and Somatic Cell Genetics of Plants*, Acad. Press, Orlando, Vol. 1, 1984, and Vol. III (1986); and Fitch et al., "Somatic Embryogenesis and Plant Regeneration from Immature Zygotic Embryos of Papaya (*Carica papaya L.*)," *Plant Cell Rep.*, 9:320 (1990), which are hereby incorporated by reference in their entirety.

Means for regeneration vary from species to species of plants, but generally a suspension of transformed protoplasts or a petri plate containing explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. Efficient regeneration will depend on the medium, on the genotype, and on the history of the culture. If these three variables are controlled, then regeneration is usually reproducible and repeatable.

Preferably, transformed cells are first identified using a selection marker simultaneously introduced into the host cells along with the nucleic acid construct of the present invention. Suitable selection markers include, without limitation, markers encoding for antibiotic resistance, such as the nptII gene which confers kanamycin resistance (Fraley et al., "Expression of Bacterial Genes in Plant Cells," *Proc. Natl. Acad. Sci. USA*, 80:4803–4807 (1983), which is hereby incorporated by reference in its entirety), and the genes which confer resistance to gentamycin, G418, hygromycin, streptomycin, spectinomycin, tetracycline, chloramphenicol, and the like. Cells or tissues are grown on a selection medium containing the appropriate antibiotic, whereby generally only those transformants expressing the antibiotic resistance marker continue to grow. Other types of markers are also suitable for inclusion in the expression cassette of the present invention. For example, a gene encoding for herbicide tolerance, such as tolerance to sulfonylurea is useful, or the dhfr gene, which confers resistance to methotrexate (Bourouis et al., *EMBO J.*, 2:1099–1104 (1983), which is hereby incorporated by reference in its entirety). Similarly, "reporter genes," which encode for enzymes providing for production of an identifiable compound are suitable. The most widely used reporter gene for gene fusion experiments has been uidA, a gene from *Escherichia coli* that encodes the β-glucuronidase protein, also known as GUS (Jefferson et al., "GUS Fusions: β Glucuronidase as a Sensitive and Versatile Gene Fusion Marker in Higher Plants," *EMBO J.*, 6:3901–3907 (1987), which is hereby incorporated by reference in its entirety). Similarly, enzymes providing for production of a compound identifiable by luminescence, such as luciferase, are useful. The selection marker employed will depend on the target species; for certain target species, different antibiotics, herbicide, or biosynthesis selection markers are preferred.

Plant cells and tissues selected by means of an inhibitory agent or other selection marker are then tested for the acquisition of the transgene by Southern blot hybridization analysis, using a probe specific to the transgenes contained in the given cassette used for transformation (Sambrook et al., "*Molecular Cloning: A Laboratory Manual*," Cold Spring Harbor, N.Y., Cold Spring Harbor Laboratory Press (1989), which is hereby incorporated by reference in its entirety).

After the expression cassette is stably incorporated in transgenic plants, it can be transferred to other plants by sexual crossing. Any of a number of standard breeding techniques can be used, depending upon the species to be crossed. Once transgenic plants of this type are produced, the plants themselves can be cultivated in accordance with conventional procedure so that the nucleic acid construct is present in the resulting plants. Alternatively, transgenic seeds or propagules (e.g., cuttings) are recovered from the transgenic plants. These seeds can then be planted in the soil and cultivated using conventional procedures to produce transgenic plants.

Thus, in other embodiments, the present invention includes transgenic plants and seeds produced by transformation with the nucleic acid molecule of the present invention which restores fertility to cytoplasmic male sterile plants and modifies expression of toxic mitochondria proteins by the plant. Examples of transgenic plants include crop plants such as alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane. Other examples of transgenic plants include ornamental plants such as *Arabidopsis thaliana, Saintpaulia, petunia*, pelargonium, poinsettia, *chrysanthemum*, carnation, and *zinnia*.

The nucleic acid molecule of the present invention can be utilized to restore fertility to cytoplasmic male sterile plants for a wide variety of crop plants and ornamental plants. Thus, the present invention also relates to a method of restoring fertility to cytoplasmic male sterile plants involving transforming a cytoplasmic male sterile plant with a nucleic acid molecule of the present invention under conditions effective to restore fertility to the cytoplasmic male sterile plant. The plant can have 2 or more copies of the nucleic acid molecule.

The nucleic acid molecule of the present invention can be utilized in a method for identifying genes affecting male fertility or mitochondrial gene expression in other species. The first PPR gene family member whose function was characterized is crp1, a gene involved in RNA processing in chloroplasts (Fisk et al., "Molecular Cloning of the Maize Gene crp1 Reveals Similarity Between Regulators of Mitochondrial and Chloroplast Gene Expression," *EMBO J.*, 18: 2621–2630 (1999), which is hereby incorporated by reference in its entirety). Rf-PPR592 and crp1 exhibit some sequence similarity, though there are other PPR motif proteins in the databases with greater similarity to Rf-PPR592. Both of these genes affect accumulation of particular RNA transcripts.

Thus, another aspect of the present invention relates to a method of identifying a candidate gene restoring fertility in plants. The method involves analyzing the candidate gene for the presence of the above nucleic acid molecule in accordance with the present invention.

Identification of the nucleic acid molecules of the present invention suggests new strategies for identification of restorers or nuclear male sterility (ms) alleles in crop species that are more important agriculturally than *petunia*. Thus, another aspect of the present invention relates to a method of identifying a candidate plant suitable for breeding with a cytoplasmic male sterile plant. The method involves analyzing the candidate plant for the presence, in its genome, of the above nucleic acid molecule of the present invention.

For example, it is possible that a nucleic acid molecule of the present invention corresponds to a restorer allele in rice. Since the complete genome sequence of rice is publicly available, using the above-described method for identifying PPR motif-containing genes, candidates for rice restorer genes can be identified in the rice chromosomal region which is genetically linked to the rice restoration phenotype. Using standard methods of cloning and rice transformation, the candidate rice restorer gene can be introduced as a transgene into a rice CMS line and the fertility of the transformants can be evaluated to determine whether the PPR gene is actually a restorer gene.

The fact that the nucleic acid molecules of the present invention can be a PPR motif gene can also be used to identify putative genes in other species that might encode male sterility when disrupted. The homolog of a restorer gene in one species could, when mutated, be a male sterility-encoding gene in another species. Creating a male sterile line can be valuable for certain applications. For example, flowers of *petunia* and some other horticultural species undergo a phenomenon called pollination-induced senescence (Xu et al., "Programmed Cell Death During Pollination-Induced Petal Senescence in *Petunia*," *Plant Phys.*, 122:1323–1333 (2000), which is hereby incorporated by reference in its entirety). Flowers are triggered to senesce when pollinated. A male sterile flower will last longer when the plant is male sterile, because no self pollen will be available to pollinate it.

Since it is possible to introduce genes into yeast mitochondria, it is likely that methods for introducing genes into plant mitochondria can be developed. When it becomes possible to introduce the pcf gene or a toxic homolog containing the sequences on which the nucleic acid molecule of the present invention operates, then a new CMS/restorer system can be created in a different species. In such a system, a male sterile line is created by introducing pcf or a pcf homolog into the mitochondrial genome. This CMS line can then be crossed with a line containing the nucleic acid molecule of the present invention in the nuclear genome, introduced by standard transformation methods, to create hybrid seed that will give rise to fertile progeny plants.

Thus, the present invention also relates to a method of producing hybrid plant seed. The method first involves providing a cytoplasmic male sterile plant. Next, a second plant containing the above nucleic acid molecule in accordance with the present invention is provided. Finally, the cytoplasmic male sterile plant and the second plant are bred under conditions effective to produce hybrid progeny seed which yield fertile plants.

Another aspect of the present invention relates to a method of producing plant seeds for an inbred line of plants. The method first involves providing a cytoplasmic male sterile plant. Next, a second plant containing the above nucleic acid molecule in accordance with the present invention is provided. Then, the cytoplasmic male sterile plant and the second plant are bred under conditions effective to produce hybrid progeny seed which yield fertile plants. Next, hybrid fertile plants are produced from the hybrid progeny seeds Finally, the hybrid fertile plants and the second plant are backcrossed to produce seed which yield inbred progeny plants.

Backcrossing methods can be used with the present invention to improve or introduce a characteristic into the present cultivar. The term backcrossing refers to the repeated crossing of a hybrid progeny back to one of the parental plants for that hybrid. The parental plant which contributes the locus for the desired characteristic is termed the nonrecurrent or donor parent. This terminology refers to the fact that the nonrecurrent parent is used one time in the backcross protocol and, therefore, does not recur. The parental plant to which the locus or loci from the nonrecurrent parent are transferred is known as the recurrent parent as it is used for several rounds in the backcrossing protocol (Poehlman et al., *Breeding Field Crops*, 4th Ed., Ames, Iowa, Iowa State University Press, (1995); Fehr, ed., *Principles of Cultivar Development*, Vol. 1: Theory and Technique, New York, N.Y., Macmillan Publishing Company (1987); and Fehr, ed., *Principles of Cultivar Development*, Vol. 2: Crop Species, N.Y., N.Y., Macmillan Publishing Company (1987), which are hereby incorporated by reference in their entirety).

In a typical backcross protocol, the phenotypically and/or commercially appealing cultivar or accession (recurrent parent) is crossed with a second cultivar (nonrecurrent parent) that carries the single locus of interest (e.g., the GSB resistance gene locus) to be transferred. The resulting progeny from this cross are then crossed again to the recurrent parent and the process is repeated until a plant is obtained where essentially all of the desired morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original cultivar or accession. To accomplish this, a single locus of the recurrent cultivar is modified or substituted with the desired locus from the nonrecurrent parent, while retaining essentially all of the rest of the desired genetic, and therefore the desired physiological and morphological constitution of the original cultivar. The choice of the particular nonrecurrent parent will depend on the purpose of the backcross; one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

A technique, known as modified backcrossing, uses different recurrent parents during the backcrossing. Modified backcrossing may be used to replace the original recurrent parent with a cultivar having certain more desirable characteristics or multiple parents may be used to obtain different desirable characteristics from each.

Presently, it is possible to introduce genes into chloroplast genomes, which are maternally inherited in many species. Therefore, a CMS/restorer system can also be created by introducing the pcf locus, modified for chloroplast expression, into the chloroplast genome. The nucleic acid molecule of the present invention can be modified to replace the mitochondrial transit sequence with a chloroplast transit sequence, using standard methods (Kohler et al., "Exchange of Protein Molecules Through Connections Between Higher Plant Plastids," *Science*, 276:2039–2042 (1997), which is hereby incorporated by reference in its entirety), so that the protein encoded by the nucleic acid molecule of the present invention will turn off toxic gene expression in the chloroplast. Without the restorer, PCF in the chloroplast is likely to be toxic; PCF is toxic to *E. coli* bacteria. Thus, the present invention also relates to a method of producing plants with a cytoplasmic male sterile plant restoration system. The method first involves transforming a first plant in its chloroplast genome with a nucleic acid which causes the plant to become male sterile. Next, a second plant is transformed with the above nucleic acid molecule in accordance with the present invention whose protein product is targeted to the chloroplast. Finally, the first and second plants are crossed to produce progeny plants possessing a cytoplasmic male sterile plant restoration system.

Since the nucleic acid molecule of the present invention prevents the expression of an organelle gene, it can be used to control the expression of a chimeric gene introduced into chloroplasts. If there is a useful protein that is desired to be produced from plant chloroplasts by introduction of a gene encoding the valuable protein into the chloroplast genome, production of the valuable protein could deliberately be turned off by expressing the nucleic acid molecule of the present invention from a conditional promoter. When desired, the expression of the nucleic acid molecule of the present invention could be turned off, so that the valuable protein is produced. In further detail, the method of the present invention involves: (1) engineering a chimeric gene including the coding region of a desirable protein and the pcf gene sequences that are regulated by the nucleic acid molecule of the present invention; (2) introducing this chimeric gene into chloroplasts of a plant and obtaining a chloroplast transgenic line; (3) engineering the nucleic acid molecule of the present invention or its homologs so that the protein is targeted into chloroplasts; (4) introducing the engineered nucleic acid molecule of the present invention into the nuclear genome of a plant and obtaining a nuclear transgenic line; and (5) crossing plants to set up a regulated system. Alternatively, the plant in (2) can be made first and the gene in (3) introduced by transformation, or the plant in (4) can be made first and the gene in (2) introduced into the plant in (4). When it becomes possible to transform plant mitochondrial genomes, the chimeric gene containing the pcf sequence can be introduced into mitochondria and the product of the nucleic acid molecule of the present invention can be targeted to mitochondria to create the analogous system.

The nucleic acid molecule of the present invention must be expressed in most of the plant, because in every tissue examined, the PCF protein is reduced in the presence of the nucleic acid molecule of the present invention (Nivison et al., "Identification of a Mitochondrial Protein Associated With Cytoplasmic Male Sterility in *Petunia*," *Plant Cell*, 1:1121–30 (1989), Nivision et al., "Sequencing, Processing, and Localization of the *Petunia* CMS-Associated Mitochondrial Protein," *Plant J.*, 5:613–623 (1994), which are hereby incorporated by reference in their entirety). The PCF protein does nevertheless vary in abundance (Conley et al., "Tissue-Specific Protein Expression in Plant Mitochondria," *Plant Cell*, 6:85–91 (1994), which is hereby incorporated by reference in its entirety) and is more highly expressed in anthers. Very few promoters have been identified that confer expression in many tissues and in developing microspores at an early stage of pollen development. Thus, the promoter sequence of the nucleic acid molecule of the present invention could be useful to express any of many different coding regions in a variety of tissues.

It is also possible to dissect the regulatory sequences of the nucleic acid molecule of the present invention by standard methods to identify those regions that confer expression in particular tissue types. Typically, such regulatory sequences are 5' to the coding region, though the 3' flanking region can also be important. The most novel aspect of the regulatory sequences of the nucleic acid molecule of the present invention is that they confer expression in early microsporogenesis. Most of the published anther-specific promoters are not effective at the early stage of pollen development, when it is critical to restore proper mitochondrial function in plants carrying the CMS cytoplasm. For example, the promoter of a nucleic acid molecule of the present invention could be used with a different coding region to restore fertility to a species with a different CMS-encoding gene. Alternatively, the promoter could be used to control a gene toxic to pollen to confer male sterility, or regulatory elements from this promoter could be combined with those of another promoter to confer expression in early microsporogenesis.

Thus, another aspect of the present invention relates to a method of directing gene expression to plant mitochondria. The method involves transforming a plant with a chimeric nucleic acid molecule containing a transgene operatively linked to a promoter or a terminator from a plant gene which restores fertility to cytoplasmic male sterile plants and modifies expression of toxic mitochondria proteins by the plant under conditions effective to direct expression of the transgene in the mitochondria of the transformed plant. The promoter has a nucleotide sequence of from nucleotide 1 to 1981 of SEQ ID NO: 1. The terminator has a nucleotide sequence of from nucleotide 3761 to 4593 of SEQ ID NO: 1.

The present invention also relates to a promoter from a plant gene which restores fertility to cytoplasmic male sterile plants and modifies expression of toxic mitochondria proteins by the plant under conditions effective to direct expression of the transgene in the mitochondria of the transformed plant. The promoter has a nucleotide sequence of from nucleotide 1 to 1981 of SEQ ID NO: 1.

Another aspect of the present invention relates to a terminator from a plant gene which restores fertility to cytoplasmic male sterile plants and modifies expression of toxic mitochondria proteins by the plant under conditions effective to direct expression of the transgene in the mitochondria of the transformed plant. The terminator has a nucleotide sequence of from nucleotide 3761 to 4593 of SEQ ID NO: 1.

Another aspect of the present invention relates to a nucleic acid construct. The nucleic acid construct includes: (i) a promoter or a terminator from a plant gene which restores fertility to cytoplasmic male sterile plants and modifies expression of toxic mitochondria proteins by the plant under conditions effective to direct expression of the transgene in the mitochondria of the transformed plant and (ii) a nucleic acid heterologous to and operatively coupled to the promoter or the terminator. The promoter has a nucleotide sequence of from nucleotide 1 to 1981 of SEQ ID NO: 1. The terminator has a nucleotide sequence of from nucleotide 3761 to 4593 of SEQ ID NO: 1.

Other embodiments of the present invention include isolated expression systems, host cells, transgenic plants, and transgenic plant seeds containing the nucleic acid construct of the present invention.

Another aspect of the present invention is a method of expressing a gene preferentially in roots of a plant. The method involves transforming a plant with a nucleic acid construct containing a promoter suitable for driving expression preferentially in roots having a nucleotide sequence of from 1 to 1388 of SEQ ID NO: 44; a nucleic acid heterologous to the promoter, where the promoter is operatively coupled 5' to the nucleic acid to induce transcription of the nucleic acid; and a terminator having a nucleotide sequence of from nucleotide 3168 to 4016 of SEQ ID NO: 44, where the terminator is operably coupled 3' to the nucleic acid. This method can be used to express genes in roots of a plant, but not in stems, leaves, or buds.

The nucleic acid molecule of the present invention or its homologues could also be used to deliberately alter floral morphology to produce novel flowers. Thus, in another embodiment, the present invention is a method of altering plant floral morphology in ornamental plants by transforming an ornamental plant with a nucleic acid molecule of the present invention which restores fertility to cytoplasmic male sterile plants and modifies expression of toxic mitochondria proteins by the plant. Combinations of certain nuclear genes with particular mitochondrial backgrounds have been found to result in altered floral morphology in some genera. For example, in tobacco, combinations of the nuclear genome of one species with the cytoplasm of another sometimes results in very abnormal flowers, such as flowers in which anthers have been converted to petals. While these particular plants may not be desirable horticulturally, it is possible that the coding region or expression of the nucleic acid molecule of the present invention could be manipulated so that interesting, valuable floral alterations could be obtained. For example, flowers with a second set of petals in place of anthers could be attractive. A similar strategy could be pursued with other species in which novel floral morphology is desirable. Manipulation of the nucleic acid molecule of the present invention could occur, for example, by overexpressing it on a different promoter, changing the coding region, or using standard antisense or gene silencing methods to underexpress homologous genes.

Figure 7B:
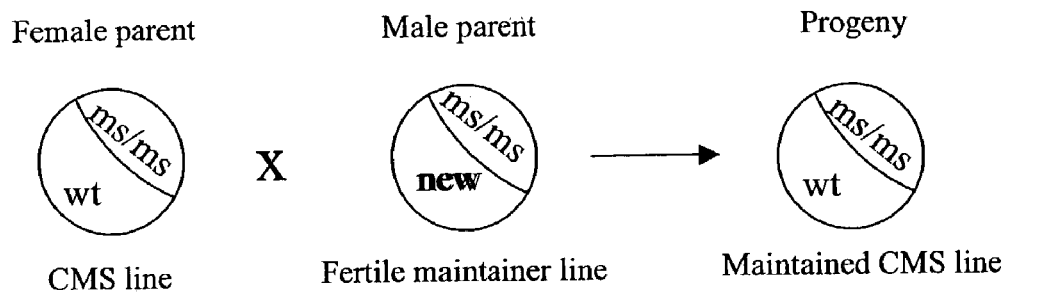

Another aspect of the present invention relates to a method of producing plants with a cytoplasmic male sterile plant restoration system. The method first involves mutagenizing a first plant having a nucleic acid which encodes a protein. The protein has a motif having an amino acid sequence corresponding to any of SEQ ID NOs: 3 to 18 or an amino acid sequence identified with a METAMEME software using the amino acid sequence of SEQ ID NO: 2 as input or an amino acid sequence identified as significantly similar to SEQ ID NO: 2 using a NCBI BLAST software (threshold=E less than or equal to 15) with SEQ ID NO: 2 as input. Next, the mutagenized first plant is crossed with a wild-type plant having mitochondrial DNA polymorphisms compared to mitochondrial DNA in the mutagenized first plant to produce progeny plants. Finally, it is determined if the progeny plants are fertile, whereby fertile progeny plants can be used as a fertile maintainer line, where the mutagenized first plant, the fertile maintainer line, and a wild-type allele present in the first plant before mutagenesis comprises a new cytoplasmic male sterile plant restoration system. FIGS. 7A–B show this aspect of the present invention in detail.

The *Arabidopsis thaliana* genome sequence contains a PPR gene highly similar to the nucleic acid molecule of the present invention. There are existing, publicly available insertional element collections that can be screened by standard methods to find a mutant in which the homolog of the nucleic acid molecule of the present invention is disrupted. The mutant can be examined to determine whether it encodes male sterility. Because the nucleic acid molecule of the present invention is important for nuclear/organelle interaction to produce male fertility, its homologs in other species are likely to be essential for proper pollen development in those species.

Figure 7B:
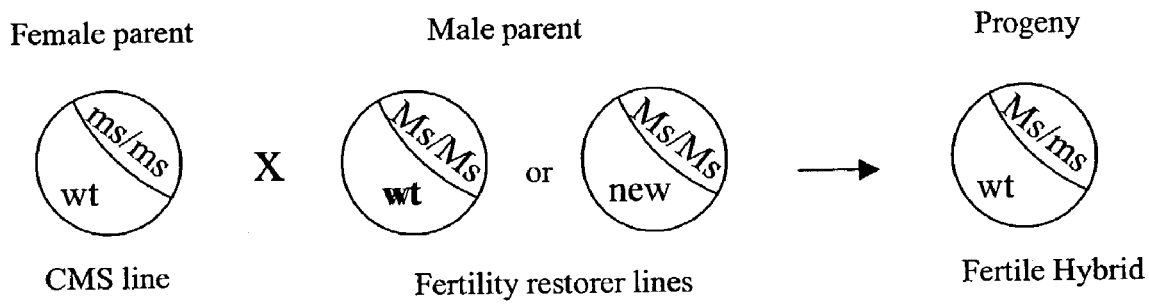

By mutating a PPR gene in a plant that does not have a CMS/restorer system, such a system can be created. In this strategy, a PPR gene is mutated and the plant becomes male sterile. The mutated PPR alleles are then crossed with plants carrying other cytoplasms, present in other varieties of the plant or in intercrossable species. If a cytoplasm can be found in which the plant is fertile in the presence of the two mutated PPR alleles, then a new CMS/restorer system will have been created. A line carrying the new cytoplasm plus the mutated alleles becomes the maintainer line. The line carrying the first cytoplasm plus the mutated alleles becomes rf/rf CMS. A line carrying an unmutated allele plus a mutated allele in the presence of the CMS cytoplasm becomes Rf/rf CMS. These lines can then be exploited just as standard maintainer, sterile, and restored lines are currently used in hybrid seed production (FIG. 7).

For example, tomato does not have a CMS/restorer system. It is known that markers near *petunia* Rf map to a region of the tomato genome where two nuclear male sterility alleles exist. Possibly, the tomato ortholog of the nucleic acid molecule of the present invention, when mutated, results in male sterility. If so, then the cytoplasms of the intercrossable wild tomato species can be tested to determine whether they can confer male fertility to a tomato line homozygous for the mutated PPR gene.

The nucleic acid molecule of the present invention may not be usable directly to restore fertility to CMS lines of most other species. Current information indicates that different mitochondrial genes are present in different CMS lines. In most cases, restorer genes will have a specific mechanism of action—suppression of expression of the abnormal mitochondrial gene. However, by chance, there may be a few species that carry a CMS cytoplasm whose abnormality can be ameliorated by the nucleic acid molecule of the present invention. This can be determined by introducing the nucleic acid molecule of the present invention into the other species and determining whether the transgenic plants become male fertile. If so, the nucleic acid molecule of the present invention can be used as a fertility restorer for this species.

EXAMPLES

The following examples are provided to illustrate embodiments of the present invention but are by no means intended to limit its scope.

Example 1

Identification of Two PPR-Containing ORFs as Potential Candidates for the Rf Gene Previously, the isolation of a 37.5-kb BIBAC clone, SB5, that cosegregates with the Rf gene has been reported (Bentolila et al., "Identification of a BIBAC Clone That Co-Segregates With the *Petunia* Restorer of Fertility (Rf) Gene," *Mol. Genet. Genomics*, 266:223–230 (2001), which is hereby incorporated by reference in its entirety). SB5 is part of a contig that was constructed by screening a *Petunia* BIBAC library with a marker, EACA/MCTC, tightly linked to Rf. No recombination was identified between EACA/MCTC and Rf after examining 1,078 meiotic events. The genetic delimitation of the Rf locus was achieved only partially on the BIBAC contig. One extremity of the contig was separated from Rf by the occurrence of four recombination events, whereas no crossing-over was found between Rf and the other extremity (Bentolila et al., "Identification of a BIBAC Clone That Co-Segregates With the *Petunia* Restorer of Fertility (Rf) Gene," *Mol. Genet. Genomics* 266:223–230 (2001), which is hereby incorporated by reference in its entirety). Because of the possibility that Rf might lie further away in the area not covered by the contig, a walk was initiated by screening the BIBAC library with a probe lying on the extremity that cosegregates with Rf. Unfortunately, the only hits were clones already isolated in the contig, demonstrating the presence of a gap in the *Petunia* BIBAC library.

Before increasing the redundancy of the library to find new clones covering the gap, it was determined whether the Rf gene might lie in the SB5 clone. Because the BIBAC vector is a binary vector allowing *Agrobacterium*-mediated plant transformation (Hamilton, "A Binary-BAC System for Plant Transformation With High-Molecular-Weight DNA," *Gene,* 200:107–116 (1997), which is hereby incorporated by reference in its entirety), SB5 was used to restore fertility to CMS plants. Unfortunately, although SB5 is stable in *E. coli,* it underwent multiple rearrangements when introduced into *A. tumefaciens,* thus precluding its use in transgenic experiments. Randomly chosen clones of various sizes did not show this instability in *A. tumefaciens,* pointing to special features in the sequence of the SB5 insert.

To address whether Rf might lie in the SB5 clone, shotgun sequencing of the entire clone was carried out and the predicted ORFs for candidate Rf genes were examined.

Because of difficulties in contig assembly caused by the presence of repeated sequences, BamHI subclones rather than the entire BIBAC clone were used as the starting material for shotgun sequencing. DNA was sonicated into 1- to 3-kb fragments, which were gel purified (Geneclean Spin Kit, Bio 101, Vista, Calif.), end-repaired with T4 DNA polymerase (GIBCO/BRL, Rockfield, Md.) in the presence of all four dNTPs, and ligated at a mass ratio of 3 inserts to 1 vector into the SmaI site of the pTrueBlue vector (Genomics One, Buffalo, N.Y.). The ligation product was introduced into Electromax DH10B *Escherichia coli* cells (GIBCO/BRL), and DNA obtained from the white colonies by minipreparation was sequenced with the T7 primer in the Cornell BioResource Center. The sequences were assembled into contigs with SEQUENCHER (Gene Codes, Ann Arbor, Mich.).

ORFs from BIBAC SB5, their promoter region, and poly(A) signals were predicted by using GENSCAN (Burge et al., "Prediction of Complete Gene Structures in Human Genomic DNA," *J. Mol. Biol.,* 268:78–94 (1997), which is hereby incorporated by reference in its entirety) with the *Arabidopsis* parameter matrix. Duplicated blocks in the Rf locus were determined by aligning the genomic sequence against itself by using the dot-plot feature from the MEGA-LIGN program (DNAstar, Madison, Wis.) with a 90% match. The presence of a transit peptide in the ORFs was determined by using PREDOTAR version 0.5, TARGETP (Emanuelsson et al., "Predicting Subcellular Localization of Proteins Based on Their N-Terminal Amino Acid Sequence," *J. Mol. Biol.,* 300:1005–1016 (2000); Nielsen et al., "Identification of Prokaryotic and Eukaryotic Signal Peptides and Prediction of Their Cleavage Sites," *Prot. Eng.,* 10:1–6 (1997), which are hereby incorporated by reference in their entirety), and MITOPROT (Scharfe et al., *Nucleic Acids Res.,* 28:155–158 (2000), which is hereby incorporated by reference in its entirety). The length of the transit peptide was predicted by TARGETP and MITOPROT.

PPR motifs were identified in Rf-PPR592 and Rf-PPR591 by the MEME software (Bailey et al., in "Proceedings of the Second International Conference on Intelligent Systems for Molecular Biology," in Altman, eds. (Am. Assoc. Artificial Intelligence Press, Menlo Park, Calif.), pp. 28–36 (1994), which is hereby incorporated by reference in its entirety). The parameters for motif searching were set as minimum width=35, maximum width=35. The PPR consensus motif computed from the comparison of 1,303 motifs has been described previously (Small et al., "The PPR Motif—A TPR-Related Motif Prevalent in Plant Organellar Proteins," *Trends Biochem. Sci.,* 25:46–47 (2000), which is hereby incorporated by reference in its entirety).

Because the Rf gene is expected to be targeted to mitochondria where it can act upon the pcf gene to prevent its expression, an ORF predicted to carry mitochondrial transit sequences was searched. Two ORFs with putative mitochondrial targeting signals were identified. The two ORFs are adjacent to each other and appear to have originated from duplications in the promoter and coding region, but carry divergent 3' flanking regions (FIG. 1A). The ORFs were 92% identical at the nucleotide level, and the predicted proteins were 93% similar, with C termini that differ completely in their final 12 aa. Both ORFs carry PPR motifs; one encodes 591 aa and the other encodes 592 aa, and were therefore named Rf-PPR591 and Rf-PPR592. A third PPR-containing ORF might lie in the vicinity of the two PPR-containing ORFs shown in FIG. 1A. On the left extremity lies a genomic block that shares high similarity with the end of the coding sequence of Rf-PPR592 and its terminator region.

According to cleavage prediction programs, both putative proteins exhibited 28-residue mitochondrial transit peptides. Predicted transit peptides of Rf-PPR592 and Rf-PPR591 differed by only one substitution. To determine whether the predicted transit peptide could target a passenger protein to mitochondria, 44 codons from the 5' end of the Rf-PPR592 coding region were inserted 5' to the coding region of an enhanced GFP. DNAs of this construct and of one known to target GFP to mitochondria were bombarded into onion epidermal cells. Both GFPs appeared to be localized to the same type of organelle in the single cells shown in FIGS. 1B and C. Because the predicted transit peptides of Rf-PPR592 and Rf-PPR591 differed by only one amino acid, it was expected that not only Rf-PPR592 but also Rf-PPR591 would be mitochondrially localized.

Most of the predicted mature protein (87%) of Rf-PPR592 consisted of 14 PPRs (FIG. 1D). These repeats extended from the amino acid in position 54 to the amino acid in position 544 and are organized in two sets of tandem repeats, one set containing 3 PPRs from amino acid 54 to amino acid 158, the other set containing 11 PPRs from amino acid 160 to amino acid 544. Because the Rf-PPR591 and Rf-PPR592 proteins are 93% similar and differ mainly in the last 12 C-terminal amino acids, their organization with respect to PPRs is identical. There was a very good agreement between the consensus motif derived from the 14 PPRs found in Rf-PPR592 (hereafter designated 14 PPR consensus) and the consensus motif derived from 1,303 PPRs (hereafter designated 1303 PPR consensus) reported previously (Small et al., "The PPR Motif—A TPR-Related Motif Prevalent in Plant Organellar Proteins," *Trends Biochem. Sci.,* 25:46–47 (2000), which is hereby incorporated by reference in its entirety) (FIG. 1D). Whenever a discrepancy occured between the consensus motif of the 14 PPRs in Rf-PPR592 and the 1303 PPR consensus, the difference usually was a conservative substitution. For instance, the aspartic acid in the first position of the 14 PPR consensus is replaced by a glutamic acid in the 1303 PPR consensus. Moreover, when the most frequent amino acid in the 14 PPR consensus at a given position differed from the corresponding amino acid found in the 1303 PPR consensus, the amino acid in the 1303 consensus was generally the second most frequent in the 14 PPR consensus (glutamic acid at position 1, asparagine at position 18, alanine at position 28, tyrosine at position 29; FIG. 1D).

It has been demonstrated that Rf-PPR592, a gene encoding a 592-aa protein containing 14 PPRs, was able to restore fertility to CMS plants. The PPR motif, a degenerate 35-aa repeat, has been found in a very large gene family in the Arabidopsis genome (Small et al., "The PPR Motif—A TPR-Related Motif Prevalent in Plant Organellar Proteins," *Trends Biochem. Sci.*, 25:46–47 (2000), which is hereby incorporated by reference in its entirety). The repeats are organized in tandem arrays with the number of motifs per peptide ranging from 2 to 26. About two-thirds of these *Arabidopsis* PPR proteins are predicted to be targeted to either mitochondria or chloroplasts (Small et al., "The PPR Motif—A TPR-Related Motif Prevalent in Plant Organellar Proteins," *Trends Biochem. Sci.*, 25:46–47 (2000), which is hereby incorporated by reference in its entirety). Although distinct from the tetratricopeptide repeat (TPR), a motif that is likely to be involved in protein binding, the PPR motif shares with the former a predicted spatial structure consisting of two α-helices (Small et al., "The PPR Motif—A TPR-Related Motif Prevalent in Plant Organellar Proteins," *Trends Biochem. Sci.*, 25:46–47 (2000); Das et al., "The Structure of the Tetratricopeptide Repeats of Protein Phosphatase 5: Implications for TPR-Mediated Protein—Protein Interactions," *EMBO J.*, 17:1192–1199 (1998), which are hereby incorporated by reference in their entirety). Tandem PPRs are thought to form a superhelix with a central spiral groove that presumably serves as the ligand-binding surface in a similar way as the one predicted for the tandem TPRs (Small et al., "The PPR Motif—A TPR-Related Motif Prevalent in Plant Organellar Proteins," *Trends Biochem. Sci.*, 25:46–47 (2000), which is hereby incorporated by reference in its entirety). However, unlike in the TPR motif, the side chains lining the central groove of the PPR are almost exclusively hydrophilic, suggesting that some or all of the PPR motifs are RNA-binding rather than protein-binding motifs. This hypothesis is supported by the involvement in RNA metabolism and/or translation of the very few PPR motif-containing proteins characterized so far: maize chloroplast CRP1, involved in chloroplast petD RNA processing and petD and petA translation (Fisk et al., "Molecular Cloning of the Maize Gene Crp1 Reveals Similarity Between Regulators of Mitochondrial and Chloroplast Gene Expression," *EMBO J.*, 18:2621–2630 (1999), which is hereby incorporated by reference in its entirety), *Chlamydomonas* MCA1, required for the accumulation of the chloroplast petA transcript (Lown et al., "*Chlamydomonas* Nuclear Mutants That Fail to Assemble Respiratory or Photosynthetic Electron Transfer Complexes," *Biochem. Soc. Trans.*, 29:452–455(2001), which is hereby incorporated by reference in its entirety), yeast PET309, required for the stability and translation of the coxI mitochondrial mRNA (Manthey et al., "The Product of the Nuclear Gene PET309 is Required for Translation of Mature mRNA and Stability or Production of Intron-Containing RNAs Derived from the Mitochondrial COX1 Locus of *Saccharomyces cerevisiae*," *EMBO J.*, 14:4031–4043 (1995), which is hereby incorporated by reference in its entirety), and *Drosophila* BSF, which binds to and stabilizes the bicoid mRNA (Mancebo et al., "BSF Binds Specifically to the bicoid mRNA 3' Untranslated Region and Contributes to Stabilization of bicoid mRNA," *Mol. Cell. Biol.*, 21:3462–3471 (2001), which is hereby incorporated by reference in its entirety). That *Petunia* Rf belongs to this family is consistent with its similarity of action to crp1, mca1, and pet309. Mutations in these three genes result in lack of accumulation of a particular transcript and reduced abundance of an organelle protein. Likewise, in *Petunia* restored plants, among the population of pcf transcripts with different 5' termini, the ones with termini at −121 exhibit reduced abundance and the amount of the PCF protein is greatly reduced (Pruitt et al., "Transcription of the *Petunia* mitochondrial CMS-Associated Pcf Locus in Male Serile and Fertility-Restored Lines," *Mol. Gen. Genet.*, 227:348–355 (1991); Nivison et al., "Identification of a Mitochondrial Protein Associated with Cytoplasmic Male Sterility in *Petunia*," *Plant Cell*, 1:1121–1130 (1989), which are hereby incorporated by reference in their entirety). However, the alleles of the other PPR genes that are known to reduce RNA and/or protein accumulation are recessive, whereas the *Petunia* Rf allele is dominant. Rf genes from other species have been shown to alter the RNA transcript profile of the CMS-associated genes (Wise et al., "Mutator-Induced Mutations of the rf1 Nuclear Fertility Restorer of T-Cytoplasm Maize Alter the Accumulation of T-urf13 Mitochondrial Transcripts," *Genetics*, 143:1383–1394 (1996); Singh et al., "Suppression of Cytoplasmic Male Sterility by Nuclear Genes Alters Expression of a Novel Mitochondrial Gene Region," *Plant Cell*, 3:1349–1362 (1991); Tang et al., "Transcript Processing Internal to a Mitochondrial Open Reading Frame is Correlated with Fertility Restoration in Male-Sterile *Sorghum*," *Plant J.*, 10:123–133 (1996); Moneger et al., "Nuclear Restoration of Cytoplasmic Male Sterility in Sunflower is Associated with the Tissue-Specific Regulation of a Novel Mitochondrial Gene," *EMBO J.*, 13:8–17 (1994), which are hereby incorporated by reference in their entirety). In some cases, restoration has been shown to result from enhanced processing of the CMS-associated transcripts (Tang et al., "Transcript Processing Internal to a Mitochondrial Open Reading Frame is Correlated with Fertility Restoration in Male-Sterile *Sorghum*," *Plant J.*, 10:123–133 (1996); Menassa et al., "Post-Transcriptional and Developmental Regulation of a CMS-Associated Mitochondrial Gene Region by a Nuclear Restorer Gene," *Plant J.*, 17:491–499 (1999), which are hereby incorporated by reference in their entirety). Taken together, these observations suggest that Rfs in other species could also be PPR-containing genes like the *Petunia* Rf.

The data presented here show that a pair of duplicated PPR-containing genes, denoted Rf-PPR591 and Rf-PPR592, lie in the *Petunia* Rf locus. A third related PPR gene might lie in the area not covered by the SB5 BIBAC clone as suggested by the high similarity between the sequence available at the end of the clone and the sequence present at the end of the coding sequence of Rf-PPR592 and in its terminator region.

In *Brassica napus*, the restorer locus has been shown to affect the transcripts of several mitochondrial genes, two of them being associated with the nap and pol CMS (Singh et al., "Nuclear Genes Associated With a Single *Brassica* CMS Restorer Locus Influence Transcripts of Three Different Mitochondrial Gene Regions," *Genetics*, 143:505–516 (1996); Li et al., "Restorer Genes for Different Forms of *Brassica* Cytoplasmic Male Sterility Map to a Single Nuclear Locus That Modifies Transcripts of Several Mitochondrial Genes," *Proc. Natl. Acad. Sci. USA*, 95:10032–10037 (1998), which are hereby incorporated by reference in their entirety). At the same locus have been mapped Rfp, the restorer gene to the pol CMS, that modifies the transcripts of the pol CMS-associated orf224/atp6mitochondrial DNA region, Rfn, the restorer gene to the nap CMS that modifies the transcripts of the nap CMS-associated orf222/nad5c/orf139 mitochondrial DNA region, and Mmt (modifier of mitochondrial transcripts), a gene that modifies the transcripts of the nad4 gene and another gene possibly involved in cytochrome c biogenesis (Li et al., "Restorer Genes for Different Forms of *Brassica* Cytoplasmic Male Sterility Map to a Single Nuclear Locus That Modifies Transcripts of Several Mitochondrial Genes," *Proc. Natl. Acad. Sci. USA*, 95:10032–10037 (1998), which is hereby incorporated by reference in its entirety). The resolution of the genetic mapping in these studies did not allow the authors to address whether the three genes represent different alleles of a single gene or whether the restorer locus might contain multiple, related, tightly linked genes. A similar situation occurs in *Sorghum*, where at the Rf3 locus, one of the two restorers to A3 CMS, has been mapped a gene that regulates the transcript-processing activity of A3 CMS-associated orf107 and the Mmt1 gene that enhances the transcript processing of urf209 (Tang et al., "Cosegregation of Single Genes Associated with Fertility Restoration and Transcript Processing of *Sorghum* Mitochondrial orf107 and urf209," *Genetics* 150:383–391 (1998), which is hereby incorporated by reference in its entirety). As in *Brassica napus*, either a multiallelic model or tightly linked genes could account for this result.

It will be worthwhile to determine whether Rf-PPR591 affects the profile of mitochondrial transcripts other than pcf in transgenic plants. If so, it would strengthen the hypothesis that Rf alleles arise as modifications, perhaps through duplication, of existing alleles that control mitochondrial gene expression. According to this theory, once CMS occurs in a plant species, there maybe strong selective pressure for the plant to overcome it by recruiting preexisting activities and redirecting them to down-regulate the expression of CMS-encoding genes. Conceivably, recombination among closely related PPR-containing genes could have led to the appearance of the Rf-PPR592 gene.

Example 2

Figure 2:
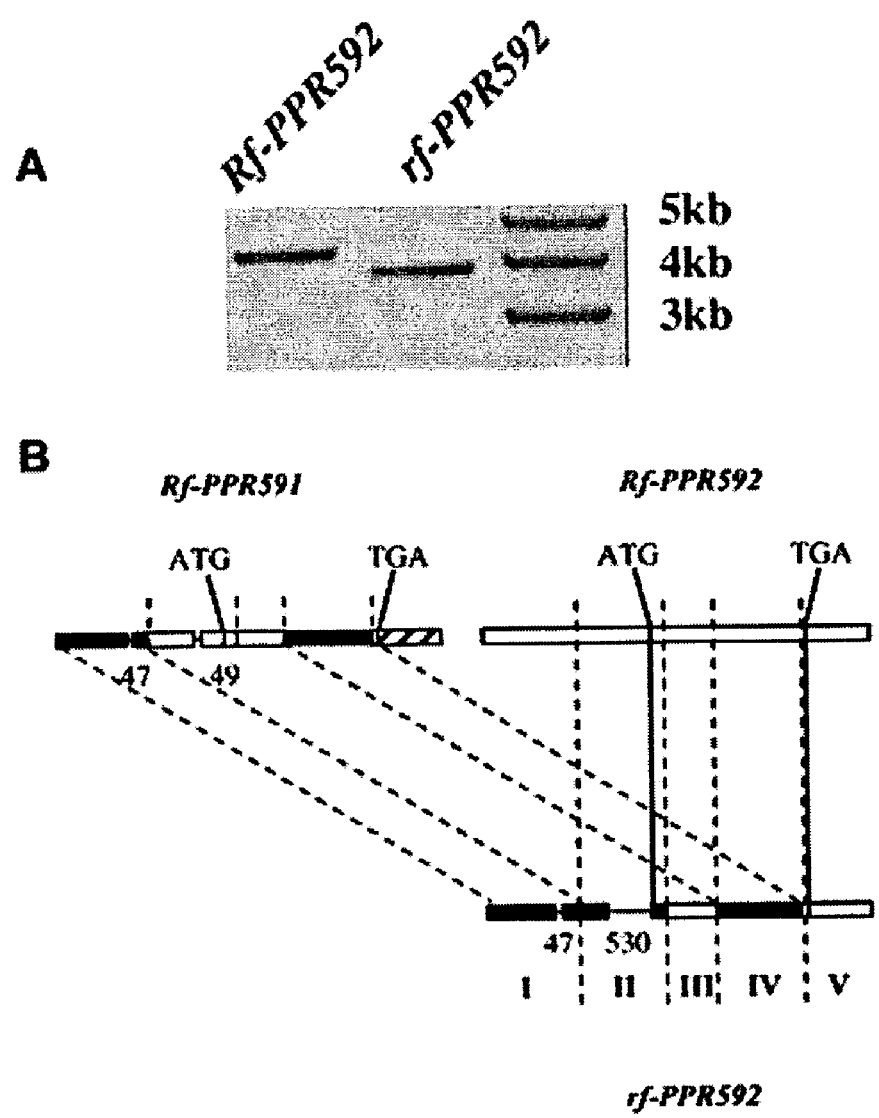
FIGS. 2A–B show the genetic structure of the rf-PPR592 gene.

A Deletion in the Promoter of rf-PPR592 Prevents Its Expression in CMS Floral Buds If one of the candidate ORFs, Rf-PPR591 or Rf-PPR592, is the Rf gene, some sequence polymorphism between the allele of these ORFs found in a restorer line (Rf/Rf) and the allele found in a CMS plant (rf/rf) might be expected. Presumably some difference in the sequences of the dominant Rf allele vs. the recessive nonrestoring allele rf must reflect their opposite restoring ability. The sequence of rf-PPR592 was obtained by amplifying genomic DNA of a *Petunia hybrida* rf/rf plant, where rf was inherited from a *P. hybrida* line called 2423, with the Pfu Turbo Hotstart DNA polymerase (Stratagene, La Jolla, Calif.) and PCR primers flanking Rf-PPR591 (5'-TGCACAGTGTTATATTTACAT-ACCC-3'; SEQ ID NO: 46) and Rf-PPR592 (5'-TTTAT-GATACATGGATTTCAACGAC-3'; SEQ ID NO: 47). A PCR product was obtained only with a primer specific to the 3' flanking region of Rf-PPR592, not with a primer specific to the 3' flanking region of Rf-PPR591. The rf-PPR592 PCR product showed a reduction in size of about 500 nt compared with the Rf-PPR592 PCR product amplified from the genomic DNA of an Rf/Rf line (FIG. 2A). Using the same primers, a PCR product similar in size to rf-PPR592 was amplified from another nonrestoring *P. hybrida* line as well as from a nonrestoring *Petunia parodii* line. The rf-PPR592 PCR product amplified from the *P. hybrida* 2423 sequence was cloned into the pCR-Blunt II-TOPO vector (Invitrogen, Carlsbad, Calif.) and sequenced, revealing a gene 97% identical to Rf-PPR591 and 94% identical to Rf-PPR592 in the coding region, with the predicted proteins 98% and 94% similar, respectively. Because of the primer design, the rf-PPR592 sequence lacks 35 nt available for Rf-PPR592. Similarity blocks between rf-PPR592, Rf-PPR592, and Rf-PPR591 were determined by comparing the aligned sequences with SEQUENCHER. Percent similarity was computed by using the MEGALIGN program. Comparison of the similarities of regions of the three different PPR genes revealed that the 5' promoter region of rf-PPR592 is most similar to Rf-PPR591, whereas the 3' flanking region of rf-PPR592 is most similar to Rf-PPR592. The genomic structure of rf-PPR592 was consistent with the past occurrence of recombination between two genes similar to Rf-PPR591 and Rf-PPR592 (FIG. 2B). Because PCR amplification could have resulted in an artificial recombination between Rf-PPR591 and Rf-PPR592 due to their high similarity, the Rf-PPR592 PCR product was resequenced as a control experiment. The sequences of three rf-PPR592 and Rf-PPR592 clones were determined. No evidence of recombination was found in any of the sequenced Rf-PPR592 clones, thus precluding PCR amplification as the source of the genetic mosaic found in the rf-PPR592 ORF.

rf-PPR592 carries a 530-nt deletion from –556 to –27 relative to the start codon of Rf-PPR592. This deletion is responsible for the observed difference in the sizes of the respective amplicons. Rf-PPR591 has a 49-nt gap within the same region, from –273 to –224 relative to the start codon of Rf-PPR592 (FIG. 2B).

RT-PCR experiments were performed to determine whether both Rf-PPR592 and rf-PPR592 are expressed in *Petunia* floral buds. The RT reaction was performed with Superscript II RNase H—reverse transcriptase (GIBCO), and the PCR was performed with the Pfu Turbo Hotstart DNA polymerase. The reverse primer R3 used for reverse transcription (RT)-PCR lies in the 3' untranslated region of the Rf-PPR592 gene at position +430 to +454. The forward primer used for the PCR lies in the coding sequence and is specific to the rf or Rf allele, F2S or F2, respectively, because of DNA polymorphisms between rf and Rf in this area. Primer pairs F2SR3 amplified a 1333-bp product and F2R3 amplified a 1507-bp product. R3, 5'-

```
R3,
5'-TGAAAATGACAATCGTAACAGAAAA-3';    (SEQ ID NO:48)

F2,
5'-AACATTCCTCCAGACATTATTACA-3';     (SEQ ID NO:49)

F2S,
5'-GACGCTGAGGAAATAATGAGATAC-3'.     (SEQ ID NO:50)
```

Figure 3:
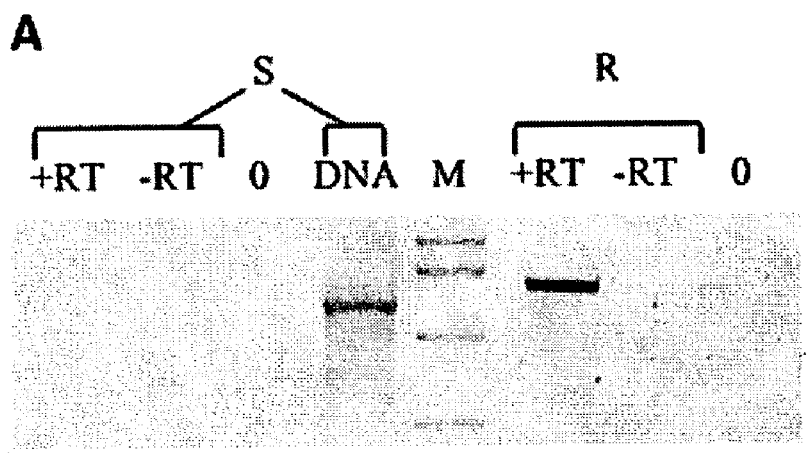
FIGS. 3A–B show the expression pattern of rf-PPR592 and Rf-PPR592.
Figure 3:
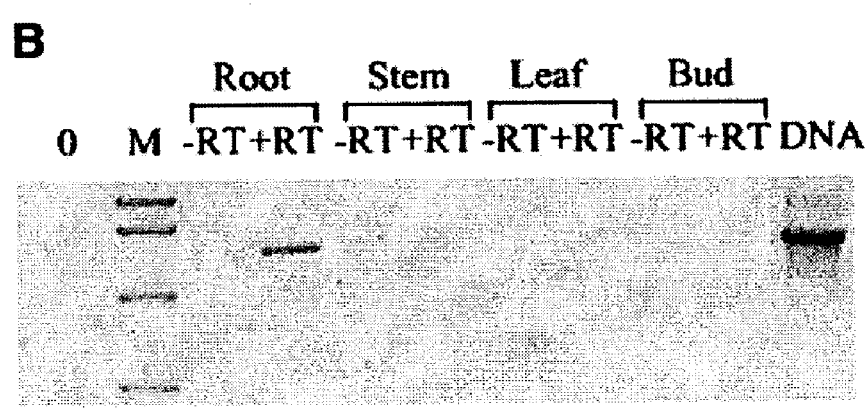

An Rf-PPR592 transcript was detected in floral buds in lines carrying the Rf allele, but no transcripts of rf-PPR592 were detected in a homozygous nonrestoring rf/rf line (FIG. 3A). The absence of the upstream 530-nt region in rf-PPR592 is likely to prevent the expression of PPR592 in the floral buds of nonrestoring lines.

Since rf-PPR592 encodes a protein that is very similar to the one encoded by Rf-PPR592, a survey of its expression was conducted in tissues other than the floral buds. From all of the tissues analyzed, an rf-PPR592 transcript was detected only in roots of a nonrestoring rf/rf line (FIG. 3B).

A deletion of 530 nt in the promoter area of the rf-PPR592 gene is the likely cause of its nonexpression in the floral buds of CMS plants. That the rf-PPR592 gene, which encodes a protein 98% similar to Rf-PPR591 and 94% similar to Rf-PPR592, has not yet accumulated missense mutations suggests either a recent deletion in the promoter or a functional expression in plant organs other than the floral buds. This latter possibility was supported by the finding of an rf-PPR592 transcript in the roots of homozygous nonrestoring rf/rf line.

Sequence inspection demonstrated that a recombination event between two genes similar to Rf-PPR591 and Rf- PPR592 can explain the formation of rf-PPR592. Perhaps once Rf-PPR592 was generated and happened to prevent the expression of pcf, its maintenance required the presence of the CMS-associated gene. The absence of the CMS-associated gene in new nucleocytoplasmic combinations might have resulted in recombination between Rf-PPR591 and Rf-PPR592 because of their high similarity. In Brassica and related genera, Rfn is found only in association with the nap cytoplasm, suggesting that the evolutionary appearance of the nap cytoplasm and the attending male sterility may have provided the selective pressure for the origin, and possibly the continued presence, of Rfn in B. napus (Li et al., "Restorer Genes for Different Forms of Brassica Cytoplasmic Male Sterility Map to a Single Nuclear Locus That Modifies Transcripts of Several Mitochondrial Genes," Proc. Natl. Acad. Sci. USA, 95:10032–10037 (1998), which is hereby incorporated by reference in its entirety). Sampling of more rf-PPR592 genes from different Petunia species should help in understanding the evolution of CMS and fertility restoration in this genus.

Example 3

Rf-PPR592 Is Able to Restore Fertility to CMS Plants

A sequence encoding the N-terminal 44 aa of Rf-PPR592 was inserted 5' to the green fluorescent protein (GFP) sequence in the pOL vector (Peeters et al., "Duplication and Quadruplication of Arabidopsis thaliana Cysteinyl- and Asparaginyl-tRNA Synthetase Genes of Organellar Origin," J. Mol. Evol., 50:413–423 (2000), which is hereby incorporated by reference in its entirety) to use in transient assay of protein localization. As a control, a vector carrying GFP fused with a known mitochondrial coxIV transit peptide (Akashi et al., "Potential Dual Targeting of an Arabidopsis Archaebacterial-Like Histidyl-Trna Synthetase to Mitochondria and Chloroplasts," FEBS Lett., 431:39–44 (1998), which is hereby incorporated by reference in its entirety) was also used in the transient assays. DNAs of GFP constructs were bombarded into onion epidermal cells as described in Scott et al., "Model System For Plant Cell Biology: GFP Imaging In Living Onion Epidermal Cells," BioTechniques, 26:1125, 1128–1132 (1999), which is hereby incorporated by reference in its entirety.

For the stable transformation experiments, genomic DNA from the Rf-PPR592 gene was amplified from the SB5 BIBAC clone with the Pfu Turbo Hotstart DNA polymerase and the primers incorporated by reference in its entirety). Petunia transformation and regeneration were performed as described in Horsch et al., "A Simple and General-Method for Transferring Genes Into Plants," Science, 227:1229–1231 30 (1985), which is hereby incorporated by reference in its entirety. Transformants were selected on 300 mg/liter kanamycin, 100 mg/liter ticarcillin/clavulanic acid (15:1, Duchefa Biochemie, Harlem, The Netherlands). Shoots were rooted on N13 medium (O'Connell et al., "Somatic Hybridization Between Lycopersicon-Esculentum and Lycopersicon-Pennellii," Theor. Appl. Genet., 70:1–12 (1985), which is hereby incorporated by reference in its entirety) before transfer to soil.

Figure 4:
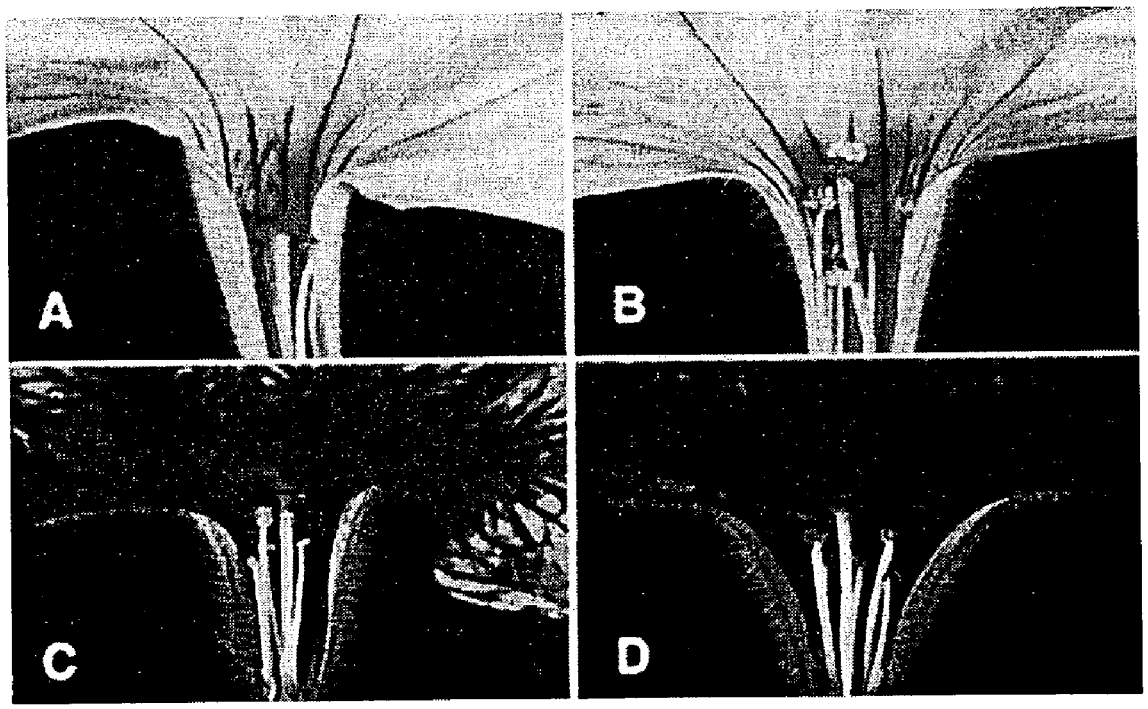
FIGS. 4A–D illustrate the restoration of fertility to CMS *Petunia* lines by transformation with a 4.6-kb genomic sequence carrying Rf-PPR592.

To determine whether Rf-PPR592 could restore fertility to rf/rf CMS lines, a 4.6-kb fragment carrying the entire coding region was introduced into the binary vector pGPTVKan. This fragment carries 2007 nt upstream of the start codon and 861 nt downstream of the stop codon. The pGPTVKan-4.6 kb Rf-PPR592 vector was transferred into A. tumefaciens strain LBA4404, which was used to transform a P. parodii rf/rf CMS line (FIG. 4A) and a P. hybrida rf/rf CMS line (FIG. 4C). More than two dozen independent transformants were obtained and grown to flowering. Fertile transformants were observed after transformation of both lines (FIGS. 4B and D). Among these were several fertile transformants carrying a single copy of the introduced Rf-PPR592 genomic DNA. Flowers of one of the P. parodii primary transformant plants were selfed, and a population of 40 T1 progeny was grown to flowering.

DNA extractions and Southern blotting were performed as described in Bentolila et al., "Locating the Petunia Rf Gene on a 650 kb DNA Fragment," Theor. Appl. Genet., 96:980–988 (1998), which is hereby incorporated by reference in its entirety. Floral bud protein was prepared for cell culture protein as described in Kohler et al., "The Green Fluorescent Protein as a Marker to Visualize Plant Mitochondria in vivo," Plant Journal, 11:613–621 (1997), which is hereby incorporated by reference in its entirety. After separation by SDS/PAGE (15%), immunoblots on Hybond-P poly(vinylidene difluoride) membranes (PVDF; Amersham Pharmacia, Picataway, N.J.) were prepared as previously described (Reed et al., "High-Level Expression of a Synthetic Red-Shifted GFP Coding Region Incorporated into Transgenic Chloroplasts," Plant J., 27:257–2653 (2001), which is hereby incorporated by reference in its entirety) and probed with a 1:5000 dilution of the anti-PCF antibody (Nivison et al., "Sequencing, Processing, and Localization of the Petunia CMS-Associated Mitochondrial

```
F11-XbaI     (5'-TCTAGAAAAAATGAAGGGGGAATCAAT-3';    SEQ ID NO:51)

and R11-EcoRI  (5'-GAATTCACTTTGCTCTCACGATAAACTAAGA-3'; SEQ ID NO:52)
```

(underlined are the restriction sites added to the 5' end of the primers for further use in the cloning of the PCR product). The PCR product was first cloned into the pCR-Blunt II-TOPO vector, and its sequence was checked to be free of possible mutations generated by the polymerase. The PCR product was then released from the pCR-Blunt II-TOPO vector by digestion with XbaI and EcoRI, gel purified, and cloned into XbaI/EcoRI-digested binary vector pGPTVKan (Becker et al., "New Plant Binary Vectors With Selectable Markers Located Proximal to the Left T-DNA Border," Plant Mol. Biol., 20:1195–1197 29 (1992), which is hereby Protein," Plant J., 5:613–623 (1994), which is hereby incorporated by reference in its entirety).

Figure 5:
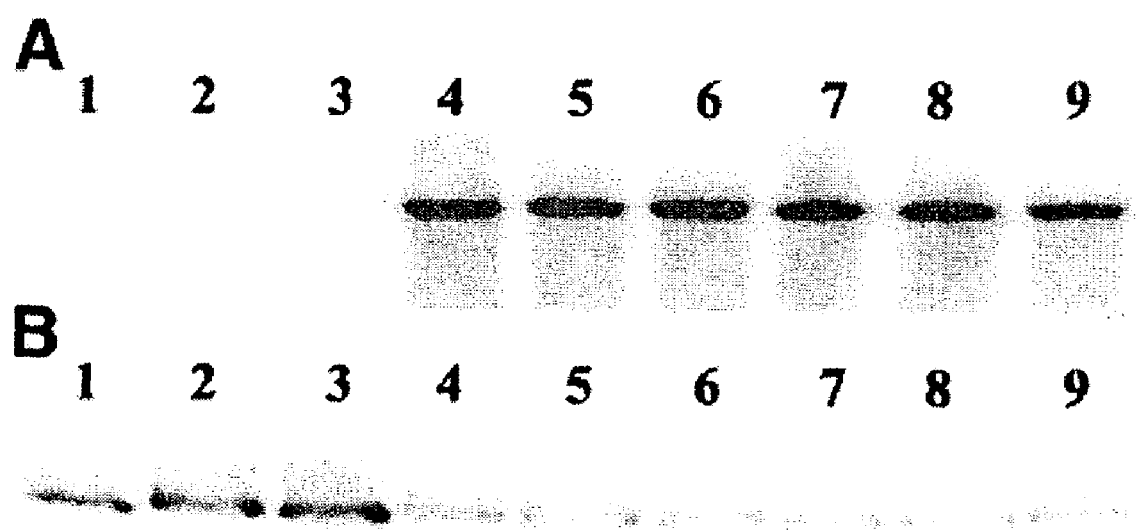
FIGS. 5A–B illustrate the cosegregation of the Rf-PPR592 transgene, restoration of fertility, and reduction of PCF.

DNA blot hybridization revealed that the fertile phenotype cosegregated with the Rf-PPR592 transgene (FIG. 5A). The T1 progeny were also surveyed for the presence of the CMS-associated 19.5-kDa PCF protein. The 19.5-kDa protein was found to be decreased about 10-fold in fertile progeny restored by Rf-PPR592 relative to sterile progeny and the parental CMS line (FIG. 5B). Thus, Rf-PPR592 was capable of restoring fertility by decreasing the amount of the PCF protein.

The cloning of a gene that can restore fertility to male-sterile *Petunia* lines will facilitate elucidation of the mechanism by which expression of the CMS-associated mitochondrial gene is suppressed. The reduced amount of the PCF protein could be due to a reduction in the abundance of one of the *Petunia* CMS-associated transcripts, which was reported previously (Pruitt et al., "Transcription of the *Petunia* Mitochondrial CMS-Associated pcf Locus in Male Sterile and Fertility-Restored Lines," *Mol. Gen. Genet.*, 227:348–355 (1991), which is hereby incorporated by reference in its entirety), or to a translation defect that destabilizes the transcript. In yeast, mutation in a transcript-specific translation factor destabilizes the particular transcript with which the factor normally interacts (Poutre et al., "PET111, a *Saccharomyces cerevisiae* Nuclear Gene Required for Translation of the Mitochondrial mRNA Encoding Cytochrome C Oxidase Subunit II," *Genetics*, 115:637–647 (1987), which is hereby incorporated by reference in its entirety).

A number of fertility restorer genes in other species are known to alter transcript profiles and mitochondrial gene product accumulation (Moneger et al., "Nuclear Restoration of Cytoplasmic Male Sterility in Sunflower is Associated with the Tissue-Specific Regulation of a Novel Mitochondrial Gene," *EMBO J.*, 13:8–17 (1994); Singh et al., "Nuclear Genes Associated With a Single *Brassica* CMS Restorer Locus Influence Transcripts of Three Different Mitochondrial Gene Regions," *Genetics*, 143:505–516 (1996); Dewey et al., "Novel Recombinations in the Maize Mitochondrial Genome Produce a Unique Transcriptional Unit in the Texas Male-Sterile Cytoplasm," *Cell*, 44:439–49 (1986); Wise et al., "Mitochondrial Transcript Processing and Restoration of Male Fertility in T-Cytoplasm Maize," *J Hered*, 90:380–385 (1999), which are hereby incorporated by reference in their entirety). In addition to the molecular phenotype of restoration, the *Petunia* Rf locus and Rf loci from other species may be similar in genomic organization (Li et al., "Restorer Genes for Different Forms of *Brassica* Cytoplasmic Male Sterility Map to a Single Nuclear Locus That Modifies Transcripts of Several Mitochondrial Genes," *Proc. Natl. Acad. Sci. USA*, 95:10032–10037 (1998); Tang et al., "Cosegregation of Single Genes Associated with Fertility Restoration and Transcript Processing of *Sorghum* Mitochondrial orf107 and urf209," *Genetics*, 150:383–391 (1998), which are hereby incorporated by reference in their entirety). The identification of *Petunia* Rf as a PPR family member suggests that searching for PPR motif genes near known restorer loci should be a useful strategy to identify candidate restorer genes in other species. Further studies of Rf-PPR592 and other PPR motif-containing genes in plants, fungi, and animals will be required to determine whether the motif has a direct role in RNA-protein and/or protein—protein interactions.

Example 4

Use of Rf-PPR592 or its Homologs/Derivatives to Create Novel Floral Structures

Figure 6:
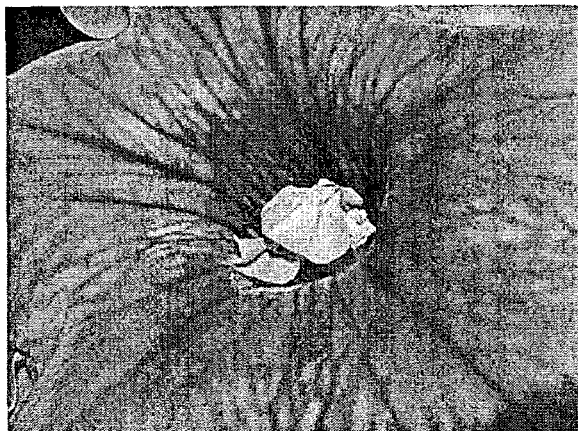
FIGS. 6A–B illustrate abnormal flowers on plants obtained by introducing Rf-PPR592 into a CMS background.
Figure 6:

In *Petunia*, recombination events near the Rf locus in standard sexual crosses resulted in plants with abnormal floral appearance. Moreover, a few of the initial transgenic plants transformed by Rf-PPR592 produced flowers with abnormal appearance. Furthermore, a number of transgenic plants transformed by Rf-PPR592 and Rf-PPR591 exhibit abnormalities in floral and vegetative structures. An example of abnormal flowers seen in some transgenic plants are shown in FIG. 6.

Example 5

Identification of a Rice Fertility Restorer Gene

The complete rice genome sequence, which has been deposited in EMBL/GenBank/DDBJ, was examined for genes similar to the *petunia* Rf gene, using BLASTP. The gene most similar to the *petunia* Rf locus was termed as Rice homolog of *Petunia* restorer 1 (Rhpr1). This gene is located very close to the rice Rf4 marker C1261. There were a total of 10 PPR genes in the vicinity of this marker on rice chromosome 10, which were termed as Rhpr1 to Rhpr10 (SEQ ID NOs: 20, 22, 24, 26, 28, 30, 32, 34, 36, and 38).

The most immediate usefulness of identification of the rice restorer gene is in marker-assisted selection. This facilitates introduction of the natural wild abortive-restorer Rf4 gene, which can restore fertility to the wild abortive cytoplasm by traditional crosses into elite breeding lines for use as a parent in a three-line breeding scheme. This use of the information does not involve genetically modified organisms and, therefore, can proceed without any of the attendant issues. Random screening has identified some molecular markers that are already being used to transfer Rf genes in certain nuclear backgrounds (Ichikawa et al., "A Rapid PCR-Aided Selection of a Rice Line Containing the Rf-I Gene Which is Involved in Restoration of the Cytoplasmic Male Sterility," *Molecular Breeding*, 3:195–202 (1997); Jing et al., "Mapping Fertility-Restoring Genes of Rice WA Cytoplasmic Male Sterility Using SSLP Markers," *Bot. Bull. Acad. Sin.*, 42:167–171 (2001), which are hereby incorporated by reference in their entirety). Knowing the actual Rf gene sequence makes laborious screening for markers suitable between different breeding lines unnecessary.

The next possibility is to more rapidly transfer the Rf4 gene into existing elite breeding lines by transformation rather than by sexual crosses. In such a strategy, the entire natural Rf4 gene would be used to transform a rice line for the three-line hybrid rice production method.

Because the three-line method for hybrid rice production requires time-consuming breeding and labor, presently there are attempts to exploit temperature-sensitive male sterility mutants for a two-line method of hybrid seed production. The three-line method for hybrid rice production involves construction of three lines. Two lines are backcrossed repeatedly so that they contain the same nuclear genome. One contains the CMS cytoplasm ("CMS parent") and is male sterile while the other ("Fertile Maintainer") contains the normal cytoplasm but no restorer of fertility (Rf) alleles. By crossing the maintainer as male and the CMS line as female, seeds of the CMS line with a known nuclear background can be produced in large quantity. The third line is homozygous for one or more fertility restoration loci. Hybrid seed is produced by crossing the third line with the CMS parent. The nuclear genomes of the third line and the CMS line are selected by breeders to optimize heterosis and desirable characteristics for the region in which the hybrid rice will be grown.

Rice plants have been found that contain a mutant allele that encodes male sterility at high temperatures but fertility at low temperatures (Dong et al., "Molecular Mapping of a Rice Gene Conditioning Thermosensitive Genic Male Sterility Using AFLP, RFLP and SSR Techniques," *Theor Appl Genet.*, 100:727–734 (2000), which is hereby incorporated by reference in its entirety). By growing the rice at high temperatures, it can be used as the sterile parent in a cross with an elite breeding line. The mutant rice can be propagated by selfing when grown at low temperatures. The use of this method in the field on large-scale has not been reported in the literature, so the feasibility of using a natural temperature-sensitive mutant is not known.

Figure 8:
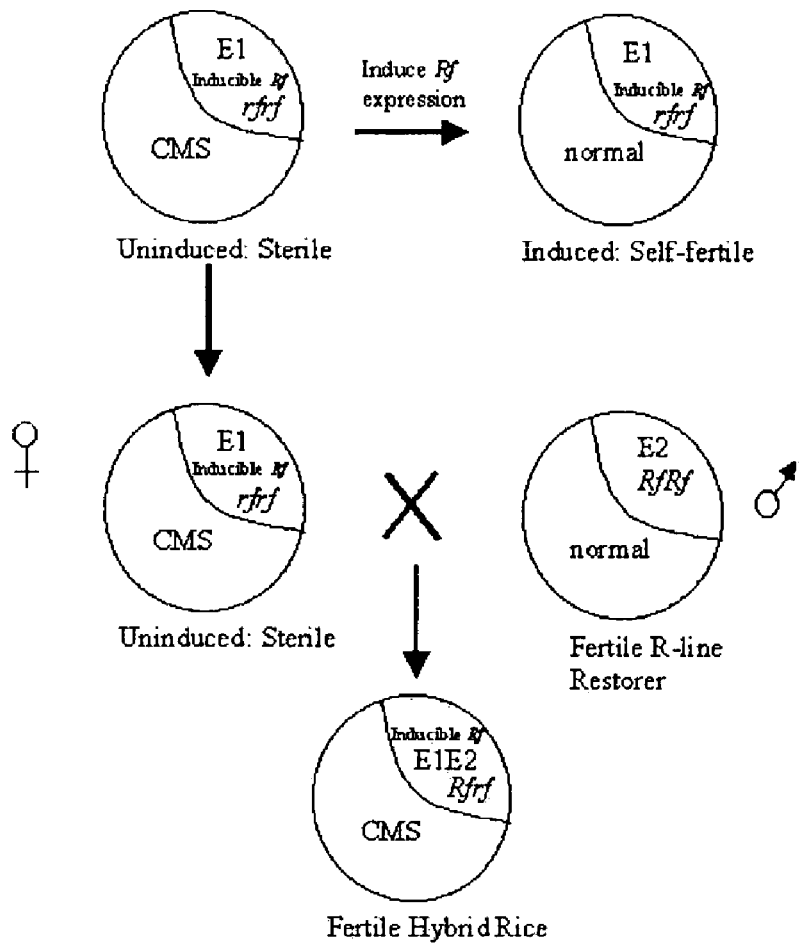
FIG. 8 shows a two-line method for hybrid rice production, using an engineered inducible restorer gene.

A cloned Rf4 gene could also be used in a two-line method. In this scheme, the Rf4 gene regulatory sequences would be engineered so that it could be turned on when desired. Then, both a CMS line and a maintainer line, which requires multiple crosses over a number of years to produce, are not needed. A single line, the CMS line containing the engineered Rf4 gene, would serve both as CMS parent and as its own maintainer line (FIG. 8). The CMS line would be propagated by selfing by turning on the Rf4 gene. Without induction of the engineered Rf4 gene, however, the line would be sterile and therefore could be used as a CMS parent.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. An isolated nucleic acid molecule which restores fertility to cytoplasmic male sterile plants and modifies expression of toxic mitochondria proteins by the plant, wherein the nucleic acid molecule encodes a protein having the amino acid sequence of SEQ ID NO: 2 or has the nucleotide sequence of nucleotides 1982 to 3760 of SEQ ID NO: 1.

2. The isolated nucleic acid molecule according to claim 1, wherein the nucleic acid molecule encodes a protein having the amino acid sequence of SEQ ID NO: 2.

3. The isolated nucleic acid molecule according to claim 1, wherein the nucleic acid molecule has the nucleotide sequence of nucleotides 1982 to 3760 of SEQ ID NO: 1.

4. An isolated expression system comprising the nucleic acid molecule of claim 1.

5. The isolated expression system according to claim 4, wherein the nucleic acid molecule is in proper sense orientation.

6. An isolated host cell comprising the nucleic acid molecule of claim 1, wherein the host cell is a *petunia* plant cell.

7. The isolated host cell according to claim 6, wherein the nucleic acid molecule is in an expression system.

8. The isolated host cell comprising the nucleic acid molecule of claim 1, wherein the host cell is a bacterial cell.

9. A transgenic *petunia* plant transformed with the nucleic acid molecule according to claim 1.

10. The transgenic plant according to claim 9, wherein the nucleic acid molecule encodes a protein having the amino acid sequence of SEQ ID NO: 2.

11. The transgenic plant according to claim 9, wherein the nucleic acid molecule has the nucleotide sequence of nucleotides 1982 to 3760 of SEQ ID NO: 1.

12. A transgenic *petunia* plant seed transformed with the nucleic acid molecule according to claim 1.

13. The transgenic plant seed according to claim 12, wherein the nucleic acid molecule encodes a protein having the amino acid sequence of SEQ ID NO: 2.

14. The transgenic plant seed according to claim 12, wherein the nucleic acid molecule has the nucleotide sequence of nucleotides 1982 to 3760 of SEQ ID NO: 1.

15. A method of restoring fertility to cytoplasmic male sterile *petunia* plants comprising:

transforming a cytoplasmic male sterile *petunia* plant with a nucleic acid molecule according to claim 1 under conditions effective to restore fertility to the cytoplasmic male sterile *petunia* plant.

16. The method according to claim 15, wherein the nucleic acid molecule encodes a protein having the amino acid sequence of SEQ ID NO: 2.

17. The method according to claim 15, wherein the nucleic acid molecule has the nucleotide sequence of nucleotides 1982 to 3760 of SEQ ID NO: 1.

18. The method according to claim 15, wherein the plant has 2 or more copies of the nucleic acid molecule.

19. A method of altering plant floral morphology in *petunia* plants comprising:

transforming a *petunia* plant with a nucleic acid molecule according to claim 1.

20. The method according to claim 19, wherein the nucleic acid molecule encodes a protein having the amino acid sequence of SEQ ID NO: 2.

21. The method according to claim 19, wherein the nucleic acid molecule has the nucleotide sequence of nucleotides 1982 to 3760 of SEQ ID NO: 1.

* * * * *

SEQUENCE LISTING

<160> NUMBER OF SEQ ID NOS: 52

<210> SEQ ID NO 1
<211> LENGTH: 4593
<212> TYPE: DNA
<213> ORGANISM: Petunia sp.

<400> SEQUENCE: 1

```
atatatatat acaaactgat tttttctgtc tatttgcaca gtgttatatt tacatacect     60 tgaaaaaggg tagctccgct aataatgtta tctttacaaa aaataacaat aattttttta    120
cataatatat acaaaactca ttgttatgta ttgtaaatat gataaaaata ttgttatttt    180
ttgtaatata gctattaggt agtcatgtgg tgtaatattt cctaaaaata tttacctgag    240
tcggccattt ggctaaaaat attttatttt atagtcgcat atactccaag cttgtatatc    300
ccatagcgac agtataccta tacgatatct tctattattt accttttag tattcgtata     360 ccccaatag tatacaagtt tgacaccgca atagtgtacc ccaatgttgt ggttgtgtgg     420
ctataaaatg tttaaacaaa atttgagtga tggtagtgta atttttagt gtaagctggg     480 tagttttaaa aacattcttt ttgaaaattg tagttcaagt catagtacaa aaaactgaaa     540
tatttatatg tttcttgatt ttggctggtc ttctaaaaat tttgaaatgc tggctagttt     600
tcatttagcg agggcaaat agactacatg gccaaatttt tacgttaaaa gaagtgttgt     660
ctgggaaagt attcgaaaag attgtacgga caagtgttgc ctagacaaca cgtcaaatta    720
tgtagaaaaa tgtaggaaga aattcaaaag caaatattgc ttaagcaaaa ggcagtcaaa    780
gacaatgctg ccttagggag tgagaaatgg gcatcactat aagattgtat ttccattcga    840
tatttattca ttataaactt aaggaaaagt gcaaggaaaa gccacttttt ggcttgcctt     900
taccgttgaa gctactttca aagaaaaaga gctagttttt agcttttttg gaactttaat    960
cattgtgggc cgaacttcag accttgtggg ccgaacttca tacattcaca agtaaaaaat   1020
tagctcacag gccactttta ccactagtat ttggtttgaa gtcatttttt tattggtttt    1080
acatgagaga ccacttttttg gaacttcaat ctttgtgcgc ttgaacttca tgcctaagtt    1140
attaagttca acttcaatcc gtaagggctg aattttttagg catagatgcg taaacttcaa    1200
ccttgtggac tgaagttgaa cttcgcccct tatggtggcc tgaagttgaa cttcaatcct    1260
tgtgggctga acttgtgtga agttcaaccc acaaggatta aagtttcaaa aaatgacctc    1320
tcaagcaaaa tctgcaaaaa aaagtggtct ctcatgcact tttacccatt cgcaaagtag    1380
gctgaagttc agcccacaat tattcaagtt ccaaaaaatt tcacaatata tacctcctta    1440
tctcggttat gatcttttgt atgatttagc aaaatggacg gggaaagtgc acgaaagacc   1500
```

```
acttttgcca ttggtctttg ggtacaggcc actaatacca aaatatttag tttgtggcta    1560
cttttgctta aagagataga acttcagtcc agaggccgga ttgaagttca gtccttaaag    1620
attgaacttc gatccagtgc catatggact gaagttcagt caagtcctta agatggaact    1680
tcagtccaga gccatatgga ctgaagttca atccttaaag atagaacttc agtccagggg    1740
ccgtatggac tgaagttcag tcaattatca gaacttaagt cagtatttat ttagtaaagg    1800
cccaaaagtg gttagtataa gaccaataaa aatagaggcc taaaactaaa taacagtgtt    1860
aaaagtggct gatggacgaa atttctacaa aatggactcg aggtagcaat tcaacttcaa    1920
cctatggtgt catagtcgta caattcttcc aatcacccct actaagtgaa gtgaagcgaa    1980
gatgatgaga attgcagtgc gttactgtct caatggtaat ccctttttct cattctttgc    2040
ttattcaatt gcaccccgac attattctac caatacatgt tccatttcag ttaaagggaa    2100
ttttggggtt tctaatgaat ttgagaatgt taagtgttta gatgatgctt tcagtttgtt    2160
ccgtcaaatg gttacaacta agcctcttcc ttctgctgtc tctttctcta aattgttgaa    2220
agctttggta catatgaagc attactcttc tgttgtttct atttttcgag aaatccacaa    2280
attacgtatt cctgttgatg ctttcgcctt gagcactgtg gttaacagtt gttgccttat    2340
gcatcgtacc gatctcggat tttctgtatt agccattcac ttcaagaaag gtattccata    2400
taatgaagtc acctttacta ccttaataag gggactttt gctgaaaata aggtcaaaga    2460
tgctgttcat ttgttcaaaa agttggtgag ggagaatata tgtgagcctg atgaagtcat    2520
gtatgggacg gtcatggatg ggctttgcaa gaagggccat actcaaaaag cttttgattt    2580
gctccggtta atggaacaag gaattactaa gcccgataca tgcatctaca acattgttat    2640
cgatgccttt tgcaaagatg ggatgctaga tggtgctacc agccttttga acgagatgaa    2700
acaaaaaaac attcctccag acattattac atataacctca ttgatcgatg gtttgggtaa    2760
gttaagtcag tgggaaaagg ttaggacttt gttccttgag atgatacatc ttaatattta    2820
tccagatgtg tgcaccttca actccgtcat tgatggacta tgcaagagg ggaaagttga    2880 agatgccgag gaaataatga catacatgat cgaaaaaggt gtagaaccta atgagataac    2940
ctacaatgtg gtaatggatg gatattgctt gcgtggtcaa atgggtagag cgaggagaat    3000
ttttgattcc atgatagata agggcattga gcctgatatc attagctata ccgcactaat    3060
aaatggatac gtcgagaaaa agaaaatgga taaggccatg caattgtttc gtgaaatttc    3120
tcaaaatgga ttgaaaccta gtattgttac ctgcagtgtt ctcttgcgtg gtctttttga    3180
agttggaaga actgaatgtg caaaaatatt ctttgatgag atgcaagctg cggggcacat    3240 acctaatta tacactcatt gcactttgct tggtggttat tttaagaatg gacttgttga    3300
agaggctatg tcacacttcc ataagttgga aaggaggaga gaagatacaa atattcaaat    3360
ttacacggct gtcattaatg gattgtgcaa aaatggtaag ctcgacaaag ctcatgctac    3420
gtttgagaag cttcccttga taggcttaca tcctgatgtg ataacataca ctgcaatgat    3480
tagtggatat tgtcaagaag ggttgttaga tgaagctaaa gatatgctaa ggaaaatgga    3540
ggacaatggt tgtttgccag acaaccgaac atacaatgtt attgtgcggg attttttcag    3600
aagcagtaaa gttagtgaaa tgaaggcttt tctgaaggaa atagctggga agagcttctc    3660
atttgaggca gctactgtag agttattgat ggatattata gcagaggatc cttcttttgct    3720 taacatgatt ccagaatttc accgggataa taagaagtga ataacttttg cacctgtttt    3780
ttttgacgat atcaccatta ttctgctatt tcctttcatc ttagcaaaag aaattgcatc    3840
cagtggaatt gcggaagctg aaaaaatggc aagaagaaca ttgcttaagc tttcctggca    3900
```

```
agcttatatc ggagggacat cattttggtt gttttggctc tcttctttat cttggaaatc   3960
aaatgttctg cgctcttaat atcagaaaca atgtgaactc ccatatatgt acgagttata   4020
agtttcggaa tatgatttca atggtttcag tattctattt ttgatatgga attaattttt   4080
gagcgaccca gtgttgacca ttgcctacct tcggttatta tatgattgaa attccctcca   4140
atctccaata ctcacttcat tttgtcttgt tgaattttc aattttctt tttctgttac     4200 gattgtcatt tcaccgcct tgagtatcca tcaggttcca gttgaaaaag aatcattttt    4260
tgccatgacc atcatgcttt ctgagtgcaa gatcaagaga ggtactttc tctctaagaa   4320 cctcttggtt ttttaagtgt tctgggttct ttcagtactt ttaagctatt ttctaatcct   4380
ttgaagagat tcatacatat ctgtgcatgt gtttgtttct tttttcggg tgatactttg    4440 ttttatagct aaggattgaa aaggtaattt tcattttcat tagcaataga tatgaaacag   4500
ctttgtaagg actctggagt ctcctaaaaa ttttggctat gcaaatagcc tattgcatca   4560
atttgtcgtt gaaatccatg tatcataaaa aaa                                4593
```

<210> SEQ ID NO 2
<211> LENGTH: 592
<212> TYPE: PRT
<213> ORGANISM: Petunia sp.

<400> SEQUENCE: 2

```
Met Met Arg Ile Ala Val Arg Tyr Cys Leu Asn Gly Asn Pro Phe Phe
 1               5                  10                  15

Ser Phe Phe Ala Tyr Ser Ile Ala Pro Arg His Tyr Ser Thr Asn Thr
            20                  25                  30

Cys Ser Ile Ser Val Lys Gly Asn Phe Gly Val Ser Asn Glu Phe Glu
        35                  40                  45

Asn Val Lys Cys Leu Asp Asp Ala Phe Ser Leu Phe Arg Gln Met Val
    50                  55                  60

Thr Thr Lys Pro Leu Pro Ser Ala Val Ser Phe Ser Lys Leu Leu Lys
65                  70                  75                  80

Ala Leu Val His Met Lys His Tyr Ser Ser Val Val Ser Ile Phe Arg
                85                  90                  95

Glu Ile His Lys Leu Arg Ile Pro Val Asp Ala Phe Ala Leu Ser Thr
            100                 105                 110

Val Val Asn Ser Cys Cys Leu Met His Arg Thr Asp Leu Gly Phe Ser
        115                 120                 125

Val Leu Ala Ile His Phe Lys Lys Gly Ile Pro Tyr Asn Glu Val Thr
    130                 135                 140

Phe Thr Thr Leu Ile Arg Gly Leu Phe Ala Glu Asn Lys Val Lys Asp
145                 150                 155                 160

Ala Val His Leu Phe Lys Lys Leu Val Arg Glu Asn Ile Cys Glu Pro
                165                 170                 175

Asp Glu Val Met Tyr Gly Thr Val Met Asp Gly Leu Cys Lys Lys Gly
            180                 185                 190

His Thr Gln Lys Ala Phe Asp Leu Leu Arg Leu Met Glu Gln Gly Ile
        195                 200                 205

Thr Lys Pro Asp Thr Cys Ile Tyr Asn Ile Val Ile Asp Ala Phe Cys
    210                 215                 220

Lys Asp Gly Met Leu Asp Gly Ala Thr Ser Leu Leu Asn Glu Met Lys
225                 230                 235                 240

Gln Lys Asn Ile Pro Pro Asp Ile Ile Thr Tyr Thr Ser Leu Ile Asp
```

```
                        245                 250                 255
Gly Leu Gly Lys Leu Ser Gln Trp Glu Lys Val Arg Thr Leu Phe Leu
                260                 265                 270
Glu Met Ile His Leu Asn Ile Tyr Pro Asp Val Cys Thr Phe Asn Ser
                275                 280                 285
Val Ile Asp Gly Leu Cys Lys Glu Gly Lys Val Glu Asp Ala Glu Glu
            290                 295                 300
Ile Met Thr Tyr Met Ile Glu Lys Gly Val Glu Pro Asn Glu Ile Thr
305                 310                 315                 320
Tyr Asn Val Val Met Asp Gly Tyr Cys Leu Arg Gly Gln Met Gly Arg
                325                 330                 335
Ala Arg Arg Ile Phe Asp Ser Met Ile Asp Lys Gly Ile Glu Pro Asp
                340                 345                 350
Ile Ile Ser Tyr Thr Ala Leu Ile Asn Gly Tyr Val Glu Lys Lys Lys
                355                 360                 365
Met Asp Lys Ala Met Gln Leu Phe Arg Glu Ile Ser Gln Asn Gly Leu
            370                 375                 380
Lys Pro Ser Ile Val Thr Cys Ser Val Leu Leu Arg Gly Leu Phe Glu
385                 390                 395                 400
Val Gly Arg Thr Glu Cys Ala Lys Ile Phe Phe Asp Glu Met Gln Ala
                405                 410                 415
Ala Gly His Ile Pro Asn Leu Tyr Thr His Cys Thr Leu Leu Gly Gly
                420                 425                 430
Tyr Phe Lys Asn Gly Leu Val Glu Glu Ala Met Ser His Phe His Lys
            435                 440                 445
Leu Glu Arg Arg Arg Glu Asp Thr Asn Ile Gln Ile Tyr Thr Ala Val
        450                 455                 460
Ile Asn Gly Leu Cys Lys Asn Gly Lys Leu Asp Lys Ala His Ala Thr
465                 470                 475                 480
Phe Glu Lys Leu Pro Leu Ile Gly Leu His Pro Asp Val Ile Thr Tyr
                485                 490                 495
Thr Ala Met Ile Ser Gly Tyr Cys Gln Glu Gly Leu Leu Asp Glu Ala
            500                 505                 510
Lys Asp Met Leu Arg Lys Met Glu Asp Asn Gly Cys Leu Pro Asp Asn
        515                 520                 525
Arg Thr Tyr Asn Val Ile Val Arg Gly Phe Phe Arg Ser Ser Lys Val
            530                 535                 540
Ser Glu Met Lys Ala Phe Leu Lys Glu Ile Ala Gly Lys Ser Phe Ser
545                 550                 555                 560
Phe Glu Ala Ala Thr Val Glu Leu Leu Met Asp Ile Ile Ala Glu Asp
                565                 570                 575
Pro Ser Leu Leu Asn Met Ile Pro Glu Phe His Arg Asp Asn Lys Lys
            580                 585                 590

<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence:  Consensus
      motif derived from 1,303 PPRs reported by Small &
      Peeters

<400> SEQUENCE: 3

Glu Glu Ala Leu Tyr Met Gly Pro Asn Thr Tyr Asn Ala Leu Ile Asn
 1               5                  10                  15
```

```
Ala Tyr Ala Lys Gly
            20

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence:  Consensus
      motif derived from the 14 PPRs found in Rf-PPR592

<400> SEQUENCE: 4

Asp Ala Phe Met Gly Pro Asp Thr Tyr Leu Ile Gly Leu Cys Lys Gly
 1               5                  10                  15

<210> SEQ ID NO 5
<211> LENGTH: 35
<212> TYPE: PRT
<213> ORGANISM: Petunia sp.

<400> SEQUENCE: 5

Asp Asp Ala Phe Ser Leu Phe Arg Gln Met Val Thr Thr Lys Pro Leu
 1               5                  10                  15

Pro Ser Ala Val Ser Phe Ser Lys Leu Leu Lys Ala Leu Val His Met
                20                  25                  30

Lys His Tyr
         35

<210> SEQ ID NO 6
<211> LENGTH: 35
<212> TYPE: PRT
<213> ORGANISM: Petunia sp.

<400> SEQUENCE: 6

Ser Ser Val Val Ser Ile Phe Arg Glu Ile His Lys Leu Arg Ile Pro
 1               5                  10                  15

Val Asp Ala Phe Ala Leu Ser Thr Val Val Asn Ser Cys Cys Leu Met
                20                  25                  30

His Arg Thr
         35

<210> SEQ ID NO 7
<211> LENGTH: 35
<212> TYPE: PRT
<213> ORGANISM: Petunia sp.

<400> SEQUENCE: 7

Asp Leu Gly Phe Ser Val Leu Ala Ile His Phe Lys Lys Gly Ile Pro
 1               5                  10                  15

Tyr Asn Glu Val Thr Phe Thr Thr Leu Ile Arg Gly Leu Phe Ala Glu
                20                  25                  30

Asn Lys Val
         35

<210> SEQ ID NO 8
<211> LENGTH: 35
<212> TYPE: PRT
<213> ORGANISM: Petunia sp.

<400> SEQUENCE: 8

Asp Ala Val His Leu Phe Lys Lys Leu Val Arg Glu Asn Ile Cys Glu
 1               5                  10                  15
```

-continued

```
Pro Asp Glu Val Met Tyr Gly Thr Val Met Asp Gly Leu Cys Lys Lys
            20                  25                  30

Gly His Thr
        35

<210> SEQ ID NO 9
<211> LENGTH: 35
<212> TYPE: PRT
<213> ORGANISM: Petunia sp.

<400> SEQUENCE: 9

Gln Lys Ala Phe Asp Leu Leu Arg Leu Met Glu Gln Gly Ile Thr Lys
 1               5                  10                  15

Pro Asp Thr Cys Ile Tyr Asn Ile Val Ile Asp Ala Phe Cys Lys Asp
            20                  25                  30

Gly Met Leu
        35

<210> SEQ ID NO 10
<211> LENGTH: 35
<212> TYPE: PRT
<213> ORGANISM: Petunia sp.

<400> SEQUENCE: 10

Asp Gly Ala Thr Ser Leu Leu Asn Glu Met Lys Gln Lys Asn Ile Pro
 1               5                  10                  15

Pro Asp Ile Ile Thr Tyr Thr Ser Leu Ile Asp Gly Leu Gly Lys Leu
            20                  25                  30

Ser Gln Trp
        35

<210> SEQ ID NO 11
<211> LENGTH: 35
<212> TYPE: PRT
<213> ORGANISM: Petunia sp.

<400> SEQUENCE: 11

Glu Lys Val Arg Thr Leu Phe Leu Glu Met Ile His Leu Asn Ile Tyr
 1               5                  10                  15

Pro Asp Val Cys Thr Phe Asn Ser Val Ile Asp Gly Leu Cys Lys Glu
            20                  25                  30

Gly Lys Val
        35

<210> SEQ ID NO 12
<211> LENGTH: 35
<212> TYPE: PRT
<213> ORGANISM: Petunia sp.

<400> SEQUENCE: 12

Glu Asp Ala Glu Glu Ile Met Thr Tyr Met Ile Glu Lys Gly Val Glu
 1               5                  10                  15

Pro Asn Glu Ile Thr Tyr Asn Val Val Met Asp Gly Tyr Cys Leu Arg
            20                  25                  30

Gly Gln Met
        35

<210> SEQ ID NO 13
<211> LENGTH: 35
<212> TYPE: PRT
```

<213> ORGANISM: Petunia sp.

<400> SEQUENCE: 13

Gly Arg Ala Arg Arg Ile Phe Asp Ser Met Ile Asp Lys Gly Ile Glu
1               5                   10                  15

Pro Asp Ile Ile Ser Tyr Thr Ala Leu Ile Asn Gly Tyr Val Glu Lys
            20                  25                  30

Lys Lys Met
        35

<210> SEQ ID NO 14
<211> LENGTH: 35
<212> TYPE: PRT
<213> ORGANISM: Petunia sp.

<400> SEQUENCE: 14

Asp Lys Ala Met Gln Leu Phe Arg Glu Ile Ser Gln Asn Gly Leu Lys
1               5                   10                  15

Pro Ser Ile Val Thr Cys Ser Val Leu Leu Arg Gly Leu Phe Glu Val
            20                  25                  30

Gly Arg Thr
        35

<210> SEQ ID NO 15
<211> LENGTH: 35
<212> TYPE: PRT
<213> ORGANISM: Petunia sp.

<400> SEQUENCE: 15

Glu Cys Ala Lys Ile Phe Phe Asp Glu Met Gln Ala Ala Gly His Ile
1               5                   10                  15

Pro Asn Leu Tyr Thr His Cys Thr Leu Leu Gly Gly Tyr Phe Lys Asn
            20                  25                  30

Gly Leu Val
        35

<210> SEQ ID NO 16
<211> LENGTH: 35
<212> TYPE: PRT
<213> ORGANISM: Petunia sp.

<400> SEQUENCE: 16

Glu Glu Ala Met Ser His Phe His Lys Leu Glu Arg Arg Arg Glu Asp
1               5                   10                  15

Thr Asn Ile Gln Ile Tyr Thr Ala Val Ile Asn Gly Leu Cys Lys Asn
            20                  25                  30

Gly Lys Leu
        35

<210> SEQ ID NO 17
<211> LENGTH: 35
<212> TYPE: PRT
<213> ORGANISM: Petunia sp.

<400> SEQUENCE: 17

Asp Lys Ala His Ala Thr Phe Glu Lys Leu Pro Leu Ile Gly Leu His
1               5                   10                  15

Pro Asp Val Ile Thr Tyr Thr Ala Met Ile Ser Gly Tyr Cys Gln Glu
            20                  25                  30

Gly Leu Leu

<210> SEQ ID NO 18
<211> LENGTH: 35
<212> TYPE: PRT
<213> ORGANISM: Petunia sp.

<400> SEQUENCE: 18

Asp Glu Ala Lys Asp Met Leu Arg Lys Met Glu Asp Asn Gly Cys Leu
1               5                   10                  15
Pro Asp Asn Arg Thr Tyr Asn Val Ile Val Arg Gly Phe Phe Arg Ser
            20                  25                  30
Ser Lys Val
        35

<210> SEQ ID NO 19
<211> LENGTH: 8440
<212> TYPE: DNA
<213> ORGANISM: Petunia sp.

<400> SEQUENCE: 19

| | |
|---|---:|
| ggatccaaaa tttcactaaa ggttaaacgc gaggatactg aagttggaga gcaatgtggt | 60 |
| atcttggtgc atggacggag tcatgggggt atagttgctg gctatttagc taactggaga | 120 |
| actgttgtga ggaattattt aaagaatgct actttctcgt ccacataaac atgtccaaat | 180 |
| attttctact tgatagagag ttcaaggaaa tagtgtggat ttcttcccaa acacaaacga | 240 |
| tttgagaaaa ctgaagtgaa ggctgaagag aaaactaaag agaactggaa gctaagaaac | 300 |
| acagaagcac aaacctataa acatagacac tggcatgttg cagaaaattt taactttcga | 360 |
| ttctccagta gaaagacaca aatacatcag taaattttct ttaggctcaa gcaaggatac | 420 |
| atcttggtag aatttgcatt ataccaacat aataagctca aaaaaataac taagctgcaa | 480 |
| ctagctactt ggtccgagaa gcttttgcta tcaggaagtt ccacagttcc aaaaccaagg | 540 |
| tagactatca agctagttcc caccagtcat tttcttagac tttgctctca cgataaacta | 600 |
| agatcatttt tttatgatac atggatttca acgacaaatt gatgcaatag gctatttgca | 660 |
| tagccaaaat ttttaggaga ctccagagtc cttacaaagc tgtttcatat ctattgctaa | 720 |
| tgaaaatgaa aattaccttt tcaatcctta gctataaaac aaagtatcac ccgaaaaaaa | 780 |
| gaaacaaaca catgcacaga tatgtatgaa tctcttcaaa ggattagaaa atagcttaaa | 840 |
| agtactgaaa gaacccagaa cacttaaaaa accaagaggt tcttagagag aaaagtacct | 900 |
| ctcttgatct tgcactcaga aagcatgatg gtcatggcaa aaaatgattc ttttttcaact | 960 |
| ggaacctgat ggatactcaa ggcggtgaaa atgacaatcg taacagaaaa agaaaaattg | 1020 |
| aaaaattcaa caagacaaaa tgaagtgagt attggagatt ggagggaatt tcaatcatat | 1080 |
| aataaccgaa ggtaggcaat ggtcaacact gggtcgctca aaaattaatt ccatatcaaa | 1140 |
| aatagaatac tgaaaccatt gaaatcatat tccgaaactt ataactcgta catatatggg | 1200 |
| agttcacatt gtttctgata ttaagagcgc agaacatttg atttccaaga taagaagag | 1260 |
| agccaaaaca accaaaatga tgtccctccg atataagctt gccaggaaag cttaagcaat | 1320 |
| gttcttcttg ccatttttc agcttccgca attccactgg atgcaatttc ttttgctaag | 1380 |
| atgaaaggaa atagcagaat aatggtgata tcgtcaaaaa aacaggtgc aaaagttatt | 1440 |
| cacttcttat tatcccggtg aaattctgga atcatgttaa gcaaagaagg atcctctgct | 1500 |
| ataatatcca tcaataactc tacagtagct gcctcaaatg agaagctctt cccagctatt | 1560 |

```
tccttcagaa aagccttcat ttcactaact ttactgcttc tgaaaaatcc ccgcacaata    1620
acattgtatg ttcggttgtc tggcaaacaa ccattgtcct ccattttcct tagcatatct    1680
ttagcttcat ctaacaaccc ttcttgacaa tatccactaa tcattgcagt gtatgttatc    1740
acatcaggat gtaagcctat caagggaagc ttctcaaacg tagcatgagc tttgtcgagc    1800
ttaccatttt tgcacaatcc attaatgaca gccgtgtaaa tttgaatatt tgtatcttct    1860
ctcctccttt ccaacttatg gaagtgtgac atagcctctt caacaagtcc attcttaaaa    1920
taaccaccaa gcaaagtgca atgagtgtat aaattaggta tgtgccccgc agcttgcatc    1980
tcatcaaaga atattttgc acattcagtt cttccaactt caaaaagacc acgcaagaga    2040
acactgcagg taacaatact aggtttcaat ccattttgag aaatttcacg aaacaattgc    2100
atggccttat ccattttctt tttctcgacg tatccattta ttagtgcggt atagctaatg    2160
atatcaggct caatgcccct atctatcatg gaatcaaaaa ttctcctcgc tctacccatt    2220
tgaccacgca agcaatatcc atccattacc acattgtagg ttatctcatt aggttctaca    2280
cctttttcga tcatgtatgt cattatttcc tcggcatctt caactttccc ctctttgcat    2340
agtccatcaa tgacggagtt gaaggtgcac acatctggat aaatattaag atgtatcatc    2400
tcaaggaaca aagtcctaac cttttcccac tgacttaact tacccaaacc atcgatcaat    2460
gaggtatatg taataatgtc tggaggaatg ttttttttgtt tcatctcgtt caaaaggctg    2520
gtagcaccat ctagcatccc atctttgcaa aaggcatcga taacaatgtt gtagatgcat    2580
gtatcgggct tagtaattcc ttgttccatt aaccggagca atcaaaagc ttttgagta    2640 tggcccttct tgcaaagccc atccatgacc gtcccataca tgacttcatc aggctcacat    2700
atattctccc tcaccaactt tttgaacaaa tgaacagcat cttgacctt attttcagca    2760 aaaagtcccc ttattaaggt agtaaaggtg acttcattat atggaatacc tttcttgaag    2820
tgaatggcta atacagaaaa tccgagatcg gtacgatgca taaggcaaca actgttaacc    2880
acagtgctca aggcgaaagc atcaacagga atacgtaatt tgtggatttc tcgaaaaata    2940
gaaacaacag aagagtaatg cttcatatgt accaaagctt tcaacaattt agagaaagag    3000
acagcagaag gaagaggctt agttgtaacc atttgacgga acaaactgaa agcatcatct    3060
aaacacttaa cattctcaaa ttcattagaa accccaaaat tccctttaac tgaaatggaa    3120
catgtattgg tagaataatg tcggggtgca attgaataag caaagaatga gaaaaggga    3180 ttaccattga gacagtaacg cactgcaatt ctcatcatct tcgcttcact tcacttagta    3240
ggggtgattg gaagaattgt acgactatga caccataggt tgaagttgaa ttgctacctc    3300
gagtccattt tgtagaaatt tcgtccatca gccacttta acactgttat ttagtttag    3360 gcctctattt ttattggtct tatactaacc acttttgggc ctttactaaa taaatactga    3420
cttaagttct gataattgac tgaacttcag tccatacggc ccctggactg aagttctatc    3480
tttaaggatt gaacttcagt ccatatggct ctggactgaa gttccatctt aaggacttga    3540
ctgaacttca gtccatatgg cactggatcg aagttcaatc tttaaggact gaacttcaat    3600
ccggcctctg gactgaagtt ctatctcttt aagcaaaagt agccacaaac taaatatttt    3660
ggtattagtg gcctgtaccc aaagaccaat ggcaaaagtg gtctttcgtg cactttcccc    3720
gtccattttg ctaaatcata caaaagatca taaccgagat aaggaggtat atattgtgaa    3780
attttttgga acttgaataa ttgtgggctg aacttcagcc tactttgcga atgggtaaaa    3840
gtgcatgaga gaccactttt ttttgcagat tttgcttgag aggtcatttt ttgaaacttt    3900
aatccttgtg ggttgaactt cacacaagtt cagcccacaa ggattgaagt tcaacttcag    3960
```

```
gccaccataa ggggcgaagt tcaacttcag tccacaaggt tgaagtttac gcatctatgc   4020
ctaaaaattc agcccttacg gattgaagtt gaacttaata acttaggcat gaagttcaag   4080
cgcacaaaga ttgaagttcc aaaaagtggt ctctcatgta aaaccaataa aaaaatgact   4140
tcaaaccaaa tactagtggt aaaagtggcc tgtgagctaa tttttttactt gtgaatgtat   4200 gaagttcggc ccacaaggtc tgaagttcgg cccacaatga ttaaagttcc aaaaaagcta   4260
aaaactagct cttttctttt gaaagtagct tcaacggtaa aggcaagcca aaaagtggct   4320
tttccttgca cttttcctta agtttataat gaataaatat cgaatggaaa tacaatctta   4380
tagtgatgcc catttctcac tccctaaggc agcattgtct ttgactgcct tttgcttaag   4440
caatatttgc ttttgaattt cttcctacat ttttctacat aatttgacgt gttgtctagg   4500
caacacttgt ccgtacaatc ttttcgaata ctttcccaga caacacttct tttaacgtaa   4560
aaatttggcc atgtagtcta tttgcccctc gctaaatgaa aactagccag catttcaaaa   4620 ttttagaag accagccaaa atcaagaaac atataaatat ttcagttttt tgtactatga   4680
cttgaactac aattttcaaa agaatgtttt ttaaaactac ccagcttaca ctaaaaaatt   4740
acactaccat cactcaaatt ttgtttaaac atttttatagc cacacaacca caacattggg   4800
gtacactatt gcggtgtcaa acttgtatac tattgggggt atacgaatac taaaaaggta   4860
aataatagaa gatatcgtat aggtatactg tcgctatggg atatacaagc ttggagtata   4920
tgcgactata aaataaaata ttttttagcca aatggccgac tcaggtaaat attttttagga   4980 aatattacac cacatgacta cctaatagct atattcaaaa aaataacaat attttttatca   5040 tatttacaat acataacaat gagttttgta tatattatgt aaaaaaatta ttgttatttt   5100
ttgtaaagat aacattatta gcggagctac ccttttttcaa gggtatgtaa atataacact   5160
gtgcaaatag acagaaaaaa tcagtttgta tatatatatc agatattgat tccccccttca   5220 ttttttcgta tgtttacttt tttatatttta tatatcccctt agtaaaaata ctggctccgc   5280
cactgccagt aaggtagtat tagtttgcgt cgctcaataa agtaacatct atcgtttatt   5340
tttcatcaac attaaaaagg aagattcact atccacatag gcatcatcat tatcaaagaa   5400
tatcagttca tacattgtat atatataact ttctcaaata aactaacttt aaaatgaagt   5460
acattaaaaa ggaagattca ctatcctttt aatatttcgt atatttactt atttatattt   5520
tgatactcct tagtaaaaat actggctccg ccactaccag tgatgtaata ttaattcgcg   5580
tccctcacta aagtaacacc tataatttaa ttttcatgaa gtcagagtta gcattggaaa   5640
gggatataag cacatgcatt gtgtatatat atataacttg ctcaaataaa ctaacttaaa   5700
aatgaaattt tacttttcct agtacaatga actatgcatc aatgcgtaat tagttgaggt   5760
cggctatatg aatatgttat taatttgaaa gcaaaacata ataactgata gaagaattttt   5820 gcacctaaaa attgaacttg agctgcttca gttactatct cattttttcac tatatatgtg   5880 tgtatcagct aattctatga tttaattaaa caaattgtaa gtattaacaa ataacgaat   5940 aaatatggaa aataagtact tgatgaacgt agggccggag ttggccgagg tgaccggaga   6000
caatggaaag cagagttact attttttgact aaatagccac aaaagaatca ttgttttttac   6060 aatgtagcaa gttggcacga ttatgattct tgacacaata gccacattat agaaagataa   6120
tgtggcacta atgaggtaat tttcattatg gaatgataac aaacaaataa gtacacgatt   6180
aaaacaaact gaagggtttt tgcgcgataa tttaatcatt gttttacgaa aatactcatc   6240
aaaatcaaaa tatttatctg cctctgcatg taagtttcat atttactcgt cttgccataa   6300
```

```
tttatatgaa aaaatttact cacaccggat atatatacct aaccatagca attaactatg    6360
gtaatgtgat gtaatgaaga gagaatgtct attaattaat tatggctaag tgatagtagt    6420
gtattgtaaa caaatgacgt gcatttgttg attagacact tacaaaaata cccacgaaat    6480
ctaaaataat tacagccact atccactact ttcaaatatt atctggccta cccattaaaa    6540
tatttactca ctctacccct ccagacttat atattataag gtataaaaag gtaaacaata    6600
ataaatggtc ctccagactt ttataccata atttatgcag ccttaaaggt atacacctat    6660
aaacaaaggt atacaataaa aaatgggtat gttgggtaaa tacttttagt tttatgggta    6720
gagtaatttt taatgggtat gacttgtaaa tactttaaat ttcatgggta tagagtgtaa    6780
aaattccttt gttgattggg tatatacacc cgatgtgggt aagtacttgc ctaatttttg    6840
ccctaaggta aatatagact tatagtataa aaaaaaatac gcagtgtgat agatactttg    6900
aatttcatga gtaatgtaat ttttaatagg tatagtaagg taaatacttt atattccaag    6960
ggtacacatt gtaaaagct caatatttta ttccaaagaa taagagacca aacaatgtgt    7020
ttgagattta ttactttgtt gtccaccaaa ctaaaaagaa aactttagaa gtctaaatta    7080
caataatctt aacatgcatt ttacgaataa atatcacaaa atctcaaact attagagata    7140
atgtcgtgga tgatgttaac atattggact acacaaccca ttgtacaata attttgaagc    7200
atgtatatgc acgaccaaga ctccatcatc atagatcaaa tgaatgttca ttttaatgca    7260
tgaaacctaa gtagaacatt tatgccttaa tgaactaaaa ccaagcaaaa agatacatct    7320
acttgtgcaa ttgaatgaat tctaccgtat atactaatat acaccagagg ttagtttaac    7380
acttggaact tcaaaaggtg tacaaccata gagtttcctt tacattgatg gtttctttca    7440
tttcactaac tgataaaatg aaggctggta tagtctacca aatccctagt tccctgtgaa    7500
cttgcatccc ttctagctac atgcagaaca tgtcctttag atcccatagg tgtattgcca    7560
tttgccactg aacaatggag gacaatgtat aattgtcctc ctcacccatt gcacatactc    7620
tgtcatttgc tgcacatcta catgccttt ctgaatattc ttctgagtca aataagcatc    7680
atgagacatc tgtcaagtat ctttgaatgg gataatcaca tttccaaatc gaaaggttct    7740
tgtcttaaca agtcaagctg catctcgaca aagagacttc gttgatgaaa tgcgaccata    7800
aagagcacat gcaaaccagt tgttaaaagc attgtacaca tatacctact tctgatgtga    7860
ataaaagaaa gtcgatcaat gacagaggaa aacagtcaat ctataaccac aaaaatactt    7920
ttctttaaaa gtacgaccac atagataact ataatttccc gtagatgtca aactcttatt    7980
gaataaaaaa taaacaaaca tgtactattt gctcatttat ccgactgtca caaggatttt    8040
cttaatgatg gtataatagg agcaatccct tttatgacag atgcactaat ttgtttgggt    8100
gcatatttca atgcagaact gtggggtata taatctaaaa tatcattcaa atcaaacctg    8160
ggaacgattg agagaagatt agcatggcct ctgcacaagg atgacacgca taaatcgaga    8220
aatgttccaa ataaggaaa tatatatatt acctgtttca attggcatag ttcttaaaga    8280
agttttggca gttaaagtat taatagttta ccttgtttcg attgtgggat ttagccttgg    8340
ggttgtctgg gacggacctg tgattattct gctaatctcc ttgtatattc atgcaatgtg    8400
cagtttaatc cagtgcattt tgcgtgttat ggatggatcc                          8440
```

<210> SEQ ID NO 20
<211> LENGTH: 2637
<212> TYPE: DNA
<213> ORGANISM: Oryza sativa

<400> SEQUENCE: 20

-continued

```
atggcgcgcc gcgtccctac ccgcccgcgc ggcggtggcg gcggcggcgt cccacgctcg      60
gagggctcga tccaagggcg aggaggccgc gcggggggca gtggcgccga ggacgcacgc     120
cacgtgttcg acgaattgct ccggcgtggc aggggcgcct cgatctacgg cttgaaccgc     180
gccctcgccg acgtcgcgcg tcacagcccc gcggccgccg tgtcccgcta caaccgcatg     240
gcccgagccg cgccggcaa ggtaactccc accgtgcaca cctatgccat cctcatcggc      300
tgctgctgcc gtgcgggccg cttggacctc ggtttcgcgg ccttgggcaa tgtcgtcaag     360
aagggattta gagtggatgc catcaccttc actcctctgc tcaagggcct ctgtgccgac     420
aagaggacga gcgacgcaat ggacatagtg ctccgcagaa tgaccgagct cggctgcata     480
ccagatgtct tctcctacaa taatcttctc aagggtctgt gtgatgagaa cagaagccaa     540
gaagctctcg agctgctgca catgatggct gatgatcgag gaggaggtag cccacctgat     600
gtggtgtcgt ataacactgt cctcaatggc ttcttcaaag agggggattc agacaaagct     660
tacagtacat accatgaaat gctggaccgg gggattttac cagatgttgt gacctacagc     720
tctattattg ctgcgttatg caaggctcaa gctatggaca aagccatgga ggtacttaac     780
accatggtta agaatggtgt catgcctgat tgcatgacat ataatagtat tctgcatgga     840
tattgctctt cagggcagcc aaaagaggct attggaacac tcaaaaagat gcgcagtgat     900
ggcgtcgaac caaatgttgt tacttatagt tcactgatga attatctttg caagaatgga     960
agatccaccg aagctagaaa gattttcgat tctatgacca agaggggcct agagcctgat    1020
attgctacct atcgtaccct gcttcagggg tatgctacca aaggagccct tgttgagatg    1080
catgctctct tggatttgat ggtacgaaat ggtatccaac cggatcatca tgtattcaac    1140
attctaatat gtgcatacgc taaacaagag aaagtagatc aggcaatgct tgtattcagc    1200
aaaatgaggc agcatggatt gaatccgaat gtagtgtgct atggaacagt tatagatgta    1260
cttttgcaagt caggcagtgt agatgatgct atgctttatt ttgagcagat gatcgatgaa    1320
ggactaaccc ctaacattat tgtgtatacc tccctaattc atggtctgtg cacctgtgac    1380
aaaatgggaca aggctgaaga gttaattctt gaaatgttgg atcgaggcat ctgtctgaac    1440
actatttcct ttaattcaat aattgacagt cattgcaaag aagggagggt tatagaatct    1500
gaaaaactct ttgacttgat ggtacgaatt ggtgtgaagc ccgatatcat tacgtacaat    1560
acactcatcg atggatgctg cttagctggt aagatggatg aagcaacgaa gttacttgcc    1620
agcatggtct cagttggggt gaaacctgat attgttacct atggcacctt gattaatggc    1680
tactgtagag ttagcaggat ggatgacgca ttagctcttt tcaaagagat ggtgagcagt    1740
ggtgttagtc ctaatattat tacgtataac ataattctgc aaggtttatt tcataccaga    1800
agaactgctg ctgcaaaaga actctatgtc agtattacca aaagtggaac acagcttgaa    1860
cttagcacgt acaacataat ccttcatgga ctttgcaaaa acaatctcac tgacgaggca    1920
cttcgaatgt ttcagaacct atgtttgacg gatttacagc tggagactag gactttaac    1980
attatgattg gtgccttact taatgtggaa gaatggatg aagctaagga tttgtttgct    2040
gctcactcgg ctaacggttt agtgccagat gttaggacct acagtttaat ggcagaaaat    2100
cttatagagc aggggtcgct agaagaattg gatgatctat ttctttcaat ggaggagaat    2160
ggctgttccg ccgactcccg catgctaaat tccattgtta ggaaactgtt acagagggt    2220
gatataacca gggctggcac ttacctgttc atgattgatg agaagcactt ctccctcgaa    2280
gcatccactg cttccttctt gttagaatct tccccaatcg tctgggagca aatatcaaga    2340
```

-continued

```
atatcacact tgtctgtaaa tttgaaatta attaagcagc ccaaatgcac ctgtgagtta    2400
ggcccaaagt ggtcccaaaa tctgcctaaa cctggcacaa attcggtcgg tagtgtcgca    2460
cagtttcact tatcgcgcgg cggttatcgc gcttaccgcg ggggtacgac ggttaccgca    2520
ctaccgcagg gtgacggtaa ccccggccca aacgataagg taaaccctgg tcgcacaaat    2580
ttggcccaaa accgaccagt tatcgcgcta ccgcgggatg cctcagtagg accttag      2637
```

<210> SEQ ID NO 21
<211> LENGTH: 878
<212> TYPE: PRT
<213> ORGANISM: Oryza sativa

<400> SEQUENCE: 21

```
Met Ala Arg Arg Val Pro Thr Arg Pro Arg Gly Gly Gly Gly Gly
 1               5                  10                  15

Val Pro Arg Ser Glu Gly Ser Ile Gln Gly Arg Gly Arg Ala Gly
                20                  25                  30

Gly Ser Gly Ala Glu Asp Ala Arg His Val Phe Asp Glu Leu Leu Arg
            35                  40                  45

Arg Gly Arg Gly Ala Ser Ile Tyr Gly Leu Asn Arg Ala Leu Ala Asp
        50                  55                  60

Val Ala Arg His Ser Pro Ala Ala Val Ser Arg Tyr Asn Arg Met
 65                  70                  75                  80

Ala Arg Ala Gly Ala Gly Lys Val Thr Pro Thr Val His Thr Tyr Ala
                85                  90                  95

Ile Leu Ile Gly Cys Cys Cys Arg Ala Gly Arg Leu Asp Leu Gly Phe
                100                 105                 110

Ala Ala Leu Gly Asn Val Val Lys Lys Gly Phe Arg Val Asp Ala Ile
            115                 120                 125

Thr Phe Thr Pro Leu Leu Lys Gly Leu Cys Ala Asp Lys Arg Thr Ser
        130                 135                 140

Asp Ala Met Asp Ile Val Leu Arg Arg Met Thr Glu Leu Gly Cys Ile
145                 150                 155                 160

Pro Asp Val Phe Ser Tyr Asn Asn Leu Leu Lys Gly Leu Cys Asp Glu
                165                 170                 175

Asn Arg Ser Gln Glu Ala Leu Glu Leu Leu His Met Met Ala Asp Asp
            180                 185                 190

Arg Gly Gly Gly Ser Pro Pro Asp Val Val Ser Tyr Asn Thr Val Leu
        195                 200                 205

Asn Gly Phe Phe Lys Glu Gly Asp Ser Asp Lys Ala Tyr Ser Thr Tyr
    210                 215                 220

His Glu Met Leu Asp Arg Gly Ile Leu Pro Asp Val Thr Tyr Ser
225                 230                 235                 240

Ser Ile Ile Ala Ala Leu Cys Lys Ala Gln Ala Met Asp Lys Ala Met
                245                 250                 255

Glu Val Leu Asn Thr Met Val Lys Asn Gly Val Met Pro Asp Cys Met
            260                 265                 270

Thr Tyr Asn Ser Ile Leu His Gly Tyr Cys Ser Ser Gly Gln Pro Lys
        275                 280                 285

Glu Ala Ile Gly Thr Leu Lys Lys Met Arg Ser Asp Gly Val Glu Pro
    290                 295                 300

Asn Val Val Thr Tyr Ser Ser Leu Met Asn Tyr Leu Cys Lys Asn Gly
305                 310                 315                 320

Arg Ser Thr Glu Ala Arg Lys Ile Phe Asp Ser Met Thr Lys Arg Gly
```

-continued

```
                325                 330                 335
Leu Glu Pro Asp Ile Ala Thr Tyr Arg Thr Leu Leu Gln Gly Tyr Ala
                340                 345                 350
Thr Lys Gly Ala Leu Val Glu Met His Ala Leu Leu Asp Leu Met Val
                355                 360                 365
Arg Asn Gly Ile Gln Pro Asp His His Val Phe Asn Ile Leu Ile Cys
                370                 375                 380
Ala Tyr Ala Lys Gln Glu Lys Val Asp Gln Ala Met Leu Val Phe Ser
385                 390                 395                 400
Lys Met Arg Gln His Gly Leu Asn Pro Asn Val Val Cys Tyr Gly Thr
                405                 410                 415
Val Ile Asp Val Leu Cys Lys Ser Gly Ser Val Asp Asp Ala Met Leu
                420                 425                 430
Tyr Phe Glu Gln Met Ile Asp Glu Gly Leu Thr Pro Asn Ile Ile Val
                435                 440                 445
Tyr Thr Ser Leu Ile His Gly Leu Cys Thr Cys Asp Lys Trp Asp Lys
                450                 455                 460
Ala Glu Glu Leu Ile Leu Glu Met Leu Asp Arg Gly Ile Cys Leu Asn
465                 470                 475                 480
Thr Ile Phe Phe Asn Ser Ile Ile Asp Ser His Cys Lys Glu Gly Arg
                485                 490                 495
Val Ile Glu Ser Glu Lys Leu Phe Asp Leu Met Val Arg Ile Gly Val
                500                 505                 510
Lys Pro Asp Ile Ile Thr Tyr Asn Thr Leu Ile Asp Gly Cys Cys Leu
                515                 520                 525
Ala Gly Lys Met Asp Glu Ala Thr Lys Leu Leu Ala Ser Met Val Ser
                530                 535                 540
Val Gly Val Lys Pro Asp Ile Val Thr Tyr Gly Thr Leu Ile Asn Gly
545                 550                 555                 560
Tyr Cys Arg Val Ser Arg Met Asp Asp Ala Leu Ala Leu Phe Lys Glu
                565                 570                 575
Met Val Ser Ser Gly Val Ser Pro Asn Ile Ile Thr Tyr Asn Ile Ile
                580                 585                 590
Leu Gln Gly Leu Phe His Thr Arg Arg Thr Ala Ala Ala Lys Glu Leu
                595                 600                 605
Tyr Val Ser Ile Thr Lys Ser Gly Thr Gln Leu Glu Leu Ser Thr Tyr
                610                 615                 620
Asn Ile Ile Leu His Gly Leu Cys Lys Asn Asn Leu Thr Asp Glu Ala
625                 630                 635                 640
Leu Arg Met Phe Gln Asn Leu Cys Leu Thr Asp Leu Gln Leu Glu Thr
                645                 650                 655
Arg Thr Phe Asn Ile Met Ile Gly Ala Leu Leu Lys Cys Gly Arg Met
                660                 665                 670
Asp Glu Ala Lys Asp Leu Phe Ala Ala His Ser Ala Asn Gly Leu Val
                675                 680                 685
Pro Asp Val Arg Thr Tyr Ser Leu Met Ala Glu Asn Leu Ile Glu Gln
                690                 695                 700
Gly Ser Leu Glu Glu Leu Asp Asp Leu Phe Leu Ser Met Glu Glu Asn
705                 710                 715                 720
Gly Cys Ser Ala Asp Ser Arg Met Leu Asn Ser Ile Val Arg Lys Leu
                725                 730                 735
Leu Gln Arg Gly Asp Ile Thr Arg Ala Gly Thr Tyr Leu Phe Met Ile
                740                 745                 750
```

```
Asp Glu Lys His Phe Ser Leu Glu Ala Ser Thr Ala Ser Phe Leu Leu
        755                 760                 765
Glu Ser Ser Pro Ile Val Trp Glu Gln Ile Ser Arg Ile Ser His Leu
            770                 775                 780
Ser Val Asn Leu Lys Leu Ile Lys Gln Pro Lys Cys Thr Cys Glu Leu
785                 790                 795                 800
Gly Pro Lys Trp Ser Gln Asn Leu Pro Lys Pro Gly Thr Asn Ser Val
                805                 810                 815
Gly Ser Val Ala Gln Phe His Leu Ser Arg Gly Gly Tyr Arg Ala Tyr
            820                 825                 830
Arg Gly Gly Thr Thr Val Thr Ala Leu Pro Gln Gly Asp Gly Asn Pro
        835                 840                 845
Gly Pro Asn Asp Lys Val Asn Pro Gly Arg Thr Asn Leu Ala Gln Asn
    850                 855                 860
Arg Pro Val Ile Ala Leu Pro Arg Asp Ala Ser Val Gly Pro
865                 870                 875

<210> SEQ ID NO 22
<211> LENGTH: 3660
<212> TYPE: DNA
<213> ORGANISM: Oryza sativa

<400> SEQUENCE: 22
```

| | | | | | |
|---|---|---|---|---|---|
| atggcgcgcc | gcgccgcttc | ccgcgtccgc | gccggcgctg | ttggcgccct | tcgctcggag | 60 |
| ggctcgaccc | aagggcgagg | gggccgcacg | ggggcagtg | gcgccgagga | cgcacgccac | 120 |
| gtgttcgacg | aattgctccg | gcgtggcagg | ggcgcctcga | tctacggctt | gaactgcgcc | 180 |
| ctcgccgacg | tcgcgcgtca | cagccccgcg | gccgccgtgt | cccgctacaa | ccgcatggcc | 240 |
| cgagccggcg | ccgacgaggt | aactcccaac | ttgtgcacct | acggcattct | catcggttcc | 300 |
| tgctgctgcg | cgggccgctt | ggacctcggt | ttcgcggcct | tgggcaatgt | cattaagaag | 360 |
| ggatttagag | tggacgccat | cgccttcact | cctctgctca | agggcctctg | tgctgacaag | 420 |
| aggacgagcg | acgcaatgga | catagtgctc | cgcagaatga | cccagcttgg | ctgcatacca | 480 |
| aatgtcttct | cctacaatat | tcttctcaag | gggctgtgtg | atgagaacag | aagccaagaa | 540 |
| gctctcgagc | tgctccaaat | gatgcctgat | gatggaggtg | actgcccacc | tgatgtggtg | 600 |
| tcgtatacca | ctgtcatcaa | tggcttcttc | aaggaggggg | atctggacaa | agcttacggt | 660 |
| acataccatg | aaatgctgga | ccgggggatt | ttaccaaatg | ttgttaccta | cagctctatt | 720 |
| attgctgcgt | tatgcaaggc | tcaagctatg | acaaagcca | tggaggtact | taccagcatg | 780 |
| gttaagaatg | gtgtcatgcc | taattgcagg | acgtataata | gtatcgtgca | tgggtattgc | 840 |
| tcttcagggc | agccgaaaga | ggctattgga | tttctcaaaa | agatgcacag | tgatggtgtc | 900 |
| gaaccagatg | ttgttactta | taactcgctc | atggattatc | tttgcaagaa | cggaagatgc | 960 |
| acggaagcta | gaaagatgtt | cgattctatg | accaagaggg | gcctaaagcc | tgaaattact | 1020 |
| acctatggta | ccctgcttca | ggggtatgct | accaaaggag | cccttgttga | gatgcatggt | 1080 |
| ctcttggatt | tgatggtacg | aaacggtatc | caccctaatc | attatgtttt | cagcattcta | 1140 |
| atatgtgcat | acgctaaaca | agggaaagta | gatcaggcaa | tgcttgtgtt | cagcaaaatg | 1200 |
| aggcagcaag | gattgaatcc | ggatacagtg | acctatggaa | cagttatagg | catactttgc | 1260 |
| aagtcaggca | gagtagaaga | tgctatgcgt | tattttgagc | agatgatcga | tgaaagacta | 1320 |
| agccctggca | acattgttta | taactcccta | attcatagtc | tctgtatctt | tgacaaatgg | 1380 |

-continued

```
gacaaggcta aagagttaat tcttgaaatg ttggatcgag gcatctgtct ggacactatt      1440
ttctttaatt caataattga cagtcattgc aaagaaggga gggttataga atctgaaaaa      1500
ctctttgacc tgatggtacg tattggtgtg aagcccgata tcattacgta cagtactctc      1560
atcgatggat attgcttggc aggtaagatg gatgaagcaa cgaagttact tgccagcatg      1620
gtctcagttg gaatgaaacc tgattgtgtt acatataata ctttgattaa tggctactgt      1680
aaaattagca ggatggaaga tgcgttagtt cttttttaggg agatggagag cagtggtgtt      1740
agtcctgata ttattacgta taatataatt ctgcaaggtt tatttcaaac cagaagaact      1800
gctgctgcaa aagaactcta tgtcgggatt accgaaagtg aacgcagct tgaacttagc       1860 acatacaaca taatccttca tgggctttgc aaaaacaatc tcactgacga ggcacttcga      1920
atgtttcaga acctatgttt gacggattta cagctggaga ctaggacttt taacattatg      1980
attggtgcat tgcttaaagt tggcagaaat gatgaagcca aggatttgtt tgcagctctc      2040
tcggctaacg gttagtgcc agatgttagg acctacagtt taatggcaga aaatcttata      2100 gagcagggt tgctagaaga attggatgat ctatttcttt caatggagga gaatggctgt      2160
actgccaact cccgcatgct aaattccatt gttaggaaac tgttacagag gggtgatata      2220
accagggctg gcacttacct gttcatgatt gatgagaagc acttctccct cgaagcatcc      2280
actgcttcct tgttttaga tcttttgtct ggggggaaaat atcaagaata tcatagttgt      2340
attagaggag ggatcttctc tttatgtgta aatagcgagg ttcaagaaaa tcatttgttg      2400
gattcagaat ctggtgtcca ttttcttctt aaattattaa atcctccagt gaatcttgtt      2460
gattccaaag caccatcgat aggttccaaa cttcttggaa tcagtaaagt tcaaatgctt      2520
aatggatcaa ataaggattc tgactgcatt tcagaggaaa tcctttcaaa agttgaagag      2580
attctcttaa gctgtcaagt gatcaagtcg ctcgacaaag atgacaagaa aacaacaagg      2640
ccagaactgt gtccaaagtg gcttgctttg ttgacaatgg aaaatgcatg cttgtctgct      2700
gtttcagtag aggagacttc tgacacagtg tccagagttg gaggaaattt taagagaca       2760 ttaagggaga tgggaggtct tgatagtatt tttgacgtta tggtggatt tcattcaaca       2820 ttggagaatc tcataaagga tacatccact tcagctttgg accgaaatga aggaacatct      2880
ttgcaaagtg ctgctctcct cttgaaatgt ttgaaaatat tggaaaatgc catatttcta      2940
agcgatgata acaagaccca tttgcttaat atgagtagaa aattgaaccc gaaacgctcc      3000
ttgctttctt ttgttggtgt cattatcaat actattgagt tattatcagc tctttcaata      3060
cttcagaatt cttctgttgt ttccagctct acatatccga aatcgtctaa agtctctcaa      3120
cagagttact ctgtggtgat ggcgggggc gaccgtggcc gaggcgtgga gtgccatccg       3180
catcagggtg tatcggccgc gctgctccgc cctggtccgc aggctttggc ggcgagctgg      3240
cggcggaggg agactgtggt gagatcggat ttcgccgctg gtggtgtcgc taccatgggg      3300
gattcgccgc aggcgctctc agatcggtta tgcgggagcg caacaaaagt atggcgtggc      3360
ggcgcggagt ggacggccga ggcgttcgcg cggaatgggg ctgcgggacc gagccagtct      3420
cgcttgccgg taacgcggaa ccgagctcag cactacattg caaagatttg gcaactctg       3480 acaatttcca tgttctacaa gcttgacgtc gagggaatgg agaacctgcc accgaatagt      3540
agccctgcta tctatgttgc gaaccatcag agttttttgg atatctatac ccttctaact      3600
ctaggaaggt gtttcaagtt tataagcaag acaagtatat ttatgttccg aattatttga      3660
```

<210> SEQ ID NO 23
<211> LENGTH: 1219

<212> TYPE: PRT
<213> ORGANISM: Oryza sativa

<400> SEQUENCE: 23

```
Met Ala Arg Arg Ala Ala Ser Arg Val Arg Ala Gly Ala Val Gly Ala
 1               5                  10                  15

Leu Arg Ser Glu Gly Ser Thr Gln Gly Arg Gly Arg Thr Gly Gly
            20                  25                  30

Ser Gly Ala Glu Asp Ala Arg His Val Phe Asp Glu Leu Leu Arg Arg
            35                  40                  45

Gly Arg Gly Ala Ser Ile Tyr Gly Leu Asn Cys Ala Leu Ala Asp Val
 50                  55                  60

Ala Arg His Ser Pro Ala Ala Val Ser Arg Tyr Asn Arg Met Ala
 65              70                  75                  80

Arg Ala Gly Ala Asp Glu Val Thr Pro Asn Leu Cys Thr Tyr Gly Ile
                85                  90                  95

Leu Ile Gly Ser Cys Cys Ala Gly Arg Leu Asp Leu Gly Phe Ala
                100                 105                 110

Ala Leu Gly Asn Val Ile Lys Lys Gly Phe Arg Val Asp Ala Ile Ala
            115                 120                 125

Phe Thr Pro Leu Leu Lys Gly Leu Cys Ala Asp Lys Arg Thr Ser Asp
130                 135                 140

Ala Met Asp Ile Val Leu Arg Arg Met Thr Gln Leu Gly Cys Ile Pro
145                 150                 155                 160

Asn Val Phe Ser Tyr Asn Ile Leu Leu Lys Gly Leu Cys Asp Glu Asn
                165                 170                 175

Arg Ser Gln Glu Ala Leu Glu Leu Leu Gln Met Met Pro Asp Asp Gly
            180                 185                 190

Gly Asp Cys Pro Pro Asp Val Val Ser Tyr Thr Thr Val Ile Asn Gly
        195                 200                 205

Phe Phe Lys Glu Gly Asp Leu Asp Lys Ala Tyr Gly Thr Tyr His Glu
210                 215                 220

Met Leu Asp Arg Gly Ile Leu Pro Asn Val Val Thr Tyr Ser Ser Ile
225                 230                 235                 240

Ile Ala Ala Leu Cys Lys Ala Gln Ala Met Asp Lys Ala Met Glu Val
                245                 250                 255

Leu Thr Ser Met Val Lys Asn Gly Val Met Pro Asn Cys Arg Thr Tyr
            260                 265                 270

Asn Ser Ile Val His Gly Tyr Cys Ser Ser Gly Gln Pro Lys Glu Ala
        275                 280                 285

Ile Gly Phe Leu Lys Lys Met His Ser Asp Gly Val Glu Pro Asp Val
290                 295                 300

Val Thr Tyr Asn Ser Leu Met Asp Tyr Leu Cys Lys Asn Gly Arg Cys
305                 310                 315                 320

Thr Glu Ala Arg Lys Met Phe Asp Ser Met Thr Lys Arg Gly Leu Lys
                325                 330                 335

Pro Glu Ile Thr Thr Tyr Gly Thr Leu Leu Gln Gly Tyr Ala Thr Lys
            340                 345                 350

Gly Ala Leu Val Glu Met His Gly Leu Leu Asp Leu Met Val Arg Asn
        355                 360                 365

Gly Ile His Pro Asn His Tyr Val Phe Ser Ile Leu Ile Cys Ala Tyr
    370                 375                 380

Ala Lys Gln Gly Lys Val Asp Gln Ala Met Leu Val Phe Ser Lys Met
385                 390                 395                 400
```

-continued

Arg Gln Gln Gly Leu Asn Pro Asp Thr Val Thr Tyr Gly Thr Val Ile
            405                 410                 415
Gly Ile Leu Cys Lys Ser Gly Arg Val Glu Asp Ala Met Arg Tyr Phe
            420                 425                 430
Glu Gln Met Ile Asp Glu Arg Leu Ser Pro Gly Asn Ile Val Tyr Asn
            435                 440                 445
Ser Leu Ile His Ser Leu Cys Ile Phe Asp Lys Trp Asp Lys Ala Lys
            450                 455                 460
Glu Leu Ile Leu Glu Met Leu Asp Arg Gly Ile Cys Leu Asp Thr Ile
465                 470                 475                 480
Phe Phe Asn Ser Ile Ile Asp Ser His Cys Lys Glu Gly Arg Val Ile
                485                 490                 495
Glu Ser Glu Lys Leu Phe Asp Leu Met Val Arg Ile Gly Val Lys Pro
            500                 505                 510
Asp Ile Ile Thr Tyr Ser Thr Leu Ile Asp Gly Tyr Cys Leu Ala Gly
            515                 520                 525
Lys Met Asp Glu Ala Thr Lys Leu Leu Ala Ser Met Val Ser Val Gly
530                 535                 540
Met Lys Pro Asp Cys Val Thr Tyr Asn Thr Leu Ile Asn Gly Tyr Cys
545                 550                 555                 560
Lys Ile Ser Arg Met Glu Asp Ala Leu Val Leu Phe Arg Glu Met Glu
                565                 570                 575
Ser Ser Gly Val Ser Pro Asp Ile Ile Thr Tyr Asn Ile Ile Leu Gln
            580                 585                 590
Gly Leu Phe Gln Thr Arg Arg Thr Ala Ala Lys Glu Leu Tyr Val
            595                 600                 605
Gly Ile Thr Glu Ser Gly Thr Gln Leu Glu Leu Ser Thr Tyr Asn Ile
            610                 615                 620
Ile Leu His Gly Leu Cys Lys Asn Asn Leu Thr Asp Glu Ala Leu Arg
625                 630                 635                 640
Met Phe Gln Asn Leu Cys Leu Thr Asp Leu Gln Leu Glu Thr Arg Thr
                645                 650                 655
Phe Asn Ile Met Ile Gly Ala Leu Leu Lys Val Gly Arg Asn Asp Glu
                660                 665                 670
Ala Lys Asp Leu Phe Ala Ala Leu Ser Ala Asn Gly Leu Val Pro Asp
            675                 680                 685
Val Arg Thr Tyr Ser Leu Met Ala Glu Asn Leu Ile Glu Gln Gly Leu
            690                 695                 700
Leu Glu Glu Leu Asp Asp Leu Phe Leu Ser Met Glu Glu Asn Gly Cys
705                 710                 715                 720
Thr Ala Asn Ser Arg Met Leu Asn Ser Ile Val Arg Lys Leu Leu Gln
                725                 730                 735
Arg Gly Asp Ile Thr Arg Ala Gly Thr Tyr Leu Phe Met Ile Asp Glu
            740                 745                 750
Lys His Phe Ser Leu Glu Ala Ser Thr Ala Ser Leu Phe Leu Asp Leu
            755                 760                 765
Leu Ser Gly Gly Lys Tyr Gln Glu Tyr His Ser Cys Ile Arg Gly Gly
            770                 775                 780
Ile Phe Ser Leu Cys Val Asn Ser Glu Val Gln Glu Asn His Leu Leu
785                 790                 795                 800
Asp Ser Glu Ser Gly Val His Phe Leu Leu Lys Leu Leu Asn Pro Pro
                805                 810                 815

-continued

```
Val Asn Leu Val Asp Ser Lys Ala Pro Ser Ile Gly Ser Lys Leu Leu
                820                 825                 830

Gly Ile Ser Lys Val Gln Met Leu Asn Gly Ser Asn Lys Asp Ser Asp
            835                 840                 845

Cys Ile Ser Glu Glu Ile Leu Ser Lys Val Glu Glu Ile Leu Leu Ser
        850                 855                 860

Cys Gln Val Ile Lys Ser Leu Asp Lys Asp Lys Lys Thr Thr Arg
865                 870                 875                 880

Pro Glu Leu Cys Pro Lys Trp Leu Ala Leu Leu Thr Met Glu Asn Ala
                885                 890                 895

Cys Leu Ser Ala Val Ser Val Glu Glu Thr Ser Asp Thr Val Ser Arg
            900                 905                 910

Val Gly Gly Asn Phe Lys Glu Thr Leu Arg Glu Met Gly Gly Leu Asp
        915                 920                 925

Ser Ile Phe Asp Val Met Val Asp Phe His Ser Thr Leu Glu Asn Leu
930                 935                 940

Ile Lys Asp Thr Ser Thr Ser Ala Leu Asp Arg Asn Glu Gly Thr Ser
945                 950                 955                 960

Leu Gln Ser Ala Ala Leu Leu Leu Lys Cys Leu Lys Ile Leu Glu Asn
                965                 970                 975

Ala Ile Phe Leu Ser Asp Asp Asn Lys Thr His Leu Leu Asn Met Ser
            980                 985                 990

Arg Lys Leu Asn Pro Lys Arg Ser Leu Leu Ser Phe Val Gly Val Ile
        995                 1000                1005

Ile Asn Thr Ile Glu Leu Leu Ser Ala Leu Ser Ile Leu Gln Asn Ser
1010                1015                1020

Ser Val Val Ser Ser Ser Thr Tyr Pro Lys Ser Ser Lys Val Ser Gln
1025                1030                1035                1040

Gln Ser Tyr Ser Val Val Met Ala Gly Gly Asp Arg Gly Arg Gly Val
                1045                1050                1055

Glu Cys His Pro His Gln Gly Val Ser Ala Ala Leu Leu Arg Pro Gly
            1060                1065                1070

Pro Gln Ala Leu Ala Ala Ser Trp Arg Arg Arg Glu Thr Val Val Arg
        1075                1080                1085

Ser Asp Phe Ala Ala Gly Gly Val Ala Thr Met Gly Asp Ser Pro Gln
1090                1095                1100

Ala Leu Ser Asp Arg Leu Cys Gly Ser Ala Thr Lys Val Trp Arg Gly
1105                1110                1115                1120

Gly Ala Glu Trp Thr Ala Glu Ala Phe Ala Arg Asn Gly Ala Ala Gly
                1125                1130                1135

Pro Ser Gln Ser Arg Leu Pro Val Thr Arg Asn Arg Ala Gln His Tyr
            1140                1145                1150

Ile Ala Lys Ile Trp Ala Thr Leu Thr Ile Ser Met Phe Tyr Lys Leu
        1155                1160                1165

Asp Val Glu Gly Met Glu Asn Leu Pro Pro Asn Ser Ser Pro Ala Ile
1170                1175                1180

Tyr Val Ala Asn His Gln Ser Phe Leu Asp Ile Tyr Thr Leu Leu Thr
1185                1190                1195                1200

Leu Gly Arg Cys Phe Lys Phe Ile Ser Lys Thr Ser Ile Phe Met Phe
                1205                1210                1215

Arg Ile Ile
```

<210> SEQ ID NO 24

<211> LENGTH: 2859
<212> TYPE: DNA
<213> ORGANISM: Oryza sativa

<400> SEQUENCE: 24

| | | | | | |
|---|---|---|---|---|---:|
| atggcgcgcc | gcgccgcttc | ccgcgctgtt | ggcgcccttc | gctcggacgg | ctcgatccaa | 60 |
| gggcgaggag | gccgcgcggg | gggcagtggc | gccgaggacg | cacgccacgt | gttcgacgaa | 120 |
| ttgctccggc | gtggcagggg | cgcctcgatc | tacggcttga | accgcgccct | cgccgacgtc | 180 |
| gcgcgtcaca | gccccgcggc | cgccgtgtcc | cgctacaacc | gcatggcccg | agctggcgcc | 240 |
| gacgaggtaa | ctcccgactt | gtgcacctac | ggcattctca | tcggttgctg | ctgccgcgcg | 300 |
| ggccgcttgg | acctcggttt | cgcggccttg | ggcaatgtca | ttaagaaggg | atttagagtg | 360 |
| gaagccatca | ccttcactcc | tctgctcaag | ggcctctgtg | ccgacaagag | gacgagcgac | 420 |
| gcaatggaca | tagtgctccg | cagaatgacc | gagctcggtt | gcataccaaa | tgtcttctcc | 480 |
| tacaataatc | ttctcaacgg | gctgtgtgat | gagaacagaa | gccaagaagc | tctcgagttg | 540 |
| ctgcacatga | tggctgatga | tcgaggagga | ggtagcccac | tgatgtggt | gtcgtatacc | 600 |
| actgtcatca | atggcttctt | caaagagggg | gattcagaca | aagcttacag | tacataccat | 660 |
| gaaatgctgg | accgggggat | tttacctgat | gttgtgacct | acagctctat | tattgctgcg | 720 |
| ttatgcaagg | tcaagctat | ggacaagcca | tggagtcatt | gcaaagaagg | gagggttata | 780 |
| gaatctgaaa | aactctttga | cctgatggta | cgtattggtg | tgaagcctga | tatcattaca | 840 |
| tacagtacac | tcatcgatgg | atattgcttg | gcaggtaaga | tggatgaagc | aatgaagtta | 900 |
| ctttctggca | tggtctcagt | tgggttgaaa | cctaatactg | ttacttatag | cactttgatt | 960 |
| aatggctact | gcaaaattag | taggatggaa | gacgcgttag | ttcttttaa | ggagatggag | 1020 |
| agcagtggtg | ttagtcctga | tattattacg | tataacataa | ttctgcaagg | tttatttcaa | 1080 |
| accagaagaa | ctgctgctgc | aaaagaactc | tatgtcagga | ttaccgaaag | tggaacgcag | 1140 |
| attgaactta | gcacatacaa | cataatcctt | catggacttt | gcaaaaacaa | actcactgat | 1200 |
| gatgcacttc | agatgtttca | gaacctatgt | ttgatggatt | tgaagcttga | ggctaggact | 1260 |
| ttcaacatta | tgattgatgc | attgcttaaa | gttggcagaa | atgatgaagc | caaggatttg | 1320 |
| tttgttgctt | tctcgtctaa | cggtttagtg | ccgaattatt | ggacgtacag | gttgatggct | 1380 |
| gaaaatatta | taggacaggg | gttgctagaa | gaattggatc | aactctttct | ttcaatggag | 1440 |
| gacaatggct | gtactgttga | ctctggcatg | ctaaatttca | ttgttaggga | actgttgcag | 1500 |
| agaggagtag | tggtggtggt | gagtggtgaa | tctgccacca | ccccaccacc | aactctcaaa | 1560 |
| attctgacat | gtgggatcac | tgtcaatccc | ttctccaaga | catgtgggat | cactgtcaat | 1620 |
| cccttctcca | aaccaattgt | gcagacaggt | gcttgcggtc | aggttaaaga | agttggcaaa | 1680 |
| aatgcttctg | aagaaaggtt | aattgttgtt | tcatctcagg | agattccaga | tgatccagtg | 1740 |
| tctccaacaa | ttgaggcgct | tattttgctc | catagtaaag | caagtacact | tgctgagaac | 1800 |
| caccagttga | caacacggct | tgttgtacca | tcaaacaaag | ttggttgtat | tcttggggaa | 1860 |
| ggtggaaagg | taattactga | aatgagaaga | cggactgggg | ctgaaatccg | agtctactca | 1920 |
| aaagcagata | aacctaagta | cctgtctttt | gatgaggagc | ttgtgcagca | tatcagcctt | 1980 |
| atcttggttg | atcggcatgc | tggacgagca | catctgttgt | cgcatcaact | gctgactgct | 2040 |
| atatatgtgc | tggtgctgaa | tcgatcgatt | gtcgtcgcgg | aagtgaagaa | caaccacggc | 2100 |
| actgctgcct | gctgggctct | agccgccatc | agttataacc | gtacaaactt | cagtgatttg | 2160 |
| ctggtttcac | attggtttat | aataaaggcc | tccgttttta | gtttcacgct | gggccttcag | 2220 |

-continued

```
aatctcagga ccggccctgc tcatgatcct tacaccgtgt atcctgtaga gtacttctct      2280
aaaagagagt accctagtgg aagtagcaaa gttgcaccat ctgcttcata cgaaagatat      2340
gcagcaacta ctcgcttgcc taatggagaa ctgccctcat ctattagtcc tggtgccgat      2400
tatatgtcct gccgttctta tcttgaccaa gtacctactg ataggtactc taatagggtt      2460
acactacaat taggcctctc gagagccggg aatagtaatg tgcaacaatt aggaatcacc      2520
agagctggaa attccaatgc ttatgattat actgaggctg ctgagcagat ccatggacgt      2580
gaggattacc gaagactgtc aggtctcact gggtatccag gtggctcttc gaattgtgga      2640
ttccaaatag ttaactggag tctgtcattg gtgttggtga tctctggtgc gagagtgaag      2700
ttgcacgaag cccatcctgg ttcttccgag tccattgtgg agatccaggg cattccggat      2760
caagtgaaag ccgcacagag ccttctgcaa ggcttcatcg gcgcaagcag caacagcagg      2820
caggcgcccc agtcctctcg catggcccat tatttttag                             2859
```

<210> SEQ ID NO 25
<211> LENGTH: 952
<212> TYPE: PRT
<213> ORGANISM: Oryza sativa

<400> SEQUENCE: 25

```
Met Ala Arg Arg Ala Ala Ser Arg Ala Val Gly Ala Leu Arg Ser Asp
  1               5                  10                  15

Gly Ser Ile Gln Gly Arg Gly Gly Arg Ala Gly Gly Ser Gly Ala Glu
             20                  25                  30

Asp Ala Arg His Val Phe Asp Glu Leu Leu Arg Arg Gly Arg Gly Ala
         35                  40                  45

Ser Ile Tyr Gly Leu Asn Arg Ala Leu Ala Asp Val Ala Arg His Ser
     50                  55                  60

Pro Ala Ala Val Ser Arg Tyr Asn Arg Met Ala Arg Ala Gly Ala
 65                  70                  75                  80

Asp Glu Val Thr Pro Asp Leu Cys Thr Tyr Gly Ile Leu Ile Gly Cys
                 85                  90                  95

Cys Cys Arg Ala Gly Arg Leu Asp Leu Gly Phe Ala Ala Leu Gly Asn
            100                 105                 110

Val Ile Lys Lys Gly Phe Arg Val Glu Ala Ile Thr Phe Thr Pro Leu
        115                 120                 125

Leu Lys Gly Leu Cys Ala Asp Lys Arg Thr Ser Asp Ala Met Asp Ile
    130                 135                 140

Val Leu Arg Arg Met Thr Glu Leu Gly Cys Ile Pro Asn Val Phe Ser
145                 150                 155                 160

Tyr Asn Asn Leu Leu Asn Gly Leu Cys Asp Glu Asn Arg Ser Gln Glu
                165                 170                 175

Ala Leu Glu Leu Leu His Met Met Ala Asp Asp Arg Gly Gly Gly Ser
            180                 185                 190

Pro Pro Asp Val Val Ser Tyr Thr Thr Val Ile Asn Gly Phe Phe Lys
        195                 200                 205

Glu Gly Asp Ser Asp Lys Ala Tyr Ser Thr Tyr His Glu Met Leu Asp
    210                 215                 220

Arg Gly Ile Leu Pro Asp Val Thr Tyr Ser Ser Ile Ile Ala Ala
225                 230                 235                 240

Leu Cys Lys Gly Gln Ala Met Asp Lys Pro Trp Ser His Cys Lys Glu
                245                 250                 255
```

```
-continued

Gly Arg Val Ile Glu Ser Glu Lys Leu Phe Asp Leu Met Val Arg Ile
            260                 265                 270

Gly Val Lys Pro Asp Ile Ile Thr Tyr Ser Thr Leu Ile Asp Gly Tyr
        275                 280                 285

Cys Leu Ala Gly Lys Met Asp Glu Ala Met Lys Leu Leu Ser Gly Met
    290                 295                 300

Val Ser Val Gly Leu Lys Pro Asn Thr Val Thr Tyr Ser Thr Leu Ile
305                 310                 315                 320

Asn Gly Tyr Cys Lys Ile Ser Arg Met Glu Asp Ala Leu Val Leu Phe
                325                 330                 335

Lys Glu Met Glu Ser Ser Gly Val Ser Pro Asp Ile Ile Thr Tyr Asn
            340                 345                 350

Ile Ile Leu Gln Gly Leu Phe Gln Thr Arg Arg Thr Ala Ala Ala Lys
        355                 360                 365

Glu Leu Tyr Val Arg Ile Thr Glu Ser Gly Thr Gln Ile Glu Leu Ser
    370                 375                 380

Thr Tyr Asn Ile Ile Leu His Gly Leu Cys Lys Asn Lys Leu Thr Asp
385                 390                 395                 400

Asp Ala Leu Gln Met Phe Gln Asn Leu Cys Leu Met Asp Leu Lys Leu
                405                 410                 415

Glu Ala Arg Thr Phe Asn Ile Met Ile Asp Ala Leu Leu Lys Val Gly
            420                 425                 430

Arg Asn Asp Glu Ala Lys Asp Leu Phe Val Ala Phe Ser Ser Asn Gly
        435                 440                 445

Leu Val Pro Asn Tyr Trp Thr Tyr Arg Leu Met Ala Glu Asn Ile Ile
    450                 455                 460

Gly Gln Gly Leu Leu Glu Glu Leu Asp Gln Leu Phe Leu Ser Met Glu
465                 470                 475                 480

Asp Asn Gly Cys Thr Val Asp Ser Gly Met Leu Asn Phe Ile Val Arg
                485                 490                 495

Glu Leu Leu Gln Arg Gly Val Val Val Val Ser Gly Glu Ser Ala
            500                 505                 510

Thr Thr Pro Pro Pro Thr Leu Lys Ile Leu Thr Cys Gly Ile Thr Val
        515                 520                 525

Asn Pro Phe Ser Lys Thr Cys Gly Ile Thr Val Asn Pro Phe Ser Lys
    530                 535                 540

Pro Ile Val Gln Thr Gly Ala Cys Gly Gln Val Lys Glu Val Gly Lys
545                 550                 555                 560

Asn Ala Ser Glu Glu Arg Leu Ile Val Val Ser Ser Gln Glu Ile Pro
                565                 570                 575

Asp Asp Pro Val Ser Pro Thr Ile Glu Ala Leu Ile Leu Leu His Ser
            580                 585                 590

Lys Ala Ser Thr Leu Ala Glu Asn His Gln Leu Thr Thr Arg Leu Val
        595                 600                 605

Val Pro Ser Asn Lys Val Gly Cys Ile Leu Glu Gly Gly Lys Val
    610                 615                 620

Ile Thr Glu Met Arg Arg Arg Thr Gly Ala Glu Ile Arg Val Tyr Ser
625                 630                 635                 640

Lys Ala Asp Lys Pro Lys Tyr Leu Ser Phe Asp Glu Glu Leu Val Gln
                645                 650                 655

His Ile Ser Leu Ile Leu Val Asp Arg His Ala Gly Arg Ala His Leu
            660                 665                 670

Leu Ser His Gln Leu Leu Thr Ala Ile Tyr Val Leu Val Leu Asn Arg
```

-continued

```
                675                 680                 685
Ser Ile Val Val Ala Glu Val Lys Asn Asn His Gly Thr Ala Ala Cys
    690                 695                 700
Trp Ala Leu Ala Ala Ile Ser Tyr Asn Arg Thr Asn Phe Ser Asp Leu
705                 710                 715                 720
Leu Val Ser His Trp Phe Ile Ile Lys Ala Ser Val Phe Ser Phe Thr
                725                 730                 735
Leu Gly Leu Gln Asn Leu Arg Thr Gly Pro Ala His Asp Pro Tyr Thr
            740                 745                 750
Val Tyr Pro Val Glu Tyr Phe Ser Lys Arg Glu Tyr Pro Ser Gly Ser
            755                 760                 765
Ser Lys Val Ala Pro Ser Ala Ser Tyr Glu Arg Tyr Ala Ala Thr Thr
    770                 775                 780
Arg Leu Pro Asn Gly Glu Leu Pro Ser Ser Ile Ser Pro Gly Ala Asp
785                 790                 795                 800
Tyr Met Ser Cys Arg Ser Tyr Leu Asp Gln Val Pro Thr Asp Arg Tyr
                805                 810                 815
Ser Asn Arg Val Thr Leu Gln Leu Gly Leu Ser Arg Ala Gly Asn Ser
            820                 825                 830
Asn Val Gln Gln Leu Gly Ile Thr Arg Ala Gly Asn Ser Asn Ala Tyr
            835                 840                 845
Asp Tyr Thr Glu Ala Ala Glu Gln Ile His Gly Arg Glu Asp Tyr Arg
    850                 855                 860
Arg Leu Ser Gly Leu Thr Gly Tyr Pro Gly Gly Ser Ser Asn Cys Gly
865                 870                 875                 880
Phe Gln Ile Val Asn Trp Ser Leu Ser Leu Val Leu Ile Ser Gly
                885                 890                 895
Ala Arg Val Lys Leu His Glu Ala His Pro Gly Ser Ser Glu Ser Ile
            900                 905                 910
Val Glu Ile Gln Gly Ile Pro Asp Gln Val Lys Ala Ala Gln Ser Leu
            915                 920                 925
Leu Gln Gly Phe Ile Gly Ala Ser Ser Asn Ser Arg Gln Ala Pro Gln
    930                 935                 940
Ser Ser Arg Met Ala His Tyr Phe
945                 950
```

<210> SEQ ID NO 26
<211> LENGTH: 1737
<212> TYPE: DNA
<213> ORGANISM: Oryza sativa

<400> SEQUENCE: 26

```
atgccgctcg ccacgctgct cggccacctc gccgccggcc gcttcggcct cgtgcaggcg    60
ctcaccggcg ccgcgaccgc ggcggccgcg caccgactcc tccacctcct cctccgcaca   120
gcgccgccgc ctccctcccc ggacctcgtc tccctcgcgc ggtggtcgcg cgcccacttc   180
cgcgcgccgc tccgctccg gctccacggg ctcctcctcg cccgcctcgc ctccaagggg   240
ctctaccccc tcctccgctc cgagctccac gtcctcgccg cggcgcgcct ccactccccc   300
gcatccatcc tccgcgctct cccctccccg tccgcgtccg cgtccgcatc cacgccgctc   360
atcgccgaca tgctcgtcct cgccctcgcc agggcatccc agcccctcag gcgtacgac   420
gcgttcctcc tcgccgggga gagccacccg cggcaccgcc cctccacctc ctccgtgaac   480
gcccttctcg ccggcctcgt cggcgccaag cgggtcgacc tcgccgagaa ggcgttcagg   540
```

```
agcgcgctgc ggcggcgcgt gtcaccggac atctacacct tcaacaccgt catctccggc    600
ctctgcagga tcggccagct ccgcaaagcc ggcgatgtcg ccaaggacat caaggcatgg    660
ggtctggctc cctctgtggc cacctacaat agcctcatcg atgggtactg caagaagggt    720
ggagctggga acatgtacca tgtcgacatg cttttgaagg agatggtcga agccgggatc    780
tcaccgactg cagttacatt tggtgtgttg atcaatgggt attgcaagaa ctcgaatact    840
gcggccgcag tgagagtctt cgaggagatg aagcagcagg ggatcgctgc gagtgtcgtg    900
acgtataatt cgctaatttc aggtctctgc agtgagggta aggtggagga agggtgaag    960
ctgatggagg agatggagga tttggggctg tcacccaatg aaatcacctt tggctgtgtt   1020
ctgaaagggt tttgtaagaa gggaatgatg gcagatgcca atgattggat tgatggtatg   1080
acagagagga atgtggaacc tgatgtggtt atttacaata tcttgatcga tgtgtatcgc   1140
cgtcttggaa aaatggagga tgcaatggcg gtgaaggagg caatggcaaa gaaggggatc   1200
agtcccaatg tcacaacata taattgcttg ataacagggt ttagccgcag tggggattgg   1260
aggagtgctt ctggccttct ggatgagatg aaggagaaag gtattgaagc agacgtcgtc   1320
acttacaatg tgcttattgg tgctttgtgc tgcaaaggtg aggtacggaa agctgtaaag   1380
ctcttggatg aaatgtcgga agttggattg gaaccaaacc atctgaccta caataccata   1440
atacaggggt tctgtgataa gggtaacatt aagtctgcct atgaaattag aaccaggatg   1500
gaaaaatgtc ggaaacgggc aaatgtggtt acgtacaatg tgttcatcaa gtatttctgc   1560
cagatagga agatggatga agctaatgat ctactcaatg agatgttgga caaatgtcta   1620
gttccaaacg ggatcactta tgaaacgata aagaggggga tgatggaaaa aggctataca   1680
ccagatatta gagggtgcac tgtctcacaa gcttctgaaa acccagcatc atcctga      1737
```

<210> SEQ ID NO 27
<211> LENGTH: 578
<212> TYPE: PRT
<213> ORGANISM: Oryza sativa

<400> SEQUENCE: 27

```
Met Pro Leu Ala Thr Leu Leu Gly His Leu Ala Ala Gly Arg Phe Gly
 1               5                  10                  15

Leu Val Gln Ala Leu Thr Gly Ala Ala Thr Ala Ala Ala His Arg
                20                  25                  30

Leu Leu His Leu Leu Leu Arg Thr Ala Pro Pro Pro Leu Pro Asp
             35                  40                  45

Leu Val Ser Leu Ala Arg Trp Ser Arg Ala His Phe Arg Ala Pro Leu
     50                  55                  60

Pro Leu Arg Leu His Gly Leu Leu Ala Arg Leu Ala Ser Lys Gly
 65                  70                  75                  80

Leu Tyr Pro Leu Arg Ser Glu Leu His Val Leu Ala Ala Arg
                85                  90                  95

Leu His Ser Pro Ala Ser Ile Leu Arg Ala Leu Pro Ser Pro Ser Ala
            100                 105                 110

Ser Ala Ser Ala Ser Thr Pro Leu Ile Ala Asp Met Leu Val Leu Ala
            115                 120                 125

Leu Ala Arg Ala Ser Gln Pro Leu Arg Ala Tyr Asp Ala Phe Leu Leu
            130                 135                 140

Ala Gly Glu Ser His Pro Arg His Arg Pro Ser Thr Ser Ser Val Asn
145                 150                 155                 160

Ala Leu Leu Ala Gly Leu Val Gly Ala Lys Arg Val Asp Leu Ala Glu
```

-continued

```
                165                 170                 175
Lys Ala Phe Arg Ser Ala Leu Arg Arg Arg Val Ser Pro Asp Ile Tyr
            180                 185                 190
Thr Phe Asn Thr Val Ile Ser Gly Leu Cys Arg Ile Gly Gln Leu Arg
            195                 200                 205
Lys Ala Gly Asp Val Ala Lys Asp Ile Lys Ala Trp Gly Leu Ala Pro
            210                 215                 220
Ser Val Ala Thr Tyr Asn Ser Leu Ile Asp Gly Tyr Cys Lys Lys Gly
225                 230                 235                 240
Gly Ala Gly Asn Met Tyr His Val Asp Met Leu Leu Lys Glu Met Val
            245                 250                 255
Glu Ala Gly Ile Ser Pro Thr Ala Val Thr Phe Gly Val Leu Ile Asn
            260                 265                 270
Gly Tyr Cys Lys Asn Ser Asn Thr Ala Ala Val Arg Val Phe Glu
            275                 280                 285
Glu Met Lys Gln Gln Gly Ile Ala Ala Ser Val Val Thr Tyr Asn Ser
            290                 295                 300
Leu Ile Ser Gly Leu Cys Ser Glu Gly Lys Val Glu Glu Gly Val Lys
305                 310                 315                 320
Leu Met Glu Glu Met Glu Asp Leu Gly Leu Ser Pro Asn Glu Ile Thr
            325                 330                 335
Phe Gly Cys Val Leu Lys Gly Phe Cys Lys Lys Gly Met Met Ala Asp
            340                 345                 350
Ala Asn Asp Trp Ile Asp Gly Met Thr Glu Arg Asn Val Glu Pro Asp
            355                 360                 365
Val Val Ile Tyr Asn Ile Leu Ile Asp Val Tyr Arg Arg Leu Gly Lys
            370                 375                 380
Met Glu Asp Ala Met Ala Val Lys Glu Ala Met Ala Lys Lys Gly Ile
385                 390                 395                 400
Ser Pro Asn Val Thr Thr Tyr Asn Cys Leu Ile Thr Gly Phe Ser Arg
            405                 410                 415
Ser Gly Asp Trp Arg Ser Ala Ser Gly Leu Leu Asp Glu Met Lys Glu
            420                 425                 430
Lys Gly Ile Glu Ala Asp Val Val Thr Tyr Asn Val Leu Ile Gly Ala
            435                 440                 445
Leu Cys Cys Lys Gly Glu Val Arg Lys Ala Val Lys Leu Leu Asp Glu
            450                 455                 460
Met Ser Glu Val Gly Leu Glu Pro Asn His Leu Thr Tyr Asn Thr Ile
465                 470                 475                 480
Ile Gln Gly Phe Cys Asp Lys Gly Asn Ile Lys Ser Ala Tyr Glu Ile
            485                 490                 495
Arg Thr Arg Met Glu Lys Cys Arg Lys Arg Ala Asn Val Val Thr Tyr
            500                 505                 510
Asn Val Phe Ile Lys Tyr Phe Cys Gln Ile Gly Lys Met Asp Glu Ala
            515                 520                 525
Asn Asp Leu Leu Asn Glu Met Leu Asp Lys Cys Leu Val Pro Asn Gly
            530                 535                 540
Ile Thr Tyr Glu Thr Ile Lys Glu Gly Met Met Glu Lys Gly Tyr Thr
545                 550                 555                 560
Pro Asp Ile Arg Gly Cys Thr Val Ser Gln Ala Ser Glu Asn Pro Ala
            565                 570                 575
Ser Ser
```

<210> SEQ ID NO 28
<211> LENGTH: 1365
<212> TYPE: DNA
<213> ORGANISM: Oryza sativa

<400> SEQUENCE: 28

```
atggctgatg atggtcgctg cccacctgat gtggtgtcgt ataataccat cattgatggt      60
ctcttcaaag agggtgatgt ggacaaagct tacatcacat accatgaaat gctggaccgg     120
agggtttctc cagatgctgt gacttacaac tctatcattg ctgccttaag caaggctcaa     180
gctatggaca gggccatgga ggtacttaca gtgatggtta tgcccaattg cttcacatat     240
aatagtatta tgcatggata ttgttcttca ggacagtcgg aaaaggctat tggtattttc     300
agaaagatgt gcagtgatgg tattgaacca gatgttgtta cttataactc gttgatggac     360
tatctctgca gaacggaaa atgcacagaa gccagaaaga ttttgattc tatggtcaag      420
aggggtctca agcctgatat tactacctat ggtaccctgc ttcatgggta tgcttccaaa     480
ggagctcttg ttgagatgca tgatctctta gctttgatgg tacaaaatgg catgcaactt     540
gatcatcatg tcttcaacat attaatatgt gcatacacta acaagaaaaa agtagacgag     600
gtcgtgcttg tattcagcaa aatgaggcag caaggattga ctccgaacgc agtgaactat     660
agaacagtga tagatggact ttgcaagtta ggtagactag atgatgctat gcttaatttt     720
gagcagatga ttgataaagg actgacacct aacgttgttg tttataccct cctaattcat     780
gctctctgta cctatgacaa atgggagaag gccgaggagt taatttttga aatattggat     840
caaggtatca atcccaacat tgtgtttttt aatacaatat tggacagtct ttgcaaagaa     900
gggagggtta tagaatctaa aaaactcttt gacctgttgg gacatattgg tgtgaatcct     960
gatgtcatta catacagtac actcatcgat ggatattgct tagctggtaa gatggatgga    1020
gcaatgaagt tactcactgg catggtctca gttgggttga aacctgatag tgttacatat    1080
agcactttga ttaatggtta ctgtaaaatt aatagaatgg aggacgcatt agctctttc    1140
aaggagatgg aaagcaatgg tgttaatcct gatattatta catataacat aattctgcat    1200
ggtttatttc gcaccagaag aactgctgct gcaaaagaac tatatgccag gattaccgaa    1260
agtggaacgc agcttgaact tagcacatac aacataatcc tcatggactt tgcaaaaaca    1320
aactcactga tgatgcactt cggatgtttc agaacctatg tttga                    1365
```

<210> SEQ ID NO 29
<211> LENGTH: 454
<212> TYPE: PRT
<213> ORGANISM: Oryza sativa

<400> SEQUENCE: 29

```
Met Ala Asp Asp Gly Arg Cys Pro Pro Asp Val Val Ser Tyr Asn Thr
  1               5                  10                  15

Ile Ile Asp Gly Leu Phe Lys Glu Gly Asp Val Asp Lys Ala Tyr Ile
             20                  25                  30

Thr Tyr His Glu Met Leu Asp Arg Arg Val Ser Pro Asp Ala Val Thr
         35                  40                  45

Tyr Asn Ser Ile Ile Ala Ala Leu Ser Lys Ala Gln Ala Met Asp Arg
     50                  55                  60

Ala Met Glu Val Leu Thr Val Met Val Met Pro Asn Cys Phe Thr Tyr
 65                  70                  75                  80

Asn Ser Ile Met His Gly Tyr Cys Ser Ser Gly Gln Ser Glu Lys Ala
                 85                  90                  95
```

```
Ile Gly Ile Phe Arg Lys Met Cys Ser Asp Gly Ile Glu Pro Asp Val
            100                 105                 110
Val Thr Tyr Asn Ser Leu Met Asp Tyr Leu Cys Lys Asn Gly Lys Cys
        115                 120                 125
Thr Glu Ala Arg Lys Ile Phe Asp Ser Met Val Lys Arg Gly Leu Lys
    130                 135                 140
Pro Asp Ile Thr Thr Tyr Gly Thr Leu Leu His Gly Tyr Ala Ser Lys
145                 150                 155                 160
Gly Ala Leu Val Glu Met His Asp Leu Ala Leu Met Val Gln Asn
                165                 170                 175
Gly Met Gln Leu Asp His His Val Phe Asn Ile Leu Ile Cys Ala Tyr
            180                 185                 190
Thr Lys Gln Glu Lys Val Asp Glu Val Val Leu Val Phe Ser Lys Met
        195                 200                 205
Arg Gln Gln Gly Leu Thr Pro Asn Ala Val Asn Tyr Arg Thr Val Ile
    210                 215                 220
Asp Gly Leu Cys Lys Leu Gly Arg Leu Asp Asp Ala Met Leu Asn Phe
225                 230                 235                 240
Glu Gln Met Ile Asp Lys Gly Leu Thr Pro Asn Val Val Tyr Thr
                245                 250                 255
Ser Leu Ile His Ala Leu Cys Thr Tyr Asp Lys Trp Glu Lys Ala Glu
            260                 265                 270
Glu Leu Ile Phe Glu Ile Leu Asp Gln Gly Ile Asn Pro Asn Ile Val
        275                 280                 285
Phe Phe Asn Thr Ile Leu Asp Ser Leu Cys Lys Glu Gly Arg Val Ile
    290                 295                 300
Glu Ser Lys Lys Leu Phe Asp Leu Leu Gly His Ile Gly Val Asn Pro
305                 310                 315                 320
Asp Val Ile Thr Tyr Ser Thr Leu Ile Asp Gly Tyr Cys Leu Ala Gly
                325                 330                 335
Lys Met Asp Gly Ala Met Lys Leu Leu Thr Gly Met Val Ser Val Gly
            340                 345                 350
Leu Lys Pro Asp Ser Val Thr Tyr Ser Thr Leu Ile Asn Gly Tyr Cys
        355                 360                 365
Lys Ile Asn Arg Met Glu Asp Ala Leu Ala Leu Phe Lys Glu Met Glu
    370                 375                 380
Ser Asn Gly Val Asn Pro Asp Ile Ile Thr Tyr Asn Ile Ile Leu His
385                 390                 395                 400
Gly Leu Phe Arg Thr Arg Thr Ala Ala Lys Glu Leu Tyr Ala
                405                 410                 415
Arg Ile Thr Glu Ser Gly Thr Gln Leu Glu Leu Ser Thr Tyr Asn Ile
            420                 425                 430
Ile Leu Met Asp Phe Ala Lys Thr Asn Ser Leu Met Met His Phe Gly
        435                 440                 445
Cys Phe Arg Thr Tyr Val
    450

<210> SEQ ID NO 30
<211> LENGTH: 1386
<212> TYPE: DNA
<213> ORGANISM: Oryza sativa

<400> SEQUENCE: 30
atggcgcgcc gcgccgcttc ccgcgctgtt ggctcggagg gctcgatcca agggcgaggg    60
```

```
ggccgcgcgg ggggcaatgg cgccgaggac gcacgccacg tgttcgacga attgcttcgg      120
cgtggcaagg gcgccacgat ctacggcttg aaccgcgccc tcgacgacgt cgcgcgtcac      180
agccccgcgg ccgccgtgtc ccgctacaac cgcatggccc gagccggcgc cgacgaggta      240
actcccaact tgtacaccta cagcgttctc atcggttgct gctgccgggc gggccgcttg      300
gacctcggtt tcgcggcctt gggcaatgtc attaagaagg gatttagagt ggaagccatc      360
accttcactc ctctgctcaa gggcctctgt gccgacaaga ggacgagcga cgcaatggac      420
atagtgctct gcagaatgac ccagctcggc tgcataccaa atgtcttctc ctgcaccatt      480
cttctcaagg gtctgtgtga tgagaacaga agccaagaag ctctcgagct gctccaaatg      540
atgcctgatg atggaggtga ctgcccacct gatgtggtgt tgtacaacac cgtcatcaat      600
ggcttcttca agagggggga tccggacaaa gcttacgcta cataccatga aatgtttgac      660
caggggattt tgccagatgt tgtgacttac agctctatta tcgctgcctt atgcaaggct      720
caagctatgg acaaggccat ggaggtactt aacaccatgg ttaagaatgg tgtcatgcct      780
aattgcagga catataatag tattgtgcac ggatattgct cttcagggca gttgacagag      840
gctattggat ttctcaaaat gatgtgcagt gatggtgtcg aaccagatgt tgttacttgt      900
aacttgctga tggattatct ttgcaagaac agaagatgca cggaagctag aaagattttc      960
aattctatga ccaagtgtgg cctaaagcct gatattacta cctattgtac cctgcttcag     1020
gggtatgcta ccaaaggagc ccttgttgag atgcatgatc tcctggattt gatggtatgg     1080
aacggtatcc aacctaatca tcatgtattc aacattctaa tatgtgcata cgctaaacaa     1140
gaaaaagtag atgaggcgat gcttgtattc agcaaaatga ggcagcaagg attgagtccg     1200
aatgcagtga actacagaac agtcatagat gtactctgca agctaggcag agtatacgat     1260
gcagtgctta ccttaaagca gatgatcaat gaaggactaa cccctgacat cattgtatat     1320
acccccctaa ttcatggttt ttgtacctgt gacaaatggg agaaggctga ggagttaatt     1380
ttttaa                                                                1386
```

<210> SEQ ID NO 31
<211> LENGTH: 461
<212> TYPE: PRT
<213> ORGANISM: Oryza sativa

<400> SEQUENCE: 31

```
Met Ala Arg Arg Ala Ala Ser Arg Ala Val Gly Ser Glu Gly Ser Ile
1               5                   10                  15

Gln Gly Arg Gly Gly Arg Ala Gly Gly Asn Gly Ala Glu Asp Ala Arg
            20                  25                  30

His Val Phe Asp Glu Leu Leu Arg Arg Gly Lys Gly Ala Thr Ile Tyr
        35                  40                  45

Gly Leu Asn Arg Ala Leu Asp Asp Val Ala Arg His Ser Pro Ala Ala
    50                  55                  60

Ala Val Ser Arg Tyr Asn Arg Met Ala Arg Ala Gly Ala Asp Glu Val
65                  70                  75                  80

Thr Pro Asn Leu Tyr Thr Tyr Ser Val Leu Ile Gly Cys Cys Cys Arg
                85                  90                  95

Ala Gly Arg Leu Asp Leu Gly Phe Ala Ala Leu Gly Asn Val Ile Lys
            100                 105                 110

Lys Gly Phe Arg Val Glu Ala Ile Thr Phe Thr Pro Leu Leu Lys Gly
        115                 120                 125
```

```
Leu Cys Ala Asp Lys Arg Thr Ser Asp Ala Met Asp Ile Val Leu Cys
130                 135                 140

Arg Met Thr Gln Leu Gly Cys Ile Pro Asn Val Phe Ser Cys Thr Ile
145                 150                 155                 160

Leu Leu Lys Gly Leu Cys Asp Glu Asn Arg Ser Gln Glu Ala Leu Glu
                165                 170                 175

Leu Leu Gln Met Met Pro Asp Gly Gly Asp Cys Pro Pro Asp Val
            180                 185                 190

Val Leu Tyr Asn Thr Val Ile Asn Gly Phe Phe Lys Glu Gly Asp Pro
            195                 200                 205

Asp Lys Ala Tyr Ala Thr Tyr His Glu Met Phe Asp Gln Gly Ile Leu
        210                 215                 220

Pro Asp Val Val Thr Tyr Ser Ser Ile Ile Ala Ala Leu Cys Lys Ala
225                 230                 235                 240

Gln Ala Met Asp Lys Ala Met Glu Val Leu Asn Thr Met Val Lys Asn
                245                 250                 255

Gly Val Met Pro Asn Cys Arg Thr Tyr Asn Ser Ile Val His Gly Tyr
            260                 265                 270

Cys Ser Ser Gly Gln Leu Thr Glu Ala Ile Gly Phe Leu Lys Met Met
        275                 280                 285

Cys Ser Asp Gly Val Glu Pro Asp Val Val Thr Cys Asn Leu Leu Met
290                 295                 300

Asp Tyr Leu Cys Lys Asn Arg Arg Cys Thr Glu Ala Arg Lys Ile Phe
305                 310                 315                 320

Asn Ser Met Thr Lys Cys Gly Leu Lys Pro Asp Ile Thr Thr Tyr Cys
                325                 330                 335

Thr Leu Leu Gln Gly Tyr Ala Thr Lys Gly Ala Leu Val Glu Met His
            340                 345                 350

Asp Leu Leu Asp Leu Met Val Trp Asn Gly Ile Gln Pro Asn His His
        355                 360                 365

Val Phe Asn Ile Leu Ile Cys Ala Tyr Ala Lys Gln Glu Lys Val Asp
370                 375                 380

Glu Ala Met Leu Val Phe Ser Lys Met Arg Gln Gln Gly Leu Ser Pro
385                 390                 395                 400

Asn Ala Val Asn Tyr Arg Thr Val Ile Asp Val Leu Cys Lys Leu Gly
                405                 410                 415

Arg Val Tyr Asp Ala Val Leu Thr Leu Lys Gln Met Ile Asn Glu Gly
            420                 425                 430

Leu Thr Pro Asp Ile Ile Val Tyr Thr Pro Leu Ile His Gly Phe Cys
        435                 440                 445

Thr Cys Asp Lys Trp Glu Lys Ala Glu Glu Leu Ile Phe
450                 455                 460
```

<210> SEQ ID NO 32
<211> LENGTH: 1521
<212> TYPE: DNA
<213> ORGANISM: Oryza sativa

<400> SEQUENCE: 32

```
atggcacgcc gcgtcgctgc ccgcgcccgc gcccgcgccg gcggcgtccc gcgctcggag    60
ggtacgatcc aagaccgagc acgcgttggg agcggtggcg ccgaggacgc actcgacgtg   120
ttcgacgaat tgctccggcg aggcatcggc gctccgatcc gcagcttgaa cggcgctctc   180
gccgacgtcg cgcgcgacaa ccccgcggcc gctgtgtccc gcttcaaccg catggcacga   240
```

```
gctggtgcca gcatggtaac tcccaccgtg cacacctatg gcatcctcat cggctgctgc    300
tgcagtgcgg gccgcttaga cctcggtttc gcggccttgg gccatgtcgt taagaaggga    360
ttcagagtgg aacccatcat ctttaatcct ctgctcaagg gcctctgtgc agacaagagg    420
acggacgacg caatggacat agtgctccgt ggaatgaccg agctcagctg cgtgccaaat    480
gtcttctccc acaccattat tctcaaggga ctctgtcatg agaacagaag ccaagaagct    540
ctcgagctgc tccacatgat ggctgatgat ggaggaggct gcttacctaa tgttgtgtca    600
tacagcaccg tcatcgatgg cctcttgaaa ggagggatc cggacaaagc ctacgctaca    660
taccgtgaaa tgcttgaccg gaggattttg ccaaatgttg tgatttacag ctccattatt    720
gctgccctat gcaagggtca agcaatggac aaggccatgg aggtacacga taggatggtt    780
aagaatggag ttacacccaa ttgcttcacg tatactagtc ttgtgcatgg attttgctct    840
tcagggcagt tgacagaggc tattaaattt ctagaaaaga tgtgcagcaa tggtgttgaa    900
ccaaatgttg ttacttatag ctcgtttatg gactatctct gcaagaacgg aagatgcaca    960
gaagctagaa agatttttga ttctatggtc aagagggggcc taaagcctga tattactacc   1020
tacagtagct tacttcatgg gtatgctatc gaaggagctc ttgttgagat gcatggtctc   1080
tttgatttga tggtacaaag tgatatgcaa cccgatcatt atgtcttcaa cacactaata   1140
tatgcatccg ccaagcaagg aaaagtagat gaggccatgc ttgtatttag caaaatgagg   1200
cagcaaggat tgaaacctaa ttgtgttacg tatagcactt tgattaatgg ctactgtaaa   1260
attactagga tggagaatgc tttagcactt ttccaagaga tggtgagcaa tggtgttagt   1320 cctaattta tcacatataa cataatgctg caaggtttat ttcgtacagg aagaactgct   1380
actgcaaaag aattctatgt acagattatc aaaagtggca aaaagatct tatagaacag   1440 gggttgctag aagaattgga tgatctattt ctttcaatgg aggacaatga ctgtagtact   1500
gtgtcgactc ctgcatgcta a                                              1521
```

<210> SEQ ID NO 33
<211> LENGTH: 506
<212> TYPE: PRT
<213> ORGANISM: Oryza sativa

<400> SEQUENCE: 33

```
Met Ala Arg Arg Val Ala Ala Arg Ala Arg Ala Gly Gly Val
  1               5                  10                  15

Pro Arg Ser Glu Gly Thr Ile Gln Asp Arg Ala Arg Val Gly Ser Gly
                20                  25                  30

Gly Ala Glu Asp Ala Leu Asp Val Phe Asp Glu Leu Leu Arg Arg Gly
            35                  40                  45

Ile Gly Ala Pro Ile Arg Ser Leu Asn Gly Ala Leu Ala Asp Val Ala
        50                  55                  60

Arg Asp Asn Pro Ala Ala Ala Val Ser Arg Phe Asn Arg Met Ala Arg
    65                  70                  75                  80

Ala Gly Ala Ser Met Val Thr Pro Thr Val His Thr Tyr Gly Ile Leu
                    85                  90                  95

Ile Gly Cys Cys Cys Ser Ala Gly Arg Leu Asp Leu Gly Phe Ala Ala
                100                 105                 110

Leu Gly His Val Val Lys Lys Gly Phe Arg Val Glu Pro Ile Ile Phe
            115                 120                 125

Asn Pro Leu Leu Lys Gly Leu Cys Ala Asp Lys Arg Thr Asp Asp Ala
        130                 135                 140
```

```
Met Asp Ile Val Leu Arg Gly Met Thr Glu Leu Ser Cys Val Pro Asn
145                 150                 155                 160

Val Phe Ser His Thr Ile Ile Leu Lys Gly Leu Cys His Glu Asn Arg
                165                 170                 175

Ser Gln Glu Ala Leu Glu Leu Leu His Met Met Ala Asp Asp Gly Gly
            180                 185                 190

Gly Cys Leu Pro Asn Val Val Ser Tyr Ser Thr Val Ile Asp Gly Leu
        195                 200                 205

Leu Lys Gly Gly Asp Pro Asp Lys Ala Tyr Ala Thr Tyr Arg Glu Met
    210                 215                 220

Leu Asp Arg Arg Ile Leu Pro Asn Val Val Ile Tyr Ser Ser Ile Ile
225                 230                 235                 240

Ala Ala Leu Cys Lys Gly Gln Ala Met Asp Lys Ala Met Glu Val His
                245                 250                 255

Asp Arg Met Val Lys Asn Gly Val Thr Pro Asn Cys Phe Thr Tyr Thr
                260                 265                 270

Ser Leu Val His Gly Phe Cys Ser Ser Gly Gln Leu Thr Glu Ala Ile
            275                 280                 285

Lys Phe Leu Glu Lys Met Cys Ser Asn Gly Val Glu Pro Asn Val Val
290                 295                 300

Thr Tyr Ser Ser Phe Met Asp Tyr Leu Cys Lys Asn Gly Arg Cys Thr
305                 310                 315                 320

Glu Ala Arg Lys Ile Phe Asp Ser Met Val Lys Arg Gly Leu Lys Pro
                325                 330                 335

Asp Ile Thr Thr Tyr Ser Ser Leu Leu His Gly Tyr Ala Ile Glu Gly
                340                 345                 350

Ala Leu Val Glu Met His Gly Leu Phe Asp Leu Met Val Gln Ser Asp
            355                 360                 365

Met Gln Pro Asp His Tyr Val Phe Asn Thr Leu Ile Tyr Ala Ser Ala
370                 375                 380

Lys Gln Gly Lys Val Asp Glu Ala Met Leu Val Phe Ser Lys Met Arg
385                 390                 395                 400

Gln Gln Gly Leu Lys Pro Asn Cys Val Thr Tyr Ser Thr Leu Ile Asn
                405                 410                 415

Gly Tyr Cys Lys Ile Thr Arg Met Glu Asn Ala Leu Ala Leu Phe Gln
                420                 425                 430

Glu Met Val Ser Asn Gly Val Ser Pro Asn Phe Ile Thr Tyr Asn Ile
            435                 440                 445

Met Leu Gln Gly Leu Phe Arg Thr Gly Arg Thr Ala Thr Ala Lys Glu
450                 455                 460

Phe Tyr Val Gln Ile Ile Lys Ser Gly Lys Lys Asp Leu Ile Glu Gln
465                 470                 475                 480

Gly Leu Leu Glu Glu Leu Asp Asp Leu Phe Leu Ser Met Glu Asp Asn
                485                 490                 495

Asp Cys Ser Thr Val Ser Thr Pro Ala Cys
                500                 505

<210> SEQ ID NO 34
<211> LENGTH: 1884
<212> TYPE: DNA
<213> ORGANISM: Oryza sativa

<400> SEQUENCE: 34
atggcgcgcc gcgccgcttc ccgcgctgct ggcgcccttc gctcggaggg ctcgatccaa      60
```

-continued

| | |
|---|---|
| gggcgagggg gccgcgcggg gggcagtggc ggtggcgcgg aggacgcacg ccacgtgttc | 120 |
| gacgaattgc tccgtcgtgg cataccagat gtcttctcct acaatattct tctcaacggg | 180 |
| ctgtgtgatg agaacagaag ccaagaagct ctcgagttac tgcacataat ggctgatgat | 240 |
| ggaggtgact gcccacctga tgtggtgtcg tacagcaccg tcatcaatgg cttcttcaag | 300 |
| gaggggatc tggacaaaat gcttgaccag aggatttcgc caaatgttgt gacctacaac | 360 |
| tctattattg ctgcgctatg caaggctcaa actgtggaca aggccatgga ggtacttacc | 420 |
| accatggtta agagtggtgt catgcctgat tgcatgacat ataatagtat tgtgcatggg | 480 |
| ttttgctctt cagggcagcc gaaagaggct attgtatttc tcaaaaagat gcgcagtgat | 540 |
| ggtgtcgaac cagatgttgt tacttataac tcgctcatgg attatctttg caagaacgga | 600 |
| agatgcacgg aagcaagaaa gattttgat tctatgacca gaggggcct aaagcctgat | 660 |
| attactacct atggtaccct gcttcagggg tatgctacca aggagccct tgttgagatg | 720 |
| catggtctct ggatttgat ggtacgaaac ggtatccacc ctaatcatta tgttttcagc | 780 |
| attctagtat gtgcatacgc taaacaagag aaagtagaag aggcaatgct tgtattcagc | 840 |
| aaaatgaggc agcaaggatt gaatccgaat gcagtgacct atggaacagt tatagatgta | 900 |
| ctttgcaagt caggtagagt agaagatgct atgctttatt ttgagcagat gatcgatgaa | 960 |
| ggactaagac ctgacagcat tgtttataac tccctaattc atagtctctg tatctttgac | 1020 |
| aaatgggaga aggctgaaga gttatttctt gaaatgttgg atcgaggcat ctgtcttagc | 1080 |
| actattttct ttaattcaat aattgacagt cattgcaaag aagggagggt tatagaatct | 1140 |
| ggaaaactct ttgacttgat ggtacgaatt ggtgtgaagc ccgatatcat tacccttggc | 1200 |
| aggttttgg ggagcgcaag gcgcgactac tcactgttcg tcaacatcta cttcatcttc | 1260 |
| accaacatgt cgaacactgg agacaaggag aaggagactc ccgtcaacac caacggaggc | 1320 |
| aatactgcct caaactccag cggaggacca ttcttgggca catacaacat aatccttcat | 1380 |
| ggactttgca aaaacaaact cactgatgat gcacttcgaa tgtttcagaa cctatgtttg | 1440 |
| atggatttga agcttgaggc taggactttc aacattatga ttgatgcatt gcttaaagtt | 1500 |
| ggcagaaatg atgaagccaa ggatttgttt gttgctttct cgtctaacgg tttagtgccg | 1560 |
| aattattgga cgtacagatt gatggctgaa aatattatag acagggggtt gctagaagaa | 1620 |
| ttggatcaac tctttctttc aatggaggac aatggctgta ctgttgactc tggcatgcta | 1680 |
| aatttcattg ttagggaact gttgcagaga ggtgagataa ccagggctgg cacttacctt | 1740 |
| tccatgattg atgagaagca cttttccctc gaagcatcca ctgcttcctt gtttatagat | 1800 |
| cttttgtctg ggggaaaata tcaagaatat catatatttc tccctgaaaa atacaagtcc | 1860 |
| tttatagaat ctttgagctg ctga | 1884 |

<210> SEQ ID NO 35
<211> LENGTH: 627
<212> TYPE: PRT
<213> ORGANISM: Oryza sativa

<400> SEQUENCE: 35

Met Ala Arg Arg Ala Ala Ser Arg Ala Ala Gly Ala Leu Arg Ser Glu
1               5                   10                  15

Gly Ser Ile Gln Gly Arg Gly Gly Arg Ala Gly Gly Ser Gly Gly Gly
            20                  25                  30

Ala Glu Asp Ala Arg His Val Phe Asp Glu Leu Leu Arg Arg Gly Ile
        35                  40                  45

```
Pro Asp Val Phe Ser Tyr Asn Ile Leu Leu Asn Gly Leu Cys Asp Glu
    50                  55                  60

Asn Arg Ser Gln Glu Ala Leu Glu Leu Leu His Ile Met Ala Asp Asp
 65              70                  75                  80

Gly Gly Asp Cys Pro Pro Asp Val Val Ser Tyr Ser Thr Val Ile Asn
                 85                  90                  95

Gly Phe Phe Lys Glu Gly Asp Leu Asp Lys Met Leu Asp Gln Arg Ile
            100                 105                 110

Ser Pro Asn Val Val Thr Tyr Asn Ser Ile Ile Ala Ala Leu Cys Lys
            115                 120                 125

Ala Gln Thr Val Asp Lys Ala Met Glu Val Leu Thr Thr Met Val Lys
            130                 135                 140

Ser Gly Val Met Pro Asp Cys Met Thr Tyr Asn Ser Ile Val His Gly
145                 150                 155                 160

Phe Cys Ser Ser Gly Gln Pro Lys Glu Ala Ile Val Phe Leu Lys Lys
                165                 170                 175

Met Arg Ser Asp Gly Val Glu Pro Asp Val Val Thr Tyr Asn Ser Leu
            180                 185                 190

Met Asp Tyr Leu Cys Lys Asn Gly Arg Cys Thr Glu Ala Arg Lys Ile
            195                 200                 205

Phe Asp Ser Met Thr Lys Arg Gly Leu Lys Pro Asp Ile Thr Thr Tyr
            210                 215                 220

Gly Thr Leu Leu Gln Gly Tyr Ala Thr Lys Gly Ala Leu Val Glu Met
225                 230                 235                 240

His Gly Leu Leu Asp Leu Met Val Arg Asn Gly Ile His Pro Asn His
                245                 250                 255

Tyr Val Phe Ser Ile Leu Val Cys Ala Tyr Ala Lys Gln Glu Lys Val
                260                 265                 270

Glu Glu Ala Met Leu Val Phe Ser Lys Met Arg Gln Gln Gly Leu Asn
            275                 280                 285

Pro Asn Ala Val Thr Tyr Gly Thr Val Ile Asp Val Leu Cys Lys Ser
290                 295                 300

Gly Arg Val Glu Asp Ala Met Leu Tyr Phe Glu Gln Met Ile Asp Glu
305                 310                 315                 320

Gly Leu Arg Pro Asp Ser Ile Val Tyr Asn Ser Leu Ile His Ser Leu
            325                 330                 335

Cys Ile Phe Asp Lys Trp Glu Lys Ala Glu Glu Leu Phe Leu Glu Met
            340                 345                 350

Leu Asp Arg Gly Ile Cys Leu Ser Thr Ile Phe Phe Asn Ser Ile Ile
            355                 360                 365

Asp Ser His Cys Lys Glu Gly Arg Val Ile Glu Ser Gly Lys Leu Phe
            370                 375                 380

Asp Leu Met Val Arg Ile Gly Val Lys Pro Asp Ile Ile Thr Leu Gly
385                 390                 395                 400

Arg Phe Leu Gly Ser Ala Arg Arg Asp Tyr Ser Leu Phe Val Asn Ile
                405                 410                 415

Tyr Phe Ile Phe Thr Asn Met Ser Asn Thr Gly Asp Lys Glu Lys Glu
            420                 425                 430

Thr Pro Val Asn Thr Asn Gly Gly Asn Thr Ala Ser Asn Ser Ser Gly
            435                 440                 445

Gly Pro Phe Leu Gly Thr Tyr Asn Ile Ile Leu His Gly Leu Cys Lys
450                 455                 460

Asn Lys Leu Thr Asp Asp Ala Leu Arg Met Phe Gln Asn Leu Cys Leu
```

-continued

```
                                 465                 470                 475                 480
            Met Asp Leu Lys Leu Glu Ala Arg Thr Phe Asn Ile Met Ile Asp Ala
                            485                 490                 495

Leu Leu Lys Val Gly Arg Asn Asp Glu Ala Lys Asp Leu Phe Val Ala
                        500                 505                 510

Phe Ser Ser Asn Gly Leu Val Pro Asn Tyr Trp Thr Tyr Arg Leu Met
                    515                 520                 525

Ala Glu Asn Ile Ile Gly Gln Gly Leu Leu Glu Leu Asp Gln Leu
                530                 535                 540

Phe Leu Ser Met Glu Asp Asn Gly Cys Thr Val Asp Ser Gly Met Leu
            545                 550                 555                 560

Asn Phe Ile Val Arg Glu Leu Leu Gln Arg Gly Glu Ile Thr Arg Ala
                            565                 570                 575

Gly Thr Tyr Leu Ser Met Ile Asp Glu Lys His Phe Ser Leu Glu Ala
                        580                 585                 590

Ser Thr Ala Ser Leu Phe Ile Asp Leu Leu Ser Gly Gly Lys Tyr Gln
                    595                 600                 605

Glu Tyr His Ile Phe Leu Pro Glu Lys Tyr Lys Ser Phe Ile Glu Ser
                610                 615                 620

Leu Ser Cys
            625
```

<210> SEQ ID NO 36
<211> LENGTH: 1554
<212> TYPE: DNA
<213> ORGANISM: Oryza sativa

<400> SEQUENCE: 36

| | |
|---|---|
| atggcgagaa gaggacgacg atactgtaga gcagagggaa cagaggagcg gggcactggt | 60 |
| gctccggtgg ctgggaggtg gcgacgtcgg cggccgaatg tgttcccgag cgccgcgctg | 120 |
| gagagccccg agctgcgacg gcatcacgcc gactaccggc cgtgggcggc gcacatggag | 180 |
| gcaaagccgg tctacttcgc gtcgaggcgt gcctccgggc ggcccgagct gcagcagcag | 240 |
| ctcgtccggc ccaccccaat ctgggccgat tgggccgatc tcagcctccc ggagcggaga | 300 |
| ccgatctggg ccgtccatcc gcgccgccca gccaatcgga cggtgggtgt attactgtac | 360 |
| tgccaggtcg gtgaccctcc gccgccgcg gcggcggcg cggcggcagg catggcgcgc | 420 |
| cgtgtcacca cccttacccg cgcccgcacc cgcgcccgcg gcggcggcgt ccccagcgcg | 480 |
| cagggtggta cgacccaaga cctagggcgc gcggggggca gtggcaccga gggcgcacgc | 540 |
| cacgtgctcg acgaattgcc gctacggggc tgggcgcct cgatctacag cttcaaccgc | 600 |
| accctcaccg acgtcgcgcg tgacagccca gccgcagcag tttcgctctt caaccgcatg | 660 |
| gcccgagccg cgccgacga ggtaactccc gacttgtgca cctacagcat tctcatcggt | 720 |
| tgctgctgcc gcgcgggccg cttggacctc ggtttcgcgg ccttgggcaa tgtcattaag | 780 |
| aagggattta gagtggaagc catcaccttc gctcctctgc tcaagggcct ctgtgccgac | 840 |
| aagaggacga gcgacgcaat ggacatagtg ctccgcagaa tgaccgagct cagctgcatg | 900 |
| ccagatgttt tctcctgcac cattcttctc aagggtctgt gtgatgagaa cagaagccaa | 960 |
| gaagctctcg agctgctgca catgatggcg gatgatcgag aggaggtag cccacctgat | 1020 |
| gtggtgtcgt ataccactgt catcaatggc ttcttcaaag agggggattc agacaaagct | 1080 |
| tacagtacat accatgaaat gcttgatcgg aggatttcac caaatgttgt gacctacagc | 1140 |
| tctattattg ctgcgttatg caaggctcaa gctatggaca aagccatgga ggtacttaac | 1200 |

-continued

```
accatggtta agaatggtgt catgcctgat tgcatgacat ataatagtat tctgcatgga    1260
tattgctctt cagggcagcc aaaagaggct attggaacac tcaaaaagat gcgcagtgat    1320
ggcgtcgaac caaatgttgt tacttataga tcactgatga attatctttg caagaatgga    1380
agatgcaccg aagctagaaa gattttcgat tctatgacca agagggggcct agagcctgat    1440 attgctacct atcgtaccct gcttcagggg tatgctacca aaggagccct tgttgagatg    1500
catgctctct tggatttgat ggatcctgag ttctacaagt atttggagaa gtga          1554
```

<210> SEQ ID NO 37
<211> LENGTH: 517
<212> TYPE: PRT
<213> ORGANISM: Oryza sativa

<400> SEQUENCE: 37

```
Met Ala Arg Arg Gly Arg Arg Tyr Cys Arg Ala Glu Gly Thr Glu Glu
 1               5                  10                  15

Arg Gly Thr Gly Ala Pro Val Ala Gly Arg Trp Arg Arg Arg Pro
            20                  25                  30

Asn Val Phe Pro Ser Ala Ala Leu Glu Ser Pro Glu Leu Arg Arg His
        35                  40                  45

His Ala Asp Tyr Arg Pro Trp Ala Ala His Met Glu Ala Lys Pro Val
    50                  55                  60

Tyr Phe Ala Ser Arg Arg Ala Ser Gly Arg Pro Glu Leu Gln Gln Gln
65                  70                  75                  80

Leu Val Arg Pro Thr Pro Ile Trp Ala Asp Trp Ala Asp Leu Ser Leu
                85                  90                  95

Pro Glu Arg Arg Pro Ile Trp Ala Val His Pro Arg Arg Pro Ala Asn
            100                 105                 110

Arg Thr Val Gly Val Leu Leu Tyr Cys Gln Val Gly Asp Pro Pro
        115                 120                 125

Pro Ala Ala Ala Ala Ala Ala Gly Met Ala Arg Arg Val Thr Thr
    130                 135                 140

Leu Thr Arg Ala Arg Thr Arg Ala Arg Gly Gly Gly Val Pro Ser Ala
145                 150                 155                 160

Gln Gly Gly Thr Thr Gln Asp Leu Gly Arg Ala Gly Ser Gly Thr
                165                 170                 175

Glu Gly Ala Arg His Val Leu Asp Glu Leu Pro Leu Arg Gly Trp Gly
            180                 185                 190

Ala Ser Ile Tyr Ser Phe Asn Arg Thr Leu Thr Asp Val Ala Arg Asp
        195                 200                 205

Ser Pro Ala Ala Val Ser Leu Phe Asn Arg Met Ala Arg Ala Gly
    210                 215                 220

Ala Asp Glu Val Thr Pro Asp Leu Cys Thr Tyr Ser Ile Leu Ile Gly
225                 230                 235                 240

Cys Cys Cys Arg Ala Gly Arg Leu Asp Leu Gly Phe Ala Ala Leu Gly
                245                 250                 255

Asn Val Ile Lys Lys Gly Phe Arg Val Glu Ala Ile Thr Phe Ala Pro
            260                 265                 270

Leu Leu Lys Gly Leu Cys Ala Asp Lys Arg Thr Ser Asp Ala Met Asp
        275                 280                 285

Ile Val Leu Arg Arg Met Thr Glu Leu Ser Cys Met Pro Asp Val Phe
    290                 295                 300

Ser Cys Thr Ile Leu Leu Lys Gly Leu Cys Asp Glu Asn Arg Ser Gln
```

-continued

```
            305                 310                 315                 320
        Glu Ala Leu Glu Leu Leu His Met Met Ala Asp Asp Arg Gly Gly Gly
                        325                 330                 335

Ser Pro Pro Asp Val Val Ser Tyr Thr Thr Val Ile Asn Gly Phe Phe
                        340                 345                 350

Lys Glu Gly Asp Ser Asp Lys Ala Tyr Ser Thr Tyr His Glu Met Leu
                        355                 360                 365

Asp Arg Arg Ile Ser Pro Asn Val Val Thr Tyr Ser Ser Ile Ile Ala
                        370                 375                 380

Ala Leu Cys Lys Ala Gln Ala Met Asp Lys Ala Met Glu Val Leu Asn
        385                 390                 395                 400

Thr Met Val Lys Asn Gly Val Met Pro Asp Cys Met Thr Tyr Asn Ser
                        405                 410                 415

Ile Leu His Gly Tyr Cys Ser Ser Gly Gln Pro Lys Glu Ala Ile Gly
                        420                 425                 430

Thr Leu Lys Lys Met Arg Ser Asp Gly Val Glu Pro Asn Val Val Thr
                        435                 440                 445

Tyr Arg Ser Leu Met Asn Tyr Leu Cys Lys Asn Gly Arg Cys Thr Glu
                        450                 455                 460

Ala Arg Lys Ile Phe Asp Ser Met Thr Lys Arg Gly Leu Glu Pro Asp
        465                 470                 475                 480

Ile Ala Thr Tyr Arg Thr Leu Leu Gln Gly Tyr Ala Thr Lys Gly Ala
                        485                 490                 495

Leu Val Glu Met His Ala Leu Leu Asp Leu Met Asp Pro Glu Phe Tyr
                        500                 505                 510

Lys Tyr Leu Glu Lys
                515

<210> SEQ ID NO 38
<211> LENGTH: 2784
<212> TYPE: DNA
<213> ORGANISM: Oryza sativa

<400> SEQUENCE: 38
atgcccttcc gaccgcgcct cccgctcccc ctcctcctcc tcctcctgcc tcacctccgg      60
cgccgccgct cctcccccg cccgcccgtg ccgcgtgga gaccgctctc gtattatccc       120
tcggcggcgg ccgcggcggc ggaggtgacg gagtccgagg aggacgcggc ggctgttggc     180
agggacaccc gagcccctcc ctccatcggc gggattgcac gggagcgcc tagggttggc      240 tgcaatggcg gggggctgc cgatgacgag gaggtcgaga ggaaggcccg cgctgtcgcg      300
cggatcaagc tctgccatga gcttctgcgg gagaggaggt ggcgcgcgat gcgggcagcc    360
ttggcgcagc tggtgactga gcaaggtgag catgctatga attttcccca ttctgattat    420
caactctact catgtggtat ctgaataact atggtgattg gtgtgaggag gcgtaggaat   480
ggcatcggta gttttgaact tctgatcgat atgaatgtgt gacacaggat atattgtttt  540
tccagaggca ttatcaattg atcattacca tataaaaaac agtaagaaaa gggtcgaaag    600
caatgcatac atagttgtat ttggtgtagt attattactg taattcgttt tttactagaa  660
ggtctctgca agtatgacaa actagtaaca taaaaattgt tcgcgtttaa tcttattgcg   720
cttcctgctg taggatctgg gtctgcagct gctctctgtg acatcttatg gaacagattc     780
agagagtgtg attccaacgg ttgtgtatgg gatgctctag cgaacagtta tgctagagct   840
cagatggttc atgatgccct ttacgttctt agtaaaatga gcagcctaaa catgcaaatc    900
```

```
tcggtgttca cctatgacag tttattgcac ggcttaagga tgacagacgt ggcattggag      960
cttttttgaag aaatggagtc ttgtggtgtc tctcccagtg aatattcgca tagtattatt   1020
attaatggcc tctgtaagca agataaggtt ggagaagctt tatctttcct tcaggaagct    1080
aggaaggagg gaaagtttaa acccttggga atgaccttta acattcttat gtctgcattg    1140
tgtaattggg ggtttgttca gtctgcaaaa tcatttttat gcctgatgct gaaatatgga    1200
ttagtccctg acaggtatac cttttctacc cttatacacg gtctatgtaa agtaggttca    1260
atggaggaag cattggatct tttcgagaga gtgacaaaag aaggaatgga acttgagatt    1320
gtgacctaca atagccttat caatgggtac cgattgcttg gtttaacaaa agaaattcct    1380
aaaatcatcc agatgatgag aggccaaggt gttgaacctg atcttgttac atatactata    1440
cttattgctg gtcactgcga aagtggtgat gttgaagaag gaatgaaggt aaggaaggat    1500
gtcctagacc aaggtttgca gttgaatatt gtcacatata gtgtccttct caatgctctc    1560
ttcaaaaaag gcatgttctg cgaaattgac aacctactcg gcgagatcta caatattggt    1620
ttggatatgg atgttatcgc atattccatc cttatccatg gtattgcaa gctaggggaa     1680
attgaaaagg ctcttcaagt atgtaatgca atgtgcagtt ctcagagggt aatgccaaca    1740
tcactgaacc attttttctat tcttctagga cttttgcaaga aaggattgtt agttgaagca   1800
aggtggtatt tggaaaatgt agctagaaaa tatcagccaa ctgatgtagt gttctataat    1860
gtcgttattg atggttatgc aaaacttggt gatattgtaa atgctgttcg tttgtatgat    1920
cagatcactg tagctggtat gcacccaacc attgtcacat gcaattctct tctatatggg   1980
tattgtaaaa ttggggatct gcaacttgcc gagagctatt ttagggctat tcagctaagt   2040
ggacttctac caacagcagt gacatacact accttgatgg atgcactctc tgaagctgga   2100
gaagttaata ccatgctaag tcttttttgat gaaatggttg caaagaggat caaggcaaat  2160
gcagtaactt acagtgtcat tgttaaaggg ctttgtaagc agctcagatt tgatgaggct   2220
atcaatgttc tcaaagatat ggatagcaaa ggtattaatg ctgacccgat aacttacaat   2280
accettatac aaggtttctg tgaatcagaa aacgttcaga tggctttcca catacatgac   2340
atcatgttat gccgtggcct tgtgccgaca cctgttactt ataacttgct tattaatgtg   2400
ctgtgtttga agggaaaagt tattcaagca gaaatacttt tggagtccct cagagaaaat   2460
ggcattaagt tgagaaaatt tgcgtacaca acacttatca aagctcagtg cgcaaaagga   2520
atgcctatca atgctgtttt gttagttggt aagcttctag atgcaggatt tgaagcttct   2580
attgaagatt tcagtgcagc aatcaatcga ctttgcaaaa gacaatttgc caaagaagcc   2640
tttatgtttg tcccgattat gctatctgtt ggtatttacc cagatactca aatatattgt   2700
gtgctaggca gagctctgca gaaaaatagt gagcttgtct atctacccat attaaatgca   2760
cttgctgtta aaactggtat ttaa                                           2784
```

<210> SEQ ID NO 39
<211> LENGTH: 811
<212> TYPE: PRT
<213> ORGANISM: Oryza sativa

<400> SEQUENCE: 39

```
Met Pro Phe Arg Pro Arg Leu Pro Leu Pro Leu Leu Leu Leu Leu
  1               5                  10                  15

Pro His Leu Arg Arg Arg Arg Ser Ser Pro Arg Pro Pro Val Pro Ala
                 20                  25                  30

Trp Arg Pro Leu Ser Tyr Tyr Pro Ser Ala Ala Ala Ala Ala Ala Glu
```

-continued

```
            35                  40                  45
Val Thr Glu Ser Glu Glu Asp Ala Ala Val Gly Arg Asp Thr Arg
     50                  55                  60

Ala Pro Pro Ser Ile Gly Gly Ile Ala Arg Gly Ala Pro Arg Val Gly
 65                  70                  75                  80

Cys Asn Gly Gly Ala Ala Asp Asp Glu Glu Val Glu Arg Lys Ala
                 85                  90                  95

Arg Ala Val Ala Arg Ile Lys Leu Cys His Glu Leu Leu Arg Glu Arg
                100                 105                 110

Arg Trp Arg Ala Met Arg Ala Ala Leu Ala Gln Leu Val Thr Glu Gln
                115                 120                 125

Gly Ser Gly Ser Ala Ala Ala Leu Cys Asp Ile Leu Trp Asn Arg Phe
         130                 135                 140

Arg Glu Cys Asp Ser Asn Gly Cys Val Trp Asp Ala Leu Ala Asn Ser
145                 150                 155                 160

Tyr Ala Arg Ala Gln Met Val His Asp Ala Leu Tyr Val Leu Ser Lys
                165                 170                 175

Met Ser Ser Leu Asn Met Gln Ile Ser Val Phe Thr Tyr Asp Ser Leu
             180                 185                 190

Leu His Gly Leu Arg Met Thr Asp Val Ala Leu Glu Leu Phe Glu Glu
         195                 200                 205

Met Glu Ser Cys Gly Val Ser Pro Ser Glu Tyr Ser His Ser Ile Ile
 210                 215                 220

Ile Asn Gly Leu Cys Lys Gln Asp Lys Val Gly Glu Ala Leu Ser Phe
225                 230                 235                 240

Leu Gln Glu Ala Arg Lys Glu Gly Lys Phe Lys Pro Leu Gly Met Thr
                245                 250                 255

Phe Asn Ile Leu Met Ser Ala Leu Cys Asn Trp Gly Phe Val Gln Ser
             260                 265                 270

Ala Lys Ser Phe Leu Cys Leu Met Leu Lys Tyr Gly Leu Val Pro Asp
         275                 280                 285

Arg Tyr Thr Phe Ser Thr Leu Ile His Gly Leu Cys Lys Val Gly Ser
     290                 295                 300

Met Glu Glu Ala Leu Asp Leu Phe Glu Arg Val Thr Lys Glu Gly Met
305                 310                 315                 320

Glu Leu Glu Ile Val Thr Tyr Asn Ser Leu Ile Asn Gly Tyr Arg Leu
                325                 330                 335

Leu Gly Leu Thr Lys Glu Ile Pro Lys Ile Ile Gln Met Met Arg Gly
             340                 345                 350

Gln Gly Val Glu Pro Asp Leu Val Thr Tyr Thr Ile Leu Ile Ala Gly
         355                 360                 365

His Cys Glu Ser Gly Asp Val Glu Glu Gly Met Lys Val Arg Lys Asp
     370                 375                 380

Val Leu Asp Gln Gly Leu Gln Leu Asn Ile Val Thr Tyr Ser Val Leu
385                 390                 395                 400

Leu Asn Ala Leu Phe Lys Lys Gly Met Phe Cys Glu Ile Asp Asn Leu
                405                 410                 415

Leu Gly Glu Ile Tyr Asn Ile Gly Leu Asp Met Asp Val Ile Ala Tyr
             420                 425                 430

Ser Ile Leu Ile His Gly Tyr Cys Lys Leu Gly Glu Ile Glu Lys Ala
         435                 440                 445

Leu Gln Val Cys Asn Ala Met Cys Ser Ser Gln Arg Val Met Pro Thr
 450                 455                 460
```

```
Ser Leu Asn His Phe Ser Ile Leu Leu Gly Leu Cys Lys Lys Gly Leu
465                 470                 475                 480

Leu Val Glu Ala Arg Trp Tyr Leu Glu Asn Val Ala Arg Lys Tyr Gln
                485                 490                 495

Pro Thr Asp Val Val Phe Tyr Asn Val Val Ile Asp Gly Tyr Ala Lys
            500                 505                 510

Leu Gly Asp Ile Val Asn Ala Val Arg Leu Tyr Asp Gln Ile Thr Val
            515                 520                 525

Ala Gly Met His Pro Thr Ile Val Thr Cys Asn Ser Leu Leu Tyr Gly
530                 535                 540

Tyr Cys Lys Ile Gly Asp Leu Gln Leu Ala Glu Ser Tyr Phe Arg Ala
545                 550                 555                 560

Ile Gln Leu Ser Gly Leu Leu Pro Thr Ala Val Thr Tyr Thr Thr Leu
                565                 570                 575

Met Asp Ala Leu Ser Glu Ala Gly Glu Val Asn Thr Met Leu Ser Leu
            580                 585                 590

Phe Asp Glu Met Val Ala Lys Arg Ile Lys Ala Asn Ala Val Thr Tyr
            595                 600                 605

Ser Val Ile Val Lys Gly Leu Cys Lys Gln Leu Arg Phe Asp Glu Ala
610                 615                 620

Ile Asn Val Leu Lys Asp Met Asp Ser Lys Gly Ile Asn Ala Asp Pro
625                 630                 635                 640

Ile Thr Tyr Asn Thr Leu Ile Gln Gly Phe Cys Glu Ser Glu Asn Val
                645                 650                 655

Gln Met Ala Phe His Ile His Asp Ile Met Leu Cys Arg Gly Leu Val
            660                 665                 670

Pro Thr Pro Val Thr Tyr Asn Leu Leu Ile Asn Val Leu Cys Leu Lys
            675                 680                 685

Gly Lys Val Ile Gln Ala Glu Ile Leu Leu Glu Ser Leu Arg Glu Asn
690                 695                 700

Gly Ile Lys Leu Arg Lys Phe Ala Tyr Thr Thr Leu Ile Lys Ala Gln
705                 710                 715                 720

Cys Ala Lys Gly Met Pro Ile Asn Ala Val Leu Leu Val Gly Lys Leu
                725                 730                 735

Leu Asp Ala Gly Phe Glu Ala Ser Ile Glu Asp Phe Ser Ala Ala Ile
            740                 745                 750

Asn Arg Leu Cys Lys Arg Gln Phe Ala Lys Glu Ala Phe Met Phe Val
            755                 760                 765

Pro Ile Met Leu Ser Val Gly Ile Tyr Pro Asp Thr Gln Ile Tyr Cys
770                 775                 780

Val Leu Gly Arg Ala Leu Gln Lys Asn Ser Glu Leu Val Tyr Leu Pro
785                 790                 795                 800

Ile Leu Asn Ala Leu Ala Val Lys Thr Gly Ile
                805                 810
```

<210> SEQ ID NO 40
<211> LENGTH: 1779
<212> TYPE: DNA
<213> ORGANISM: Arabidopsis thaliana

<400> SEQUENCE: 40

```
atgaaggctt tgagattgat tcagcctcat ctcttgaaga caggtagtct tagaactgat      60
ttgctctgta ccatttcgag tttcttttct agctgcgaac gagactttc aagtattagc     120
```

-continued

```
aatgggaatg tctgtttcag agagagattg agaagtggta ttgttgatat taagaaagat    180
gatgctattg ctctgttcca agaaatgatt aggtctcgtc ctcttcctag tcttgttgat    240
ttcagtagat tctttagtgc cattgccaga acaaaacagt tcaatctcgt gttagatttc    300
tgcaagcaac tggaattgaa tgggattgct cataacatct acactttgaa tatcatgatc    360
aactgctttt gccggtgttg taaaacttgt tttgcttatt ctgttttggg aaaagtaatg    420
aagcttgggt atgagcctga cacaaccacg tttaacactc tgatcaaagg actctttctt    480
gagggtaaag tgtctgaagc tgtggtttta gtcgatagga tggtggaaaa cggatgtcaa    540
cctgatgtgg ttacttataa ttcgattgta aatgggatat gtagatcagg agatacttct    600
ttggccttgg atttgctcag aaagatggaa gaaagaaatg ttaaggctga tgtgtttact    660
tacagtacaa tcattgatag tctttgtaga gatggttgca tagacgctgc aattagcctt    720
ttcaaggaaa tggagacgaa agggattaaa tctagtgttg ttacgtataa ttctcttgtg    780
agaggtcttt gtaaagccgg taaatggaat gatggggcac tgttgttgaa ggatatggtg    840
agtagggaaa tcgtccctaa tgtcatcact ttcaatgtat tacttgatgt ttttgtcaaa    900
gaagggaagc ttcaggaggc taatgaattg tacaaagaga tgatcacaag aggtatatca    960
cctaatatta ttacttataa taccttgatg gatgggtatt gtatgcagaa ccgtcttagt   1020
gaggccaaca atatgttgga tcttatggtt aggaataagt gcagtcctga tatcgtgact   1080
tttacaagtc tcatcaaagg atattgtatg gtgaaaagag ttgacgatgg tatgaaggtc   1140
ttccgcaata tttctaagag aggcttggtt gccaatgcag ttacttatag cattcttgtc   1200
caagggtttt gtcaatccgg gaaaataaag ctcgcagagg aacttttcca agaaatggtt   1260
tcacacggtg ttcttcctga tgttatgacg tatggtattt tgcttgatgg cttgtgtgac   1320
aatgggaagc ttgaaaaggc attggaaatt tttgaggatt tacaaaagag taagatggat   1380
cttggtattg ttatgtatac aaccatcatc gagggggatgt gcaagggtgg aaaagtggaa   1440
gatgcctgga atttattctg tagcctacct tgtaaaggag tgaagcctaa tgttatgaca   1500
tacaccgtga tgatttcagg attatgtaag aaagggtcac tgtctgaagc aaacatcttg   1560
cttagaaaaa tggaggaaga tgggaatgcg ccaaatgatt gtacatacaa cacactaatc   1620
cgggcacatc tccgagatgg tgacttaact gcatcagcta aacttattga agaaatgaag   1680
agttgtgggt tctcagcaga tgcttccagt attaagatgg ttatcgatat gttattgagt   1740
ggtgaattgg acaaaagctt tctagatatg ctttcgtaa                          1779
```

<210> SEQ ID NO 41
<211> LENGTH: 592
<212> TYPE: PRT
<213> ORGANISM: Arabidopsis thaliana

<400> SEQUENCE: 41

```
Met Lys Ala Leu Arg Leu Ile Gln Pro His Leu Leu Lys Thr Gly Ser
  1               5                  10                  15

Leu Arg Thr Asp Leu Leu Cys Thr Ile Ser Ser Phe Ser Ser Cys
                 20                  25                  30

Glu Arg Asp Phe Ser Ser Ile Ser Asn Gly Asn Val Cys Phe Arg Glu
             35                  40                  45

Arg Leu Arg Ser Gly Ile Val Asp Ile Lys Lys Asp Asp Ala Ile Ala
         50                  55                  60

Leu Phe Gln Glu Met Ile Arg Ser Arg Pro Leu Pro Ser Leu Val Asp
 65                  70                  75                  80
```

-continued

```
Phe Ser Arg Phe Phe Ser Ala Ile Ala Arg Thr Lys Gln Phe Asn Leu
                85                  90                  95
Val Leu Asp Phe Cys Lys Gln Leu Glu Leu Asn Gly Ile Ala His Asn
            100                 105                 110
Ile Tyr Thr Leu Asn Ile Met Ile Asn Cys Phe Cys Arg Cys Cys Lys
        115                 120                 125
Thr Cys Phe Ala Tyr Ser Val Leu Gly Lys Val Met Lys Leu Gly Tyr
    130                 135                 140
Glu Pro Asp Thr Thr Thr Phe Asn Thr Leu Ile Lys Gly Leu Phe Leu
145                 150                 155                 160
Glu Gly Lys Val Ser Glu Ala Val Val Leu Val Asp Arg Met Val Glu
                165                 170                 175
Asn Gly Cys Gln Pro Asp Val Val Thr Tyr Asn Ser Ile Val Asn Gly
            180                 185                 190
Ile Cys Arg Ser Gly Asp Thr Ser Leu Ala Leu Asp Leu Leu Arg Lys
        195                 200                 205
Met Glu Glu Arg Asn Val Lys Ala Asp Val Phe Thr Tyr Ser Thr Ile
    210                 215                 220
Ile Asp Ser Leu Cys Arg Asp Gly Cys Ile Asp Ala Ala Ile Ser Leu
225                 230                 235                 240
Phe Lys Glu Met Glu Thr Lys Gly Ile Lys Ser Ser Val Val Thr Tyr
                245                 250                 255
Asn Ser Leu Val Arg Gly Leu Cys Lys Ala Gly Lys Trp Asn Asp Gly
            260                 265                 270
Ala Leu Leu Leu Lys Asp Met Val Ser Arg Glu Ile Val Pro Asn Val
        275                 280                 285
Ile Thr Phe Asn Val Leu Leu Asp Val Phe Val Lys Glu Gly Lys Leu
    290                 295                 300
Gln Glu Ala Asn Glu Leu Tyr Lys Glu Met Ile Thr Arg Gly Ile Ser
305                 310                 315                 320
Pro Asn Ile Ile Thr Tyr Asn Thr Leu Met Asp Gly Tyr Cys Met Gln
                325                 330                 335
Asn Arg Leu Ser Glu Ala Asn Asn Met Leu Asp Leu Met Val Arg Asn
            340                 345                 350
Lys Cys Ser Pro Asp Ile Val Thr Phe Thr Ser Leu Ile Lys Gly Tyr
        355                 360                 365
Cys Met Val Lys Arg Val Asp Asp Gly Met Lys Val Phe Arg Asn Ile
    370                 375                 380
Ser Lys Arg Gly Leu Val Ala Asn Ala Val Thr Tyr Ser Ile Leu Val
385                 390                 395                 400
Gln Gly Phe Cys Gln Ser Gly Lys Ile Lys Leu Ala Glu Glu Leu Phe
                405                 410                 415
Gln Glu Met Val Ser His Gly Val Leu Pro Asp Val Met Thr Tyr Gly
            420                 425                 430
Ile Leu Leu Asp Gly Leu Cys Asp Asn Gly Lys Leu Glu Lys Ala Leu
        435                 440                 445
Glu Ile Phe Glu Asp Leu Gln Lys Ser Lys Met Asp Leu Gly Ile Val
    450                 455                 460
Met Tyr Thr Thr Ile Ile Glu Gly Met Cys Lys Gly Lys Val Glu
465                 470                 475                 480
Asp Ala Trp Asn Leu Phe Cys Ser Leu Pro Cys Lys Gly Val Lys Pro
                485                 490                 495
Asn Val Met Thr Tyr Thr Val Met Ile Ser Gly Leu Cys Lys Lys Gly
```

```
                500             505             510
    Ser Leu Ser Glu Ala Asn Ile Leu Leu Arg Lys Met Glu Glu Asp Gly
            515                 520                 525

Asn Ala Pro Asn Asp Cys Thr Tyr Asn Thr Leu Ile Arg Ala His Leu
            530                 535                 540

Arg Asp Gly Asp Leu Thr Ala Ser Ala Lys Leu Ile Glu Glu Met Lys
    545                 550                 555                 560

Ser Cys Gly Phe Ser Ala Asp Ala Ser Ser Ile Lys Met Val Ile Asp
                        565                 570                 575

Met Leu Leu Ser Gly Glu Leu Asp Lys Ser Phe Leu Asp Met Leu Ser
                580                 585                 590

<210> SEQ ID NO 42
<211> LENGTH: 6711
<212> TYPE: DNA
<213> ORGANISM: Petunia sp.

<400> SEQUENCE: 42
atatatatat acaaactgat tttttctgtc tatttgcaca gtgttatttt tacatacccc      60
tgaaaaaggg tagctccgct aataatgtta tctttacaaa aaataacaat acttttttta    120
cataatatat acaaaactca ttcttatgta ttgtaaatat gataaaaata ttgttatttt    180
ttgtaatata gctattaggt agtcatgttg tgtaaatttt cctaaaaata tttacctgag    240
tcggccattt ggctaaaaat atttcatttt atagtcgcat atactccaag cttgtatatc    300
ccagagcgac agtatacttc aatggtatac gatatcttct attatacacc ttttttagtat   360 tcgtataccc ccaatagtat acaagtttga caccgcaata gtgtacccca atgttgtggt    420
tgtgtggcta caaatttga gtgatggtag tgtaattttt tagtgtaagc tgggtagttt     480
tgaaaacatt cttttttgaaa attgtagttc aagtcatagt acaaaaaact gaaatattta    540
tatgtttctt gattctggct ggtcttctaa aaattttgaa atgctggcta gttttcattt     600
agcgaggggc aaataggcta catggccaaa tttttacgtt aaaagataag tgttgtctgg     660
gaaagtattc gaaagattg tagggacaag tgttgcctag acaacacgtc aaattatgta      720
gaaaaatgca cgaagaaatt caaaagcaaa tattgcttaa gcaagaggca gtcaaagaca     780
agtgctgcct tagggagtga gaaatgggca tcactataag attgtatttc catccgatat    840
ttattcatta taaacttaag gaaaagtgca ggaaaaacca ctagttttta gctatttttt     900 ggaacttaa tcattatggg ctgaacttca gactttgtgg gccgaacttc atacattcgc      960
aagtaaaaat ttagctcaca ggccactttt accactagta tttggtttga agtcattttt    1020
tattggtttt acatgagaga ccacttttg gaacttcaat cttttgtgcgc ttgaacttca    1080 tgcctaagtt attaagttca acttcaatcc gtaagggctg aatttttagg catagatgcg    1140
taaacttcaa ccttgtggac tgaagttgaa cttcgcccct tatggtggcc tgaagttgaa    1200
cttcaatcct tgtgggctga acttgtgtga agttcaaccc acaaggatta agtttcaaa     1260 aaatgacctc tcaagcaaaa tctgtaaaaa aagtggtct ctcatgcact tttacccatt     1320
cgcaaagtag gctgaagttc agcccacaat tattcaagtt ccaaaaaatt tcacaatata    1380
tacctcctta tctcggttat gatcttttgt atgatttagc aaaatggacg gggaaagtgc    1440
acgaaagacc acttttgcca ttggtctttg ggtacaggcc actaatacca aaatatttag    1500
tttgtggcta ctttttgctta aagagttgaa cttcagtcca gaggccggat tgaagttcag    1560 tcctaaaga ttgaacttcg atccagtgcc atatggactg aagttcagtc aagtccttaa     1620
```

-continued

```
gatggaactt cagtccagag ccatatggac tgaagttcag tcaattatca gaacttaagt    1680
caatatttat ttagtaaagg cccaaaagtg gttagtataa gaccaataaa aatagcggcc    1740
taaaactaaa taacagtgtt aaaagtggct gatggacgaa atttctacaa aatggactcg    1800
aggtagcaat tcaacttcaa cctatggtgt catagttgta caattcttcc aatcacccct    1860
actaagtgaa gtgaagcgaa gatgatgaga atttcagtgc gttactgtct caatggtaat    1920
ccctttttct cattctttgc ttattcaatt gcaccccgac attattctac caatacatgt    1980
tccatttcag ttaaagggaa ttttgggggtt tctaatgaat tcagaatgt taagtgttta    2040 gatgatgctt tcagtttgtt ccgtcaaatg gttagaacta agcctcttcc ttctgttgcc    2100
tctttctcta aattgttgaa agctatggta catatgaagc attactcttc tgttgtttct    2160 cttttttcgag aaatccacaa attacgaatt cctgttcatg aattcatctt gagcattgtg    2220
gttaacagtt gttgccttat gcatcgtacc gatctcggat tttctgtatt agccattcac    2280
ttcaagaaag gcattccata taatgaagtc acctttacta ccttaataag gggacttttt    2340
gctgaaaata aggtcaaaga tgctgttcat ttgttcaaaa agttggtgag ggagaatata    2400
tgtgagccta atgaagtcat gtatggaacg gtcatgaatg ggctttgcaa aaagggccat    2460
actcaaaaag cttttgattt gctccggtta atggaacaag gaagcactaa gcccaataca    2520
cgcacttaca ccattgtcat agacgccttt tgcaaagatg gatgctaga tggtgctacc    2580 agccttttga atgagatgaa acaaaaaagc attcctcccg acattttttac ttatagcact    2640 ttaattgatg ctttgtgtaa gttaagtcag tgggaaaatg ttaggacttt gttccttgag    2700
atgatacatc ttaatatttta tccaaatgtg tgcaccttca actccgtcat tgatggacta    2760
tgcaaagagg ggaaagtaga agacgctgag gaaataatga gatacatgat tgaaaaaggt    2820
gtagaccctg atgtgatcac ctataatatg ataattgacg gatatggctt gcgtggtcaa    2880
gtggatagag cacggaaat ttttgattcc atgatcaata agagcattga gcccgatatt    2940
attagctata atatactaat aaatggatat gccaggcaaa agaaaataga cgaggcaatg    3000
caagtctgcc gtgaaatttc tcaaaaggga ttgaaaccta gtattgttac ctgcaatgtt    3060
ctcttgcatg gtctttttga acttggaaga actaaatctg cacaaaattt ctttgatgag    3120
atgctatctg cggggcacat ccctgattta tacactcatt gtactttgct tggtggttat    3180
tttaagaatg gacttgttga agaggctatg tcacacttcc ataagttgga aagaaggaga    3240
gaagatacaa atattcaaat ttacacggct gtcattgatg gattgtgcaa aaatggtaag    3300
ctcgacaaag ctcatgctac gtttgagaag cttcccttga taggcttaca tcctgatgtg    3360
ataacataca ctgcaatgat tagtggatat tgtcaagaag ggttgttaga tgaagctaaa    3420
gatatgctaa ggaaaatgga ggacaatggt tgtttggcag acaaccgaac atacaatgtt    3480
attgtgcggg gatttctcag aagcaataaa gttagtgaaa tgaaggcttt tctggaggaa    3540
atagctggga agagcttctc atttgaggca gctactgtag agttattgat ggatattata    3600
gcagaggatc catccataac acgcaaaatg cactggatta aactgcacat tgcatgaata    3660
tacaaggaga ttagcagaat aatcacaggt ccgtcccaga caaccccaag gctaaatccc    3720
acaatcgaaa caaggtaaac tattaatact ttaactgcca aaacttcttt aagaactatg    3780
ccaattgaaa caggtaatat atatatttcc tttatttgga acatttctcg atttatgcgt    3840
gtcatccttg tgcagaggcc atgctaatct tctctcaatc gttcccaggt ttgatttgaa    3900
tgatatttta gattatatac cccacagttc tgcattgaaa tatgcaccca aacaaattag    3960
tgcatctgtc ataaaaggga ttgctcctat tataccatca ttaagaaaat ccttgtgaca    4020
```

```
gtcggataaa tgagcaaata gtacatgttt gtttattttt tattcaataa gagtttgaca    4080
tctacgggaa attatagtta tctatgtggt cgtactttta aagaaaagta tttttgtggt    4140
tatagattga ctgttttcct ctgtcattga tcgactttct tttattcaca tcagaagtag    4200
gtatatgtgt acaatgcttt taacaactgg tttgcatgtg ctctttatgg tcgcatttca    4260
tcaacgaagt ctctttgtcg agatgcagct tgacttgtta agacaagaac ctttcgattt    4320
ggaaatgtga ttatcccatt caaagatact tgacagatgt ctcatgatgc ttatttgact    4380
cagaagaata ttcagaaaag gcatgtagat gtgcagcaaa tgacagagta tgtgcaatgg    4440
gtgaggagga caattataca ttgtcctcca ttgttcagtg gcaaatggca atacacctat    4500
gggatctaaa ggacatgttc tgcatgtagc tagaagggat gcaagttcac agggaactag    4560
ggatttggta gactatacca gccttcattt tatcagttag tgaaatgaaa gaaaccatca    4620
atgtaaagga aactctatgg ttgtacacct tttgaagttc caagtgttaa actaacctct    4680
ggtgtatatt agtatatacg gtagaattca ttcaattgca caagtagatg tatctttttg    4740
cttggtttta gttcattaag gcataaatgt tctacttagg tttcatgcat taaaatgaac    4800
attcatttga tctatgatga tggagtcttg gtcgtgcata tacatgcttc aaaattattg    4860
tacaatgggt tgtgtagtcc aatatgttaa catcatccac gacattatct ctaatagttt    4920
gagattttgt gatatttatt cgtaaaatgc atgttaagat tattgtaatt tagacttcta    4980
aagttttctt tttagtttgg tggacaacaa agtaataaat ctcaaacaca ttgtttggtc    5040
tcttattctt tggaataaaa tattgagctt tttacaatgt gtaccctgg aatataaagt     5100 atttaccta ctatacctat taaaaattac attactcatg aaattcaaag tatctatcac      5160
actgcgtatt tttttttata ctataagtct atatttacct tagggcaaaa attaggcaag    5220
tacttaccca catcgggtgt atataccaa tcaacaaagg aattttaca ctctatacc       5280 atgaaattta agtatttac aagtcatacc cattaaaaat tactctaccc ataaaactaa     5340
aagtatttac ccaacatacc catttttttat tgtataccttt tgtttataagg tgtataccttt  5400 taaggctgca taaattatgg tataaaagtc tggaggacca tttattattg tttaccttttt    5460 tataccttat aatatataag tctggagggg tagagtgagt aaatatttta atgggtaggc    5520 cagataaatat ttgaaagtag tggatagtgg ctgtaattat tttagatttc gtgggtattt    5580
ttgtaagtgt ctaatcaaca aatgcacgtc atttgtttac aatacactac tatcacttag    5640
ccataattaa ttaatagaca ttctctcttc attcatcac attaccatag ttaattgcta      5700
tggttaggta tatatatccg gtgtgagtaa attttttcat ataaattatg gcaagacgag    5760
taaatatgaa acttacatgc agaggcagat aaatattttg attttgatga gtattttcgt     5820
aaaacaatga ttaaattatc gcgcaaaacc ctttcagttt gttttaatcg tgtacttatt    5880
tgtttgttat cattccataa tgaaaattac ctcattagtg ccacattatc tttctataat    5940
gtggctattg tgtcaagaat cataatcgtg ccaacttgct acattgtaaa aacaatgatt    6000
cttttgtggc tatttagtca aaaatagtaa ctctgctttc cattgtctcc ggtcacctcg    6060
gccaactccg gccctacgtt catcaagtac ttattttcca tatttattcg ttattttgtt    6120
aatacttaca atttgtttaa ttaaatcata gaattagctg atacacacat atatagtgaa    6180
aaatgagata gtaactgaag cagctcaagt tcaatttta ggtgcaaaat tcttctatca      6240
gttattatgt tttgctttca aattaataac atattcatat agccgacctc aactaattac    6300
gcattgatgc atagttcatt gtactaggaa agtaaaaatt tcatttttaa gttagtttat    6360
```

-continued

```
ttgagcaagt tatatatata tacacaatgc atgtgcttat atccctttcc aatgctaact    6420
ctgacttcat gaaaattaaa ttataggtgt tactttagtg agggacgcga attaatatta    6480
catcactggt agtggcggag ccagtatttt tactaaggag tatcaaaata taaataagta    6540
aatatacgaa atattaaaag gatagtgaat cttcctttt aatgtacttc attttaaagt     6600
tagtttattt gagaaagtta tatatataca atgtatgaac tgatattctt tgataatgat    6660
gatgcctatg tggatagtga atcttccttt ttaatgttga tgaaaaataa a             6711
```

<210> SEQ ID NO 43
<211> LENGTH: 591
<212> TYPE: PRT
<213> ORGANISM: Petunia sp.

<400> SEQUENCE: 43

| Met | Met | Arg | Ile | Ser | Val | Arg | Tyr | Cys | Leu | Asn | Gly | Asn | Pro | Phe | Phe |
|---|---|---|---|---|---|---|---|---|---|---|---|---|---|---|---|
| 1 | | | | 5 | | | | | 10 | | | | | 15 | |

| Ser | Phe | Phe | Ala | Tyr | Ser | Ile | Ala | Pro | Arg | His | Tyr | Ser | Thr | Asn | Thr |
| | | | 20 | | | | | 25 | | | | | 30 | | |

| Cys | Ser | Ile | Ser | Val | Lys | Gly | Asn | Phe | Gly | Val | Ser | Asn | Glu | Phe | Gln |
| | | 35 | | | | | 40 | | | | | 45 | | | |

| Asn | Val | Lys | Cys | Leu | Asp | Asp | Ala | Phe | Ser | Leu | Phe | Arg | Gln | Met | Val |
| | 50 | | | | 55 | | | | 60 | | | | | | |

| Arg | Thr | Lys | Pro | Leu | Pro | Ser | Val | Ala | Ser | Phe | Ser | Lys | Leu | Leu | Lys |
| 65 | | | | | 70 | | | | 75 | | | | | 80 | |

| Ala | Met | Val | His | Met | Lys | His | Tyr | Ser | Ser | Val | Ser | Leu | Phe | Arg |
| | | | | 85 | | | | 90 | | | | | 95 | |

| Glu | Ile | His | Lys | Leu | Arg | Ile | Pro | Val | His | Glu | Phe | Ile | Leu | Ser | Ile |
| | | | 100 | | | | | 105 | | | | | 110 | | |

| Val | Val | Asn | Ser | Cys | Cys | Leu | Met | His | Arg | Thr | Asp | Leu | Gly | Phe | Ser |
| | | 115 | | | | | 120 | | | | | 125 | | | |

| Val | Leu | Ala | Ile | His | Phe | Lys | Lys | Gly | Ile | Pro | Tyr | Asn | Glu | Val | Thr |
| | 130 | | | | 135 | | | | 140 | | | | | | |

| Phe | Thr | Thr | Leu | Ile | Arg | Gly | Leu | Phe | Ala | Glu | Asn | Lys | Val | Lys | Asp |
| 145 | | | | | 150 | | | | 155 | | | | | 160 | |

| Ala | Val | His | Leu | Phe | Lys | Lys | Leu | Val | Arg | Glu | Asn | Ile | Cys | Glu | Pro |
| | | | | 165 | | | | 170 | | | | | 175 | |

| Asn | Glu | Val | Met | Tyr | Gly | Thr | Val | Met | Asn | Gly | Leu | Cys | Lys | Lys | Gly |
| | | | 180 | | | | | 185 | | | | | 190 | | |

| His | Thr | Gln | Lys | Ala | Phe | Asp | Leu | Leu | Arg | Leu | Met | Glu | Gln | Gly | Ser |
| | | 195 | | | | | 200 | | | | | 205 | | | |

| Thr | Lys | Pro | Asn | Thr | Arg | Thr | Tyr | Thr | Ile | Val | Ile | Asp | Ala | Phe | Cys |
| | 210 | | | | 215 | | | | 220 | | | | | | |

| Lys | Asp | Gly | Met | Leu | Asp | Gly | Ala | Thr | Ser | Leu | Leu | Asn | Glu | Met | Lys |
| 225 | | | | | 230 | | | | 235 | | | | | 240 | |

| Gln | Lys | Ser | Ile | Pro | Pro | Asp | Ile | Phe | Thr | Tyr | Ser | Thr | Leu | Ile | Asp |
| | | | | 245 | | | | 250 | | | | | 255 | |

| Ala | Leu | Cys | Lys | Leu | Ser | Gln | Trp | Glu | Asn | Val | Arg | Thr | Leu | Phe | Leu |
| | | | 260 | | | | | 265 | | | | | 270 | | |

| Glu | Met | Ile | His | Leu | Asn | Ile | Tyr | Pro | Asn | Val | Cys | Thr | Phe | Asn | Ser |
| | | 275 | | | | | 280 | | | | | 285 | | | |

| Val | Ile | Asp | Gly | Leu | Cys | Lys | Glu | Gly | Lys | Val | Glu | Asp | Ala | Glu | Glu |
| | 290 | | | | 295 | | | | 300 | | | | | | |

| Ile | Met | Arg | Tyr | Met | Ile | Glu | Lys | Gly | Val | Asp | Pro | Asp | Val | Ile | Thr |
| 305 | | | | | 310 | | | | 315 | | | | | 320 | |

```
Tyr Asn Met Ile Ile Asp Gly Tyr Gly Leu Arg Gly Gln Val Asp Arg
                325                 330                 335

Ala Arg Glu Ile Phe Asp Ser Met Ile Asn Lys Ser Ile Glu Pro Asp
            340                 345                 350

Ile Ile Ser Tyr Asn Ile Leu Ile Asn Gly Tyr Ala Arg Gln Lys Lys
        355                 360                 365

Ile Asp Glu Ala Met Gln Val Cys Arg Glu Ile Ser Gln Lys Gly Leu
370                 375                 380

Lys Pro Ser Ile Val Thr Cys Asn Val Leu His Gly Leu Phe Glu
385                 390                 395                 400

Leu Gly Arg Thr Lys Ser Ala Gln Asn Phe Phe Asp Glu Met Leu Ser
            405                 410                 415

Ala Gly His Ile Pro Asp Leu Tyr Thr His Cys Thr Leu Leu Gly Gly
            420                 425                 430

Tyr Phe Lys Asn Gly Leu Val Glu Glu Ala Met Ser His Phe His Lys
        435                 440                 445

Leu Glu Arg Arg Arg Glu Asp Thr Asn Ile Gln Ile Tyr Thr Ala Val
450                 455                 460

Ile Asp Gly Leu Cys Lys Asn Gly Lys Leu Asp Lys Ala His Ala Thr
465                 470                 475                 480

Phe Glu Lys Leu Pro Leu Ile Gly Leu His Pro Asp Val Ile Thr Tyr
            485                 490                 495

Thr Ala Met Ile Ser Gly Tyr Cys Gln Glu Gly Leu Leu Asp Glu Ala
            500                 505                 510

Lys Asp Met Leu Arg Lys Met Glu Asp Asn Gly Cys Leu Ala Asp Asn
        515                 520                 525

Arg Thr Tyr Asn Val Ile Val Arg Gly Phe Leu Arg Ser Asn Lys Val
        530                 535                 540

Ser Glu Met Lys Ala Phe Leu Glu Glu Ile Ala Gly Lys Ser Phe Ser
545                 550                 555                 560

Phe Glu Ala Ala Thr Val Glu Leu Leu Met Asp Ile Ile Ala Glu Asp
            565                 570                 575

Pro Ser Ile Thr Arg Lys Met His Trp Ile Lys Leu His Ile Ala
            580                 585                 590

<210> SEQ ID NO 44
<211> LENGTH: 1779
<212> TYPE: DNA
<213> ORGANISM: Petunia sp.

<400> SEQUENCE: 44
atgatgagaa ttgcagtgcg ttactgtctc aatggtaatc ccttttctc attctttgct      60 tattcaattg cacccgaca ttattctacc aatacacgtt ccatttcagt taaagggaat     120
tttggggttt ctaatgaatt tgagaatgtt aagtgtttag atgatgcttt cagtttgttc     180
cgtcaaatgg ttagaactaa gcctcttcct tctgttgtct ctttctctaa attgttgaaa     240
gctttggtac atatgaagca ttactcttct gttgtttctc ttttcgaga aatccacaaa     300 ttacgtattc ctgttcatga attcatcttg agcattgtgg ttaacagttg ttgccttatg     360
catcgtaccg atctcggatt ttctgtatta gccattcact tcaagaaagg tattccattt     420
aatcaagtta tctttaacac cttactaagg ggactctttg ctgaaaataa ggttaaagat     480
gctgttcatt tgttcaaaaa gttggtgagg gagaatatat gtgagcctaa tgaagtcatg     540
tatggaacgg tcatgaatgg gctttgcaaa aagggccata ctcaaaaagc ttttgatttg     600
```

-continued

```
ctccggttaa tggaacaagg aagtactaag cccaatacat gtatctatag cattgttatc    660
gatgcctttt gcaaagatgg gatgctagat ggtgctacca gccttttgaa tgagatgaaa    720
caaaaaagca ttcctcccga cattttact tatagcactt taattgatgc tttgtgtaag    780
ttaagtcagt gggaaaatgt taggactttg ttccttgaga tgatacatct taatatttat    840
ccaaatgtgt gcaccttcaa ctccgtcatt gatggactat gcaaagaggg gaaagtagaa    900
gacgctgagg aaataatgag atacatgatt gaaaaggtg tagaccctga tgtgatcacc    960
tataatatga taattgacgg atatggcttg cgtggtcaag tggatagagc acgggaaatt   1020
tttgattcca tgatcaataa gagcattgag cccaatatta ttagctataa tatactaata   1080
aatgatatg ccaggcaaaa gaaaatagac gaggcaatgc aagtctgccg tgaaatttct   1140
caaaagggat tgaaacctag tattgttacc tgcaatgttc tcttgcatgg tctttttgaa   1200
cttgaagaa ctaaatctgc acaaaatttc tttgatgaga tgctatctgc ggggcacata   1260
cctgatttat acactcattg tactttgctt ggtggttatt ttaagaatgg acttgttgaa   1320
gaggctatgt cacacttcca taagttggaa agaaggagag aagatacaaa tattcaaatt   1380
tacacggctg tcattgatgg attgtgcaaa aatggtaagc tcgacaaagc tcatgctacg   1440
tttgagaagc ttcccttgat aggcttacat cctgatgtga taacatcac tgcaatgatt   1500
agtggatatt gtcaagaagg gttgttagat gaagctaaag atatgctaag gaaaatggag   1560
gacaatggtt gtttggcaga caaccgaaca tacaatgtta ttgtgcgggg atttctcaga   1620
agcaataaag ttagtgaaat gaaggctttt ctggaggaaa tagctgggaa gagcttctca   1680
tttgaggcag ctactgtaga gttattgatg gatattatag cagaggatcc ttctttgctt   1740
aacatgattc cagaatttca ccgggataat aagaagtga                           1779
```

<210> SEQ ID NO 45
<211> LENGTH: 592
<212> TYPE: PRT
<213> ORGANISM: Petunia sp.

<400> SEQUENCE: 45

```
Met Met Arg Ile Ala Val Arg Tyr Cys Leu Asn Gly Asn Pro Phe Phe
  1               5                  10                  15

Ser Phe Phe Ala Tyr Ser Ile Ala Pro Arg His Tyr Ser Thr Asn Thr
             20                  25                  30

Arg Ser Ile Ser Val Lys Gly Asn Phe Gly Val Ser Asn Glu Phe Glu
         35                  40                  45

Asn Val Lys Cys Leu Asp Asp Ala Phe Ser Leu Phe Arg Gln Met Val
     50                  55                  60

Arg Thr Lys Pro Leu Pro Ser Val Val Ser Phe Ser Lys Leu Leu Lys
 65                  70                  75                  80

Ala Leu Val His Met Lys His Tyr Ser Ser Val Ser Leu Phe Arg
                 85                  90                  95

Glu Ile His Lys Leu Arg Ile Pro Val His Glu Phe Ile Leu Ser Ile
            100                 105                 110

Val Val Asn Ser Cys Cys Leu Met His Arg Thr Asp Leu Gly Phe Ser
        115                 120                 125

Val Leu Ala Ile His Phe Lys Lys Gly Ile Pro Phe Asn Gln Val Ile
    130                 135                 140

Phe Asn Thr Leu Leu Arg Gly Leu Phe Ala Glu Asn Lys Val Lys Asp
145                 150                 155                 160
```

-continued

```
Ala Val His Leu Phe Lys Lys Leu Val Arg Glu Asn Ile Cys Glu Pro
                165                 170                 175
Asn Glu Val Met Tyr Gly Thr Val Met Asn Gly Leu Cys Lys Lys Gly
            180                 185                 190
His Thr Gln Lys Ala Phe Asp Leu Leu Arg Leu Met Glu Gln Gly Ser
        195                 200                 205
Thr Lys Pro Asn Thr Cys Ile Tyr Ser Ile Val Ile Asp Ala Phe Cys
    210                 215                 220
Lys Asp Gly Met Leu Asp Gly Ala Thr Ser Leu Leu Asn Glu Met Lys
225                 230                 235                 240
Gln Lys Ser Ile Pro Pro Asp Ile Phe Thr Tyr Ser Thr Leu Ile Asp
                245                 250                 255
Ala Leu Cys Lys Leu Ser Gln Trp Glu Asn Val Arg Thr Leu Phe Leu
            260                 265                 270
Glu Met Ile His Leu Asn Ile Tyr Pro Asn Val Cys Thr Phe Asn Ser
        275                 280                 285
Val Ile Asp Gly Leu Cys Lys Glu Gly Lys Val Glu Asp Ala Glu Glu
    290                 295                 300
Ile Met Arg Tyr Met Ile Glu Lys Gly Val Asp Pro Asp Val Ile Thr
305                 310                 315                 320
Tyr Asn Met Ile Ile Asp Gly Tyr Gly Leu Arg Gly Gln Val Asp Arg
                325                 330                 335
Ala Arg Glu Ile Phe Asp Ser Met Ile Asn Lys Ser Ile Glu Pro Asn
            340                 345                 350
Ile Ile Ser Tyr Asn Ile Leu Ile Asn Gly Tyr Ala Arg Gln Lys Lys
        355                 360                 365
Ile Asp Glu Ala Met Gln Val Cys Arg Glu Ile Ser Gln Lys Gly Leu
    370                 375                 380
Lys Pro Ser Ile Val Thr Cys Asn Val Leu Leu His Gly Leu Phe Glu
385                 390                 395                 400
Leu Gly Arg Thr Lys Ser Ala Gln Asn Phe Phe Asp Glu Met Leu Ser
                405                 410                 415
Ala Gly His Ile Pro Asp Leu Tyr Thr His Cys Thr Leu Leu Gly Gly
            420                 425                 430
Tyr Phe Lys Asn Gly Leu Val Glu Glu Ala Met Ser His Phe His Lys
        435                 440                 445
Leu Glu Arg Arg Arg Glu Asp Thr Asn Ile Gln Ile Tyr Thr Ala Val
    450                 455                 460
Ile Asp Gly Leu Cys Lys Asn Gly Lys Leu Asp Lys Ala His Ala Thr
465                 470                 475                 480
Phe Glu Lys Leu Pro Leu Ile Gly Leu His Pro Asp Val Ile Thr Tyr
                485                 490                 495
Thr Ala Met Ile Ser Gly Tyr Cys Gln Glu Gly Leu Leu Asp Glu Ala
            500                 505                 510
Lys Asp Met Leu Arg Lys Met Glu Asp Asn Gly Cys Leu Ala Asp Asn
        515                 520                 525
Arg Thr Tyr Asn Val Ile Val Arg Gly Phe Leu Arg Ser Asn Lys Val
    530                 535                 540
Ser Glu Met Lys Ala Phe Leu Glu Glu Ile Ala Gly Lys Ser Phe Ser
545                 550                 555                 560
Phe Glu Ala Ala Thr Val Glu Leu Leu Met Asp Ile Ile Ala Glu Asp
                565                 570                 575
Pro Ser Leu Leu Asn Met Ile Pro Glu Phe His Arg Asp Asn Lys Lys
```

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 46
tgcacagtgt tatatttaca taccc                                              25

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 47
tttatgatac atggatttca acgac                                              25

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 48
tgaaaatgac aatcgtaaca gaaaa                                              25

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 49
aacattcctc cagacattat taca                                               24

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 50
gacgctgagg aaataatgag atac                                               24

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 51
tctagaaaaa atgaaggggg aatcaat                                            27

<210> SEQ ID NO 52
<211> LENGTH: 31
<212> TYPE: DNA
<213> ORGANISM: Artificial Sequence -continued

```
<220> FEATURE:
<223> OTHER INFORMATION: Description of Artificial Sequence:  Primer

<400> SEQUENCE: 52
gaattcactt tgctctcacg ataaactaag a                                        31
```